US011053287B2

(12) United States Patent
Foster et al.

(10) Patent No.: US 11,053,287 B2
(45) Date of Patent: Jul. 6, 2021

(54) **MATERIALS AND METHODS FOR DIFFERENTIAL BIOSYNTHESIS IN SPECIES OF THE GENERA *RALSTONIA* AND *CUPRIAVIDUS* AND ORGANISMS RELATED THERETO**

(71) Applicant: INV Nylon Chemicals Americas, LLC, Wilmington, DE (US)

(72) Inventors: Alexander Brett Foster, Redcar (GB); Ana Teresa dos Santos Brito Mendes Roberts, Redcar (GB); Arghya Barman, Redcar (GB); Jonathan Kennedy, Redcar (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 16/398,365

(22) Filed: Apr. 30, 2019

(65) Prior Publication Data

US 2019/0337995 A1    Nov. 7, 2019

Related U.S. Application Data

(60) Provisional application No. 62/665,800, filed on May 2, 2018.

(51) Int. Cl.
| | | |
|---|---|---|
| *C07K 14/195* | (2006.01) |
| *C12P 7/18* | (2006.01) |
| *C12P 7/42* | (2006.01) |
| *C12P 7/54* | (2006.01) |
| *C12P 7/56* | (2006.01) |

(52) U.S. Cl.
CPC .............. *C07K 14/195* (2013.01); *C12P 7/18* (2013.01); *C12P 7/42* (2013.01); *C12P 7/54* (2013.01); *C12P 7/56* (2013.01)

(58) Field of Classification Search
CPC ... C12N 1/20; C12N 15/87; C12P 7/00; C12P 7/62; C12P 7/64
See application file for complete search history.

(56) References Cited

U.S. PATENT DOCUMENTS

| | | | |
|---|---|---|---|
| 7,384,783 B2 | 6/2008 | Kunas et al. | |
| 8,809,027 B1 | 8/2014 | Lynch et al. | |
| 8,986,960 B2 * | 3/2015 | Sichwart ................ | C12N 9/001 435/134 |
| 9,580,733 B2 | 2/2017 | Botes et al. ............ | C12P 13/02 |
| 9,637,764 B2 | 5/2017 | Botes et al. .......... | C12P 13/001 |
| 9,862,973 B2 | 1/2018 | Botes et al. ............ | C12P 5/007 |
| 9,920,339 B2 | 3/2018 | Kadi et al. ................ | C12P 7/62 |
| 10,072,150 B2 | 9/2018 | Conradie et al. ....... | C08L 77/12 |
| 10,196,657 B2 | 2/2019 | Pearlman et al. .... | C12P 13/001 |
| 2012/0003706 A1 | 1/2012 | Hickey | |
| 2012/0064622 A1 | 3/2012 | Fischer et al. | |
| 2013/0034884 A1 | 2/2013 | Burgard et al. | |
| 2013/0065285 A1 | 3/2013 | Sefton | |
| 2013/0323714 A1 | 12/2013 | Cheng et al. | |
| 2015/0315599 A1 | 11/2015 | Shetty et al. | |
| 2017/0218406 A1 | 8/2017 | Conradie et al. | |
| 2018/0023103 A1 | 1/2018 | Foster et al. | |
| 2018/0023104 A1 | 1/2018 | Cartman et al. | |
| 2018/0100160 A1 | 4/2018 | Bawdon et al. ....... | C12N 15/74 |
| 2019/0124947 A1 | 5/2019 | Pearlman et al. | |
| 2019/0300838 A1 | 10/2019 | Smith et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |

FOREIGN PATENT DOCUMENTS

| | | |
|---|---|---|
| EP | 0995490 A2 | 4/2000 |
| EP | 1728853 A1 | 12/2006 |
| EP | 1938892 A1 | 7/2008 |
| EP | 3399015 A1 | 11/2018 |
| JP | 2009225662 | 10/2009 |
| JP | 2013179909 | 9/2013 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |
| WO | 2015117019 A1 | 8/2015 |
| WO | 2015195654 A1 | 12/2015 |
| WO | 2017165244 A1 | 9/2017 |
| WO | 2018005770 A2 | 1/2018 |
| WO | 2018022595 A1 | 2/2018 |
| WO | 2018022633 A1 | 2/2018 |
| WO | 2018106549 A1 | 6/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Uniprot database, entry A0A0U2WHG0, Mar. 2016.*
Non-final office action received for U.S. Appl. No. 16/399145, dated Aug. 12, 2020, 16 pages.
Brandt et al. "Elevated poly(3-hydroxybutyrate) synthesis in mutants of Ralstonia eutropha H16 defective in lipopolysaccharide biosynthesis" Appl Microbiol. Biotechnol. 2012 95:471-483.
Byrd et al. "Bacterial Control of Agromyces ramosus in soil" Can J Microbiol 1985 31:1157-1163.

(Continued)

*Primary Examiner* — Maryam Monshipouri

(57) ABSTRACT

Methods for increasing carbon-based chemical product yield in an organism by increasing carbon uptake and/or altering a pathway to or from an overflow metabolite in the organism, nonnaturally occurring organisms having increased carbon-based chemical product yield with increased carbon uptake and/or an altered pathway to or from an overflow metabolite, and methods for producing a carbon-based chemical product with these organisms are provided.

3 Claims, 1 Drawing Sheet

Specification includes a Sequence Listing.

(56) References Cited

OTHER PUBLICATIONS

Doberstein et al. "Polythioester synthesis in Ralstonia eutropha H16: novel insights into 3,3'-thiodipropionic acid and 3,3'-dithiodipropionic acid catabolism" Journal of Biotechnology 2014 184:187-198.

Grousseau et al. "Isopropanol production with engineered Cupriavidus necator as bioproduction platform" Appl Microbiol Biotechnol 2014 98:4277-4290.

Lu et al. "Studies on the production of branched-chain alcohols in engineered Ralstonia eutropha" Appl Microbiol Biotechnol 2012 96:283-297.

Makkar, N.S. & Casida, L.E. "*Cupriavidus necator* gen. nov., sp. nov.: a Nonobligate Bacterial Predator of Bacteria in Soil" Int. J. of Systematic Bacteriology 1987 37(4): 323-326.

Orita et al. "Identification of mutation points in Cupriavidus necator NCIMB 11599 and genetic reconstitution of glucose-utilization ability in wild strain H16 for polyhydroxyalkanoate production" Journal of Bioscience and Bioengineering 2012 113(1):63-69.

Pohlmann et al. "Genome sequence of the bioplastic-producing "Knallgas" bacterium Ralsonia eutropha H16" Nature Biotechnology 2007 1-6.

Raberg et al. "A closer look on the polyhydroxybutyrate—(PHB-) negative phenotype of Ralstonia eutropha PHB-4" PLoS One. 2014; 9(5): e95907.

Rosa et al. "Tripartite ATP-Independent Periplasmic (TRAP) Transporters and Tripartite Tricarboxylate Transporters (TTT): From Uptake to Pathogenicity" Front Cell Infect. Microbiol. 2018 8:33.

Schlegel and Vollbrecht "Formation of the Dehydrogenases for Lactate, Ethanol and Butanediol in the Strictly Aerobic Bacterium Alcaligenes eutrophus" Microbiology 1980 117:475-481.

Sillman, C. E. & Casida, L. E. "Isolation of nonobligate bacterial predators of bacteria from soil" Can J Microbiol 1986 32:760-762.

Steinbüchel and Schlegel "A multifunctional fermentative alcohol dehydrogenase from the strict aerobe Alcaligenes eutrophus: purification and properties" Eur J Biochem. 1984 141(3):555-64.

Vollbrecht and Schlegel "Excretion of Metabolites by Hydrogen Bacteria I. Autotrophic and Heterotrophic Fermentations" European Journal of Applied Microbiology and Biotechnology 1978 6(2):145-155.

Vollbrecht and Schlegel "Excretion of Metabolites by Hydrogen Bacteria II. Influence of Aeration, pH, Temperature, and Age of Cells" European Journal of Applied Microbiology and Biotechnology 1978 6(2):157-166.

Vollbrecht and Schlegel "Excretion of Metabolites by Hydrogen Bacteria IV. Respiration Rate-Dependent Formation of Primary Metabolites and of Poly-3-hydroxybutanoate" European Journal of Applied Microbiology and Biotechnology 1979 7(3):267-276.

Volodina et al. "Characterization of propionate CoA-transferase from Ralstonia eutropha H16" Appl Microbiol Biotechnol. 2014 98(8):3579-89.

Winnen et al. "The tripartite tricarboxylate transporter (TTT) family" Res. Microbiol. 2003 154(7):457-65.

Zeph, L.E. & Casida, L.E. "Gram-negative versus gram-positive (actinomycete) nonobligate bacterial predators of bacteria in soil" Applied and Environmental Microbiology 1986 52(4):819-823.

Invitation to Pay Additional Fees and, Where Applicable, Protest Fee in PCT/US2019/029798 dated Jul. 22, 2019.

Alagesan, S., et al., "13C-assisted metabolic flux analysis to investigate heterotrophic and mixotrophic metabolism in Cupriavidus necator H16", Metabolomics, 2018, vol. 14, Issue 9, pp. 9.

Alagesan, S., et al., "Functional genetic elements for controlling gene expression in Cupriavidus necator H16", Applied and Environmental Microbiology, vol. 84, Oct. 2018 (Oct. 2018), pp. 1-17.

Anderson, A.J., et al., "Occurrence, metabolism, metabolic role, and industrial uses of bacterial polyhydroxyalkanoates", Microbiology Review, 1990, vol. 54, pp. 450-472.

Atlic et al., "Continuous Production of Poly([R]-3-Hydroxybutyrate) by Cupriavidus Necator in a Multistage Bioreactor Cascade", Appl Microbial Biotechnology, vol. 91, 2011, pp. 295-304.

Bramer, C.O., "The malate dehydrogenase of Ralstonia eutropha and functionality of the C(3)/C(4) metabolism in a Tn5-induced mdh mutant", FEMS Microbiol Letters, Jul. 2, 2002, vol. 212, Issue 2, pp. 159-164.

Brigham, C.J., et aL, "Correction for Whole-genome microarray and gene deletion studies reveal regulation of the polyhydroxyalkanoate production cycle by the stringent response in Ralstonia eutropha H16", Appl Environ Microbiol., 2017, vol. 83, Issue 15, pp. 1-2.

Brigham, C.J., et al., "Whole-genome microarray and gene deletion studies reveal regulation of the polyhydroxyalkanoate production cycle by the stringent response in Ralstonia eutropha HI6", Appl Environ Microbial., 2012, vol. 78, Issue 22, pp. 8033-8044.

Brown, D.R., et al., "Nitrogen stress response and stringent response are coupled in *Escherichia coli*", Nature Communications, 2014, vol. 5, 4115, pp. 8.

Chae, T.U., et al., "Metabolic engineering of *Escherichia coli* for the production of four-, five- and six-carbon lactams Metabolic Engineering", Academic Press, US, vol. 41 ,Apr. 5, 2017, pp. 82-91.

Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.

Chen, R., et al., "A highly active decarboxylating dehydrogenase with rationally inverted coenzyme specificity", PNAS, 1996, vol. 92, Issue 25, pp. 11666-11670.

Chen, R., et al. "Redesigning secondary structure to invert coenzyme specificity in isopropylmalate dehydrogenase" PNAS, 1996, vol. 93, pp. 12171-12176.

Choi, J.C., et al. "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbial Technology, 2003, vol. 32, Issue 1, pp. 178-185.

Cramm, R. J. "Genomic view of energy metabolism in Ralstonia eutropha HI6", Journal of Molecular Microbiology and Biotechnology, 2009, vol. 16, pp. 38-52.

Darani, K.K., et al., "Simulation of bioreactors for poly(3-hydroxybutyrate) production from natural gas", Iranian Journal of Chemistry and Chemical Engineering, vol. 39, 2018, pp. 1-24.

Ding, H., et al., "Glycerol utilization by Rhizobium leguminosarum requires an ABC transporter and affects competition for nodulation", Microbiology, 2012, vol. 158, pp. 1369-1378.

Du et al., "Effects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.

Eggers et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24,Dec. 2014, pp. 7702-7709.

Frng, Y., et al. "Tuning of acyl-ACP thioesterase activity directed for tailored fatty acid synthesis", Applied Microbiology and Biotechnology, Springer, De, vol. 102, No. 7 ,Feb. 22, 2018, pp. 3173-3182.

Gao, C., et al. "Lactate utilization is regulated by the FadR-type regulator LldR in Pseudomonas aeruginosa", Journal of Bacteriology, 2012, vol. 194, pp. 2687-2692.

Girdhar, A., et al., "Process Parameters for Influencing Polyhyroxyalkanoate Producing Bacterial Factories: An Overview", Petroleum & Environmental Biotechnology, 2013, vol. 4, Issue 5, pp. 9.

Gyaneshwar et al., "Sulfur and Nitrogen Limitation in *Escherichia coli* K-12: Specific Homeostatic Responses", Journal of Bacteriology, vol. 187, No. 3, Feb. 2005, pp. 1074-1090.

Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.

(56) References Cited

OTHER PUBLICATIONS

Hauryliuk, V. et al."Recent functional insights into the role of (p)ppGpp in bacterial physiology", Nature Reviews Microbiology, 2015, vol. 13, pp. 298-309.
Haushalter, R.W., et al., "Production of Odd-Carbon Dicarboxylic Acids in *Escherichia coli* Using an Engineered Biotin-Fatty Acid Biosynthetic Pathway" Journal of the American Chemical Society, vol. 139, No. 13 ,Mar. 21, 2017, pp. 4615-4618.
Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.
Hun-Suk Song et al: Enhanced isobutanolproduction from acetate by combinatorialoverexpression of acetyl-CoA synthetaseand anaplerotic enzymes in engineered*Escherichia coli*, Biotechnology and Bioengineering,vol. 115, May 2, 2018 (May 2, 2018), pp. 1971-1978.
Lenczak, J.L., et al., "High cell density strategy for poly(3-hydroxybutyrate) production by Cupriavidus necator", Brazilian Journal of Chemical Engineering, 2011, vol. 28, Issue 4, pp. 585-596.
Inoue, H., et al., "Biochemical and molecular characterization of the NAD(+)-dependent isocitrate dehydrogenase from the chemolithotrophAcidithiobacillus thiooxidans", FEMS Microbial Letters, 2002, vol. 214, Issue 1, pp. 127-132.
International Search Report and Written Opinion for International Application Serial No. PCT/US2019/025189, dated Jul. 2, 2019, pp. 12.
International Search Report and Written Opinion for International Application Serial No. PCT/US2019/025194, dated Aug. 22, 2019, pp. 24.
International Search Report and Written Opinion for International Application Serial No. PCT/US2019/025202, dated Jul. 30, 2019, pp. 15.
International Search Report and Written Opinion for International Application Serial No. PCT/US2019/025211, dated Jul. 29, 2019, pp. 16.
International Search Report and Written Opinion for International Application Serial No. PCT/US2019/025218, dated Sep. 5, 2019, pp. 17.
International Search Report and Written Opinion for International Application Serial No. PCT/US2019/029973 dated Jul. 23, 2019, Jul. 23, 2019, 5 pgs.
International Search Report and Written Opinion in PCT/US2019/029795 dated Jul. 11, 2019, pp. 10.
International Search Report and Written Opinion in PCT/US2019/029798 dated Sep. 12, 2019, p. 19.
International Search Report and Written Opinion in PCT/US2019/029817 dated Sep. 23, 2019.
International Search Report and Written Opinion in PCT/US2019/029827 dated Sep. 23, 2019.
International Search Report and Written Opinion in PCT/US2019/029956 dated Aug. 13, 2019,.
Invitation to Pay Additional Fees and, WhereApplicable, Protest Fee in PCT/US2019/029817 dated Aug. 1, 2019.
Invitation to Pay Additional Fees and, WhereApplicable, Protest Fee in PCT/US2019/029827 datedJul. 23, 2019.
Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.
Joris, Beld, et al., "Evolution of acyl-ACP thioesterases and [beta]-ketoacyl-ACP synthases revealed by protein-protein interactions", Journal of Applied Phycology, vol. 26, No. 4 ,Nov. 22, 2013, pp. 1619-1629.
Juengert, Jr, et al., "Absence of ppGpp Leads to Increased Mobilization of Intermediately Accumulated Poly(3-Hydroxybutyrate) in Ralstonia eutropha HI6" Applied and Environmental Microbiology, 2017, vol. 83, Issue 13, pp. e00755-17.

Justyna Mozejko-Ciesielska et al: "Bacterial polyhydroxyalkanoates: Still fabulous?", Microbiological Research, vol. 192, 2016, pp. 271-282.
Kaddor, C., et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbiol., 2011, vol. 77, pp. 3582-3590.
Kaddor, C., et al., "Implications of various phosphoenolpyruvate-carbohydrate phosphotransf erase system mutations on glycerol utilization and poly(3-hydroxybutyrate) accumulation in Ralstonia eutropha H16", AMB Express, 2011, vol. 1, pp. 16.
Karstens, K., et al., "Phosphotransferase protein EIIANtr interacts with SpoT, a key enzyme of the stringent response, in Ralstonia eutropha HI6", Microbiology, 2014, vol. 160, pp. 711-722.
Bruland et al. "Unravelling the C3/C4 carbon metabolism in Ralstonia eutropha H16" Journal of Applied Microbiology 2010 109:79-90.
Tan, Z., et al. "Activating phosphoenolpyruvate carboxylase and phosphoenolpyruvate carboxykinase in combination for improvement of succinate production" Appl. Environ. Microbiol, 2013, vol. 79, Issue 16, pp. 4838-4844.
Kazakov, A.E., et al., "Comparative genomics of regulation of fatty acid and branched-chain amino acid utilization in proteobacteria", Journal of Bacteriology, 2009, vol. 191, pp. 52-64.
Kim et al. "Effect of overexpression of Actinobacillus succinogenes phosphoenolpyruvate carboxykinase on succinate production in *Escherichia coli*" Applied and Environmental Microbiology, 2004, vol. 70, Issue 2, pp. 1238-1241.
Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.
Koller et al., "Potential and Prospects of Continuous Polyhydroxyalkanoate (PHA) Production", Bioengineering,May 29, 2015, pp. 94-121.
Koller, M., "A review on established and emerging fermentation schemes for microbial production of polyhydroxyalkanoate (PHA) biopolyesters", Fermentation,vol. 4, Apr. 23, 2018 (Apr. 23, 2018), pp. 1-30.
Koller, M., et al., "Continuous production mode as a viable process-engineering tool for efficient poly (hydroxyalkanoate) (PHA) bioproduction", Chemical and Biochemical Product Engineering, vol. 28, Issue 1, 2014, pp. 65-77.
Krausse et al., "Essential role of the hprK gene inRalstonia eutropha HI6", J Mol Microbiol Biotechnol, 2009, vol. 17, pp. 146-152.
Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.
Lardi M. et al., "o54-Dependent Response to Nitrogen Limitation and Virulence in Burkholderia cenocepacia Strain H111" Appl. Environ. Microbiol., 2015, vol. 81, Issue 12, pp. 4077-4089.
Lee, J.N., et al., "Metabolic Engineering of Pentose Phosphate Pathway in Ralsonia eutropha for Enhanced Biosynthesis of Poly--hydroxybutyrate", Biotechnology Progress, 2003, vol. 19, Issue 5, pp. 1444-1449.
Lee, et al., "Regulation of poly- -hydroxybutyrate biosynthesis by nicotinamide nucleotide in Alcaligene eutrophus" FEMS Microbiological letters, 1995, vol. 131, pp. 35-39.
Lee, et al. "Microbial Production of Ethanol from Acetate by Engineered Ralstonia Eutropha", Biotechnology and Bioprocess Engineering, vol. 21, 2016, pp. 402-407.
Leyn et al., "Control of proteobacterial centralcarbon metabolism by the HexR transcriptionalregulator: a case study in Shewanella oneidensis", Journal of Biological Chemistry, 2011, vol. 286, Issue 41, pp. 35782-35794.
Leyn, S.A., et al."Comparative genomics and evolution of transcriptional regulons in Proteobacteria", Microbial Genomics, 2016, pp. 1-15.
Li, Z.J., et al. "Overexpression of NAD kinase in recombinant *Escherichia coli* harboring the phbCAB operon improves poly(3-hydroxybutyrate) production", Appl Microbial Biotechnol., 2009, vol. 83, Issue 5, pp. 939-947.
Liu, X. et al., "Comparative analysis of genes frequently regulated by drugs based on connectivity map transcriptome data" PLoS One, 2017, vol. 12, Issue 6, e0179037.

(56) References Cited

OTHER PUBLICATIONS

Marc, J., et al., "Over expression of GroESL in Cupriavidus necator for heterotrophic and autotrophic isopropanol production", Metabolic Engineering, vol. 42, 2017, pp. 74-84.

March, J.C., et al., "Expression of an anaplerotic enzyme, pyruvate carboxylase, improves recombinant protein production in *Escherichia coli*" Applied and Environmental Microbiology, 2002, vol. 68, Issue 11, pp. 5620-5624.

Martin, Koller, et al., "Continuous production mode as a viable process-engineering tool for efficient poly (hydroxyalkanoate) (PHA) bio-production", Chemical and Biochemical Engineering Quarterly, vol. 28, XP002792820, 2014, pp. 65-77.

McKinlay, J.B., et al., "Carbon dioxide fixation as a central redox cofactor recycling mechanism in bacteria" PNAS, 2010, vol. 107, Issue 26, pp. 11669-11675.

Meng, J., et al. "High-yield anaerobic succinate production by strategically regulating multiple metabolic pathways based on stoichiometric maximumin *Escherichia coli*" Microbial Cell Factories, vol. 15, 2016, pp. 13.

Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.

Nguyen, C., et al., "Trapping the dynamic acyl carrier protein in fatty acid biosynthesis", Nature, vol. 505, No. 7483, Dec. 22, 2013, pp. 427-431.

Obruca, S., et al. "Application of random mutagenesis to enhance the production of polyhydroxyalkanoates by Cupriavidus necator H16 on waste frying oil", World J Microbiol Biotechnol, 2013, vol. 29, pp. 2417-2428.

Olaya-Abril et al., "Poly(3-hydroxybutyrate) hyperproduction by a global nitrogen regulator NtrB mutant strain of Paracoccus denitrificans PD1222", FEMS Microbiology Letters, 2008, vol. 365:fnx251, pp. 8.

Papagiani, M., "Recent advances in engineering the central carbon metabolism of industrially important bacteria", Microbial Cell Factories, 2012, vol. 11, pp. 13.

Park, J-S., et al., "Metabolic Characteristics of Isocitrate Dehydrogenase Leaky Mutant of Alcaligene eutrophus and its Utilization for Poly-Hydroxybutyrate Production" Journal of Fermentation and Bioengineering, 1996, vol. 81, Issue 3, pp. 197-205.

Park, S., et al., "Oxaloacetate and malate production in engineered *Escherichia coli* by expression of codon-optimized phosphoenolpyruvate carboxylase2 gene from Dunaliella salina", Bioprocess Biosyst Eng., 2013, vol. 36, Issue 1, pp. 127-131.

Persuhn, D.C., et al. "The transcriptional activator NtrC controls the expression and activity of glutamine synthetase in Herbaspirillum seropedicae" FEMS Microbiology Letters, 2000, vol. 192, pp. 217-221.

Pryzbylski, D., et al., "Synthesis of the building block 2-hydroxyisobutyrate from fructose and butyrate by Cupriavidus necator HI6", Appl. Microbial. Biotechnol., 2013, vol. 97, 20, pp. 8875-8885.

Qi et al., "Model-driven redox pathway manipulation for improved isobutanol production in Bacillus subtilis complemented with experimental validation and metabolic profiling analysis" PLoS ONE, 2014, vol. 9, Issue 4, : e93815, pp. 1-11.

Raberg, M., "Ralstonia eutropha H16 in progress: applications beside PHAs and establishment as production platform by advanced genetic tools", Critical Reviews in Biotechnology, vol. 38, Dec. 12, 2017 (Dec. 12, 2017), pp. 494-510.

Russell, J.B., "The Energy Spilling Reactions of Bacteria and Other Organisms", Journal of Molecular Microbiology Biotechnology, vol. 13, No. 1, 2007, pp. 1-11.

Sacamboio, E.N.M., et al. "The transcriptional regulator NtrC controls glucose-6-phosphate dehydrogenase expression and polyhydroxybutyrate synthesis through NADPH availability in Herbaspirillum seropedicae" Scientific Reports, 2017, vol. 7, Article No. 13546, pp. 1-12.

Sanchez, A.M., et al., "Effect of overexpression of a soluble pyridine nucleotide transhydrogenase (UdhA) on the production of poly(3-hydroxybutyrate) in *Escherichia coli*" Biotechnol Prog., 2006, vol. 22, Issue 2, pp. 420-425.

Saur, U., et al., "The PEP-pyruvate-oxaloacetate node as the switch point for carbon flux distribution in bacteria", FEMS Microbiology Reviews, 2005, vol. 29, Issue 4, pp. 765-794.

Schlegel, H.G., et al., "Formation of the Dehydroganses for Lactate, Ethanol and Butanediol in the Strictly Aerobi Bacterium Alcaligene eutrophus" Microbiology, 1980, vol. 117, pp. 475-481.

Schobert, P., et al., "Unusual C3 and C4 metabolism in the chemoautotroph Alcaligenes eutrophus" Journal of Bacterialogy, 1984, vol. 159, Issue 1, pp. 167-172.

Schramke, h., et al., "Revisiting Regulation of Potassium Homeostasis in *Escherichia coli*: The Connection toPhosphate Limitation", Wiley Microbiologyopen, vol. 6, No. 3, 2017, pp. 1-16.

Schwartz, E., et al., "A proteomic view of the facultatively chemolithoautotrophic lifestyle of Ralstonia eutropha HI6" Proteomics, 2009, vol. 9, Issue 22, pp. 5132-5142.

Segura, D., et al., "Inactivation of pycA, encoding pyruvate carboxylase activity, increases polybeta-hydroxybutyrate accumulation in Azotobacter vinelandii on solid medium" Appl Microbial Biotechnol, 2004, pp. 65, Issue 4, pp. 414-418.

Sekar, B.S., et al., "Co-production of hydrogen and ethanol from glucose in *Escherichia coli* by activation of pentose-phosphate pathway through deletion of phosphoglucose somerase (pgi) and overexpression of glucose-6-phosphate lehydrogenase (zwf) and 6-phosphogluconate dehydrogenase ( gnd)", Biotechnology for Biofuels, 2017, vol. 10, 85, pp. 12.

Shang et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.

Shively, J.M., et al., "Something From Almost Nothing: Carbon Dioxide Fixation in Chemoautotrophs", Annu. Rev. Microbiol., vol. 52, 1998, pp. 191-230.

Silva, F., et al., "Impact of nitrogen feeding regulation on polyhydroxyalkanoates production by mixed microbial cultures", New Biotechnology, vol. 37, 2017, pp. 90-98.

Stokke, R., et al., "Biochemical characterization of isocitrate dehydrogenase from Methylococcus capsulatus reveals a unique NAD+-dependent homotetrameric enzyme" Arch Microbiol., 2007, vol. 187, Issue 5, pp. 361-370.

Sun, J., et al., "Involvement of glnB, glnZ, and glnD genes in the regulation of poly-3-hydroxybutyrate biosynthesis by ammonia in Azospirillum brasilense Sp7", Appl. Environ. Microbiol, 2002, vol. 68, Issue 2, pp. 985-988.

Sun, J., et al., "The ntrB and ntrC genes are involved in the regulation of poly-3-hydroxybutyrate biosynthesis by ammonia in Azospirillum brasilense Sp7", Appl. Environ. Microbiol., 2000, vol. 66, Issue 1, pp. 113-117.

Tanaka, K, et al., Production of Poly (D-3-Hydr0xybutyrate) From CO2, H2, and O2 by High Cell Density Autotropic Cultivation of Alcaligenes Eutrophus Biotechnology and Bioengineering, Wiley, vol. 45, No. 3, (Feb. 5, 1995), XP000489583, Feb. 5, 1995, 268-275.

Valderrama, J.A., et al., "AccR is a master regulator involved in carbon catabolite repression of the anaerobic catabolism of aromatic compounds in Azoarcus sp. CIB" Journal of Biological Chemistry, 2014, vol. 289, Issue 4, pp. 1892-1904.

Vemuri, G.N., et al., "Physiological response of central metabolism in *Escherichia coli* to deletion of pyruvate oxidase and introduction of heterologous pyruvate carboxylase" Biotechnology and Bioengineering, 2005, vol. 90, Issue 1 pp. 64-76.

Vollbrecht, D., et al., "Excretion of Metabolites by hydrogen Bacteria III. D(-)-3-hydroxybutanoate", European J. Appl. Microbiol. Biotechnol., 1979, vol. 7, pp. 259-266.

Wang, F., et al., "Poly(3-Hydroxybutyrate) Production with High Productivity and High Polymer Content by a Fed-Bath Culture of Alcaligene lat us under Nitrogen Limitation", Applied and Environmental Microbiology, 1997, vol. 63, No. 9, pp. 3703-3706.

(56) References Cited

OTHER PUBLICATIONS

Wang, R., et al., "Isocitrate dehydrogenase from *Streptococcus mutans*: biochemical properties and evaluation of a putative phosphorylation site at Ser102" PLoS One, 2013, vol. 8, Issue 3, e58918.

Weiden et al., "Cation Transport in *Escherichia coli* Vii. Potassium Requirement for Phosphate Uptake", The Journal of General Physiology, vol. 50, No. 6, 1967, pp. 1641-1661.

Weinberg, Z., et al. "Identification of 22 candidate structured RNAs in bacteria using the Cmfinder comparative genomics pipeline" Nucleic Acids Research, 2007, vol. 35, pp. 4809-4819.

Wu, M.C., et al. "A Novel Type II NAD+-Specific Isocitrate Dehydrogenase from the Marine Bacterium Congregibacter litoralis KT71" PLoS One., 2015, vol. 10, Issue 5, pp. 1-17.

Youngquist et al., "Functional Genomics Analysis of Free Fatty Acid Production under Continuous PhosphateLimiting Conditions", J. Ind. Microbial. Biotechnol., vol. 44, May 2017, pp. 759-772.

Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.

Ziesack, M., et al., "Chimeric Fatty Acyl-Acyl Carrier Protein Thioesterases Provide Mechanistic Insight into Enzyme Specificity and Expression", Applied and Environmental Microbiology, vol. 84, No. 10 ,Mar. 16, 2018, pp. 12.

International Preliminary Report on Patentability in PCT/US2019/029798 dated Nov. 3, 2020.

Kizer L et al. Application of Functional Genomics to Pathway Optimization for Increased Isoprenoid Production. Applied and Environmental Microbiology. 2008. vol. 74, No. 10. p. 3229-3241. (Year: 2008).

Non-final office action received for U.S. Appl. No. 16/398,351, dated Feb. 1, 2021, 24 pages.

Non-final office action received for U.S. Appl. No. 16/398,401 , dated Feb. 16, 2021, 29 pages.

Prather KLJ et al. De nova biosynthetic pathways: Rational design of microbial chemical factories. Current Opinion in Biotechnology, 2008. 19:468-474 (Year: 2008).

Singh RK et al. Protein Engineering Approaches in the Post-Genomic Era. 2017. Current Protein and Peptide Science. 18, 1-11. (Year: 2017).

Zhang M et al. Propagated Perturbations from a Peripheral Mutation Show Interactions Supporting WW Domain Thermostablity, 2018, Structure. 26, 1474-1485. (Year: 2018).

Devos et al., "Practical Limits of Function Prediction", PROTEINS: Structure, Function and Genetics, vol. 41, pp. 98-107 (2000).

International Preliminary Report on Patentability in PCT/US2019/029817 dated Nov. 3, 2020, 14 pages.

International Preliminary Report on Patentability in PCT/US2019/029795, dated Nov. 3, 2020, 7 pages.

International Preliminary Report on Patentability in PCT/US2019/029827, dated Nov. 3, 2020, 13 pages.

Kisselev, "Polypeptide Release Factors in Prokaryotes and Eukaryotes: Same Function, Different Structure", Structure, vol. 10, pp. 8-9 (2002).

Non-Final office action received for U.S. Appl. No. 16/398,384, dated Oct. 23, 2020, 13 pages.

Whisstock et al., "Prediction of protein function from protein sequence and structure", Quarterly Reviews of BioPhysics, vol. 36, Issue 3, pp. 307-340 (2003).

Witkowski et al., "Conversion of β-Ketoacyl Synthase to a Malonyl Decarboxylase by Replacement of the Active-Site Cysteine with Glutamine", Biochemistry, vol. 38, pp. 11643-11650 (1999).

\* cited by examiner

SEQUENCE LISTING

<160> NUMBER OF SEQ ID NOS: 169

<210> SEQ ID NO 1
<211> LENGTH: 978
<212> TYPE: DNA
<213> ORGANISM: C. necator

<400> SEQUENCE: 1

```
atgaagcgcc ccattctcag tgccgcgctg gcctgcgcgg ctgcaatcat gcccgggcct      60
gccgcctggg ccagcgatgc ttggccgagc aagccgatca aatgggttgt cccttacccg     120
cccggtggat ccaccgacat gctggcgcgc atcgtcggcc agaagctggg ggaacggctc     180
gggcaacccg tggtggtaga gaacaaggca ggcgccggcg gcaatgtcgg cactgactac     240
gtgaccaagc agccagccga tggctacacc atcgtgatgg gcaatatcgg ccccatcgcg     300
atcaatcccg cgctctatcc cgacctgccg tacaagccgg gcaaggatct cgcgccggtg     360
accatgctga tggcggtgcc caacctgctg gtcgtgaata cggcactgcc ggtgcaatcc     420
```

-continued

| | |
|---|---|
| gtgaaggacc tgatccagta cggcaagcgc caggctacgc cgctgaccta tgcaacgccg | 480 |
| ggcgccggca cctcgctgca cctggcgggc gagctgtttg ccagcaccgc cggcgtgcgc | 540 |
| atgacccacg ttccctacaa aggcagcgcg ccggggctga cgacaccgt ggcggggcat | 600 |
| gttccggtga tgttcgacaa catgccgtcg ggctgcagc tggtgaagtc cggcaagctg | 660 |
| cgcgcgctgg cgatcaccgg agcccagcgt cgccgctgc tgcccgatgt gcccaccatg | 720 |
| gcggaagccg gcctgcgcgg ctatgagatt gcaggctggt cggcgtgct ggtgcccgca | 780 |
| gcaacgccca agcccatcgt tgcccggctg gattcagagc tggaagccgt gctgaagatg | 840 |
| cccgacgtcc gcaagaagat cgatgagatg gcggcgtca tctccggagc cgggccggag | 900 |
| gcgttcggcg tctttatcga tgcggaaacg cagaagtggc gcgcgctggt gcgcagcgcc | 960 |
| cacatcaccg tccagtaa | 978 |

<210> SEQ ID NO 2
<211> LENGTH: 942
<212> TYPE: DNA
<213> ORGANISM: C. necator

<400> SEQUENCE: 2

| | |
|---|---|
| gtgaccagcg gtgctgccgc actgcctgcc gccgctgccg acgcctatcc cagccgtccg | 60 |
| atccgcctga tcgtcgccta cccgaccggc ggcatcagcg acaccgtggc gcgcgcgctc | 120 |
| ggcgagcggc tgtcggcgca gatgggcacc tcggtggtgg tcgagaacaa ggccggcgcg | 180 |
| ggcggcagca tcggcatcga tgcggtcgcc aaggctgcgc cggacggcta cgctgggc | 240 |
| ttcgccgcca ccagcccgct gacgctcaac ccgcatgtcg gccgcgtcaa ctacgacccg | 300 |
| cagaaggacg tggcgccggt gatgagcgtg atgtactcgc cggtgctggt ggtggccacc | 360 |
| gccggcttca gcgcaagggg ctttgccgac gtggtcggcc aggccagcgc caaaccgggc | 420 |
| tcggtgcgct gggcaacgtc gggcctggga acggttggcc acgtagtgct ggaacagatc | 480 |
| aagcagaagt cgaaggccga catcacgctg atcccgtata agggcgcggg ccaacagatg | 540 |
| aatgacgcgc tcggcggcca gttcgaggtg atgagcacca acgccagccc ggtgctgacc | 600 |
| cagcatatgc aggccggccg cctgcgcgcg ctggcggtgg gtgcgcccag cgcctggag | 660 |
| agcctgccct cggtgccgac gctggccgag ctgggctacc ccaaggccaa cctgacctcg | 720 |
| accttcggca tcttcgcgcc gggcaagacg cccgcggcca tcatcaaccg cctgaacgcc | 780 |
| gaactgaaca aggcgctggc cgagccggaa gtccatgagc gcctgctcaa gggcggcgaa | 840 |
| gtgccgaccg gcgtacgcc ggcgcagttt gccaaggcta ttcgcgaaga gtccgcggag | 900 |
| aacgcccgca tcgtcaggga cgcgggcatc aaggccgatt ga | 942 |

<210> SEQ ID NO 3
<211> LENGTH: 969
<212> TYPE: DNA
<213> ORGANISM: C. necator

<400> SEQUENCE: 3

| | |
|---|---|
| atgaagacca tcctgcgcgc ggccgctgcc gcactctgcc ttgccgcttc cgccggcgcc | 60 |
| gttgcctccg cctggcccgc caagccgatc acgctggtgg tgggctacac cgccggcggc | 120 |
| agcgtcgacc tggtggcccg gaccattgcc ccggagctgg caagcgcct gggccagagc | 180 |
| gtggtgatcg agaacctggg cggcgccggc ggcaccatcg cgcgcggcca ggtggtcaag | 240 |
| gccgaggccg acggctacac cctgctgatg ggctcgggca gtgaagtgtc gatcgcccgc | 300 |
| ctgaccaacc ccgccgtgcg ctacgacggc gaaaaggacc tggtgccggt gaccttcgtc | 360 |

| | |
|---|---:|
| ggcacccagc cgatggtgct ggtcggcaag cccggcctgg cggccaggaa cgcggccgag | 420 |
| ctgattgcgc tggccaaggc ccagccgggc aagctgtcgt atgcctcgtc gggcgtgggc | 480 |
| acgccgctga acctggccgg cgagctgatc aagcagcagg gcaaggtcaa tatcacgcac | 540 |
| gtgccgtaca agggcgcgtc ggccatggcc accgacctgc tcggcggcca gatcgacctg | 600 |
| gcggtaatgg tgctgtcgtc ggcgctgccg catatccagg ccggccgcgt gcaggcctac | 660 |
| ggcgtgacca cgccaagcg ctcgccgtg gcgccgaacg tgcccgcgct ggccgagacg | 720 |
| cccgcgctca agggcgtcga catgggcgtg tggttcggcc tgatgggccc ggccaggctg | 780 |
| ccgcaagcgg tggtggagcg cctgaacacc gagatgcagg ccgtgctggc catgccggat | 840 |
| gtgaagaaga agctggcaga agccggtgtg gaagtggcgc ctgccaatcc ggcgcagttc | 900 |
| ggcagcttta tcaagcgcga cgggcgc tatcgcacca tcgtgcagac cgctggcatt | 960 |
| catgaataa | 969 |

<210> SEQ ID NO 4
<211> LENGTH: 975
<212> TYPE: DNA
<213> ORGANISM: C. necator
<400> SEQUENCE: 4

| | |
|---|---:|
| atgacattca gccgccgcac cctgctgctc ggcactgccg ccgccttgct ggcccggcac | 60 |
| gggtttgcac agggctggcc ttccaggccg gtcaggatcg tggtgccgtt cgcggcggga | 120 |
| ggtccgggcg atttcgtcgc gcgcctggcc gcgaagcatc tcgcgcaggt gctggcgcag | 180 |
| ccggtcgtgt tcgagaacaa gccaggcgcc agcggcaacc tggagcgca gttcgtgctg | 240 |
| gacacggagg ccgatggcca taccctgctg ctgaacacgg tcggcatgca ggcggtcaat | 300 |
| cccctgatgt acccagccgc gcgcttcctg ccgcagcgcg atttcgtggc catcggcatt | 360 |
| gccgccaccg tgccgaacgt gctggtggtc catccgggca agctcggtgt ctcgaccatg | 420 |
| ggcgacctgg tcaggcttgg caagcagcgg cccggcaacc tcaccttgc cacctacggg | 480 |
| ccggggagtt ctccgcatat ctacggtgcg ctgctccagc ggctggccgg cttctcggcc | 540 |
| attgaagtgc cgtacaaggg cagcgcgccg gccagcagcg atgtgatggc gggccaggtg | 600 |
| gacttcctgt cgacagcat gaccacctgc gtgagccaga ttcagggcgg caagctgaag | 660 |
| gggctggcga tcacctcggc agagcggtcg ccgctgttgc cggccgtccc caccatgaag | 720 |
| gaggcgggct acggcggcct ggccatgaag tactggctgt cgctccaggc ttcggccagg | 780 |
| accccgcctg agatcgtgtc cgcgctgcgc caggccctgg ccaggcgct ggccgatccc | 840 |
| gcctatcagc gcgccctggc cgcgcgtggc gcagagccgc tcctgatcgc cccggcgcaa | 900 |
| gtgcaggcct ttgtcgaccg cgatgctgaa cgctggactg ccgcggcccg cagcattggc | 960 |
| attcgggcgg aatag | 975 |

<210> SEQ ID NO 5
<211> LENGTH: 996
<212> TYPE: DNA
<213> ORGANISM: C. necator
<400> SEQUENCE: 5

| | |
|---|---:|
| atgcaagcac tccgcagtac caggcgcctg gcgctcgcac ttgccgctgc cctgggcgca | 60 |
| atgatggcgg ccccggctgt gtccgcgcaa acgggcgcgg cgtggcctgc gcggccggtt | 120 |
| accatcatcg tgccgggcgc ggcaggggc acgatcgata ttcccatccg catgctcgcg | 180 |
| cagaaactga gccttcgcct tggccagcct gtcatcgtgg acaaccggcc cggcagcggg | 240 |

| | |
|---|---|
| ggcatcatcg gcacacaggc ggcgctacgc gcgcccgccg acggctacac gctcctggcc | 300 |
| gggaatgtcg ggccgcaggc catcaactac agcgcctaca agaccctgcc atacaagccg | 360 |
| gacgacctgg tggggattac cgatgtcatc tcttttccca gcgtcctggt cgtcaacgca | 420 |
| cagtcgccga tccggagcgc cgccgacctg gtcgcgcaaa tgagggcgca ggcgggaaag | 480 |
| ctgtccttcg gctcctccgg catcggccag accagccacc tgaccggcga actgctcaag | 540 |
| cagcgcacgg aacggatgc cattcacgtt ccctatcgcg gttccacgcc ggcgaccacc | 600 |
| gcgctgctgg ccggtgaaac gactttccag ttcgacaacc tgacccaggc cctgccgcat | 660 |
| atccgggccg gcaagctgcg cccgctcgcc gtgacgtcgg cacggcgaat ccccagcctg | 720 |
| cccgaggtgc cgaccatgga ggaaaccggg gtgggcaacc tcttgtcgac ggcgtggatc | 780 |
| ggcatctttg tgaaagccgg cacgccgccg gagatcgcag ccaggctgca tgagcacctg | 840 |
| gtcgcggtcc tgcgcgcccc ggacgtggtt accgaaatca gccggatggg cggtattcca | 900 |
| ggcggacagg cacaggagag attcgccgcc tttgtcacgg cggaacgctt gcgctggagc | 960 |
| gaaaccatca agacatcgca gctgagcctg gattga | 996 |

<210> SEQ ID NO 6
<211> LENGTH: 999
<212> TYPE: DNA
<213> ORGANISM: C. necator

<400> SEQUENCE: 6

| | |
|---|---|
| atgcgccccc ttggccactt ccgccccgcc ctcgccgcat tgacggccgg tactctgttt | 60 |
| gctgccctgt tcaccgccag cgcccccgcg cgcgccgatg actggccgtc gcagccgatc | 120 |
| cgctgggtcg tgccctatcc cgccggcggc ggcaccgacg tggtggcgcg cactgtggcg | 180 |
| caggccatca ccccggggct gggcaagcag gtggtgatcg acaaccgccc gggcgcggcc | 240 |
| accatcgtcg gcgccgatgc cgtggcgcat gccaagcccg acggctacac cgtgctgacc | 300 |
| gccgacaccg ccacgctggc cgccaatccg tcgctgtaca agaagctgcc gtacaacccg | 360 |
| gacaaggact tcgtctacat cggccagctt gcgcgcttcc cgctggtgct ggtggccaat | 420 |
| cccaacttcc cggcgcgcac gctcaaggaa gtggtcgcgt acgcgcagaa gaacccgggc | 480 |
| aaggtcaatt tcgcctcgcc gggcgcgggc agcccgcacc acctggcgat ggaactgttc | 540 |
| atggaccaga cccgggtcaa gatgacgcac gtgccctaca agggcgcggc gccggcggtg | 600 |
| caggacctgc tcgcgggcca ggtcgacctg atgttcctgg acctggcctc gggccagcag | 660 |
| aacgtgcagg cgggcaagct gcgcgcgctc ggcgtggcca cgcccaagcg ccttaccgtg | 720 |
| ctgcccggcg tgccgaccgt ggccgagggc ggcgtggccg gcttcgaggc ctacgcctgg | 780 |
| caaggcatgg tggcgccggc cggcacgccc aaggccgtgg tcacgcgcct gaatgccgag | 840 |
| ctggtcaagg cgctgaagac gcccgaggtg cagaagaagc tggaaggcgt gggcgtggag | 900 |
| gcggtctaca gcacgcccga ggaattcgcc agctacgcgc gcgccgaggg cgagcgctgg | 960 |
| ggcaagctga tcaaggccaa gggcatcacc gtcgactga | 999 |

<210> SEQ ID NO 7
<211> LENGTH: 987
<212> TYPE: DNA
<213> ORGANISM: C. necator

<400> SEQUENCE: 7

| | |
|---|---|
| atgaaacgag taataaagat ggtcgcggcc gcgctggcag tcagcgcaat gggtgtggcg | 60 |
| tcgggcgcgt acgcccagga atatcctggc ggcaagccgg tgtcggcggt ggtgccgttt | 120 |

| | |
|---|---|
| gccgcgggtg gtccgaccga caagctctcg cgcgagctga ccgcgatcat gtccaagcat | 180 |
| ctgggcgcga ccatgatcat cgagaacctc ggcggcgccg gcggcaccat cggcgccaag | 240 |
| aaggtggccc aggccaagaa cgacggccac accctgctga tccaccatat cggcatggcc | 300 |
| acggccccgg cgctgtaccg caacctgggc ttcgatccgc tcaaggactt cgagatggtc | 360 |
| ggcgaaatcg ccgacgtgcc gatgatcctg gtcggcaaca agcagctgcc gccaaacacc | 420 |
| ttcaaggacc tgctgccgta cctcaaggcc aacgccagca gctgtcgct ggccaatgcc | 480 |
| ggcatcggct cggcttcgca cctgtgcggc ctgctgttcc agagcgcgat ccagaccgaa | 540 |
| ctgaccaccg tgccgtacaa gggcgccgcg ccggcactaa ccgatatcct gggcggccag | 600 |
| gtcaacctgc tgtgcgacca gaccaccaat ctcgcaggcc acctcaaggc caactcggtc | 660 |
| aagccgtacg cggccatgca ggcacgccgc gtggaagcgt tcaaggatat cccgacggcg | 720 |
| gccgagcaag gcctgccggg cgtggaagtg aaggtctggc acgccatgta cgcgcccaag | 780 |
| ggcacgccca agccggtgat cgacaagctg tcggctgcgc tgcagaaggc cgtggccgac | 840 |
| ccgaccttcc gctccaagat ggccgagctg ggcgccgaag ccgcgccggc acagcgcgcc | 900 |
| acgccggatt cgctgcgcac cctcctgacc gccgagatca acaagtggac cccggtgatc | 960 |
| aagaaggccg cgtgtatgc ggactga | 987 |

<210> SEQ ID NO 8
<211> LENGTH: 993
<212> TYPE: DNA
<213> ORGANISM: C. necator

<400> SEQUENCE: 8

| | |
|---|---|
| atgaaccgac gcgcatcgct cgcgctggcc gctggtgggc tgattggcgg gctttcgctc | 60 |
| agcctggccc tgcccgccgc ggcacagacc tatcccgcca aaccaatccg catcgtggtg | 120 |
| ccttatgtgg ccggcggcgg cactgacacc atcgcccgtg ccatgggcga aaagctcagc | 180 |
| aagcgcctgg ccagcccgt ggtggtggac aacaaggcgg gcgcctcggg catcatcggc | 240 |
| accgacgccg tggccaaggc cgcgccggat ggctacacgt tgttgatgac cctgacgcag | 300 |
| tcggtgctga ccaaccagtt cctgtaccag aaactgccct acgacccgcg caaggacctg | 360 |
| accatgatca gcgtgctggc cgatgcgcag ctggtgctgg tggcccatcc gtcggtgccg | 420 |
| gcgcgcaccg tgcgcgaact gggcgattac gcgcgcagcc ggccgggcaa gctcagctat | 480 |
| gcctcgtggg gcgtgggttc gctgtcgcac ctgagcggcg cctactacag caagctggtg | 540 |
| catggccagg ccgcgcacgt gccctacaag ggcgaggcgc cgatgatgca ggacctgctg | 600 |
| ggcgggcagg tgcagttcgg ctttgccagc atcctgaccg ccaagcccta tatccagagc | 660 |
| ggcaagctca aggcgctggc ggtgaccggc acgcagcgca gcgcgct gcctgacatg | 720 |
| cccaccttcg ctgagtccgg catgcaggac agcgccttca agaccgtcgg ctggatcggc | 780 |
| ctggtggcgc cggtgggcgt gcccgcgccg attctcgcca ggcttgaagg cgaagtgcgc | 840 |
| gccatcctgc aggcgcccga catgcaggag cgactggtcg cgctggggct gcgcacggtg | 900 |
| ggcagctcgc cggccgaggc gcaggcgctg tatgcgcgcg actggccggt gctgaagacg | 960 |
| ctggtggcgg attcgggcgc gaagctcgac tga | 993 |

<210> SEQ ID NO 9
<211> LENGTH: 978
<212> TYPE: DNA
<213> ORGANISM: C. necator

<400> SEQUENCE: 9

```
atgcccacac gacgacaagc gctgatcgcg ctggctgccg cctgcgccgc cgggacttcc        60
ggcggcgtct tcgcccaacc ctggcccgcg cggccgatcc gcatggtggt gccgttcccg       120
ccgggctcat cgcccgacct gatcgcgcgc atcgtgaccg aaaagctggc cgccgcgctg       180
ggccagccgg tggtggtgga aaaccgtccc ggcgccggcg gcaatatcgg caccggcatg       240
gtggcgcgcg ccgctccgga tggctacacc ctgctgttca ccatcaacgg cccgctggtg       300
accgcgccga cgctgtcgcg caacctgaac tacgacccgt tccgccagct ggcgccggtc       360
acgctggtgg cgacctcgcc caacgtgctg gtggtggatg cacgcctgcc ggtgcacaac       420
ctgcgcgagt tcgtcgcgct ggcacgggcc aagccgggtg agttgaacta tggctcgccc       480
ggcaacggca gtgcctcgca cctggcgatg gagcaactca aggcgatggc gggcatcgac       540
ctgcagcacg tgccataccc cggcttcccg cagatcacca cggcgatggt gggcgggcag       600
gtgcaggcgg gtttcatggt gccggcgatc gcgatgccgc aggtcaacgc gggcaagctg       660
cgcgtgctgg ccgtgaccac gacggggcgc acggcggtgt gccgtcggt gccgacagtg        720
gcggaatccg gctacccggg cttcgaggcg atttcctggc aggcggtgct ggcgccggcg       780
ggcacgccgc aggctgtgat cgaccggctc taccgcgagc tggtggcgat catcggcagc       840
gccgacgtgc gcgacaagat gcgcgcgcag tatttcgtgc cggccggcac cgcgccggcc       900
tcgctgcgcc agaccatggt gagcgagaag gcgcgctggg acaaggtgat ccgcgccgcc       960
ggcgtgcagc cggagtag                                                    978
```

<210> SEQ ID NO 10
<211> LENGTH: 987
<212> TYPE: DNA
<213> ORGANISM: C. necator

<400> SEQUENCE: 10

```
gtgatttcga agacacagtt ccttgccgcg gcgctggccg cgccggcatt gccggggatg        60
ccggcgcgcg cggacagcgg cgccgcggca tggccgcgcc atccggtgcg gctggtggtg       120
actttcccgc cgggcgggtc cagcgacatc gtggcgcggc tgctggcacc ggtgctgcag       180
gaaaagctgg ggcagccatt cgtgaccgac aaccggccgg gggcgggatc gacgattggc       240
gcggctgcgg tcgccgcggc gcccaatgac ggctacacgc tgctgatgtc gaactcggcg       300
gcgctgagca tctcgccgtt cctgctcagg cggcccgcct acgacccggt acgcagcttc       360
acgcacgtgc attacatcgg cgcggtgccg accgtctttg ccgtgcatcc gtcggtgccg       420
gcgcgcaacc tcgcggagct ggcggcgtgg atcgcgcgc agcgcgagcc ggtgccgttc        480
ggcagcggcg gggcggcgtc ggtggcgcat atcgtcggcg agctgtttgg ccagcaggcg       540
gggttgcggc tgacccatgt gccatacaag ggcgcgggtc cgatgcgcgc cgacctgctc       600
ggcggacaga tcccgtttgc ggtggatgcc ctgccgcaga acctgccgtt gctgcagtcc       660
ggcgccttgc gcctgctggc ggtgacctcg gcgcaacgcg tgccgcaggc gccccagctg       720
cccaccgtgg cgcaagccgg ctatcccggc ctggtggccg aaaacttcgt cggcgtctcc       780
gcgccggcca acctgcctga ggacatcgtg caacgcttgc atcaacaact gcaggtcatc       840
ctgcaacaac cggccctgcg cggccgcctg gaagcccagg gctttgtgct ggccgagcgc       900
cggcccgatg agtttgccgc ctacgtacgc cagcaggcgc aggcctgggg tcctgtggtc       960
gtggcaaccg gggcgacgct gtcatga                                          987
```

```
<210> SEQ ID NO 11
<211> LENGTH: 1020
<212> TYPE: DNA
<213> ORGANISM: C. necator

<400> SEQUENCE: 11
atgcctactt cgtcccgcct gcttccgcgc ttgtccttcc gttccgctac cggcctggcc      60
gcgctgtgcg ccgccgctgc catcagcacg gtcagctcgc ccgcccgcgc gcaaggggag     120
tggccgacgc agccggtgac gatcctgatg ggctttactg ccggctccgg cgtcgacatc     180
gtcggccgca cgctgcagga atcgctgcag aagtcgctga aggccaccat catctacgac     240
taccggccgg gcgccggcgg caacgtcgcc tccgaggtgg tggcgcatgc caggccggat     300
ggctacacgc tgctgctggg caccgccgcc acgcacggca tcaacccggc gctgtacaag     360
aacctgccgt cgacgccga ggccgatttc accccgatcg cgccgctggt cgaggtctcc     420
aacgtgctga ccgtcaaccc ggcggtgctg acgtgaagt cggtcaagga gtttatcgag     480
aaggtcaagg ccaaccccgg gcaagtacaac tttgcctcca ccggcaacgg caccggcacg     540
cacctggcct ttgccgagtt caatgcgcgc gccggcctgg acatggtcca cgtgccctac     600
aagggcggcc ccgacgcgct gcaggcggtg gtgaagggcg aggtctgctg catcttcaac     660
caggtgcaga gcgtgctgcc gcagtaccgc gccggcaagg tgcgcctgct gggcgtgacc     720
accaagcagc gcgtgcaagt gattcccgac gtgccgacca ttgccgagag cggcctgccc     780
ggcttcaaca gcaccatctg gttcggcttc ttcgggccca aggggctgga tccgaagatc     840
gcgcgcaagg tcaacgatgc ggtgaaggtg gcgctggaaa cgccggcgat ccgccagaag     900
ctgatcgatg ccggcaacac gccgcgggtc gagaccgtgg atcagttcaa ggctacggtg     960 aaggggggatc ggcagaagtg ggcgggggtg gtcaagaccg tgggcgcgtc gatcgactga    1020

<210> SEQ ID NO 12
<211> LENGTH: 969
<212> TYPE: DNA
<213> ORGANISM: C. necator

<400> SEQUENCE: 12
atgcaagctg gcaaactcgc actgaccctg gccctggccg ccgccgccac cgcggcgcag      60
gcccagagct accccaccaa gccgatccga ctgatcattc cgttcgcacc cggcggcacc     120
accgacatcg tcggccgcgg cgccgcggac cagatgagcc gcatcctggg ccagcccgtg     180
gtggtggaga accgcgccgg cggggggcggt tcgatcggtg ccgacgcgat cgccaaggcc     240
gcgccggacg gctacaccat cggcatctcc acggtctcga ccatggccgt gaacccggcc     300 tgcaaccccca gctgtcgta cgacccgatc aaggacttca gcccatcac caacctggcc     360 aacgtggcca acgtgatcgc cgtgaacccg agcttcccgg ccaaggacta caaggagttc     420
ctggccgtgc tgaaggccaa cccgggcaag tattcgtacg cctcgtcggg cacctgcggc     480 ttcgccaca tgctgggcga gcagttcaag gtctcgacca gaccttcat ggtccatatc     540 ccgtaccgcg gcgcgggccc ggcgctgaac gacgtgctgg ccggccaggt gccgatcatg     600
gtggacaacc tgccctcttc gatccccta atcaaggccg gcaagctgcg cccgatcgtg     660
gtggcctgga acaagcgcct ggaatccatg cccaacgtgc cgaccttcgg cgaaatgggc     720
ctgaaggagc cgaacgaccc ggcctggtac ggcctggtgg cgccggccgg cacgcctgac     780
gacgtcatca agaagctcaa cgaggccgcc gtcaaggccc tgcaggacaa ggacttccag     840
cagcgcctgc gcaccgccgg cgccgagccg tcgggcaaca cgccggcgca gcatgcggcc     900
```

```
gagatcaaga aggaattcga caagatgaag aatcttgtga aggtgcagaa catcaagctg    960
gagcaatga                                                            969

<210> SEQ ID NO 13
<211> LENGTH: 981
<212> TYPE: DNA
<213> ORGANISM: C. necator

<400> SEQUENCE: 13
atgaaattcc agaacatcct gcgcgcggcg cttgcgacgg cgctctgcct gccgctgctg     60
cacggcgcgg cgcaagccga agcgtatccc gacaagccga tccgcatgat cgtgccgttt    120
gctgccggca gcgccaccga cctgctcgca cgcatcgtca gcgccagat cggcaccagc     180 tcgaacatgc agatcgtggt ggacaaccgc cccggcgcgg gtgggaccat cggcaccgcg    240
gtggtggcca aggcgcccgc ggacggctac acgctgctgc tgacctccgc cgggcatgcg    300
gtcaatccca cgctctatcc caagctgccg tacgacacca cccgcgacct gaagggcatc    360
tccacggtgg cgaccatgcc ctacctgctg gtggtcagcg cctccagccc ctaccgcacg    420
ctcaaggacc tgctggcggc tgcgcgcgcc aggcccgatt ccgtcaccta cagctcggcg    480
ggcagtggca gctcttcgca cctgagcggc gagctgttca cgtgaccgc gggcgtgcag     540 acccggcata tcccgtacaa gggcgcgccg gcggcgatca ccgatgtgat gagcgggcgc    600
gtcgacatgt tcttcgcgcc gtccatcact gcgctgcagt cgtcaagga cggcaagctg     660 cgcatcctgg gcgtggccac ggcggcgcgg gtgccgtcgc tgccggacgt gcccaccatc    720
gccgaagcgg gcgtgccggg ctatgtcttc gatgcctggt cggcgtgct ggcgcccgca     780 ggcacgccca aggatgtcgt cgcccgcctg aacacggcga tgcagcaagc gctcagcgcg    840
ccggcgacca aggagaagct cattgcgcaa ggcgccgagg ccaagccctc gacgccggct    900
gccttcgaca gctgatcgc cgccgacatc gccaagctcg agcccatcgt caagcgctcg    960
ggcgcacagc cgggccagta a                                             981

<210> SEQ ID NO 14
<211> LENGTH: 987
<212> TYPE: DNA
<213> ORGANISM: C. necator

<400> SEQUENCE: 14
atgcaacgtc gccatcttct ccgcctcctg gccaccgctt cggccgccgc cgctgccggc     60
atctccttca gcgccatggc ccaggccggc tatccgacca gccgatcac gctggtggtg    120 cccttccccg ccggcggcac cacggacatc gtcgcgcgca tcgtcgccga caagctcggc    180
cagcaactgg gccaggccgt ggtggttgac aaccgcggcg cgccggtgg cagcatcggc    240 accgcttcc tgtccaaggc ggcgccggac ggctacacgc tgggcattgc cacggcctcg    300
acccatggca tcaatccggc ggtctacccg cgcctgtcct acgatgcaac caaggacttc    360
acaaccatca ccaacctggc ctcggtgccc aacgtgatga gcatcaaccc ggcggtcaag    420
gccaccgaca tgaagtcctt catcgcgctg gcgcagtcgc agcccaacaa gctggcctat    480
ggctcggcgg gcaacggcag cgtctcgcac atgatggggg aactgttcaa gatgagcagc    540
aagaccgaac tgctgcacgt gccctacaag ggcgtgggcc cggcgctgaa cgacgcgctg    600
gccggccagg tgcaggtgct gttcgacaac ctgccgtcgt cgctgccatt cattgaaggc    660
ggcaagctgc gtcgctcgc cgtggcagcg cccaagcgcg tggccgcgct gcccaacgtg    720
ccgaccttcg ccgagctggg cctgggcgag gtcaacgacg ccgcctggtt cggcctgatc    780
```

```
gcgccggcca acctgccggc ggatatccag accaggctcc acaccgccgc ggtcaaggtg    840
ctggcactgc cggaagtgaa ggccaagctc gagaagctgg gcgcgacccc ggtaggcgat    900
acgccggcgc actttgccgc ccagatcaag agcgaagtgg ccaagaacaa gcgcgtggcc    960
gccgccgcca ggatctcgct cgactga                                       987
```

<210> SEQ ID NO 15
<211> LENGTH: 990
<212> TYPE: DNA
<213> ORGANISM: C. necator

<400> SEQUENCE: 15

```
atgcgattcc cccaccgtat cgcgcgcgcc ctttgcgccg cactgtgcgc gccgggcctg     60
ctggctggcg tgagcgcgcc ggccgccgcg cagccgtggc cggacaagcc gatccggctg    120
gtcgtcaact tcccggccgg cggggccgcg gatacgctgg cgcgcggcat ctcgcccggt    180
ctgtccgagg cgctgaagcg tccggtggtg atcgacaacc gccccggcgc caacggcatc    240
gtcggcggcg atgccgtggc caaggcgccg gccgatggct ataccttcct gctgacctcg    300
ggcggcgcgg tggcgatcga tcccttcctc tacaagaaga tgccgtacga tccgatcaag    360
gatctgaccc cggtcgcgtc ggtggcgctg gtgcgggtct acctgctggt gcatccgtcg    420
gtgccggcga agacgctgga agcgttcatc gcctatgtgc gcgagcatcc gggcaggctt    480
agctacggct cggccggcaa cggcagcacg ccgcatatcg ctgccgagat gttcaaacgc    540
gccggcaagc tggacgccgt gcacgtgccg tacaagggcg cggccccggc cctgagcgac    600
ctgctggcag gcaggtgcga gttcatgttc gatcccggcc ccggcctgca gcacgtggcc    660
agcggcaagc tcaggctgct ggcggtggcc agcgccaagc gcgcggcgca atacccggac    720
gtgccgacgc tggccgaggc cggcctgcag gacgtggacg cgactcgac cttcggcgtc    780 tatgcgcccg ccggcacgcc gccggccatc gtcgagcgca tgaaccgcga gatcaaccgc    840
acgctcgccg gcgcgcagct gcaggaaaac gtcaacaagc tgggcggcgc cgtggcgccg    900
ctgagcatcc aggcgtttgc cgagcggcag aacgtggatc gcgcgcgcta tggcaggttc    960
atccggcagg cgggcatcac cgtggactga                                    990
```

<210> SEQ ID NO 16
<211> LENGTH: 993
<212> TYPE: DNA
<213> ORGANISM: C. necator

<400> SEQUENCE: 16

```
atgtcctggc aatttcatac gacccacgcg ctgcgtgccg cagccttcgg cctggcctgc     60
ctggcaggca cgggcgccgc actggcgcag acctatcccg cgcagccgat ccgcatggtg    120
gtgccttacg caccgggcgg aaccaccgac atcatcgcca ggcaactggc gcagcgcatg    180
tccgagaagc tgggccagcc ggtggtggtg gaaaacaaga gcggcgccaa taccgtgatc    240
ggcgccgacg cggtggccaa ggcgcagccc gacggctaca cgctgctgct gaccaacgat    300
gccaccttcg tgctcaaccc ggtggtgctg ccgtcggtgt cgtacaacgt cgcgcgcgac    360
tttgccccgg tggcgacgat cggctacgtg ccgctcgtca tggccgtctc gggcagcctg    420
ccggtggaca gcgtcaagga cctggccgca tatgccaagg ccgtccgca gccctcagc    480 tacggctcgt tcggcagcgg cagccagccg cacctgatgg gcgcgctgtt caacaagctg    540
gccggcaccg acctggtcca cgtgccgtac aagggctcgg cgccggcggt ggcagacgtc    600
gtcggcggcc agatcctgat gaccttcccg gcgctgccga cgatccagag ctttgttgcg    660
```

```
gcaaagaaac tcaaggtgct cgccgtcagc ggcgacaagc gcacgcgcgc gctgccgcag    720
gtgcccacct ttgccgaggc cggctacaag gacatggaca tctcggccgt ctacggcgtg    780
ctggccccgg ccaaggtgcc gcgcgcggtg gtcgacaagc tgaacgccac catccgcgag    840
atcctggacg acaaggactt cgtcgagaag cacttcgccg cgcaggggat ggtgccgatg    900
aagctgagcc cggcgcagtt ctcgcagtac atcgagacgc agacgcgcca gacgcgcaag    960
ctggtcgagc tgtccggcgt cagggtcgag tag                                 993
```

<210> SEQ ID NO 17
<211> LENGTH: 981
<212> TYPE: DNA
<213> ORGANISM: C. necator

<400> SEQUENCE: 17

```
atgaaatccg tattgaaccg ttttggccgt accctgggcg cgatcgcatt ggctgcctgc     60
gccaccagcg cgctggcaca aggcggatat cccaaccggc caatccgcat catcgtgccg    120
tggccggcag gcggcggcgt cgatgccgtc acccgcacgg tggccgagaa gatgaccgcc    180
agcctcgggc agcaagtcgt ggtcgacaac cgccccgggg cgaccggcaa tatcggcgcc    240
ggcatgggcg ccaaggcggc gccggatggc tacacgctgc tggtcgccag cgcgccgatg    300
gcgatcaacg ccagcctgca taagaacctg cccttcgaca tgggcaagga cttcgcgccg    360
ctggggctga tggcaagctc gccgtacatg ttggtggtca cccgtccgt gggcggctcg    420 gtcaaggaac tggtggcacg ggccaaggcg agcccggca agctcagcta tgcctcgccc    480
ggcccgggca cccagcagaa cgtgatcagc gaggtgttca aggaaaccgc gcatatcaac    540
gtcgtgcacg cgccgtacaa gggcggaccc caggcgctga ccgacatggt gggaggccat    600
atccacatga tgttccacgg cgtgccggcg gtgatgccgt cgtcaaggg cggccagctc    660 aagggcatcg ccgtggccag caagcagcgg ctgccgttgt ccccgacgt gccgaccatg    720 gcggaagccg gcttcccggg catagaagcc agcgaatggt atggcctggt cgcgcctgcc    780
ggcacgccca gggagatcgt tgcgctgctg agcaaggaaa tcgacaaggc gctgaatgcg    840
ccaggtgtgc gccagcagct tgtcagcaag ggctatgagc cggccagcca gagctctccg    900
gaccagtttg cgacgttcat ggcggcagag cagaagaaat gggcgctcgc catcaagcag    960
accgggttcc ggctggagta g                                              981
```

<210> SEQ ID NO 18
<211> LENGTH: 969
<212> TYPE: DNA
<213> ORGANISM: C. necator

<400> SEQUENCE: 18

```
atgcgcatga agtccctgat cgcgatggca gcgatggcgt ggagcgccgc ctgcggtgcc     60
cagagctacc cgtcgcgtcc catcaccgtt gttgtcccgg gccgcccgg cggcgccacc    120 gacaccgtgg cgcgcgcact ggccgaggac atgggcaagc gtctcgggca aaccatcatc    180
gtcgacaaca gcccggcgg cgcgggcgtg atcgcggtgc aggccatcac gcgcagcgcg    240
ccggacggct acaccatcct gctcacccac tcctcgccgc tgatcaacac gccgcacctg    300
taccgcaacg tgccgtatga cgtgcgccgg gacctggcct tgtcaccga actctgcatc    360 gccaagatcg tgctggccgt gaaccgggac gtgccggtaa agaacgtgca gcagttcctc    420
gactgggccg cgaagaacaa gggcaaggtc agctacggct cctatggcgt cggcaccttc    480
```

```
ccgcaccttg tcggcgcgca cctgaaccag gtgcgcggcc tggacatggc gcatgtggcc      540
tacaagggtg aagcgccaat ggcgcaggac atgatcgccg gcaatatcgc ctgggcgatc      600
ggctcgatga gcacgctcgg cccgcatatc aagagcggcc ggcttaccgc cctcgccgtg      660
atgggcgaca gcgcatcaa ggagctgccc gacgtaccga ccatggccga ggccgggctg       720
aaggagcagg aactgcgctc gcccgcctgg cttggcctgt tcgcgcgctc cggcacgccg      780
gcggcggtgc tgtcgcggct ggaagcgaa gcgcgggcgt cggtccagtc gccgaccatg       840
cgcgcgcggc tcgaggcact ggccatggat ccggtgggca actcgccggc ggagttccgg      900
cgcgaattcg acgcgaccga gcccgtggtc gcccagatga tcaaggccag cggcgccacc     960
gcggaataa                                                             969

<210> SEQ ID NO 19
<211> LENGTH: 1002
<212> TYPE: DNA
<213> ORGANISM: C. necator

<400> SEQUENCE: 19
gtgaaagaag aacggaggca ctccttgaaa gcagttatca gcgccggcgc agccgcctgc      60
atcgcggccc ttggcctggc ccacggcctg gcccaagccc agtcctaccc caacaagccg     120
atccgcctga tcgttccgtt cgcggccggc ggcaccaccg acatcgttgc gcgcgcggtc     180
tccgacggcc ttggccgcga gctgggccag ccggtggtgg tggaaaaccg cggcggcggc     240
ggcggcgcga tcggcgccga cgcgctcgcc aagtccgccc ggacggcta cacgctgggc      300 atcgccaccc tcagcacgat ggcgaccaac cccgccacca accccaagaa cccgtacgac     360
ccgctcaagg acttcgcgcc gatcaccaac ctggtcaacg tgccgaacgt gctgacggtc     420
aacccgaagg tgccggccaa daccccttaag gagttcgtcg cgatgctgca ggccagcccc    480
ggcaagtaca gctacgcctc ggccggcaag ggcagcatct cgcacctgga cggcgagctg     540
ttcaaggaca tcaccaagac cgacatggtc catatcccct accgcggatc gggccctgcg     600
ctgaacgaca cgctggccgg ccaggtcaac gcgcagttcg acaacctgcc gtcgtcgatg     660
ccgcatatcc aggtcggcaa gctgcgcgcg ctggcagtgg cggcgcccaa gcgggtcgag     720
ggcctgccag acgtgccgac cttttgccgaa gccggcatga aggacatgaa caacatggcc     780
tggtacggcc tggtggcccc ggccggcacg ccggcggcaa tcatcacgcg cgtgcatgat     840
gccgcggtca aggcgctgca ggaccccaac gtcaagcgcc gcctggccga cagcggtgcc     900
tacaccgacg gcaacacccc ggcgcagtac ccgcccagag tcaagcgcga gctggacctg     960
cgcaagaaga tcgcacgcga ccagaacatc acactggaat aa                        1002

<210> SEQ ID NO 20
<211> LENGTH: 1047
<212> TYPE: DNA
<213> ORGANISM: C. necator

<400> SEQUENCE: 20
atgaagaccg ctgtgaaacc tgatgtggaa gctgccgtga agcccgccgt aaaacctgtc       60
cttcgacgca tggccatgcg ctgcatgctt gcctgcatcg cggcctgcgc cccgtggctc     120
gctgccgcac ccgcgctggc ccagccgcct gggtaccccg ccaagccggt gcgcatcgtg     180
gtgccgttcg ccgccggcgg ggccgccgat gtgctcggcc gcgcggttgg cgaaggcatc     240
gccaaggcca ccgccagag cgtgctggtg gagaacaagg ccggcgctgc cggcaccatc      300
ggcgtcgaca tggtggccaa ggccgcgccc gacggctata cgctggcgct ggtgccggtc      360
```

| | | | |
|---|---|---|---|
| ggcaatatcg | cggtgaaccc cacgctgatg ccgaacctgc cgtacaagcc | ggccgatctg | 420 |
| gcgccggtgg | cgatgctggc caccgccgag aacgtgctgg tggtcaatgc | ggccacgcca | 480 |
| gtcaaatcgc | tggcggaact gctcaagctg gccgggcaga agccgggtga | gctgagcttt | 540 |
| gcttcgcccg | cgccggcag ccaggcgcac ctggccggcg aactgctgca | gctggatgcc | 600 |
| catgtcaagc | tgaaccacgt gccgtacaag ggcatcagcc cggccatgac | cgatgtggtc | 660 |
| ggcggccagg | tgacgatgat gttcgcgcag atgtcggcgg cgctgcccta | tatcaaggcc | 720 |
| ggcaagctgc | cccgctgggt gtggccagc ccaagcgct cggcggtgct | gcccgatgta | 780 |
| ccgaccatcg | ccgaacaggg cttccgaag ttcgaggcgt tgtcgtggta | tgcgctgatg | 840 |
| gccccggccg | gtacgcccgc ggagatcgtg cgcaagctca gtcagcatgt | tgatgcagtg | 900 |
| ctggctgatg | cgacgctgaa ggaaaagctg gcaacgctgg ggatggaagc | ggccggcggc | 960 |
| acgccgcagc | agcttgccac caccatccag aaggaaagcg cgcgctgggc | cggcgtgatt | 1020 |
| cggcagcggc | atatcactat cgactga | | 1047 |

<210> SEQ ID NO 21
<211> LENGTH: 1017
<212> TYPE: DNA
<213> ORGANISM: C. necator

<400> SEQUENCE: 21

| | | | |
|---|---|---|---|
| atgaacttca | tggtatcagt ggggcgcttt gctggaagcg ccaagggagg | cgttcgcctt | 60 |
| gtgggcgccg | ctgcgacgct gttcgccgca atgtgggcgg ccaatccggc | aaacgctcaa | 120 |
| ccggggtgga | cgcccactaa accgattcgg ctggtcgttc cgtatgcgcc | aggcggggga | 180 |
| acggatgtac | tcgcccgcct tgtcgtggcg ggcattggta acggacttgg | ccaacccatc | 240 |
| gtggtggaga | accggccggg tgccaacggc gtgattggtg ccaatgtcgc | ttatgcatcg | 300 |
| ccaccggatg | gtacacgtt gctgtttgcg ccgccgact ttatttcagt | cgcaccgtat | 360 |
| attcacaaga | aggtcgtcca gtttcagccc aatggcttcc ggccgttgc | tcccgtagcc | 420 |
| aagatgggct | tcgttctggc aagtcgtcca gatgccgaga ccaggactgt | ccaggacatc | 480 |
| gtcgcgaagg | caaaagccag ctcactttcc tatggtcatt gggggccggg | gagcatggcg | 540 |
| caaatgggca | tggaattgct caagaccaag gcgcacatca acaacatgct | cgaagtgccg | 600 |
| ttcggcggcg | ctgcaccggt catgacagct gtcatgggtg gtcaagttga | ctatgcattc | 660 |
| attcccacac | ttttggcggt cgccaacaag accaaactgc ggctttatgc | attgggatct | 720 |
| cctgagcgct | tcccgtcaat caaggagatt cctacgctca ccgaaagtgg | ctatgccatc | 780 |
| gacgctgaca | cctggtttgg cgtgctcgct ccgccaaata cgccgcaagt | ggtggttgat | 840 |
| gccatccagg | cgcaggtgac tcgcgccacg tcccaaccag agttccgtgc | acgcctcgcc | 900 |
| gacatgggct | atacgccaat cacgattgac cccaagaagt tcggtgaatt | tgtccaggct | 960 |
| gagaatcaac | gatggggcgc ggctgtcaag gcggcaagga tacggattga | ggagtaa | 1017 |

<210> SEQ ID NO 22
<211> LENGTH: 984
<212> TYPE: DNA
<213> ORGANISM: C. necator

<400> SEQUENCE: 22

| | | | |
|---|---|---|---|
| atgcaacgcc | gccacttcat cgcccgcgcg ggcatcgccg ccgccaccgc | ggcactgggc | 60 |
| cttgccgcca | tgcccgccca ggcacaggcc gacaagttcc cgcagcgccc | gatccgcctg | 120 |

| | | |
|---|---|---|
| gtgatcggct acaccgccgg cggctccacg gatatcccgt tccgcgtgct cgccgacaac | 180 | |
| gcctccaaga tcctgggcca gcccgtgatc gtcgagaaca agcccggcgc gggtggcgtg | 240 | |
| ctgcccgcgc agatgatgca gtccaccgcg ccggacggct acacgctggc ccaggtcgcc | 300 | |
| atgccggtct accgcctgcc gtacaccacc aagatcaact gggacccggt caaggacctg | 360 | |
| aactacatca tcaacctcgc cggctattcg ttcggcctgg tggtgccggc cgattcgccg | 420 | |
| atcaagacga tgcaggagta cattgcctac gccaaggcca atccgggcaa gctgacctac | 480 | |
| ggttcgccgg gctcgatgac cacgctgcac ctgaccatga agagctggc gatgaagcag | 540 | |
| ggcgtgcagt tctcgcacat cccctacaag ggcaattccg agtcgatgca ggcgctgctg | 600 | |
| ggcggccacg tgatgtcggt ggccgacacg ccggcatggg caccgtacgt tgagcagggc | 660 | |
| aagctgcgcc tgctgtcgac ctggggcgag aagcgctcgg cgcgcttccc cagcgtgccg | 720 | |
| acgctgaagg aactgggcat cggcatcgtg cagacctcgc cgttcggcct ggtcgcgccc | 780 | |
| aagggcaccg atccgaagat cgtgcagaag ctgcatgacg ccttcaagaa ggccatggac | 840 | |
| atgcccaact accgcgaatc gctggccaag ttcgacatgg agccgtacta catgaacagc | 900 | |
| cagcaatacg cgcagtttgc ggccgagacc gtcaagaagg aaaaggcgat catcgagaag | 960 | |
| ctggggctgg ccaaggcaca gtaa | 984 | |

<210> SEQ ID NO 23
<211> LENGTH: 993
<212> TYPE: DNA
<213> ORGANISM: C. necator

<400> SEQUENCE: 23

| | | |
|---|---|---|
| atgaaacact tgttcagcgc gctcgccgcc ggcacccttg cattcggcgc gaccatgccc | 60 | |
| ggcatcgccg cgcgctcga gttcccggcc aagccggtgc gcatcatcgt gccgtacccg | 120 | |
| ccgggcggca ccaccgacat ggtggcccgg ctgatcggcg agcaactggc cacgcaatgg | 180 | |
| aagcagtcgg tggtggtcga caaccgcccc ggcgcgggcg catcgtcgg caccggcacg | 240 | |
| gccgccaagt ccacggcgga cggctacacc ctgctgatgg gctcggtggg cgagttcggc | 300 | |
| atcaacccgg ccttgtacaa gaagctgccc tatgatgccg acgccgactt cgcgccggtc | 360 | |
| gcgatggtgg cgcgcgtacc caacgtggtg gtgctgtcgc cggcgtttgc ggaacgcgcg | 420 | |
| cgcgtgcaga cgctgcccga gttcatcgcc tacctgaaag ccaatcccaa gcgcgtcaac | 480 | |
| atggcgtcgg ccggaaatgg cacgtccacg cacctcgcgg gcgagctgtt ccagcgcatg | 540 | |
| accagcacgg agatgagcca cgtcgcctac aagggcagca gcccggccat cgccgacctg | 600 | |
| atgggcggca gcgtcgacgt gatgttcgac aacctgccgg cgtcgctgcc gtttatccgc | 660 | |
| tcgggcaagc tcaggccgct ggccgtgacc acgccggcgc gctcgtcggc gcttccgaat | 720 | |
| gtgccgacgg tcgccgccgc gggccccgtc cccggctttg atgccagccc ttggttcggc | 780 | |
| ctgcttgcgc cgcgcggggt gcccacggcg gtggcgcaga gatcagcca ggacctgacg | 840 | |
| cgcgtgctca acgagccagg cgtgcaggcg aaaatgcgcg agctgggcgc ggaaccggcg | 900 | |
| cccagctcgc cggaggcatt tgccgacgtg ttgaagaagg accgccagaa gtggggcgag | 960 | |
| atcgttcgcc tgtccggtgc ttcggtggac tga | 993 | |

<210> SEQ ID NO 24
<211> LENGTH: 924
<212> TYPE: DNA
<213> ORGANISM: C. necator

<400> SEQUENCE: 24

```
atgataagcg gctcaggctg ggcgagtggg tatccggtga agccggtgac actgatcgtt      60
ccacaagcgc ctggtggtgc caacgatgcc gtggcgagaa tcgtggcgca aagactcggt     120
gcggtgctgg ccaccccat tgtcgtcgac aaccggccgg cgccggtgg caatatcggc       180
atccaggtag ccgcgaaggc accgcgcgac ggctacacgc tactgctgac agtcggcagt     240
tcgttcacca tcaacccgtc gctataccgg aagattccgt ttgatccggt caaggacttc     300
gagccgatta cgctggtggc aacgcgcgcc tacgtgctgg tcacgaaccc cgcaatccag     360
gccaggtctg tccacgatct gattggcctg gccaggtcga agccaggaaa actggactat     420
gcctccgcgg gcaatggcac gctgaatcat ctgctcgggg aaatgctgaa ggcaaaggct     480
ggcatcgata ttactcacgt tccgtacaag agcgcagcgg cagcggctac tgacgtggtt     540
gccggccagg ttcccataac gttcggcagc ttgccaggcg tgatgccgtt cgtgaaaacg     600
gggcaactcc gcgtacttgg cgtggccaca gagaaacggt caagactgat tcccgaggtg     660
ccggcgatag gggaggccat tcccgggtac agcgcggtct cctggtatgg gttgcttgcg     720
ccagccggta cgccaaagga aattcttgcc cagcttcatg cggaggccac caaagtcctg     780
aatagcaagg acgtgcagga caagctggcc gcgcaaggag cagaggccgc atccaatacg     840
ccagagcagt tccgcgttct gatcaaggac gatctggtga aatgggcgaa ggtcgtcaag     900
gactcgggag cacaggtcga ttga                                            924

<210> SEQ ID NO 25
<211> LENGTH: 1002
<212> TYPE: DNA
<213> ORGANISM: C. necator

<400> SEQUENCE: 25
atgactatcc agctttcgcg ccggcgcctg ctgcaggcgg cgtgcggcgc cgtgccggca      60
atgcttgtgc cgtccttgct gcgggctgaa gcgccctatc cgggcaaccc gatcgtcgtc     120
aaggtcgcat ttcccgctgg gggtccggcg gacgaatcga tccgcgcggc agccgtcgtg     180
atgaaaagga gcctggggca gaacgttctt gccgacaacc ttcccggcgc aagcggatcg     240
atctgcgcca tgaacgtgct gcgcggtgcc aacgatggca cacccttgct gggcacgacc     300
ggcatcgact cctggtcgc gccacttacc atcgcatcgg cgaagtattc gccggagaag     360
ttcaggctgg caggcttcag cgggatttcg gacttcatcc tggtgtcgaa tcccctcgttg    420
cagttcaaga acgtcgacga agtcattgcc tacgcgaaga acccgaagaa ccgcccgctg     480
tcgctggcgc attggggccc tggctcggga ccccacctgg tcggggccga cttccaggcc     540
cgcaccggcg cacgcttcct ggaagtcccc tacaagggcg cggcgccggt caccagcgac     600
attgccggtg cgcaggtaga cctgaccttc attcccatgg gaggtccgac ttacgggatg     660
atcaaggccg gccgcttccg gccgatcggt gtcgccagca aggcccggca tccgtcgttg     720
cccgatgtgc cggcgctgtc ggaatacaag gacctggccg acttcgagta cagccagtgg     780
gcgggcgtgc tggccccgcc gaatacaccg gatgccgtga cggcacgggt ggtggaggcc     840
atgaatgcgt gggtggggcag cccggaaaac cgtacccggc gcgccgtcaa tctccagcgc     900
gcgatcgagc cgatgaccat ggcccaggcg caagccttcc tgagcaacga acacgccaag     960
ctgacccgca ttgccaagag cctcaggctg gccgggcaat aa                       1002

<210> SEQ ID NO 26
<211> LENGTH: 1014
<212> TYPE: DNA
```

<213> ORGANISM: C. necator

<400> SEQUENCE: 26

| | | | | | |
|---|---|---|---|---|---|
| atgcaatacc | gaggactacc | ccccgtcaag | cgctggatgg | cgctgagtgc | cgccatcctg | 60 |
| gggatgacac | tgaccagcgc | accaacgtcc | gccgccgacg | cctttccctc | caagccgata | 120 |
| tcgatgctgg | tggcattccc | tccgggggggg | cccgccgatg | ttctggcgcg | ggccatgcag | 180 |
| ccggcgatgg | ccaaggcgct | cggccagccc | gtggtcatcg | agaatctgcc | cggcgccggc | 240 |
| ggtgcgctgg | cagtgcagcg | gctgctcagc | cgtccggccg | acggctacac | gctgatcatg | 300 |
| ggctcgccca | tgaggctat | cctgacgccg | ctggcgctcg | ccagcgccaa | gtacaagtcg | 360 |
| gaggaactgg | ccctgctggc | gccggtctcg | aaccaccgc | tcgtcgtgat | gacgcgcagc | 420 |
| gacctgccat | acaattcgct | tgaacagatc | atcacggcca | gcaagtcggc | aggtggcaag | 480 |
| agcctgacct | tcggcaatcc | gggctacggc | accatgtacc | acatcgtcgc | cgaatacatg | 540 |
| gctcagctga | ccggcgccaa | gatgctgcag | gtgccgtaca | agggcgccac | gccgatgctg | 600 |
| gcagacctga | ccggtcgcca | gattgacatg | acgattctgc | caaacctcgg | tgcctccacg | 660 |
| cagttgctcg | aaacgcacaa | gatcaaggcg | gtcgcagtgc | tggacacaca | gcgcatgcga | 720 |
| aacctgcccg | atgtgcctgc | gatctccgaa | accagcgtcg | cgcgcaaatc | cgagttcgtg | 780 |
| tattcgatct | ggctgggcgt | catgagcaag | ccggcgtcc | ggcggagcg | tgcccgcgta | 840 |
| ttgatggatg | cctcgcagca | agcgctgcgg | tcgcccgaac | tgatcaaggc | gcttgatctc | 900 |
| tccggcgtgc | agccgatgaa | gccacaaacg | ctcgaggcct | ccgcgaagtt | ctacgtcgac | 960 |
| gagaccgaga | aattcaggaa | gatggccgcc | tcgatcaagc | tgacgccgca | gtaa | 1014 |

<210> SEQ ID NO 27
<211> LENGTH: 1023
<212> TYPE: DNA
<213> ORGANISM: C. necator

<400> SEQUENCE: 27

| | | | | | |
|---|---|---|---|---|---|
| atggagataa | gttccaagat | gactactgcc | ctggcccccc | ttttccatgc | ggcgcgggcg | 60 |
| cgcgcgcaaa | catccgccgc | gctggtgctg | acgcttgcct | gcacgctggc | gccgggcttc | 120 |
| gcgcgggcgg | aagcatggcc | cgccaagccg | gtcacgatcg | tcgtccccta | tgccgcgggc | 180 |
| ggcaccgtcg | acaaggtcgc | gcggcaggtc | caggagggcc | tgcgcaagca | gctggcgcag | 240 |
| acggtggtga | tcgacaaccg | cgcaggcgcg | ggcggcacca | tcggcacggg | gcagatcgcg | 300 |
| cgcagcgcgc | cggacggcta | caccgtcggc | atggtgttcg | acagctttgc | caccgagccg | 360 |
| catttctacc | cgaagctgcc | ctatgcctcg | caccgcgacc | tgacaggcgt | ttcctatatg | 420 |
| gtgcgctcgc | cgatggtgct | ggtcgtaccc | gccgcctcgc | cctacaagac | cgtgcaggac | 480 |
| tacgtgacgg | cggcacgcgt | gccgaacaag | gtgtcctacg | catcggtggg | caacggcagc | 540 |
| tcgaaccagc | tcgtggccga | agccttccac | gaggccgccg | gcaccagcgg | catccatacc | 600 |
| ccctacaagg | gcgcggcccc | ggccatcaat | gacctgctcg | gcggccacgt | cgactcgatg | 660 |
| atcgcgagcc | tgccgctggt | gctgcccctat | gtgcagtcgg | gcaagctgcg | cgcgctggcc | 720 |
| gtgacctcgc | gccagcgtga | cgcgaggctg | ccggctgtcc | ccgcggtagc | cgagtcctac | 780 |
| aagggcttcg | aggcctattc | gtgggtcggg | atgatcgcgc | cggccaagac | ccgccggaa | 840 |
| gtgctgggga | aactgaccac | cgccatgacg | tcgacgctgc | gcaatccggc | gatcgcgaaa | 900 |
| ctgctgaccg | acgcggcctt | cgacgtggtg | gccggcgacg | cacaacagac | caacaagctg | 960 |
| atccaggacg | aatcggcacg | ctggggccgg | ctaatcaagg | cgcgcaacat | cgcggtcgac | 1020 | tga                                                                      1023

<210> SEQ ID NO 28
<211> LENGTH: 954
<212> TYPE: DNA
<213> ORGANISM: C. necator

<400> SEQUENCE: 28
atgaccgccg tcgctgccgc caccttcgcc atgaccgctc cggctagcgc ggccgatgcc      60
gagccgatgc atatcatcgt cggctacgcc cccggcggcg ccgccgacag ccttgcccgc     120
ctgtatgccg agcagctgcg ccaggacggc cacggcacgg tggtggtcga aaaccgcccc     180
ggcgcgtcgg cgcgcctggc gctcgactac gtgaagcgcg ccaggcccga tggcaagacc     240
gtgttcatcg gcccctcgcc cctgttcacg atctttccgc tgacctacaa gaagctgtct     300
tacgacgccg acaaggacct ggtgcccgca gcggtactga ccgatgtgcc gaccgcggtc     360
gcgaccggcg tgcagcagcc ttaccagaac atgaaggaat acgtgagctg gccaggcgc      420 aacccgggcg gcgccagcct gggcctggcc accatcggca gcgccggcca cctcggcacg     480
gtggcgctgg caaggccga aggcatcgcc atcacgcccg cggcgtatcg cggcgcatcg      540
ccgatgctgg tggatgtggt cagcggcaat gtgtcgatcg gctgggatgc cgtggccagc     600
atgatgccgc tgtacaaggg cggcaagctg cgcttccttg gcgtgagcgg cacgcgccgc     660
gccaaggcgc tgcccgaagt gcccaccatg aaggaacagg gcttcagcca gtacgaccac     720
gccaccagct ggtacggcgt gttcgtcccg gcaggcaccc agcctgacgt ggtggcgcaa     780
gtggaaaaga tgttcctcgc ggcctcggcc aacgccgcca ccgcggccaa gctggaagcg     840
ctgggcctgg aagtggtggc gcgccccggc cacgaaggcc gccgccgcat ccagctggaa     900
cgcgccgcct ggaagccgat cgtggaggcg accggcttcc aggccgagga ctga          954

<210> SEQ ID NO 29
<211> LENGTH: 993
<212> TYPE: DNA
<213> ORGANISM: C. necator

<400> SEQUENCE: 29
atgaaacaca agctgccaga atcgctgttc aacacgtccg cggccctgct gctggcgacc      60
gccgccgcca cgctgccgct gcccgccagc gccgcgtcct ggcctgagcg ccccatcacc     120
atcatcgtgc ccggcgcgcc gggcggcacc accgacatcc gacgcgcct ggtggcgcag      180 aagctgtcgg ccatcctggg ccagccgtg gtggtcgaca acaagcccgg cagcggcggc      240
atcatcggca cgcaggcctt catgcgcgcg gcgccggacg gctacacgct gctggtcggc     300
aataccggct cgcacgcaat caactacagc gcctacaagc agttgtccta ccagccacag     360
gacttcatgc gctgacgga cctgatctcg ttcgccaacg tgctggtggt cggcgcgcag     420
gcgccggtgc gcagcgtgtc cgagctggtg gcgcagctca gcagtccccc ggggaagtat     480
tcctacgcct cggccggcat cgggcagacc acgcacctga cggcggaact gttccggctg     540
cgcactggca ccgaagtaat tcacgtgcca tacaaggggt cgacacccgc caccacctcg     600
gtgctggcgg cgaaaccac cttcatgttc gacaacctga cgcaggcgct gccgcagatc     660
cgcgccggca gctgcgcgc gcttgcggtg accagcgccg aacgcctgcc ggcactgccg     720
gacgtgccga cgatgcgca ggccggcgtg aaggatttcg tggtgatggg ctggctgggc     780
ttctttgcgc cggccaggac cccgccgcc attgccgcca cgctgcagga agcgctgggc      840

| aaggccatgc gcgaccccga ggtggtggcc aggttccgcg acatgggcgg tatccctggc | 900 |
| ggcgaaccgc agccgaagtt cgccgcgctg gtcagcggcg acatcaagcg ctggggcgag | 960 |
| accatccggg catccaaggt cagtctggac tag | 993 |

```
<210> SEQ ID NO 30
<211> LENGTH: 468
<212> TYPE: DNA
<213> ORGANISM: C. necator

<400> SEQUENCE: 30
```

| atgcagcatg cgtccggcac cactgatgtc gcctttatcc cgtacaacgg cggccccgcc | 60 |
| gcgctgcagg acctgatggg cggccggctc gacttcatgt tcagcaatac ctccgaggcc | 120 |
| atgccgctga tccgcggcgg caaggtgcgc ccgctggccg tcagcagcct gaaacgcctt | 180 |
| gcgctgctgc ccgaggtgcc gacgctcgac gagtccgggc tgaagggcta cgagaccgtg | 240 |
| gcctggggcg gcgtggtcgc gccgcgcggc acgccggcgc cggtgatcga caggatcaac | 300 |
| gccgcgctgc aagctgcgct gcaggcgccg gacgtgcgca agggcctggc cgcgctgggc | 360 |
| gccgagcctg ccggcggctc gcccgcgcag ctccggcagc tgatcgatgc cgagaccgac | 420 |
| aagtggcgtg ccccgattac gtcggcccat atcgagcagc tggactga | 468 |

```
<210> SEQ ID NO 31
<211> LENGTH: 1008
<212> TYPE: DNA
<213> ORGANISM: C. necator

<400> SEQUENCE: 31
```

| atggcatccc tgatcgcatc ccggcgccgc gcctgggtcc gccgcgcatg gctggccggc | 60 |
| atgctggcca ccgcggccgc aaccgccttg ccgtccggcg ccagcgccga gacctggcca | 120 |
| tcgcgcccgg tccagctgct gatcccctac ccgccgggcg gcagcgccga cctgctggcc | 180 |
| cgccccggtcg cagccaggct gcaggagcgc ctgggccagc ccgtggtgct ggactaccgg | 240 |
| cccggcgccg gcggcaccat cgccagccag gcgctggcgc gggccaagcc cgacggctac | 300 |
| accctgatca tggtgctggc cgcccatgcc atcaatgcca gcctgtaccc gaagctgccc | 360 |
| tatgacacgc gcaaggactt cgcgcccgtc tcgctggtgg ccagcctgcc gatgatcctg | 420 |
| gccgggagcc cctcgctgca ggccaccaac gtgaaggagc tgattgccga ggccaaggcc | 480 |
| gcgcccggca agctgacctt cgcctcggcc ggcaacggca ataccggcca cctggcgggc | 540 |
| gaattgttcg attccgtcgc gggtatcaag atgacccacg ttccgtacaa aggcagcgca | 600 |
| caagtggtga cggcaatgct gtcgggcgag gtccagctga ccttcgacag catctccacc | 660 |
| accctgccgc atgtgaagag cggcaagctg cgcgcactgg ccgtgaccgg cagccagcgc | 720 |
| gccgcggtcg cgcccgaggt gccgacgctg gccgaggccg gcgtgccggg catcagcatc | 780 |
| accggctggt acgcgatgct ggcaccggcc ggcacgccgc agcccgtgat cgaccggctc | 840 |
| agcaccgaga ttgccacggt gctgcgccag cccgaactga aggcgacgct ggccgccaac | 900 |
| ggctatgagc cggtgggctc gactcccgcc gcgctgcgca cccatatcga cgccgagatc | 960 |
| aaccgctgga gcaaggtggt gaaggactcc ggcgcacaga tccagtaa | 1008 |

```
<210> SEQ ID NO 32
<211> LENGTH: 996
<212> TYPE: DNA
<213> ORGANISM: C. necator

<400> SEQUENCE: 32
```

```
atgcaacacc gttccgcacg gctgcgcgca gccgtggccg ccatgctgct ggcggccatc        60
ccggcggcag tctgcgccgc cgatcccgcc tccgccgagc cctatccgtc gcgcccgctc       120
accatcgtgg tgccgtcggt ggcgggcaat gtgaacgacg ccgtggcgcg gctgatcggg       180
caggaactga ccaggagctg gggccagccg gtcatcgtcg acaacaagcc tggcgcgggc       240
accaccacgg gtaccaagta cgttgcccgc gcagcaaagg acggttacac cgcgctgttg       300
accttcactg cgcacgtgca gaacccgtcg ctgtaccggg gtatcggcta tgacccgatc       360
gcggacttca cgccggtcag cgaggtggcg atctcgtcca ccatcctggc ggtgtcgccg       420
gacttccagg cgcgcacgct gccggaggtg gtggcgctgc tcaaggccaa tcccggcaag       480
tatccgtacg ggtcgtatgg cgcggggacg accggccata tcctgggaga gttgctcaag       540
cgcgaggccg ggctgcagat ggaacacgtc gcctacaagg gcggcgcgcc gctggccacc       600
gacctggcgg ccggccatgt gaagctgggc tttattgccg tgggcacggc catgccgctg       660
ctgcagggcg gcaagctggc gccggtggcg atcgctggcg cggagcgttc ggcgctgctg       720
cccaaggtgc cgaccttccg ggaggccggc tacaagggct tcgagcccga tgcgtggatg       780
ggcctgctgt tccccgccgg cgtgccgaaa gcacgggtcg atgccctgtc gcgcgaggtc       840
gcgcgcatcg tgcgcctgcc ggaaatcgcg aagaagatgc aggacctgaa tctggtgccg       900
gtcggcagca cgccggaagc cttcgccacg gtgatgaaga cgaccgcga caaatggagc       960 cgcatcatca gcgatgtcgg catcacgctc gaatga                                996

<210> SEQ ID NO 33
<211> LENGTH: 987
<212> TYPE: DNA
<213> ORGANISM: C. necator

<400> SEQUENCE: 33
atgcgtggta ctgaactcgt gcgtcgtatt tccggcgtgg ccgtgctggc agccggcttt        60
atcctcagcg gcacttgcct ggcacaggaa tggccggcca gccgatcac cgtggtggtg       120 ccgttcccgt cgggcgggac taccgacgtg ctggcccgcg cgctgggcga ccagttgtcg       180
aagagcctgg gccagccgt gatcgtcgag aaccggcccg cgccggcgc caccgtgggc       240 gcggactacg tcgccaaggg caagccggac ggctacaccc tgctgatggg cgcggtccac       300
catacgattg ccagcagcgt ctacaagaag ctgcctaca gcttccagaa ggacctggca       360
cccattgcca cggtcgccat ggtgcccaac gtgctggtca tcaatgccgc caagacgccg       420
gcgaaggacg tcagcgaact ggtggccctg gcgaagaagg cagcgccgga gtttgcctat       480
ggctccaatg gcaacggcac cgcgcagcac ctgatcggca cccagttcca ggccgccacg       540
ggtgcgccgc tgctgcacgt gccctacaag ggcagtggcc cgctgaccac cgatctgctc       600
ggcggacagg tgacgatgtc gttcgatacc ctgacgccgg tgctgcagca catcaagtcg       660
ggcaagctgc gcgccctggc cgtgaccacc gcgcggcgct ccagcgtcct gcctgatgtg       720
ccgacgctgg aagaggcggg gctgaagggc ttcgatatcg gcacctggtt cggcgtgctg       780
gcgccggccg ccacgccagc gcccatcgtc acccggctga acgccgagat cgtcaagatc       840
gtgaaatcgc cggacttcca gcagcgcatg gtggcggtcg gggccgagcc gatggcgagc       900
acgccgcagg agtttgccaa gcggatccag gacgagacgg tcaagttcgc caggctggtg       960
aaggacggga aggtgacgat cgagtag                                          987

<210> SEQ ID NO 34
```

```
<211> LENGTH: 1047
<212> TYPE: DNA
<213> ORGANISM: C. necator

<400> SEQUENCE: 34
atgcaagcga cacagcaacc ggactaccaa gctcagagca ccacgcggcg gctcgccaag      60
cgacgatgcc gcgtcgccgt gagcgcgctg ggtgccatcc tgtggggcgc tgcagccagc     120
gcccagccaa cgtccactcc cggcactgat cgcatcgaca agccggtgcg catcatcgtt     180
gcttacggag ccggcggggc ttcggacagc atcgcgcgtt tcgtgggcga cggactctcc     240
aggcgtgccg gcaagcccgt gatcgtagaa aacaagtccg gtgctgacgg caacattgca     300
gccgacgctg cagtccgcgc gtcgaccgat gcttacacgc tgctggtgtc cggctcatcg     360
acgcacgcgg caaacgccac catctaccgc aaacttccct atgacccgga agcggacttc     420
acgccgctgg ccacaatggc cagcacaccc ttcgtgttgc tcgtgaatcc aaagcgtgtt     480
cacgcagcaa cgttcaagga gttcctggca tgggccagga aggagagcaa tccgctttcc     540
tttgcgagcg ccaacgtggg aggccgtatc agcggggagt tgttcaagca acgagcaggc     600
gtcaaggcag tcagcgttcc gtacaagaac agcagccagg ccatgacgga cctgcttggc     660
ggccagttcg actactacct gtgcgacatg gtcaccgcgc tgccgcagat ccaggccgga     720
accgtgcgcg ccctggcaat ctccagctcc gaacgagtgc agtcattacc tgatgtgccg     780
acactggcgg aaagcggatt cccggacttt gacgtcagtt cgtggatcgg catctggagc     840
gctaacgcgt cgacgcccca gcctgtggcc aggctgttgt cgcgctggat cgccgatacg     900
ctggactcgc ccgatggtcg tcatttcctc atcggcaagg cctgattcc ggccaaggtt      960 gccccgatgc atctgcagga gttgcagcgg cgcgacacca agctctgggg aaaaatcatc    1020
attgacgcgg gaatgcagca gccatga                                        1047

<210> SEQ ID NO 35
<211> LENGTH: 993
<212> TYPE: DNA
<213> ORGANISM: C. necator

<400> SEQUENCE: 35
atgcccatca tcactgtgcc gcggcggcgt gctgccctgg ccgcgctggc gtgcatcgcc      60
gcactgccgg cctggtcgca cgccgcggac gattctgcct atccgcaaaa gcccatccgg     120
ctggtcgtgc cattcccggc cggaggcgga tccgacaccg tggcccgctt gctcggccgc     180
gagctgacgg cgatgtgggg ccagacggtg gtggtcgaga acaggcccgg tggcagcggc     240
gcgattggca caggcgcggt cgcgaaggct gcaccggacg gctatacgct gctgttgggc     300
gcaacgccgc tggtgcagtt gcagggcgcc tacaagtcac tgccctatga caccttccgc     360
gacttcgcgc cgctggcgcg cctggcgctc tcgtcggacg tatttgccgc tccggtatcc     420
acccgcgttg ccagcgtgag cgagctgctg tccgcggccc gggccacgcc tggcaagatc     480
agctacggct cctacggcaa cggcacctcc tcccacatgc acgggaatt gctgcggatg     540 cagggggacg tcgacctgac ccacgtggcc tacaagggcg ctcgccact gatccaggac     600 ttgctgggtg ggcaggtgag ttccgggttt gtggatgtgg ccagcggcaa ggccgcgctc     660
aactccccga agatcaaggt actggccgtc acgggcgagc gccggctggc gctgctgccg     720
gaggtgccga cctttaccga actgggctac cgtgatttcg agccaaacgg ctggtatggc     780
ctgttcgtgc cggcggcgac gccgaaggcg gtgacggaca gctatccgc ggcggtgctg      840 gcaatcctgg ccaagccggc catgcaaacg gcgattcgtg agcaaggcct ggagccggga     900
```

```
acgctggagc ccgaggcatt cctgaagctg atgcggcgcg acgccgagat ctggggacgg    960
atcgcggcca acgcgcgcat cacgcttgac tga                                 993

<210> SEQ ID NO 36
<211> LENGTH: 987
<212> TYPE: DNA
<213> ORGANISM: C. necator

<400> SEQUENCE: 36
atgaagcggc gttttctttg ccaggcgcta gcctgcctcg ctgtcgtgtc cacctcgggc     60
cttgcattcg ccagcccgtc ccccgagacc ttccaggcca agcgtccttt gcgcctgatc    120
gcgccaagtt cgcccggcgg catccttgac ctgaccagcc gcctgctcgg caagacgctg    180
tctgagcagc tggggcagcc cgtcgtcgtg gagaacctgc ctggcgcggg cggcgtgatc    240
gggatgcagg ccatgctgcg cgcggaaccg gacggccaca cgctggtgat gggcagcctt    300
gcccccaatg cggccaacta cgcattgcac gacaagctgc cttacaagtt cgaggacttt    360
gcaccggtgg cgcatgtgct gacgatgccg gacgtcgtgg tggtcaaccc gaaactgccg    420
gtcaagacca ttgccgagct ggcggcctat gccaggacgc gccccaacgg cttgtccatg    480
gcggtgtcga cgagcggttc ttccggccat ctcgccgggg acctgctgaa gcagcgcgcc    540
ggcattaccg ccgtcgacgt gatctatcgg ggcgcatcgc cggcgctgac cgacctggtg    600
gcggggcaag tcgatttcat ggtggacaac ctcatcaccg cattgccgct ggtgcgagcc    660
ggcaagctgc gcgcgcttgc ggtcacgaca aggcagcgtg ccccggaact cccggatacg    720
ccgaccatgg ccgaatccgg ttaccgcgac ttcgacgttt cggtctggct cggcctcttt    780
gtctcgtcca gaacgccgcc cgcggtggtg caggcgttga atgttgccgt caacaaggcg    840
ctggccgatc ctgctctgcg cgagaagctg gcgcagcagg gcggtacggc cgcggggcggg   900 tcgacgcggc agttcgacag cttcgtgcgc gccgaaaaag cccgctggga gcaggtcatc    960
aaggacggca acatcaagcc cgagtaa                                       987

<210> SEQ ID NO 37
<211> LENGTH: 984
<212> TYPE: DNA
<213> ORGANISM: C. necator

<400> SEQUENCE: 37
atggatcgtc gaaagttcct gagcgccgcg gccatcgcgg cgaccgccgg cgtcgcgccg     60
cacgccatcg cgcagcagtg gccggcgcgc gccatccggc tggtcgtggc ctatccgcct    120
ggtggcggca ccgacgtggt ggcacgtttg tttgccgact acctgacgcg cgtgaccggg    180
cagtcggtgg tggtggagaa caagcccggc ggggccacca ttcccgccac gcaggacgtg    240
atccgcgcca ggaatgacgg gcagacgctg ctggtgacgc tgggttcctc ggccacctcg    300
ggcgcgcata tcaaccgcgt tccttacgac ccgttgaccg acctcaccgc gctgcggaa     360 cttggccgcg ccccggtgct gctggcggcc aacaaggatg cgccgtactc cacgctgaag    420
gaactgatcg cctattccaa ggcgaatccg accaagccga tccactcggc ctcgtacggt    480
ccgggcacct cgtcgcactt cggtccgctg ctgttcaacc ggctggcagg caccaaccht    540
gaaccggtgc tgtacaaggg ctcggcgccg gccacgcagg acctcgtggg cggcgtggtg    600
ccgctgatga tcgacggcct gaccaccggc gtgccgctat accaggccgg caagaccaag    660
gcgctggcca ccaccatccc ggaacgctct gatctggcgc ccggggcgcc taccttccgt    720
```

```
gagcagggct tcctgagat ggagcagctc agcggctatt tcgcgctgtt cggcccaag    780 gccatgccca aggccacggt cgatgcggtc tctgctgcgg tgcgcaaggt gctggccgac    840
ccggcctacc agaagcggct ggcaggcgtt ggcgtgctgc cgccgcaggc ggtcacgcct    900
gaggccttcg ccgcgcagat ccggaccgat catgcgcgct gggggcagtt catcaaggat    960
atcggcttca agatcgatgg gtga                                          984
```

<210> SEQ ID NO 38
<211> LENGTH: 993
<212> TYPE: DNA
<213> ORGANISM: C. necator
<400> SEQUENCE: 38

```
atgaaacagg tggcgaagtg gatggggccg ctggcacgcg gcatgatgtg gatgagcctg     60
ggcgcggcgg tgatcccggg cgcgcaggcg caggagtgga agccggccaa gccggtgcgc    120
ctgctggtgg gctttgcgcc cggcggctcg gccgatctgc tggcgcgcct ggtgcaggcg    180
ccgctgtcgg aaagcctggg ggttccggtg gtggtggaga cgtgccgggg tgcgggtggc    240
aatatcgccg ccgacaagct ggccaaggcc ccggccgacg gctacaccat cggcatgggc    300
gccgccggcg cgatggcggt gacccacgtg ctcaaccccca agggcacgcc atacaaggcg    360
gatgatttca cgcccatcgc catgctggcc acccagccga atgtcgtgat cgtcaatccg    420
gccctgccgg tcaagaccat ggccgacttc gtcgcctacg tcaaaaagac gccgcaggtc    480
acctacggca ccgccggcgt cggcacgtca aatcacctga ttgccgaaac catgctgcac    540
cgtcttggca tcgacatggt ccatgcgccg tacaagggtg ccaccccggt gatcaccgac    600
ctgatgggcg gcatatcgc catgacggtc gacaacatca ccaccgcggc gacgctggcc    660
aagaccggca aggtcaaggc gctggcagtc accggcagca gcgctcgcc cctgttgccg    720 gacgtgccga cgcttgccga gagcggactg aaggacttca acatgccgac ctggcaaggc    780
atcttcgggc cgaaggacct gccgaaggca atcgtggtcc gctacaacca ggcgctggtc    840
aaggccttgg cgaacccgga agtcaggaag aagatggctg aattcggctc cgagcccgtg    900
ggcgatacgc cggagcattt cgccgggttc ctcgcccagg accgcaagat gtgggccgat    960
gtcatcaaga cggccaagat cacgctcgag taa                                993
```

<210> SEQ ID NO 39
<211> LENGTH: 1017
<212> TYPE: DNA
<213> ORGANISM: C. necator
<400> SEQUENCE: 39

```
atgaagcaag cccttcaacg caagtccgcc atgcccgcac ggcgcaaggc cgtagccgcc     60
acgctggcgg cactcggtgc ggcatggttc gcgcccgtcg ccctggcgca ggacggtacc    120
tatcccgccc gtccggtgac gctggtggta tcggccgcgg ccggtggcac caccgacatc    180
gcggcgcgca tgattgcgga accgctgtcc aaggcgctcg ccagccggt ggtggtggac    240 aaccgtcccg gcggcaacgg cagcatcgcc gcgcaactgg tggcgcgggc caagccggac    300
ggctacacgc tgatgctgca gtactcgggc ttccacgtga tcgcgcct gctggtcaag    360 aacctgtcgt gggacccggt caaggacttt gcgccggtgg ccaacatcct gtcggcgccg    420
caggtgctgg tggtgcgccc gagcctgccg gtcaagtcgc tgaaggaact ggtggcctac    480
gccaaggcca atccggacaa gctcaactac gcctcgtcgg gcaacggctc gctgcagcac    540
gtctcgaccg agctgctgaa ccagatggcc ggcacgaaaa tcacgcacgt gccctacaag    600
```

| | |
|---|---|
| ggtaccggtc cggccatgac cgacctgctg ggcggctcgg tggacctgac catcaccacg | 660 |
| ccgccgccgc tgatggccca tatcgccgcc ggcaagctgc gtccgctggt ggtgaccagc | 720 |
| aagacccgcc tgcccagcct gaaggacgtg ccgtcggcgc ccgaggccgg ctaccccgac | 780 |
| ctggacgtgt cgtcgtggtt cgcgatgtac gcaccggcag gcacgcccaa gccggtgatc | 840 |
| gacaagctga ctggcgaaat cgacaagatc atgcgcaccg aagccttccg caagaaggcc | 900 |
| gaggacctgg cgccgaggc caagtacatg aacccgcagc agctgggtca gtaccagaag | 960 |
| gcggaactcg cgcgctgggg caaggtgatc aagtccgccg acatccacgc ggaatga | 1017 |

<210> SEQ ID NO 40
<211> LENGTH: 2040
<212> TYPE: DNA
<213> ORGANISM: C. necator

<400> SEQUENCE: 40

| | |
|---|---|
| atgagcaaga caatacccttg cgtgctgatg cgagccggca cctcgcgcgg gccgttcttt | 60 |
| ctgcgggagt ggctgcccga aagcgtagag gctcgcgacc aggcgttgat cggtgccatc | 120 |
| ggtgcctccg acccgcttca actggacggg gtgggcggcg gtagcacgct gaacagcaag | 180 |
| gtggcgattg tttcgcgatc cacgcaaccc ggctgtgacc ttgactacct gttcgtacag | 240 |
| gtaggagtgg gtaactcctc ggtggacacc cggcccaact gcggcaatat gctttccgga | 300 |
| gtcgcaccct ttgcgatcga gcaaggcctg gttgcagccc aactcggctc aacccgcgtg | 360 |
| cgcgttcaca acgtcaatac aggctcgcga atcgatgtga cggtccgcac gcctaatggg | 420 |
| cgggtcacct atgacggcga cactcgaatc gatggcgttg cgggcactgg gtcaccaatc | 480 |
| ttgctcgatt tcgtcgatgc gtggggcgca gtgaccggaa aggtctttcc gacgggcaac | 540 |
| cgcgttgacc tgattgacgg catcgaagtg acttgtatcg atgcggcgat gccattgatg | 600 |
| ctcgtccggg cacgcgacct cggtgtcagt ggacgcgagg cgccggccac gctcgacaat | 660 |
| gatccgatac tgcttgcgcg tctggaagcg ctgcgcttgc aggctgggca gttgatgggg | 720 |
| ctgggcgacg tctcggacag cgttattcca aagccagtcc tggtcagccc cggcgattcg | 780 |
| ccggaaagca ttacgtcgcg ctactttacg ccccgcaaat gtcatgcgtc gcatgcagtc | 840 |
| accggcgcca tcggcgttgc cagcgcattc gccttacctg ggacggttgc tagccaattg | 900 |
| acccgattgc ccgccgcca cgcacttgtc gtcttgcacc cagcgggacg gatcgaagtg | 960 |
| gaggtggaat tggagggga gggcgatgcg gctactgtaa caagagcggc tctcgttcga | 1020 |
| acggcacgca agatcataga aggtcagctc catctgcccg aatatgtctt ctcgcggccg | 1080 |
| gaaggcagcc gagtaaagca ggcctcggct cggcattcat tgcggatcat cgtaccaacc | 1140 |
| cgtgccggag gcgcaacga tcttgtggca catcttattg gtcccaggct tgggcgactg | 1200 |
| ctggggcatg acgtcatcat cgataaccgt cccggtgcca acggcggcat cgcctgcgag | 1260 |
| tacgtggcgc gggcagtacc cgatggtcag acgctcttgc tcggctatat tggaactcat | 1320 |
| tcaatgaatc cggccctgca acctgttggg tatgatccgg tttcgtcttt ttctccggtc | 1380 |
| gggcttatag gatcgtcacc gatattgttg gtggcgaatc caatgcagac gccgcttgac | 1440 |
| ctgggtacgc tggtcgccca catgaagcgc gagcctggaa ggtttcgcta cgcgtccgca | 1500 |
| ggggacggta caccgccgca ctttgccgca gagcttttcc aactggccac tggcacttcg | 1560 |
| atgcgcagta ctaccttcga gggcgcagcg cctgccatcg cgtcgaccat tgatggacgg | 1620 |
| acacaggtta tgttcgcgag cctgctgaca gcgtatcggc cggtgggtgc cggtcagttg | 1680 |

| | |
|---|---|
| cgagcactgg cagtcgccgg acccaaacgt ctgccagtgc tgccagaagt accgacgctt | 1740 |
| gcggagttgg gcgtgagggg catggaattg actcagtggt atggtctgtt tgccccggcg | 1800 |
| ggaactgctg ccacgatggt ggagcagctc aatggcgcct tggctgcagt cctacgggat | 1860 |
| ccagaggtca agagggcttc gagagctac ggcgcagccc ccgagccggg cggttccgaa | 1920 |
| cttctcgcaa gacgggtgga gactgaacta gagcgctggc agcgcattgt tagggtgtca | 1980 |
| ggtcttgcgc cgtcgtcgat cgacggtgac ccggtgcaac agtttctgga gccctgctaa | 2040 |

<210> SEQ ID NO 41
<211> LENGTH: 972
<212> TYPE: DNA
<213> ORGANISM: C. necator

<400> SEQUENCE: 41

| | |
|---|---|
| atgcaatcat cgaagcgact tttactttgc agcattgcga tcgcggtatc acttggcagc | 60 |
| gtcagcgcct ttggtgcgtt ccctgacaag agaatttcgc tggtagtgcc caccgcagcg | 120 |
| ggaggcgcta atgacgccat ggcgcgggta gttggccagg caatgtcgac cattctcaat | 180 |
| cagacaatcg tggtcgacaa caaagcgggg gcgaacggcg cgattgccag tgagtttgtc | 240 |
| atgcgtgccc caccggacgg ctacacgttg ctactcggct acgtggcgac acatgccatg | 300 |
| aaccctgcgc tgcagaagct tcggtacgat cccgttaagg attttgtgcc cgttggcatg | 360 |
| gtgggttctt cggcaaccgt gatggtcgtc aatccaaacc tgaaggccaa cgatgccaag | 420 |
| ggagtcgtga cgctactcaa agcaacgcca ggaaagatca gttacgcgtc ggcgggcaat | 480 |
| ggaaccgctc cgcattttgc cgcggagatg ttcaaactct cgaccggcac cgagatgctt | 540 |
| catgtgccgt ataaggggtc agctccggcg attaacgaca cagttgccgg gcagacacaa | 600 |
| gtgatgtttc cgagtctttt caccgccatg ccccagttga gaacggcaa gctgaaggcg | 660 |
| gtcgggattg caggcagcaa gcgctcttcg ctgatgccag agttgcccac gctgaaggaa | 720 |
| caagggatcg acgacgttga tgtttcccag tggtatgcca tcttcgcccc cgcgaacaca | 780 |
| ccagccccccg ttgtagaagc attgaacaag gcattaaacc aggcgttgaa ggataaagcc | 840 |
| gttgtccagc gttttgaggg acaaggcgca gaggttacga ccatgtccac ggcccagatg | 900 |
| cgaacattta ttcaggagga acaggtcaag tggaagaaag tagttcaggc ggcaaaactg | 960 |
| aaggcggact ga | 972 |

<210> SEQ ID NO 42
<211> LENGTH: 978
<212> TYPE: DNA
<213> ORGANISM: C. necator

<400> SEQUENCE: 42

| | |
|---|---|
| gtgaagtcct tcagcaatgc ctttgccagc ctggtgctcg ggtgcaccgc ggcgctggcc | 60 |
| gccaccccgg cgctgtcggc cgatgaattc ccgtccaggc cgctgcgcct ggtggtgccg | 120 |
| ttcgctgccg gcagcggcac cgatgccgtg gcccgcctga ctgccaaata cctgggcgag | 180 |
| gcgctgcagc agccggtggt ggtggacaac aagcccggcg ccaacggcac cattgccgcc | 240 |
| gagttcgtgg ccaaggcccc ggccgatggc tacacgctgt tcatgaccac caacaccacg | 300 |
| cattcggcca accgtcgct gatgaagcag ctgcgctatg accggtcaa ggatttcacg | 360 |
| ccggtctcgc gcatgggcaa cctgccgttc atgctggtgg tcaacccggc gctgccggtg | 420 |
| aagacgctgc gcgagttcat cgactatgcc agggcgcatc cgggcctgag ctatgccagc | 480 |
| ggcaacagca ccggcatcgt ctcgggcgcc acgctgtcga agatggccgg gctgaacatg | 540 |

```
ctgcacgtgc catacaagag cacgccgccg gcgatgaccg atgtgatggg tggccaggtg      600
caggcgatgt tcgtcgactt tgccgcaggc atcgccaacg tgcgcgccgg caagctgcgc      660
gcgctggcgg tgaccaccgc gcagcgcagc gagctgctgc ccgacctgcc gccgctggcg      720
agcgtgccga agctgaaggg tttcgacgtg acctcatgga acggcgtgtt cgcgccggcc      780
ggggtgccgg cgccggtggt gcagcggctc aatcgtgaac tggttgccat cgccaccagc      840
aagcagcatg cgccgcggtt ccacgcgctg ggcttcgagc cgttcggcag cacgccggcc      900
gagctcagcc agtttgtcgt ggccgagctg cagaagtggt cgcggctggt gaaagacgct      960
ggcatccagc cggaatag                                                   978

<210> SEQ ID NO 43
<211> LENGTH: 996
<212> TYPE: DNA
<213> ORGANISM: C. necator

<400> SEQUENCE: 43
atgctgaaga aactgcttgc cgccgcgctg accgcggccc tgctgccgcc gccgccgtg       60 gcggccacca atgcctaccc gaccaagccg gtccgcttcg tggtgcccta ccccgccggc      120
ggcccgctcg acaccgtcgc gcgcgccatc ggcgagaagc tgcgcgacag cctgggccag      180
ccggtggtgg tcgagaacaa gccggccgcg ggcggcaacc tgggcgcgga ctacgtcgcc      240
aagcagccgg ccgacggcta caccatcgtc atgggcgcgg tggccacgca cgccatcaac      300
ccgacgctgt tcagcaagat gccgtacgac ccggtcaagg acttcgcgcc gatcacgctg      360
gtggccgacg tccccaacgt gctggtgatg cacccgggca aggccgccga cctgcatatc      420
aacaatgtgc gcgacctggt cgcgtacgcg cgcaagaatc cggcaagct ggattacgcc       480 tcgggcggca acggcagcgc cggccacctg tcgggcgagc tgttcaagag catggcgaag      540
gtcagcatgg tccatatccc gtacaacggc gccgcaccgg cgcagctgtc ggtgctgtcg      600
ggccagaccg acctgatctt cgacaacctg gcttcggcct cggccaatat caaggcgggc      660
aagctgaagg ccttttgcggt caccaccgcc agccgcgccg cggccttccc ggaactgccg      720
accatcgcgg aagccggcaa ggggctgggc ctggaaggct tcgacatctc gacgtggttc      780
ggcgtgttcg cgccggccaa caccccgcgc gagatcgtcg agcggcttaa ccatgagatc      840
gtggcaatcc tgaagaccga cgagatgaag gcacgcctgg cccgcatcgg cgcacagccg      900
gcaccgacca cgcccgagca gttcgcggcg ctgatccagc gcgagctgaa gaaatacgcg      960
cagatcgtga aggtatccgg ggcgaaggtg gattga                                996

<210> SEQ ID NO 44
<211> LENGTH: 978
<212> TYPE: DNA
<213> ORGANISM: C. necator

<400> SEQUENCE: 44
atgaaatcct ggctgcgccg cttcggcatc ggccttggct gcgggctttg cctggccgcc      60
acgcccgcac tggccgatac ctatcccagc aagccgatcc gcctgatcgt gcccttcccg      120
gccagcggcg cgaccgacct gctggcacgc gccatcgcgc agaaggtggg cgccaacctg      180
ggccagcaga tcgtggtcga caaccgcccc ggcgccggcg gcgcgatcgg ctcggacatg      240
gccgccaagg ccgctcccga tggctatacg ctgctgatcg ccaccaccag cacgcactcg      300
atcgggccgt atatcaacac ccgcctgcca tacaacaccg agaccgactt caccccggtc      360
```

-continued

| | |
|---|---|
| agccaggtcg cgatcgccac caacctgctg gtggtgccga acagcctgcc ggcgaaaaac | 420 |
| gtgcgcgagc tgatcgacta cgccaagaag catcccggcg agctgaacta cgcctccagc | 480 |
| ggcaacggca ccgtggtgca cctgaccgcc gaggccttca aggcgcaggc gggcgtgttc | 540 |
| atcacccaca tcccctaccg cggcaccgcg ctggccgtgc cggacctgat ctcgggcaag | 600 |
| gtgcaggtgc tgttcgacag catcgtgtcg ggcctgccgc atgtgaagga cggcaagctc | 660 |
| aaggcactgg cagtgaccag cgccaagcgc tcgccgctgg caccggaaat ccccaccgcg | 720 |
| agtgagtcgg gcctgcccgg cttcgagtcc gacacctggt tcggcatcta tggccccaag | 780 |
| ggcctgccgg cggatatcgt caaccgcctg aatgccgagt tcaacaaggc catccagtcg | 840 |
| cccgaggtca aggaacgcct gggcaagctg ggcgccgagc cggtcggcgg cacgccggcg | 900 |
| cagttcgccg cgatggtgaa gaaggacagc gcgcgctggg gcaagctgat caaggatcgc | 960 |
| aagatcacgg cagaataa | 978 |

<210> SEQ ID NO 45
<211> LENGTH: 990
<212> TYPE: DNA
<213> ORGANISM: C. necator

<400> SEQUENCE: 45

| | |
|---|---|
| atgcatgcca acgtcgggcg ccgcctgctg ctgaagtccc tgctggcgct gccggccgct | 60 |
| gccgcgctgg caggggccgg tgcggccagt ccctatccca accgcccgat ccggctggtg | 120 |
| gtgccctacg ccgccggcgg cggtccggat atccagaccc gcaagctggc tgagttgctg | 180 |
| gcgcgagagc ttggccagcc ggtggtggtc gagaacaagg tcggtgcagg cggcatcctg | 240 |
| gccgcggagt ttgtcgcgca gcagccggcg gatggctaca cgctgatgct gggtgcctcg | 300 |
| acccatgtca cgcagaagct gctgcagccc ggcgcgaagt tcgacccgat ggcgttcacc | 360 |
| cacatcatcc gcgtcggcgt cagtccggcg gtgctggtgg tcagcgccgg ctcgccgtac | 420 |
| cggaacgtgg ccgacctggt cgccgcggcg ggcgcgcgc cgggcacgct gaactacgcc | 480 |
| tcgggcggga tcggctcggc cgcgcatgtg tcgggcgcgg cgtttgcgtc ggccaccggc | 540 |
| atcgacgtgt gcatgtgcc gtacaagggc tcggtcgaga tcgtgccatc gctgataaag | 600 |
| ggcgacacgc agttcggctt cccggtggcg cgacggcga ttccgcagat cgccagcggc | 660 |
| aaggtgcggg cctggcggt gacctcggcc agccgcgccg cggtgctgcc gcaggtgccc | 720 |
| acgctgaatg aggcgctggg ccgcaaggat ctcgatctcg acgcatggag cggcatctgg | 780 |
| gcgccgccgc atctgcccgc gccgatcgtg gcgcggctgc atgccgcggt gctgcaggcg | 840 |
| ctgggcgatc ccggcctgcg ccggcgctat gccgagatgg gcgcggtgct tgcgccgacg | 900 |
| cccacgcctg aagccttctc gcggctggtg gccgatgaga ccacccgcat ccgccaggtt | 960 |
| atcgacaaga accgcatcac catcgaatag | 990 |

<210> SEQ ID NO 46
<211> LENGTH: 1014
<212> TYPE: DNA
<213> ORGANISM: C. necator

<400> SEQUENCE: 46

| | |
|---|---|
| atgaatcgtc gtcagttcag cctggccgcg tgcgcgcgcg caacgggcgt ggccctgggc | 60 |
| ctggccggcc tggcgccgg cgcaatgctc gccgcacccg ccgcgcatgc cgacacctgg | 120 |
| ccgtccaagc ccgtcaccgt gatcgtgccg tttcccgccg gcggcggcac cgacgccttt | 180 |
| gcgcggccgc tgaccgcgca gttgtccaag cagctcggca agcagttcgt gatcgacaac | 240 |

```
cgcggcggcg ccggcggcac ggtcggcgcc agcattgcgg ccaaggccgc gccggacggc      300
tacacggtgt tcatcggcgg cgcgcaccac gcgattgcgc cgtcgttcta caagaagctg      360
gactacgaca tcgagaagga cttcatcccg gtcacggtga tcgcgcagcc gccgcaagtg      420
gtggtggtca atcccaaccg cgtcaaggcc aacacgctgc aggagctgat tgcctacgcc      480
aaggccaatc ctggcaagct gaactacggt tcggccggca acggctcgtc gcaccacctg      540
gcgggcgagc tgttcaagct ccagaccaag accttcatca cccacatccc ctacaagggt      600
gcgggcccgg cgctgtccga cctgatcgcg ggccaggtcg acctgatgtt cgacggcctg      660
ggctcgtcgg cgcagcatat ccgcgcgggc cgcatcaagg cgctggcggt ggcttcgagc      720
aaacgctcgg cggcgttccc caacgtgccg accgcggccg aggcgggcgt gcccaactat      780
gacgtgtcga cctggtatgc gatgtgggtg cccaagggta cgcccaagga gatcgtcgac      840
cgcctgtacg cagagaccga aaggcgctg aacacgtcgg agctcaagca ggtctggctt      900
aacaacggtt ccgagacgcc ggcgtttacg caggaacagt tcgcgcagtt ccagcacgcc      960
gagattcgcc gctgggccca ggtggtgcag cagtccggcg ccaagatcga ctga          1014
```

<210> SEQ ID NO 47
<211> LENGTH: 1008
<212> TYPE: DNA
<213> ORGANISM: C. necator

<400> SEQUENCE: 47

```
atgtcctctg ccgaacgcac gcggcgccgc cgcctgctgc tcaagatcct gccgctgggt       60
gccatgcccg tcccgatgct ccacgtcgct gcagccgccg gcgccgaacc gctggcgggc      120
aaccgcccga tcgcgctggt gctgccgttc ccgcctggcg ggagcgtcga catcgtggcc      180
cggcagctgc agcctgggct gaaggcgacg ctggggcagg ccgcggtggt cgacaacaag      240
ccgggtgccg gcggcctgat cgcatcgagc accgtggcgc gcgcgaagcc ggacggcacc      300
accctgttga tggccttcga cacccacgcc atcaacccct tcgcctacaa gcagctgccc      360
tacgacacct tccgcgattt ctcgccaatc tcgcagctgg tgcgctttcc gctggtgatt      420
gccgccaatc ccgcgctgcc cgtggccaat gtgcgcgagc tggtggagct ggccaaggcc      480
aggcccgacg gcgtgcgcta tgcctcgtcc ggcatcggca gcctgaacca gctggcggca      540
gaggcgctgc gaccgaagc cggcgtacgc atgctgcatg tgcctacaa gggcggcggc      600 ccggccgtgc aggcggtgct gtccaacgag gtcgatattt tcttcagcag ctacgccgcc      660
gtgcaggcgc acgtggccgc acgcaccatc aaggtgctgg gcgtgaccgg caccagccgg      720
ctgcgccagc tgccgcaggt gccgacggtg gcagagcagg ggctcaaggg cttcgaggcc      780
tactcctgga tcgcgtgtt cggcccgcc ggcctgccgg catccacggt cacgcgcatc      840
cacgacgcgc tggtcgaatc gctgcgccag ccgcgcgtgc tcgatgcgct ggccgcgcag      900
ggcttcgaga tcgtgggcgg cagcccggcc gacctcggca acctggtgcg ccgcgagcat      960
gacaaatggc aggccgtggc gcgcaaggcc aatatccagt cgaatga                   1008
```

<210> SEQ ID NO 48
<211> LENGTH: 993
<212> TYPE: DNA
<213> ORGANISM: C. necator

<400> SEQUENCE: 48

```
atgcaagccg accgccgcaa agccctgcac tggctgggag caggttccct ggcagccacc       60
```

```
gcctcgactc ttggaatcag ccgggcgtgg gcccagcagg cttacccgtc gcgcccggtg    120
cgggtggtgg tgccctaccc gcccggcggt gccaccgacg tgctggcgcg cgcgctgggc    180
gatccgctca gcaagctgtg gcagcgccct gtgatcgtcg agaaccgccc cggcgtgggt    240
ggcatgatcg gcgccgacgt ggtcgccaag gcgccggcgg acggctacac gctgctgctg    300
ggcttgccca gcctggtgca gacgccctat atggtggcca gccgccgttc gatccgctg     360 cgcgacctga ccgccatctg ccagctgtgc acctcgagcc tggtgctgac cgccagcagc    420
gccatgccgc gcacgctgcc gcagatggtc agcctggcca gtcccagcc cgacaagtat     480 tcctatggca cctatggcat tggcaccggc gcccatctct atatgcaggt ctttctcaag    540
ggagctggcg ccgaactggt ccatgtcccg tacaagggcg aagcccccat cgccaccgac    600
ctgatcggcg ccagatctc gctgggaacg ctgtcgccga tgacggtgcg ccagcatgcg    660
cgcaccggca agctccagcc gctggcggtc accggcaata cccgcgcgcc gatgctgccg    720
gatgtgccga ccttccagga actcggctac aagggcctgg acggcccggc ctggctgggc    780
ctgttcacca ccgccggcac gccgcaggcc atcgtcgaca aggtctcggc cgatgtggaa    840
acggtgatgg ccgcgccgga catccgccag cgcctcgccg agctggggct gatcgtcaag    900
acgacgcagc cggcggcgtt cgcggcgacg gccagagcgg accaggcgta ctggggcaac    960
gtgatcaagg aaaacaatat ccggctggat tga                                 993

<210> SEQ ID NO 49
<211> LENGTH: 993
<212> TYPE: DNA
<213> ORGANISM: C. necator

<400> SEQUENCE: 49
atgccccgcc cacccgacgc ccgccggcgc acactgctca aggccatgcc ggccgccgcg     60
ctcttccctg ccatgctcag cctgcccgcc accgtgcgcg cccaggcctg gccgcgcgc    120 cccatcaccc tgatcgtgcc cttcaccgcc ggcggcgcca ccgacgtgca gatgcgcgcg    180
ctgtgcctgg cggcatcgaa gaccctgggc cagcccatcg tgatccagaa ccagcccggc    240
gtcagcggca cgctcgggcc cgccgcgatg gcgcgcagcg cggcgcgcga cggctacacg    300
ctggcgctga tcacaccggc gttgttccgc ctgccgcacc tgcagccggt gaactacgac    360
gcgatcaagg acttcaccta catcatcggc ctgaccagct atgtgtacgg gatctcggtg    420
ccagcgggct cgccttggaa gcgctttggc gacttcgtcg agcacgcgcg cgccaaccct    480
ggcaaggtca acgtggcatc ggtcggcacc ggctcgctcg gccagatcac cgtgcgccgg    540
ctggaacagc aggccggcat caagctcaat ttcatccct tcaagggcgg cgccgatgcg     600
ttgtccgcgc tgctgggtgg ccatgtcgac gtgatgatcg aagccggctg gggcgccatg    660
gctgaagccg gcaaggtacg cctgctggcc gtggccgagc cgcagcgcct gaagcgctgg    720
caggccgtgc ccacgctgcg cgagctgggc tacgacatca ccgtgcagtc cgaaatcggc    780
atcgccggcc cgcgcgcgct ggaccccgcg gtggtcgcca cgctgcacga tgccttccgc    840
caggccacat cggaccctgc ctacctgcgc gcgctcgaat ccgaatcgat gcccaaccgc    900
catatgaata ccgccgacta ccagcactac gccgcttcgc aattcgccag cgacaagcgg    960
ctggtggccg agctcggcat ccggctggac tga                                993

<210> SEQ ID NO 50
<211> LENGTH: 966
<212> TYPE: DNA
<213> ORGANISM: C. necator
```

<400> SEQUENCE: 50

```
atgcagcgca gacaattcat tgtggcggca gcggccgggc tggcgatacc cagcctggtg    60
cgcgccgccg acatcgccgg cccggtgcgc attgtggtgg gcttcgcccc cggcggaggc   120
accgatgtgc tggcacgcgt gatcgggcag aagctcgggg tcatgtggaa caccagcgtg   180
ctggtggaga acaagcccgg cgctaccggc gccatcgccg ccgcctatgt ggccaagcag   240
ccgcctgacg gcaccacctt gctgatggcg catgtgaaca gccacgcgat cgccccggcg   300
ctgctggacg tcaagtacga cccgcgcacc gacttcacgc cgatttcaat ggtgggcgtc   360
acgcccaata tgctgacctg ccgtccggaa cagaaggtgc gcagcgtttc ggacatcgtg   420
gcgctgtgcc ggcagaagcc ggggaagatt cctttggct cgtccggcat cggttcggcg    480
cagcacctgg cgctggagat gttccggttg caggccaggc tcgatgtggt gcacgtgcct   540
tacaagggct cgggcccgct ggtcgcggac ctgatcggcg ccagatcga ctatgcgttc    600
gacaccatga ccgccgccac gccgtttatc cagcagggca aggtgatcgc gattgcgcag   660
acccgcctga agcgcgcggc cagccatccc aatgtgccga cgctggcgga gtccggcttc   720
cccgggctgg acgcggcgtc gtggtatggc ctggtgggcc cgaagaacat gccgccggcg   780
ctggtgcagc gcatgaacgc ggacgtcaac cgcgtgctgg ccatgcccga cgtcgccgag   840
cggctcaaga gctttggcgc cgaggactcc ggcggatcga accagcagtt cgccgccttc   900
atcgcctctg agtccaccaa gtgggccaag gtcgtgaaag acgccggcgt aaaggccgag   960
agctga                                                              966
```

<210> SEQ ID NO 51
<211> LENGTH: 1002
<212> TYPE: DNA
<213> ORGANISM: C. necator

<400> SEQUENCE: 51

```
atgcaaccca ctcgccggcg cgtcgttgcg ctgctgctgt ccgccagcct tgccgcgctc    60
gccagccagt cggcgctggc cgcagacccg tacccggcca agccgatccg gctggtggtg   120
cccttttgccg ccggcggcac caccgacatc ctggcccgcg ccgtggccgc agagctggcc   180
aggctgccgg gctggaacgt ggtggtcgac aacaaacccg gtgccggcgg caatatcggc   240
gcggacatcg tcgccaaggc cgctccggac ggctacacgc tgctgatggg caccgtgggc   300
acccatggca tcaaccagtc gctgtacggc aagctgccgt tcgatccgat caaggacttc   360
gccccgatca ccgaggtggc ggccgtgccc aacgtgctgg tgctgaaccc ggtgtttgcg   420
cagcagaaca agatcgacag cgtcaaggac ctgatcactt acgcgcgcgc caatcccggc   480
aagatcaaca tggcctccag tggcaacggc acctcgatcc acctggccgg ggagttgttc   540
aagacgcaga cccggacctt catggtccac ttcccgtaca agggcagcgg gccggcgctg   600
acggacctgg ccgggggcac catgcaggtg atgttcgaca acctgccgtc gtcgatggcg   660
ctgatcaaga gcggcaagct caaggcgctg gcggtgacca gcgccaggcc ctcgccggcg   720
ctgccgggcg tgccaaccat tgcccaggct gcgggcctgc ctcagtatga agccagctcc   780
tggttcggca tgctggcgcc ggccggcacg ccgccggacg tcatccaccg catccagcag   840
gaagtggcca aggcgctgaa cgccccggcc gtgcgcgaac gcctgcaggc gcagggcgcc   900
gagcctgtcg gcaacacgcc ggagcagttc gccgcgttca tccgcgccga gaccgccaag   960
tgggccaagg tggtcaagga ttccggcgcc aaggtggatt ga                      1002
```

<210> SEQ ID NO 52
<211> LENGTH: 999
<212> TYPE: DNA
<213> ORGANISM: C. necator

<400> SEQUENCE: 52

```
atgcagaaca aaccaagcgg acggcgcgcc tggctcgccg cgatggcagc cggcgcgggg    60
tgcgcgctgg ccatgtgggg cggagccgcg caggccgcct atcccgatcg cccgatcaag   120
ctggtggtgc cctacacccc cggcggctcg accgaccagt tcggccgcgc gctggccgac   180
ggcatgtcgc gccagctggg ccagaccgtg gtggtggaaa accgcccggg cgcggccacc   240
atgatcggca ccaccagcgt ggcgcgtgcg ccggcagacg gttacaccat ggtgctggcc   300
accaacggca gcatggtgct caaccccgatg ctgtacaaga agatcaacta cgatccgccc   360
aaggatttca agatcttcag catcggcgcc gaggtgccgc tggtggtggt gaccaacagc   420
aaggtgccgg ccagcaatat ccgcgagttc gcggcctacg ccaaggccgc gggcggcaag   480
ctcaactatg gctcggtcgg cctgggcaac gcgctccagc tggccaccga atgctcaag   540
accgagctgg gcatcagcgt cacccacgtg ccctacaacg gcagcgcccc ggcgctgtcg   600
gcgctgctgg ccaacgacgt gcaactgatg gtggatgtgg tcagcacctc gctgccgcat   660
atcaaggcag gcaagctcaa ggcgctggcg gtcaccggcc gcacccggct ggacgtgctg   720
cccgacgtgc cgaccgtggc ggaaggcggc tatcccaact tccaggccgc cacctggttc   780
ggcctggccg tgcccgcgca gacgccgccc gatgcggtgg ccaggctgca ggccgccgct   840
gccccacgtgc tcaaggacgc gcagttccgt tccaccttca gcgcgctggg actggtcgtg   900
caggcgccgc gcacgcaggc cgagatcgac cgctatatcg aagccgaccg cgagcactgg   960
ggcaaggtga tcaaggccaa taacatttcg ttggactga                          999
```

<210> SEQ ID NO 53
<211> LENGTH: 984
<212> TYPE: DNA
<213> ORGANISM: C. necator

<400> SEQUENCE: 53

```
atgactatat tcttccgcag gatcgccagc gcgctgggca gcgccgcgac actcctggcc    60
tgggcgtccc cgtcagtggc gcagacagac tacccggtgc ggcctgtccg actcatcgtt   120
ccgtaccccg ctggcgggcc gacggacacc ttcgcccgat cgctggctgc aagctggggc   180
cgcaagctga acacctcggt ggttgtcgag aacaagtcgg gggccggcac gatagtcggc   240
accgagctcg cggcgaaagc ggcaccggac ggctatacgt tgctgctgac cactgtcgcg   300
catgccgtga acccaagcat tcacgccagc ctgccgtatc gcacgatcga ggactttgcg   360
ccagtcgggc tggcggctcg tgcgccgctg gtgctggtcg tgaacaaggg cgtcccggcg   420
aaaacactgc cggaattctt cgcttatctg aagtcgcgtc ccggccaggt caactatggc   480
tcagccggag ttggcagtgc cccgcatctc gccggggaac tgctgaacta cacggcagga   540
acgaaagcgg tccacgtccc atatcggggg agcgcgcctg ccatggccga tcttatcggt   600
ggccatgtcg aattcatgat cgacagcgca ccgacagggc tggcgcaggt gcgcgcggga   660
acggtgcgat tgctgggaac gtcgatggga aaacgcctgc cgcagaccag ggagacgccg   720
gcgattgcga agccgtgtc aggctatgag gcgtacacct ggaacgcggt attcgtgcca   780
gccccgaacac cgtcggcagt tgtccagaag ctggtctcga cacttggcga tgcactcagc   840
gatcccgccc tgcaaagcaa agccttcgaa ctcggattgc agctggagac gcagcctaca   900
```

| | |
|---|---|
| ccagcggggc tcgaccagtt cctgcgcgcg gaactggaga agtggaagcg ggtggccgtc | 960 |
| gccacgaata tgaaagccga ctga | 984 |

<210> SEQ ID NO 54
<211> LENGTH: 1005
<212> TYPE: DNA
<213> ORGANISM: C. necator

<400> SEQUENCE: 54

| | |
|---|---|
| atgaacgaac gcaaacctgc ttacgcccca cggctgtcgc gccgcgccat gctggccggc | 60 |
| accgccgccg ctctgtgtac cggtggcctg ctctccaggg ccgtatgggg gcagtccgta | 120 |
| tcgcgcatca tcgtgccgtt ccgccgggga gggccggccg actacatggg ccgcctgctg | 180 |
| tccgagaagc tgaaagatgc catgggccgt accgtcatcg tcgacaaccg ccccggtgcc | 240 |
| gggacgcgcg tggcggccga atgctgaag aacgccccgg ccgacggcac caccgtgctg | 300 |
| ctggcacctg tcgatccgat gttcatcggg ccgctgatct acagcaatat gcgcttcaac | 360 |
| cccgccaccg acttcacggc gatcaccgat gtgacgggcg tccagttcgg tattgcagtc | 420 |
| agcgccagct cacccatcaa gacactggcc gacttcgtca aggccgccag gccaagccg | 480 |
| gctgactatt cgatcggcat cagcacggtt ggctcgctgc tgcatttcct tgccgtggag | 540 |
| ttcgtcagcc agtcgcgcac cggcagtacg ctggtaccgt atcgcggtgg cgcggcgatg | 600 |
| gtgacggaaa taatgggtaa ccaggtcgcg gcgggcatgg acgccatcac gagcttcacc | 660 |
| gaactgcatc gcggcggcaa gctccgcgtg ctggccgtgg caggggaaaa gcgcgctgat | 720 |
| gccttgccgg atgtgcctac gtttgcggag tctggttttcc ccaacctggt gacctcgtcg | 780 |
| cgctacctgc tttatgtccg cgccaacacg ccgcccgacg tgaccacgca gtggtatcag | 840 |
| gccgtgcgca aggtgctggc catgccggat gtgcgcgaaa agctcgcgcg cgctggctat | 900 |
| gacatcttgc cggcggcac tgctgatgag gttgccaggt atgcgagcgc gctttcggca | 960 |
| cggtggacgc cggtgatcaa ggcgtcgggt ttcaagggggg attga | 1005 |

<210> SEQ ID NO 55
<211> LENGTH: 1023
<212> TYPE: DNA
<213> ORGANISM: C. necator

<400> SEQUENCE: 55

| | |
|---|---|
| atgggcgcag tccggcgctg gctccggtct ttcctgtgcc tgtacgccct ggggtgtgcc | 60 |
| acgctggcgc ttgcggtgcc agccatgccg gcgcatgcgg ggacccagca gctcgcccgc | 120 |
| agcatgtcgt tccccgaccg cccgatgcgc ctgatcgtgc cattcccggc cggcggtgtt | 180 |
| gccgatgcgc tggcgcgcat gctggccgag cgcctctccg tccggctggg cgtgccggtg | 240 |
| gaggtcgaca accggcccgg cgccgccggc accatcgccg gcgacgtggt cgccaaggcc | 300 |
| agctccgatg ccacacccct gttgttgcac caggccaata tgctgatcca gcccggactg | 360 |
| gagccggtgc cgtacgacgt cgtgcgcgat ttcacgccgg ttgcgcgcgt ggccaccacg | 420 |
| ccgctgttcc tggtgatcga tgcccggctg cccatgcgca cgccggagca atggatgacc | 480 |
| gcggtcaggt cgaacccggg ctcctacagc tatggctacg ccagccgggg cagcccctcc | 540 |
| cacctgtacg ccgagtacgc ggtgcgcggc atccgcagcg gcgtgccgct ggtcaccgcc | 600 |
| aagggtgagg ccgccgtggt ccaggagatg ctggccggcc gcgtcagtgc ctgttttctgt | 660 |
| tcgttttgccg cggtccaggg ccaggtcaga agcggcgggc tgcgcctgct cggggtgacg | 720 |

| | |
|---|---:|
| ggcgtggccc gctcgccgct ggcgccgctg gtgccgacgc tgcaggagtc ggggctggaa | 780 |
| ggctatgccg cggctgcctg gtttggcgtg atggcgccgg ccaagacccc gcgcgcgatc | 840 |
| gtcgccaggc tggcggtcga actcgacgcg gtcatgtccg agcgcgaggt gcgttcgcgt | 900 |
| ctgcaggcgg cggggtcac gccgctgcgc gattcgccgg aggcgtttgc caccgcgatc | 960 |
| cgctcggaat ctatccaatg gcaggtgatc ctgaaggacg tctcgccgat acaggagcct | 1020 |
| tga | 1023 |

<210> SEQ ID NO 56
<211> LENGTH: 996
<212> TYPE: DNA
<213> ORGANISM: C. necator

<400> SEQUENCE: 56

| | |
|---|---:|
| gtgatccgag ccaggatgtc ccgccgccag ctgctgctgt ccggtaccgc cgccgctgcc | 60 |
| acgctggcct tgccggcaa cgcgttcgcg caagccaatt acccgacgcg cccgatccgt | 120 |
| ctgatcgtgc cgttcgcggc gggtggctcc accgacctgt cggcgcgcct ggtggcagag | 180 |
| tttgccggcc gcgagctggg ccagtcgatc gtggtcgaga caagggcgg cgccggcggc | 240 |
| tcgctgggca tggagcaggt ggccaacgcc gcgcccgatg gctacaccat cggcatggcc | 300 |
| acggtcagca cgcatggttc caaccccggcg gtgtacccga agctgaagta cgacccgatc | 360 |
| aaggactttg ccccgatcac caacgtggtg tcgatgccga gcgtattcac ggtgcatccg | 420 |
| agcgtgccgg cgaaaaccat gcaggagttt attgccttag ccaaggccaa tccggggaag | 480 |
| tattcagttg cctcgccggg cacagggacc ctcggccacg taaatcttga gaacttccag | 540 |
| atgctggcga agatccagct gctgcatgtg ccgtacaagg gcgccggcct tggactcaat | 600 |
| gacgcggtgg cagggcaggt caatgcaatc tcggacaacc tggcctccgc gctgcctcac | 660 |
| gtgaaatcgg gccgctgcg cgcgctggcg gtgcttggcg ccacgcgctc gccgcagttg | 720 |
| ccaaacgtac ccacctatgc agaactgggc tacaaggaga tgggcgacgg cggttggttc | 780 |
| ggcatcgtcg cgcccgcgaa tacgccgccc gccatcgtcg ccaggctgaa ccaggcgatc | 840 |
| cacaaggcca tgcagaaccc cgagttcaag cgcaaggtgg aagaatccgg cggcacgctg | 900 |
| gtgccgacta cgccggagca gttcaaggcg cagatccagc aggcgatggc gcgctacgcc | 960 |
| cgcgtggcca aggctgccga tatcaagctg gactga | 996 |

<210> SEQ ID NO 57
<211> LENGTH: 969
<212> TYPE: DNA
<213> ORGANISM: C. necator

<400> SEQUENCE: 57

| | |
|---|---:|
| atgcgccgta cctattcccg cctggcccat gccgtgatgg catcggccgc cgttgccgcc | 60 |
| accttcgccg ccgcgccggc ctttgcgctc gatagcgtca aggtcatgat cggcgccaac | 120 |
| cccgcggcg gctttgacca gaccggccgc tcgctgggcg ccgcgatgat tgccgcgggc | 180 |
| caggccaaga ccgcttcata cgacaacaag ggcggcgccg gcggcaccat cgcgctgacc | 240 |
| cagttcgtca ataccgacaa gggcaacccc aatgcgctga tggtggtggg gcgcggtgatg | 300 |
| gtgggcgcga tcgagaccaa caagccgccg gtcacgctga gaacgccac cccgatcgcg | 360 |
| cgcctgttcg ccgacaccat ggtcatcacc gtgccggcca gctcgccgat caagtcggtc | 420 |
| aaggacctga ccacgcagct caaggccaac ccgggcagcg tcagctgggg cggcggctcc | 480 |
| aagggttcga tcgaccacat cctggccggc ctgatcgcca aggaatcggg cgtcgatccc | 540 |

```
aagaagatca actacgtgcc gttccagggc ggcggcgaag cctcggcctc gatcatgggc    600
ggccacgtga cggtgggcat cgccggcgtg tcggaattcc tgcccttcat caagagcggc    660
aagatgcgcg cgctggcggt gacctccaag gaccgcaccg ccgatatccc gacgctcaag    720
gagcaaggcg tgaacgtcga gatctataac tggcgcgggg tgtacggcgc gcccggcatc    780
agcgccgagc agcgcaaggc catgatcgac gccgtggtca aggccaccga gagccaggcc    840
tggaaggaca cgctgcagaa gaatgactgg accccgttcc tgctgactgg cgacgagttc    900
ggcaagttcg tcgacagcga atcggcccgc ctgggcggct cgctgcgtga actgggcgtg    960
gccaagtaa                                                            969

<210> SEQ ID NO 58
<211> LENGTH: 1041
<212> TYPE: DNA
<213> ORGANISM: C. necator

<400> SEQUENCE: 58
atgcccgtgt tctgcctggt cccgtccagc ccgacccgtc tgccttcgat ccccgccgc     60 gccgcggtgc agcgcctggc catgccagcc ctggccgtgt gcgcgctggc cctgccgctg    120
tccgccgcgg cccaggggca accccaggtg gccggcggca agccgatccg gatcctggtg    180
ggcgcgcccg ccgccggcac caccgacacg ctggcgcgca ccatcgccca ggaaatgtcc    240
caggagctcg gccagccggt ggtggtcgag aaccgccccg gcgccggcgg caatatcgcc    300
gccgacctgg tcgccaaaag cgcgccggac ggcagcacgc tgctgatgag cttcaccagc    360
cacaccatca acgccaccct gtacaagaag ctgccgttcg accggtgca ggacttcacc     420 ccgatcacgc tggtggccac cgtgccgagc gtgctggtgg ccacgcctaa gctggcggcc    480
agcaatgtgc ccgagctgat ccgcctggcg cgttccgaac cgggcaagct gaactttgcc    540
atcggctcgg tggggtcgtc gctgcatatg gccggcgaca tgttcaagat gatgaccggc    600
acctatatcg tcaacattcc gtacaagggc acctcgcccg cgctcaccga cgtgctggcg    660
ggccagtgcg acctgatgtt cgccagcacc atcaacgtgc tgccgcatgt gcgcgcgggc    720
aagctcaagg tgctgggcgt gaccagcccc gcggccctgc cgcagttccc gggcgcggcg    780
ccgatcggcg ccaccgtgaa gggctttgaa tcgagcgcgt ggttcggcct gttcggtccg    840
gccggcatgc gcacgaagt cacgcaggcg ctgtaccagg ccgcgcgcaa ggggctggaa     900
acgcccgcgg tgcgcaagcg cctggagaac gacggggcgc agccgatggg cacgccgccc    960
gacgccttcg ccgccttcgt gaagcaggac gtcaggcgct gggccgccgt ggtcaagtat   1020
tcgggagcct cgccggaatg a                                             1041

<210> SEQ ID NO 59
<211> LENGTH: 966
<212> TYPE: DNA
<213> ORGANISM: C. necator

<400> SEQUENCE: 59
atgtacccat ttctcaagcc actggccgtc gccgcacttg cgctgatcct gcccgcgggg    60
caggcctggg ccgagttccc ggacaagccg atccgcttcg tggtgccgtt cgccgccggc   120
agcgccaccg accagctggc gcgtgccatt ggccaggcca tcaccgtgga cagcaaggtc   180
accgtggtgg tcgacaacaa gccgggcgcg aatggcttca tcgccgcgtc ggacgtggcc   240
aaggccgcgc cggacggcta caccgtgctg atcagcacca acaccacgca tgcggccaac   300
```

-continued

| | |
|---|---|
| gagcacctgt tcaagaagct gccctacgac ccggtcaagg actacgcgcc gatcaccgcg | 360 |
| ctgggccgcg gcggccagat catggtggtc aacccgcagg tgccggccaa gaccgtgggc | 420 |
| gagttcatcg cgctggcaaa acagcagccg ggcaagctca gcttcggcag cggcagctcg | 480 |
| tcgtcgcgca ttgccggcga gctgttccag cagatggcgc atgtggagtt gctgcacgtg | 540 |
| ccgtacaaga gcaacccgct ggccatcacc gacctgctcg gcaaccagat ccagatgatg | 600 |
| atcacggaca cggccaccgg cctgccgcag gtcaagagcg gcaagctgcg cgcgctggga | 660 |
| gtgtcgggca agacgcgctc gccgctggcg ccggacgtgc ccaccatcga cgaagccggc | 720 |
| gtcaagggct acgagatgag ctactggttc gcggcctatg cgcccgccgg cacgccgcag | 780 |
| ccggtggtgg cgaagctcaa tgcgatgatg gtcaaggccg cgcgcggcga tagcgcggct | 840 |
| ggcttctaca gtcgaccgg cactgaggtg ttcaccagca cgcccgcgga gctggcgaag | 900 |
| ttccagttgc aagagtccgg caagtgggga cgcatcatca aggcggcgaa tatccagccg | 960 |
| gagtaa | 966 |

<210> SEQ ID NO 60
<211> LENGTH: 975
<212> TYPE: DNA
<213> ORGANISM: C. necator

<400> SEQUENCE: 60

| | |
|---|---|
| atgaaactct ggcaccgcgt agcggccatc gccgcctgct cgctcttat cgccccgcc | 60 |
| ttcgcgcaga aggactttcc gtccaagccg atcatgatgg tcgtcaccta cccgccgggt | 120 |
| ggccccaccg atgccatggc gcgcacgctt gccgctgcgc tcaagaccag ccttggccag | 180 |
| ccggtggtgg tggaaaaccg cgccggcgcc ggcggcaaca tcggtgccga ggtggtggcg | 240 |
| cgcgccgagc ccgacggcta cacgctgatg ttcggcacct cggcgccgct ggcgatcaac | 300 |
| gtcagcctgt accgcaagat caactacgac ccggtcaaga gcttcgcgcc ggtgatccag | 360 |
| atcgccagc tgcccaatgt actggtggtc aacccgtccg tgccggcgaa gaacgtcgcg | 420 |
| gagctgatcg cctatggcaa ggcgcacccg ggcaagctga cctatgcctc gtccggcaac | 480 |
| ggcgcctcgt cgcacctggc gggggtgctg ttcaacaacg tcaccggcac cgatttccag | 540 |
| cacatcccgt acaagggcac cggtcccgcg ctgaacgacc tgctgggcgg gcaggtcagc | 600 |
| atgaccttca ccgatgtgct gaccgcgatg cccttcatca agagcggcaa ggtgcgcgca | 660 |
| ctgggcgtca ccaccaaggc gcgctcgcag gcgctgccgg atgtgccgac cgtggccgag | 720 |
| cagggcgtgc caggtttcga tgtatcggtg ttcttcggcg tggtcgcgcc cgccggcacg | 780 |
| ccgcccgaag tgatcggcaa gctcaaccgt gcctttgccg atgcgctcaa gcagcccgag | 840 |
| gtgcgcaaga ccctgcaggc gcagggcctg gagttcgcgc cgtcgaccac gcccgagcag | 900 |
| cttggcggct tcgtcaaggc cgaggtcggc aagtggcgcg ccgtggtgca gaagtccggc | 960 |
| gcccagcttg actga | 975 |

<210> SEQ ID NO 61
<211> LENGTH: 1023
<212> TYPE: DNA
<213> ORGANISM: C. necator

<400> SEQUENCE: 61

| | |
|---|---|
| atgtacacgt tccaacgcca gcgcgccctg cgcctgcctc actggctgcg cgcctttgcg | 60 |
| ctcggctctg tcgtcacggt ggcggccctg accgtgagcg ccgccgcata cgccgcgcca | 120 |
| caggagtggc cgcaacgccc ggtatcggtg gtggtgccgt tcccgccggg tggctccagc | 180 |

| | |
|---|---|
| gacgccatcg cgcgcatgct gaccgtgccg ctcaatgaaa agctgggcca gcccttcgtc | 240 |
| atcgacaacc gccccggcgc gaccggcgcc atcggcgcca ccttcgtcaa gcgcgcgccg | 300 |
| gcggacggct acaccatgat ggtggcgtcg atcggcgtgt atgctgtgaa cccgttcctg | 360 |
| cagaagaacc tggcctatga cccggccaag gacttcgacc tgctgaccgt ggcggtgcgc | 420 |
| gcgcccaacg tgctggtggc caatccacag ttccccggcca atacgctgca ggaactggtg | 480 |
| gcctacatga agaagaatcc gggcaaggtc agctttgcct cgtccggcgc gggctcgtcc | 540 |
| gaccacctga ctgctgcgct gttctggcag aagagcgcca ccgacggcct gcacgtgccc | 600 |
| tacaagggcg gcgccccggc catctccgac ctgcttgccg ccaggtcga cgtgtcgttc | 660 |
| cagaacgtca acgccgtgct gcagcacatc cgcaccggca agctcaaggc catggcggtg | 720 |
| acctccgaca gcgctcgcc ggtgctgccc aatgtgccga ccatggccga ggccggcgtt | 780 |
| aaggacgtcg aggtgtactc gtggcagggc gttgctgcgc gcgcggcct gccgcccgag | 840 |
| gtgaagagcc gcctgcacgg cgcgctggtg tcgtcgctga acgacccgaa gatgcgccag | 900 |
| aagctgtccg agagcggctt cgaggtggtg gccaacacgc ccgagcagtt caaccagttc | 960 |
| gaggcgcagg aactgctgcg ctggaagacc gtgatcgaga agggcaagat cgcgctggac | 1020 |
| tga | 1023 |

<210> SEQ ID NO 62
<211> LENGTH: 999
<212> TYPE: DNA
<213> ORGANISM: C. necator

<400> SEQUENCE: 62

| | |
|---|---|
| atgacccagg gacgccgcac cttcctcaag caatcctccg cactggccgc cggcctggca | 60 |
| gccggtccgc tcgcgggcct gtcctcggcg gcgcacgccg gaccggactg gcccacccgc | 120 |
| ccgatccgcc tggtggtgcc gtacaccgcc ggcggctcgt cagacatcat cgcgcgcctg | 180 |
| atcagcaagc agctgggcga ggcgctgggc cagtcagtgg tggtggacaa ccgccccggt | 240 |
| gccaacggca acgtcggcgc ggcactggtc gcgcaggcca ccgacaacca cacgctgatg | 300 |
| ctgtgcgata tcggcgcgct ggcgatcagc ccgtcggtct ataccaagct gaccttcaat | 360 |
| atcgccaagg acctcaagcc ggtgtcgatg ctggcctact cgccgcacct gctggtggtg | 420 |
| catccgtcgg tgcaggcggc cagcgtgaag gaactggtgg cgctgtcgca gcgcagccag | 480 |
| ctcaacttcg ccgtgaccgc catcggcagc gcgccgcacc tggccggcgt ggcggtggag | 540 |
| caggccaccg gcgccaagtg gcaatacgta ccctacaagg gcggctcgca ggccattgcc | 600 |
| gataccgtgg gcggcagcgc ccaggtgctg atgaacggca tgctggccac gctgccgcac | 660 |
| gtgcagtcgg gcaagctcaa gctgatcgcc cagtccaagc gcacgcgcat gccgctgctg | 720 |
| cagaacgtgc cgaccatcgc cgagcagggc gtgccgaatt ttgaatccgg aacgtggcag | 780 |
| ggcgtgatgg ctccggccag catgcccgat gcgatggtgg cgcgcctcag cggcgagctg | 840 |
| atccgcatca tccgcgcgcc ggatctgcgc gcgcagctgg tgcccagggg gcggaggtg | 900 |
| gtgacgatga cgcccgggga gaccgggaag ttctttgttg ccgagcaggc gcgatgggcg | 960 |
| ggggtggtga agcaggcggg gatcaagctg gaggcttga | 999 |

<210> SEQ ID NO 63
<211> LENGTH: 1008
<212> TYPE: DNA
<213> ORGANISM: C. necator

<400> SEQUENCE: 63

```
atgagacaag attcccagac ctccaccacg cgccgccgcc tgcttgccgc tggcgtggcg        60
ctggccacca ccatcgccgg cttgccggt gcggcccatg cgcagggcgg ctacccgacc       120
aagccgatca ccatgatcgt gccgttctcg gctggcggca ccaccgacat cctggcccgc       180
atcgtcggcc tgcagctggg caaggcgctc ggccagccgg tggtgatcga caaccgtccg       240
ggcgcgggcg gcaatatcgg cgcctcgctg gcggccaagg cgcctggcga tggctacacg       300
ctgttcatgg gcaccatcgg cacgcacgcg atcaaccagt cgctgtactc caagctgccg       360
tatgacccgg tcaaggactt cgcaccgatc acgcgcgtgg ccatggtgcc gaacctggtg       420
gtggtgaatc ccaaggtgcc ggtcaacaac gtcaaggaac tgatcaccta cgtcaaggcc       480
aacccggaca gctgtcgta cggctcgtcg ggcagcggtt cgtcgatgca cctgtcgggc       540
gagctgttca actccatgac cggcctgcat atccagcaca tcccgtacaa gggcagcgcc       600
ccggccgtga cgacctgct gggcaaccag atcggcctga tgttcgacaa catgccgtcg       660
tcgtacccgc acgtgaaggc cggcaagttg cgcgccatcg ccgtgacttc ggccaagcgc       720
tcgccgcgc tgcccaacgt gccgaccgtg gccgaatcgg gcgtgccggg ctatgaggcc       780
acctcgtggt ttgcgctgta cgccaccggc ggcacgccgc agcccatcgt cgaccgcctc       840
aacgccgaag tggtgaagat cctggccatg ccggaagtga agaagcagat ggccgaccag       900
ggtgccgaac ccaacccgga aaagccggcc cagctggccg cgttcatgaa gtcggagacg       960
gccaagtggg cgaaggtggt gaaggcttcg ggcgctacgg tggattga                    1008
```

<210> SEQ ID NO 64
<211> LENGTH: 987
<212> TYPE: DNA
<213> ORGANISM: C. necator

<400> SEQUENCE: 64

```
atgacaaccg ttttgcgcat gcgccgcgcc gtgatggccg gcctcgccgg taccgctgtg        60
ctgggcgcgc ccgccgcgtt cgccgcggac aactggccgg ccaagccgat caccctggta       120
gtgcccttcg ccagcggcgg caccaccgac atcctcgccc gcaccatcgg ccagaagctg       180
ggcgaggcgc tgcagcagcc ggtggtggtg ataaccgcc ccggcgccgg cggcacccctc       240
ggcgcggcca acgtggcgcg cgcgccggcc gacggctaca ccttcctgct ggccaccgtc       300
gcccacacca tggcgccggc catctacaag agcctgccct acgagttcac gcgcgatctc       360
gatccggtgg gcctggtggc gctgacgccc aatgtgctgg tggtcaatcc tgcgatcccg       420
gtgaagtccg tgtccgacct ggtcgcctat atcaaggcgc atcccggcaa ggtcaactac       480
ggctcggccg gcatcggcag caccgagcac ctgtccggcg agttgttccg cgcgctgacc       540
ggcaccgacg ttgcgcatgt gccgtataag gcggcgcgc cgatgatgac cgacctgatc       600
gcgggccaga tccagatggc gatcgaaacc agcccgtcgg cgtcgcagca cgtgcgcagc       660
ggcaaggtcc gggcgctggc ggtcaccacc gcgaagcgtt ccgccgccta tcccggcgtg       720
ccgacgctgg cggagagcgg cgtcagggc tacgaagtca ccacatggtt cgcgctgatg       780
gcgccgcgcg gcacgcccgc ggcgatcgag cagcgcgtct cggcggagct gggcaagctg       840
ctgaaggcgc cggaggtgca gaagcggttt gacgagcagg gcgtgaccgc tggtgacatg       900
acgccaacgc agcttgctgc ctttatccgc gccgagaccg acaagtgggg caaggtggcg       960
cgggaatcgg gggcgaaggc ggagtaa                                          987
```

```
<210> SEQ ID NO 65
<211> LENGTH: 969
<212> TYPE: DNA
<213> ORGANISM: C. necator

<400> SEQUENCE: 65
atgaagacat ggatcgccgg cgcactcgcc ggcctggcca cggtggcggc agtaacgggc      60
aatgcctggg cgcaggacac acggccggtg cggctgatgg tgggtgcagc gcccggcggc     120
ggcaccgacg tgatggcgcg catcgtctcc gacaagctcg ccgcgcagct gaagcagcca     180
gtcgtggtcg acaaccgccc cggcgcgtcc aacaccattg ccgcggattt gaccgccaag     240
gcggcgccgg acggcaatac gctgctgatg gcgtggtga cctcgcaagc gatcgcgccg     300
cacctgctca agctgcagtt cgatccgctc aaggacctgg cgccggtggc gctggtgtcg     360
tcggtgccca tgtgctggt ggtcaacaac caggtgcagg cgcgcgacgt caaggcgctg     420
gtggcgcaga tccaggccaa cccggacaag ttccgctaca gctcgtccgg ggtcggcagc     480
acccagcacc tggccggcgc gtccttcgcg cggcagatca agggcaagct gctgcacgtg     540
ccgtacaaga gcagcagcag cgcgctggtg gacctgatgg gcgggcaggt ggacatgagc     600
ttcgagacca tgccgtcggt catcagccat atcaaggccg gcaagctgcg cgcgctggcg     660
gtcaccgcgg accagcgctc ggcgctgctg cccaacgtgc ccacgctggc tgaagcgggc     720
gtgcccggca tccagatgag tgcatggtac ggtgtctatg cgccggccgg cacggcgccc     780
acgacactgc agaagctggg caacgcgctg gccacgtga tcagggaccc tgacaccgtg     840
cgccggctgg ccgatgtggg gcgggtgccc ggcgcgctga ccgcggcgca gttcgatgcc     900
ttctcgcgtg ccgagtatgt gcgctatggc aagctgatcg ctgaactggg cgtcaagctc     960
gaccaataa                                                           969

<210> SEQ ID NO 66
<211> LENGTH: 990
<212> TYPE: DNA
<213> ORGANISM: C. necator

<400> SEQUENCE: 66
atgaagaaat ccgcgagacg ccgggcattg gttgccctga cagctattgc caccctactt      60
gcgacgggcg gggccactgc gcagggcagc tatccaacca agccggtcac gcttctcgtg     120
gcctatccag ccggcggcga tacagatgtg ctggcacgcc tctttgccga aagctgact     180 gctcggcttg ggcaacctgt cgtggtggag aaccgcaccg cgccggcgg caccattggc     240 acggcgtacg tggcaaaggc tgcgccggat ggctatacgc tgctgttcgc cccgaacaca     300
atctcgatct ctccgcacgt gctgcggccc ggcacggtg cctcctacga cccgcgcaag     360
gatctgacgc cgatcacgct actcggcacg cagtcgctgt cgttgtggt caacaaggcc     420 gccggtgtca cccggattga agacttcgtc acgcatgcta aagccggtac gctgaaaacc     480
tatggcagtc cgggcaacgg atcgccaatg cacatactgg cggaactgtt caacaaatcg     540
gccggcatca agctcacgca gatccctac cgcggcagcg cccccgcggt ggtcgacttg     600
ctgggcgggc aggtgccgat gatgtactcc acgcttgggc cggtgtccca gtacttcccg     660
tcgggcaagc tgattccgct ggccgtcgcg gacaagaagc gctcgccttt cgcgccgaac     720
gtgccgtccc tggccgagct tggctacaag gatgtcgagg ttggtgcctg caggccgtg     780 gtgggccga agggcatgtc cccggaactg gttctgacgc tgaacaagca cttcaacgac     840
atcctgaaaa tgccggacgt cgtcgcccgg atggcaacgg ttgccgtgac tccgcagggc     900
```
agcgacccag ccgcccttgg caagctgatc gctgccgact acgagcgcta tggccggatc    960
gtcaaggaat tcggcattca ggccgactga                                      990

<210> SEQ ID NO 67
<211> LENGTH: 969
<212> TYPE: DNA
<213> ORGANISM: C. necator

<400> SEQUENCE: 67
atgaacttgc gttctctgtt gactgccatc accttcggcc tcgcggctca ggtaccgtcg     60
gccctggccg cctatcctga aaagccgatc cgattgatcg tgccctgggc tgccggcggc    120
agcaccgatg cgctggcccg tgcggtcgcg cagcgaatga cgaatcgat gggccagccc    180 gtggtcgtcg acaatcgcgc cggcgcctcc ggccgcatcg cgccgacat cctcgcaaag    240 tcggctcccg acggctacac gctgggcgtc atcgagctgg ctcataccgt ggcgccgtcg    300
gtgttccgcc agatgccata tgatgtgttg cgcgacttca cgccggtttc actgctcggc    360
gaggcgccgc tcatcctgtt cgcggacagc acgcactatc gcgctggcga cgtccagcgc    420
ttccttgcgg actcacgcaa ggcaggaacg ccgctgcagc ttgccaccag cgggaacggc    480
acgatcagcc atctggccgc caagatgctt gaagcgcagg cgggcatccc ggtcgatgcc    540
gtaccgtacc ggggctcggc gcccgcgctg accgatgtgt ccgcccaact ggtcaaaggc    600
catttcgcta cgctggcaag cggcagcagc ctgcttggcg tggcaagat cgcggccttg    660 atggtgacgg ggccggtgcg cgtgacttcg cttcccggtg ttccgaccgc agccgaagcc    720
aggctgccgg gaatgcaggt cagccaatgg tgggccctgg tggctcccgc gcgggcaccg    780
tctgccgtcg tgagcaggct tgcggacgaa gtccgcgcgg cattgacgaa tccgcagacc    840
aaggcacggc tcgacagcca aggtatcgac ctcgcctgc tcaactcgga    900 gaccggctgc gcgcagagac ggatcgctgg gcgaatctgg ctaagcaggc tggcattcaa    960
cccgaatga                                                            969

<210> SEQ ID NO 68
<211> LENGTH: 1002
<212> TYPE: DNA
<213> ORGANISM: C. necator

<400> SEQUENCE: 68
atgtctagcc gacttgcggc accaggccgc cagaaagcgc ttggtgccgg cgtggtggcc     60
cttgcctgcc tgctgctgcc gctgacaacg gcagcagcag gcctgacaa tgccacgcca    120 ctgaagctgg tggtcaccctt cccgcccggc ggcagcaccg acattgccgc acgcatcatc    180
cagccgaaac tggcggaggc ggccgggcgg cccgtggtca tcgaaaaccg gcccggcgca    240
gccagccagg tcgctaccca gtacgtggct cgatccgcgc cggacggcaa tacccctgctg    300 gtcgccttcg atacgcatgc aatcaacccc gtggcgaagt ccaggctccc ctatgacacg    360
ttcaaggact tcactggcgt cacgtttgcc gtgcgcttcc cgctcgtgat cggcgcatcg    420
cccaccgttc ctggcaagga cctgcgcagc ttcctcgacg ctgcgcggcg tgagccgtcc    480
aaatacagct acgcctccac cgggcttggc tcgatgaacc atcttgtggc cgaggacctg    540
aagcggcagg ctcgggtcga gttgatgcac gtgccgtacg ccggcggggg tcccgcggtc    600
caggcagtgc tggcaatgt gtccagcatc acgctgctga gctatgcggc cctgaagggc    660
cagatctctg ccaacaagat caagccgctg gccgtgacgg gcgcgcgccg cctgcccgac    720
ctgcccgatg ttccaaccgt catcgagtcc gggttcccgg acttcgaggc ctactcgtgg    780

```
atcggcatct tcgcaccggc agccacccca cctgcggtcg tcaggaaact gacggaagat        840
ttccagaccg cattgtcgga cccggaaacc aaacgaaagc tgaccgcggc cggcttcgag        900
gtcatggcca ccgatggtcc caccgtagac cgctatgcgc gcgagcaata cgagcgctgg        960
cacagcttcg tcaagaagac cgggctgaag ctggaagact ga                         1002
```

<210> SEQ ID NO 69
<211> LENGTH: 969
<212> TYPE: DNA
<213> ORGANISM: C. necator

<400> SEQUENCE: 69

```
atgttgaagc gacgcgtttt caatcgggtg gctgcaacca tggcgctggc cgccgcgctg         60
cccatgggcg cccttgccca ggacaagccc cccctcaagc tgctggtcgg cttcgcgccc        120
ggcggctcgg tcgatgtcgt ggcgcggctg ctggccgagc gcctgcgcct gccgctcggc        180
cagcaggtga tcgtcgagaa caagcccgga gccggcggtc gcctggtgct tggggaagca        240
aagcgcgcgc cggccgacgg caacacgctg gtcatttcac ccagcggcgc gttggtgatc        300
tcgccatggc tataccacct caactacgac ccggtgaagg acttcacgcc catcgcgcgc        360
gtggtgacct tcgacttcgc ggtgacggcg ggtccggcgg cgccggccgg cgacatccgc        420
gcggtgctga actggctcaa ggccaacccg gccgcgccca actacggcac ttcgggcgca        480
ggcaccgtgc cgcactttgc gggcgtgctg ctgtcgcagg cctcaggcgt gccgctcacg        540
cacgttgcct acaagggcgg cgcgccggca gtgtccgatc tgctgggcgg acagattccc        600
atcatggtgg acacgatatc ggagaccatc gagcatcacc gcgcgggccg cctgcgcatc        660
ctcgcggtca cgggtaacgc gcgatcgccg gcgctgcccg acgtggccac gctcaaggag        720
tccggaatcg acgccacagc tgaggccttc gtcggcctgt cgccccggc aggcctgccg        780 gccgacaagg tcaagcgcct gtccgacgcg atcgccgaag tgctcaaggc gcccgatctc        840
caggcgcgca tccgcgagat cggcctgaat gcgaactacg ccggcccgca gcaacttggc        900
gagacccagg tcgccgacct caggcgctgg gagcggccca tcaaggcatc gggctacaag        960
gccgaatga                                                               969
```

<210> SEQ ID NO 70
<211> LENGTH: 1008
<212> TYPE: DNA
<213> ORGANISM: C. necator

<400> SEQUENCE: 70

```
atgcccaaca aagtacaaga gccgttacgg cgcatgtcgc gccgtaacgc cctagccgcc         60
ctcgcgatcc cgctagccac tgcactgatt cccgcacagg cgcagacctg acacccgcc         120 aggccgatcc ggctgattgt cccgtatggg cccggcggaa gctcggacgc cattgcccgc        180
gtcatcgcgg cagagatgtc gaagaatctg gccaacagta tcgtggtgga caacaagggc        240
ggcggccagg gtgtcatcgc catgcaggag accgcacgcg cagcgcctga cggatacaca        300
ctggttctcg ccacgttgg cacgcttgcc gtcaatcccg ccatgatgcg caagcttccc        360
tacgatcctc tgaaggactt cacgccggtg actttgctgg cgaaagtgcc gatggtgttc        420
gcggtggggc ctaccgtcca tagcgattcc atcaaggcat tcatcgccca ggccaagacg        480
aagcctggtg ccatgaccta tggatcgcg ggcaacggaa cgctggcaa cgttgccttc        540 gagatgctca agcagactgc gcatatcgat cttgtgcacg tgccatacaa gggcaccggc        600
```

| | |
|---|---|
| gcccagattt ccgacttgct cgccggaaac atcgacgccg catcggcggg cctggcgggg | 660 |
| atcctgcaac acgccaaggc gggcaagctg cgcatcctcg ccgttggatc gtcacagcgc | 720 |
| ctcgcgccga ttcccaacgt tcccaccatt gccgaggaag ctacccggga atttgaaagc | 780 |
| tcgcaatggt ttgggctgat ggcgccagcg cgcacgccaa cgccggtggt cagccgcctg | 840 |
| catgccgagg cagtcaaggc cctggccacc ccgctggtgc gacaacgact tgccgaggac | 900 |
| gcaagcacgc ctgtcggcgc gggcagcgcc gaatttgcgt cattcattcg tgccgagcaa | 960 |
| caacgctggg gcaccgtcat ccgcagcgcg ggaatccagg caaactaa | 1008 |

<210> SEQ ID NO 71
<211> LENGTH: 966
<212> TYPE: DNA
<213> ORGANISM: C. necator

<400> SEQUENCE: 71

| | |
|---|---|
| gtgttttatc gaaccattgg ctgcctggtg gcagcaacga cgctgcttgt cagcctgtcc | 60 |
| gctgtggcgg cgtacccgga caaaccggtc cgcatcatcg tgccgaatcc tcccggcggc | 120 |
| gccgtcgacg tcgtgacgcg caaggttgcg cagaagctct ccgtgcagac agggcagagc | 180 |
| ttcgtcgtgg agaacaaacc gggcgcgtcc ggcacgatcg gcacgtccct ggtcgtgaac | 240 |
| gcacccgccg atggctacac gcttctggcg aacgacaact cctataccac cctcccctat | 300 |
| gtcttcaaga aactgaactg ggaccatcag acagctctga tccctatcgc gccgttcgca | 360 |
| ttttcgccgg tggtgcttgg cgtcaaggcc gattcgcgct tcaaggacct ggcctccctc | 420 |
| atcagctatg ccaaggcgca tcccggagaa gtgacgtttg caccggcgg ccccggtagt | 480 |
| tcgccgcatt tttctgccga ggcgttccaa caggccgcag gtatcaagct gatgcatgtg | 540 |
| ccgtacaagg gggctggcga ggccatggtc gggctgctgt ccgtagcgt ggatctgctg | 600 |
| gtcgtgtcga ccccgaccgc gctggcgccg gtcaagggta atcagatgcg tctgctgggc | 660 |
| atcagtggca agaccagggt ggatgtgttc ccgggcgtcc ctacgttcgc tgaagctggt | 720 |
| gtacccaact tcagcctgtt caactggtca ggccttgccg cgccaaaggg cacgccgaac | 780 |
| gatgtcatta cgcgcctgca aacggaaatc cagaaggcgc tccaggcgcc cgacatgaag | 840 |
| gcattccttg cgcagatggg gtcgcagccg ggcaacctgg acagccccgc gttcgcgcag | 900 |
| ctgatccagc gcgaaaccgc gcaatgggca acggttgcgc aaaaggcgca tattgagaag | 960 |
| caataa | 966 |

<210> SEQ ID NO 72
<211> LENGTH: 981
<212> TYPE: DNA
<213> ORGANISM: C. necator

<400> SEQUENCE: 72

| | |
|---|---|
| atgaaggcaa tttcccgtcg ctgcatattc atgctcgccg caggtctggt tctggcgtcc | 60 |
| gccactaccc aggccgcgcc gcaataccc accaagccca tccgcgtcat cgtgcctttt | 120 |
| cccgccggcg ggggcacgga catcattgcg cgcgaggtga ccaatacggt ggccaagtcg | 180 |
| accggctggg tctttgtggt ggagaacaag ccagggtccg gtggcaacct cggggtggac | 240 |
| gcggcagcca aggcgccggc cgatggctac accatcgtca tggggcagac cagcaacctt | 300 |
| gcaatcaatc cctcgctgta tgaacggttg ccgtatgacc cattgaagga tctggcgccc | 360 |
| atcagtctgg tcgcctccgc gccgctcgtc ctggtgacga atgtcacctc gccctacaag | 420 |
| acgatgaagg acgcgattca ggctgccaag gcaaagcccg gagcgatcaa tttcgcatcg | 480 |

```
ccgggcaacg gcacggtggc gcaccttggc ggcgagctgc ttcaaggtac cgcgaaggtg      540
aagttcaccc atgtgccgta caagggcgca gcccaggcgg tcaacgacct gatgggcggc      600
caggtcgatc tctacatggc atccgtgcca acgttgctcg gcatatcaa gaacaacagg       660 ctgcggccgc tcgcggtgac gtcgccgaag cgtttgccag acctgcccca ggtgccgaca      720
gtcgccgaac tgggctatcc cggctttgat accgcgacct ggttcggctt cgtcgcgcct      780
gccgcgacac cgaaggacat cgtggtacgc ctcaataccg agttcaacaa ggcgctcaaa      840
tccccggagc tcgccaagaa gctgaatgaa caaggtgcat cggtgctggc cggcacgcct      900
gaggcgttca gcgcgctgat caagcaggac atcggacgct gggcatcggt catcaagacc      960
tccggcacga agctggattg a                                                981

<210> SEQ ID NO 73
<211> LENGTH: 975
<212> TYPE: DNA
<213> ORGANISM: C. necator

<400> SEQUENCE: 73
atgggcgccg cgatcgtggc cggggcgctg attgccctga tgccgttggc gccggcacgg       60
gcagcgactg gtgagggcta tcccgccaag ccggtgaccc tggtcgtgcc ggggccgccc      120
ggtggcatta cggaccagct cgcgcgcctc gtcgcggccc gcatggggcg cgatttcggc      180
gtgcaggtcg tggtggacaa ccggcccggg gccggcggca atattgcggc ggagcttggc      240
gcgcgcgcgc agccggacgg ctacaccgtg ctgatgggca cgcagggcat gatggtgagc      300
aaccagttcc tctacaagtc gctgcgcttc gatccgtcga aggacttcgt tcccgcccag      360
ggacttgcgt ccatccccaa cgtgctggtg gtgagcagcc ggctgccgtt ccgttccgtc      420
agggagctgg tggactacgc ccgggcgaat cccggcaagc tgacgtcgc gtccgccggc       480 aacgggaccg gcacccatct ggtggccgaa ctgttccaga ccgaggccgg catccggctc      540
gtccacatcc cctacaaggg cagcgcgccg gtcatcaccg acctgctggc gggacaggtc      600
gacctggcct tcgactaccc cgtctcgacg cttgcgcaga tcgaagccgg caagctgcgt      660
gcgctggcgg tgaccggcgc ggcgcgcctg cccgcgctgc cgcaggtgcc gaccaccgcg      720
gagtcgggtt tcccgggcgt cgaatcgacg tcgtggatcg gcctgttctt tccggcccgg      780
accagcccgg ccatcgtggc gaagtggcag gccgacatcg gccgcctgct ggccgatccc      840
gcggtcattg ccgagatccg caagatgggc ggcgtcccgc tcgcgctcgg cggcgcgcgg      900
ctcggcagct tcgtggagtc ggagcgcggc aagtggaagg cggtcatcca gcgttccggc      960
gcgagcatcg actga                                                       975

<210> SEQ ID NO 74
<211> LENGTH: 1074
<212> TYPE: DNA
<213> ORGANISM: C. necator

<400> SEQUENCE: 74
atggcgccgg atggcggcaa ccatggcgta gcgacatctc gacaagcttt cgggccggat       60
ctggctcccc gcagtacgtg tgaggagaag acaaatatgt tgatgaagca gaagaaggcg      120
ctgctgccga tcctggcact cgcctggagt gccgccgtga tggcgcaggc ctaccccggc      180
aagccggtta cgctcatcct gccgagcgca ccagggggac tggtcgacac catcggacgg      240
gcctatggcg atgagttcac ccggcgcacg ggccagcccg tcgtcgtggt caacaagccg      300
```

```
ggtgcctcgg gcgcgctcgg cacgctggcg gcggcgcggg ccgcgcccga cggctatacg    360
ctgctgatgg cgcaatccac ggcgatcttc aatgtcccgc tgaccatgaa aaaggtgccc    420
tatgaggtgc gccgcgactt cgccttcatt acgcaggtca cgccgggac gctggtgctt     480
gccgtcaatg ccgccgtgcc ggcgcgcaac ctgcaggaat cgtggcctg gcgaagaac      540
aaccgggaca aggtgaacta tggctcgtac ggcgtgggca gcaatgcgca tctcgtcatc    600
ggccatctca acagttcccg cggcctggag atgtcgcaca ttccctatcc cagcgagatg    660
caggatctgc agggactggc aggtggctcg gtgcaactca ccatcgcctc ggccggtgcg    720
ctggcgccgt atgtgccag cggcaagatc cgcccgcttg ccgtggtcgg cgatacgcgg     780
ctgccggcga tgccggacgt gccgaccatg gcggaagcgg ggttcagcga cccggagttc    840
cgctcgcatg cctggatcgt gctgatggcg ccggcgggca taccgccgaa cgtgcaggcg    900
ttcctggaga aaacctcgcg cgagatcatc cgctcgaccc cgttgaaggc acgcttccag    960
gcctacggct tcgagccgat gggtaacagc tcggccgagt tccgccagaa cttcgaggcc    1020
gcactgcccg tgatcgggcg cctgatcaag ctatccggcg cccgtgaaga gtga          1074

<210> SEQ ID NO 75
<211> LENGTH: 978
<212> TYPE: DNA
<213> ORGANISM: C. necator

<400> SEQUENCE: 75
atgctcatca ggtgcaaaag ggcgctgcta cccgtgatgg caatcatctg gggtaccggc    60
agccttgcgc aaacctaccc cgacaagcct gtcacgctga tcgtgccggc cagcgcaggc    120
ggggtggtcg acgctctggc ccgtgcctat ggcgacgagt tcaggaagct cacggggcag    180
cccatggtgg tcgtcaacaa gccgggtgcc tcggccatgg tggggacgca gatggccgcg    240
cgctcggccc ccgatggcta cacactgttg atgacgcaag ccacgtccat cctgaacggg    300
ccgctgatga ccaaaaagat gccgtacgac gcgcggcgcg acctggcatt catcacgcag    360
gtgggtaccg ggaacctcgt cgtggccgta ggcaaggacg tccccgcccg caacatgcag    420
gagttcatcg cctgggccaa ggccaaccgt ggccaggtca actatggttc gtacggcgtc    480
ggcggcaccg cgcatctggt ctccgcctac ctgagcagtt cccgcaacct ggagatgtcg    540
cacgtccccct atccgggcga agcgccggag atccagggc ttgccggcgg cgcagtgcaa     600
tgcgccattg cttcggccgg cgcgctggcg ccccatctgg caagcggcag ggtgcgcgcg    660
ctggccgtga ttgcggacaa cgccctggca gccctgccgg acgtgccgac catggccgaa    720
gcgggtctgc gcgatccgga gttccgtccg cagtcatgga tcgtgctgat ggcaccggcg    780
ggcacgccgc agaacgtgct ggcgttcgtc gaaaagacct cgcgcgacat catccattcg    840
acgccgatga aggcgcgctt ccaggcctac ggcatcgagc cggtcggcaa cagttcggcc    900
gagttccgcc ataacttcga agcactcatg cctgtcatgg agcgcctgat caaggtatcc    960
ggcgccgcgg gggaatga                                                  978

<210> SEQ ID NO 76
<211> LENGTH: 1014
<212> TYPE: DNA
<213> ORGANISM: C. necator

<400> SEQUENCE: 76
atggcctttc atctaccccg attgccgtat tggcggcgct ggcgcctcat ggcgacatgt    60
gtggcggcgt gcgcggtggc cgcggcgtcc gcgtggatgc aaccggccct ggcgcaggcg    120
```

```
gcttacccga accgcccggt caagatcatt gtctcgctgc cgcccggcag cggcacggac    180
acgaccgcgc gctttgtcgc ccaggcactc tcggcgaagt tccaccagcc gttcgtggtg    240
gagaaccgcc caggcgccaa cggcttcatc ggcgcacgcg ccgcggccga ggctgcgccc    300
gacggctata cgctgtttgt cggcagcaac tcgaccatgg tgaccaacgt cgccgtgttc    360
aggaacctgc cgtatgaccc cgtcaaggac ttcgcgccgg tggaacgcat cgcgcgcttc    420
gcgctcgtcg tcgtggtgcc gaccggctcc ccgttccgga cgctcgcgga gctggtcgac    480
ggcgcgcgca aggcgccccg caagctcaac tacgccgccg gcagccccgg ctaccaggtg    540
ttcgtcgaac tgctcaacga gcgcttcggt atccacgccg cccgatcgc ctacaagggc    600 accgccccgg ccatgaccga cgtcgccgtc ggacaggtgg actactccat ggccgagatc    660
agcgcggtca tgccgctggt ccgggccggc cgcctgcgcg cgcttgcggt caccgacacc    720
catcggctca aggaactccc ggaggtgccc accgtggccg aaagcggcgc gccgggcttc    780
gacgtttcgg cgtggaccgg ggtcttcgcg cccgccaacg tgcccgcgcc gatcatcaag    840
agcctgtcgg acgccgtgcg cgcggccctg caggcgcccg ccggcgtgaa attcgtcgag    900
agcctgggcg gcaccgtgta caccggcagc accaccccgcc tgcgcgactt ccagctcgcc    960
gagatacaac gcacgcgcga catcgtaaag actgccggca tccccgtgga gtag         1014

<210> SEQ ID NO 77
<211> LENGTH: 1047
<212> TYPE: DNA
<213> ORGANISM: C. necator

<400> SEQUENCE: 77
atgctgtcac gaatccggag ccggcgcccc cggttccccg gcctcgcccg ccttcccagg     60
cgcttcggaa caaccctggc ggcggccgcc gcagtcgtgt gcggcctcgc cgccgcgacg    120
agcgcatcgc ccgcgcgtgc gcaggacggg tatcccgcca agccggtcac gatagtggtg    180
cccgcgccgc ccggcggcat caccgaccag cttgcccggc tcgtcgcctc gcatatggcc    240
agggacttcg ggatccaggt cgtggtcgac aaccggggcg cgccggcgg caacattgcc    300 gcggaaatcg cgcgcgtgc gcaggcctgac ggctacaccg tcctgatggg cacgcagggc    360
atgtttgccg gcaaccagtt cctctacaag gcgctgcgct tcgatccgga gaaggacttt    420
atcgcggcac aaggcctggt caccattccc aacatcctgg tggtgaacag ccggttgccg    480
ttccgctcgg tcgcggacct ggtcacgtac gccagggcca atcccggcaa gctgaccgtg    540
gcgtccgtgg gcaacggcac ggggacgcac ctggccgccg aactcttcca ggcccaggcg    600
ggagtgaagt tcgtccacat cccctacaag ggcagcgcgc ctgtcatcaa tgacctgctg    660
gcgggacagg tcgacatgac cttcgactac ccgtttcga cgctgccgca gatccaggcg    720
ggcaagctgc gcgcgctcgc ggtcacgagc aaggcacgcc tgcccgcgct ggcgcaggtg    780
ccgaccgtgg ccgaggccgg ctatcccggg gcggaagcca cgtcgtggat cggcctgttc    840
ttcccggccc gcaccagtcc ggccatcgtg gccaggtggc aggccgatat cggccgcctg    900
ctggccgatc cggcggtgac cgccgagatc agcggatgg gcgccgcgcc gctgccgctt    960
ggcggcgaac gtttccgcgc cttcgtgcaa tccgaacgcg ggaagtggaa ggccatcatc   1020
cagcgctccg gcgccagcat tgactga                                       1047

<210> SEQ ID NO 78
<211> LENGTH: 1011
<212> TYPE: DNA
```

<213> ORGANISM: C. necator

<400> SEQUENCE: 78

| | | | | | |
|---|---|---|---|---|---|
| atgaccagac | cccattcgac | acgccgccgc | cacatcctgg | cgctggccgc | cagcagcgtc | 60 |
| atccagacgc | tggcaccggc | cgcgcgggcg | caggcgcgcg | gctacccgga | ccgcccgctc | 120 |
| aggatcgtgt | ccgtcgcgag | cccgggatcg | ggcatcgacg | actacacgcg | cctgctggcc | 180 |
| aagttcctgg | cgagaagct | gggccagggc | gtggtcgtgg | agaaccggcc | cggggccaac | 240 |
| atgatcatcg | ccagcgacta | cgtggccaag | tcagcgccgg | acggctatac | gctgctgctg | 300 |
| accgcatcga | gctcgatggc | ggcgaatccc | ttcctgttcc | gccagctgcc | gtacaacccc | 360 |
| aacaaggact | tcgtgccggt | ggcccggctg | tcgacgttgc | ccatcgtgct | ggtggtgccg | 420 |
| gccgcatcgc | catacaggac | cgtggccgac | ctggtcaacg | ccgcgcgcgc | caatccgggc | 480 |
| aagctcaatg | cgccagcag | cagcaccggc | taccggctga | tggccgccgc | gttcacgcag | 540 |
| gcggcgggca | tccggacgac | cgacgtgcca | tacaaggcga | ccgccagcct | gctgacggac | 600 |
| ctgatggggg | gcagcgtcga | tttcaccatg | gtggagttcg | gggcggcgct | ggcgctgatc | 660 |
| cgctcgaaca | agctgcgtgc | gcttgccatg | ctgagtccga | agcggctgcc | gcagttgccc | 720 |
| gacgtgccga | cgctggcgga | agccggcatg | cgcaacggca | cgctggtgga | gtcggtgtcg | 780 |
| cgcatcaact | ggagcgggct | gttcgcgccc | gcgggcacac | cggcgccgat | cgtggagcgg | 840 |
| ctcgggcggc | tgtcgctgga | gttcgtcaat | tcgccgaggg | cggcggcgca | ctacgccagc | 900 |
| cggggcagcc | tggcgaatcc | cggctcgggc | ccggaactgg | gcaaggcggt | gctggacgac | 960 |
| cagcaggtct | ggaaaacgct | gatcgccgcg | gctggcgtgc | agcccgagta | g | 1011 |

<210> SEQ ID NO 79
<211> LENGTH: 972
<212> TYPE: DNA
<213> ORGANISM: C. necator

<400> SEQUENCE: 79

| | | | | | |
|---|---|---|---|---|---|
| atgaagtgga | aagcgatcgc | cggtgtggcc | atgctgttct | gcggcatcac | cgcgcgggcc | 60 |
| gacacctatc | ccagccggcc | gattacattc | gtcgtgccca | cgccgcagg | cggcgcgatg | 120 |
| gactccatcg | cccgcaccat | ggcggagacg | atgagcaagc | aactgggcca | gccaatcgtc | 180 |
| atcgacaacc | ggcccggcgc | cggcggcatg | ctcggtgccc | agtacgtggc | ccgcgccgcg | 240 |
| ccggacgggt | acacgctgct | ggtcaccacg | tccggcccga | tcctcatggc | gccgttcctg | 300 |
| tatgcaaggg | tgccctatga | cgtcaaacgc | gacttcacct | tcgtctcgca | gatttgcgac | 360 |
| ggccagctcg | tcatggcggt | caatacgcaa | aaggtgccgg | tgaagtcggt | cagggaattt | 420 |
| gtgtcttggg | cgcagcagca | caagggcagc | gtgacctatg | gctcgtacgg | catcggctcg | 480 |
| tcggcgcacc | tgatggcggc | gtacttcagc | gagtccaaca | agctggagat | gacccacgcc | 540 |
| gcctacaagg | gcgaggcgcc | gatgatgcag | gacctgatcg | gcggccagat | cgactggggc | 600 |
| atcggcacca | ccggtacgct | ggcaccgcac | ctgaaaagcg | gccgtcttcg | cgcgctggcc | 660 |
| gtcatgggca | accagaagct | ggccgagctg | cccgacgtgc | cgaccatggc | cgaggccggc | 720 |
| tttcccggcg | ccgagtacag | gaccatcggc | tggggcggca | tcctggcgcc | cgccaacgtg | 780 |
| ccggcgccgg | tgctggcaaa | gctggagcag | gcggcgcgcg | ccgccgcgca | gaccaccgcg | 840 |
| atgaaggccc | gcttccaggt | gttcggcatg | cagccgctcg | gcaccaccgg | ggcggatttc | 900 |
| aagcgcgatg | tggaggccac | ggctcccgtt | gtggaacgcc | tggtccgcct | gtccggggcg | 960 |
| cgggtggaat | aa | | | | | 972 |

<210> SEQ ID NO 80
<211> LENGTH: 1005
<212> TYPE: DNA
<213> ORGANISM: C. necator

<400> SEQUENCE: 80

| | | | | | |
|---|---|---|---|---|---|
| atggaacttc | ggaccatcac | gcgcacgctg | gcgccacgcc | ttcgccggat | cggcgcgacc | 60 |
| tgtgtggcgg | cagcggtggc | tgcgagcgat | gcgctcgcgc | agcccgctta | tcccgccagg | 120 |
| ccagtcacga | tcgtctccgt | cggaccggcc | ggcggggtca | cggatcaggc | cgcgcggctg | 180 |
| atcgccacca | aggtcggtgc | gcgccttggg | caaaccgtga | tcgtcgatga | ccgaggcggc | 240 |
| gcgggcggaa | atatcggcgc | ggagtacgcc | tcgaaagcag | cgccggacgg | ctacacgctg | 300 |
| atggtcggca | cgcagggcac | ccagtcgacc | aaccagttcc | tcttcaaatc | gttgcgcttc | 360 |
| aatcccgaga | agatttcgt | gccggtgcac | gggatcattt | cgctgcccaa | cgtgctggtg | 420 |
| gtcaatgcca | gtcgtccata | tcggtcggtg | ggtgaatttg | tcgcctatgc | caggacgcat | 480 |
| cccggcaagg | tgacggcggc | atccggaggc | aacgggaccg | gaatgcacct | tgccatcgag | 540 |
| cagttccgga | gcgtggccgg | cgtagacctg | gtgcatgtgc | cgtacaaggg | cagtccgccc | 600 |
| gcgatcaccg | atctcgtaag | cgggcaggtg | gacctgtgct | tcgactatcc | ggcgaccacc | 660 |
| gtcgccaca | tccggagcgg | caagctgcgc | gcgctcgccg | tgctggggcc | gaaccggctg | 720 |
| ccgcagttgc | cgcaggttcc | cacgattgcc | gaggccggat | tcccgcgcgc | cgaatccacc | 780 |
| gactggatcg | gcctgttcgc | ggtggccggg | acgccgcagc | cgattgtcga | ccggtggacc | 840 |
| agggaggtgg | cgctcgtcct | gcaggggcct | gatgtcatcg | cgtccttcga | gcgcatgggc | 900 |
| ggcgtgccgc | tgccgctggg | cggcgagcag | ttcggcagct | tcatcgtctc | cgagcgggtc | 960 |
| aaatggaagg | cggtgatcga | acgcaccggc | gcacggatcg | aataa | | 1005 |

<210> SEQ ID NO 81
<211> LENGTH: 990
<212> TYPE: DNA
<213> ORGANISM: C. necator

<400> SEQUENCE: 81

| | | | | | |
|---|---|---|---|---|---|
| atgaagcggc | attcacccccg | gaatgtttgg | aaacgcgcga | tcgttgcggc | cgtgctggcc | 60 |
| atcgccggca | cgggcagcgc | gctcgcccag | ccgggctatc | cggaccacac | gatccggatc | 120 |
| atcgtgccgt | tcagcgccgg | gggcagctcg | gacctgcagg | cacgcatgct | ggccgaccgg | 180 |
| ctgggcaagc | tctacaagca | atcggtggtg | gtcgagaacc | ggcccggcgc | cggcggccat | 240 |
| atcggggggca | aggccgtggt | cgatgcggcg | cccgacggct | acacgctgct | gctgggctcg | 300 |
| ctgggcctgc | acgccaccta | tgccaccttc | aagaagctga | actacaaccc | cgccaccgac | 360 |
| ctcaaggtcg | tgacggtgct | ggccgagatg | ccgcacgtgg | tggtggtcaa | cccgaagctg | 420 |
| gcggtgaaca | acctgcagca | actggccagc | ctggcgcgcc | agcagccaga | cacgcggacc | 480 |
| ttcggctcgg | ccggcgtcgg | ttcctcggtg | cacatgatgg | gcgagctgtt | ccggctcaat | 540 |
| gccaatgcgc | cgatcacgca | tgtgccgtac | aagggcagct | cagcggccat | gacggatctt | 600 |
| ctcggtggcc | agatcgacat | gatgttcgag | aatccgccca | ccacgctggc | ctatatccgc | 660 |
| tccggcaagc | tcaaggcgct | ggcggtgacc | ggcaagaccc | gctcggccgc | gctgcccgat | 720 |
| gtgcccactg | ccagcgaagc | cggctaccccg | tcgttcgtgg | cgacttcctg | gaccacggtt | 780 |
| gcggttggcg | ccagggtgcc | cgatgcgatc | gcggacaagc | tcaacgccga | tatccgccag | 840 |

```
atcgtggcca cgccggagtt ccggcaggga ctgcaagagc agggcatgac cccgtggcc    900
aatacgcgcg atgccgcgca gaagttcgtc gccgcggaga aagtgcgctg ggaccaggtg    960
atcctgaagg gcaggatcag cgccgaataa                                     990
```

<210> SEQ ID NO 82
<211> LENGTH: 969
<212> TYPE: DNA
<213> ORGANISM: C. necator

<400> SEQUENCE: 82

```
atgacacccc gtcccttcag aatactgatc gccgcagcca tgctggcggc cgcggtcccc     60
gcctgcgcgc aggatgccta cccggccaag ccggtccgcc tgatcgtcaa ctttcctgca    120
ggtggcccgc tcgacaccgt ggcacggctc attgccgagc gtgccgggcg cgacctgaag    180
cagccggtcg tggtggagaa ccgctccggc gccgcggca acatcggtgc cgaagccgtc    240
gcgcatgcga cgccggacgg ctacacgttg ctgatgtcga ctgacaccgt tgtcaccgtc    300
aatccgttcg cctatcgcaa gatgtcgttc gacccggtcc gcgacctgga gccggttggc    360
ctggccggca ccttcaatca ggtgctggtc acgcatcccg gcctgaaaat ccgcgacctg    420
aagcagttcc tggctgccgg caaggacaaa gacctgtcct atgcatcggc tggcgtagca    480
tcgccgggcc atattgtgtt cgagatgctg aaggcacgca cgcagatccg gggcacccat    540
gtcccctaca agggcaatgc gccagcgctg agcgacgtgc tcgcgggtca ggtaccggca    600
ggattcctgg ccacgccgac cgccgtgcaa tacatcaagg gcggcaagct ggtcgcgctt    660
gcggtgtccg gcctcaagcg cgacccctcg ctccgggacg tgccgacggt ggcagagacc    720
ggcatcgcca acttcgatgc cgagttcgcc ttcgtcatgt cctgccctc aggcacgccc    780
gcggccatcc gtgcgcgctg ggagcagcag ctcaagaccg tcttcgcgga cgcggatttc    840
cagaagaagc tgctggcaca gggcgtgcgg ccgcagacga gcaacggcgc ggcggcagcg    900
caatggctgg ccgcgggggcg tacgcgctgg ggcgaactga tccgcaagct cggcgtgtcg    960
ctggactga                                                            969
```

<210> SEQ ID NO 83
<211> LENGTH: 999
<212> TYPE: DNA
<213> ORGANISM: C. necator

<400> SEQUENCE: 83

```
atggatgcca tccaaccgtt gcgccggctc gctgccggca tgctggcctg cgccgcgctg     60
atgccgctgc cagtgctggc cgcccctgac aatgcggcgc gcttcccgga ccacccgata    120
cggatcatcg tgccgttctc ggcgggcggt gtggtcgact ccgtcacccg catcaccgcg    180
gagaacatgg ccaaggtact gaagcagccc gtcatcgtcg agaacaagac cggcgccggc    240
ggcgccatcg gcgcggactt cgtcgcccgg tcacccgccg acggctatac gctgctggcg    300
gtcagcccca gctatgtggt cgggccgatg ctgaacccgt cgatccaggg caagagcggc    360
aaggacttcc gcgcggtggc gggcattggt gccgtaccca acgtgatcgt ggtgccggct    420
tcgtcgccgc tgcgcacact gcctgaactg ctcgacgccg cgcagcaa gcccggcacg    480
ctgacctacg ccagcgcggg cgtcggcacc tcgaaccatc tgtcggccga actgctggcg    540
cagatgacgc acgtgaagct cacccacgtg ccctacaagg ccagcccga ggccatgagc    600
gacctgctgg gcgcgcgcgt ctcgatgatg gcgctgacct cggccattgc ccgccagcag    660
gtgcaaagcg gcaagctgcg cgcgctggcg gtgacttcgg caaaacgctc agccgtgatg    720
```

```
cccgacgtgc caccgtggc cgaggccgcg cgcctgcccg gctatgaagt gggcgggtgg    780
ttcggcctgg tcgcgccgca gggcacgccg gacgcggtgg tgccgcaagct ggccgaggcc    840 gccgcgcagg ccaccgcgga ccccgccacg gcacgccgcc tggccgaact cggcatggac    900
ctggcaccgc aatccaccgc cgcattcgac cgcttcctgg acacggaaac caagaaatgg    960
accggcgtgc tgaagaccgc cggcatcacg gcacagtag                          999
```

<210> SEQ ID NO 84
<211> LENGTH: 990
<212> TYPE: DNA
<213> ORGANISM: C. necator

<400> SEQUENCE: 84

```
atgaccccga taatcccct tcgccgccat ctgctcaaga ccaccgccgc gctgggcgcg     60
tgcgcgctgg caccaacact ggcccgcgca caggcctggc cggccaagcc gatccggctg    120
gtggtgccgt tcgcgccggg cggcagctcg gagatcgtgg cgcgctccac cgcggcggag    180
ctgaccaagc tgctaggcgt gtcagtcttc gtcgagaaca gcccggcgc ggccggcaat    240 atcgccatgg ccgaagtcgc gcgcgccgat gacaaccaca cgctgatcct cggccatatc    300
ggcacgctgg cggtcaatcc gtttatcttc ccgaagctgc cctacgaccc cgtcaaggac    360
ttccgcgcga tctcgctgct gtccaaggtg ccgagcctgt acgtggtcca ccccgacgtg    420
cccgcgaaga acctgaagga gttcgtggcg ctggccaaga gcaagcctgg caagctgaac    480
tacggttcgg ccggcaacgg cagcgccggc cacctggcct ttgaatacct gaaagccgcg    540
agcggcacct tcatcaccca tgtgccgtat cgcggcagcg gccgcagat cactgacctg    600 ttgtccggac ggctggatgc ggccgcggtc ggcgcgccgg cgatcatcca gttcatcaag    660
gccggcaagg tgcgctgcat cgccaccggc acgacccagc gcattgccca gctgcctgac    720
gtgcctacgg tcgcggaaca gggctatccc ggcttcgaaa tgacgcagtg gtacggactg    780
ctggcgccgg catcgctgcc gcaggcggcc gccgacaagc tggcggacgt caccgcaaaa    840
gccgtgaaaa gcccgacctc ggtcgagcgc ctgagcgcgg atgcggcgat tgtcgtgggc    900
ggcacgccgg ccgagttctc gcgctttatc gcgcaggaac agcagcgctg gaagcccatc    960
attgcgcgcg ccgggatcaa gccggattga                                    990
```

<210> SEQ ID NO 85
<211> LENGTH: 981
<212> TYPE: DNA
<213> ORGANISM: C. necator

<400> SEQUENCE: 85

```
atgcacgcac gccacgcgat cgccgccacg gtcgctgcca tgatcgccac caccacgctg     60
gcgcaggccg ccgacaccgc gcggcctgg ccggcacggc ccatcacgat cgtggtgaca    120
tatccgccgg gcgcggcgc ggacctgatg gcacggctga tcgcgccggg cctcgggcgc    180
gagctgggcc agaccgtcgt cgtcgagaac cgcccgggtg ccggcgggca gatcggtgcc    240
gcctatgtcg ccaaggcggc accgacggc tacacgatga tggtcgatgc ctcctcttat    300
gcggtgaatc ccagcctcta tccgcgcctg ccctacgatc cggacaaggc cttccggccg    360
gtcggcgtgc tggcgcgcta tccaacgtg ctggtggcca cggcgggctt ccccgccagc    420
aaggtcagcg acgtcctggc catgccagg caaaagccag gctcggtcgc ctttgcgtcc    480
tcgggcaatg gctcggcgca gcatctggcc ggcgtgctgt tcgagcagcg cgcggggtc    540
```

```
gatctactgc atgtgcccta caagggcggc ggccccgcca tgaccgatgt catcgccggc    600
caggtgccgc tgttctttgc caacgtcgct tcgagcctgc agcacatcaa ggccggcaag    660
ctgaagccgc tggcggtgac cagccatgcc cgcacccagg cattgccgtc cgtgcccacc    720
atgcaggaag ccggcgtggc gagctacgag gtctatgaat ggaacgcggc cttcctgccc    780
gccgcaacgc cggacccgat cgcagcgaag ctcgccgacg ccctgcggaa agtcatgacc    840
agccccgaga tccggcaacg cgtggccgag ctgggcggcg aggtcgtggc tgcgccgcca    900
gcacaggcac ggcaattcat cgacgggcag gcccggctat gggccaaggt catccgggac    960
ggcaacatca agcccgaata g                                              981
```

```
<210> SEQ ID NO 86
<211> LENGTH: 975
<212> TYPE: DNA
<213> ORGANISM: C. necator

<400> SEQUENCE: 86
atgaggaagt cagcagttca agtcctggcc gcggggatct tcggcgcgct gccatgggca     60
ccggcggccg tgcaagcggc gtggccggag aagccggtgc gcctgatcgt gccgaccgcg    120
ccgggcggcc gcccggacat cgtcgcgcgc ctgttcggcg atgcgctgtc caggcgcctc    180
ggccaggccg taatcgtcga gaaccggccg ggcgcgggcg aaatatcgg catgcaggcg     240 ctgctggccg caccgtcgga cggctatacg atcggctacg caacaatgc cacgctgtcg    300 accaatcgct tcctttacag caagctcccc tacgatccgg acaagctggt gcccatcgtc    360
ggcctggtca cgaccttcaa catcctcgcc gtcaatccgt cgctaccggt caagtccacc    420
ggggaactgg tggcatactc ccgcgccaat ccgggcaagc tctccatggg ctcggcgggc    480
aacggcacca ccagccacct gggcggcgag ctgttcaagg tcatggccaa tctcagcatc    540
acacacgtgc cctacaaggg cagcacgccg gcgctgcagg acctggtcgg caacaacgtg    600
cagttgatgt tcgacaatgt gccttcgatc ggaccgtacg tgacgtccaa ccgcgtacgc    660
gcgctggcgg tgacctcaag caagcgctcg ccgcacttcc cggatttgcc caccatggcg    720
gaggccggcc tcaagggcta tgaactgacg gcatgggcgg gcctggttgc cgcgccgggc    780
actcccaccg aggtgattga gcggatcaac cgggaaatca acgcgatcat caatgacccg    840
gcattccgtg cccaactgga caagctctca ttcgatccgc tggcggcac cgcgcgcgac    900 ttccaggcgc tgatcgcgag cgagaccgtc aagttcggcg agctggtgcg caagagcggc    960
gccagggtcg attga                                                     975
```

```
<210> SEQ ID NO 87
<211> LENGTH: 996
<212> TYPE: DNA
<213> ORGANISM: C. necator

<400> SEQUENCE: 87
atgaagacgt tattccagcg gctggcaagc accggccgcg caggggcgct ggcactggct     60
gccggcctgt cgttcgcagc gccggccgcg cacgcggcct atcccgacca tccgatccgc    120
tggatcgtgc cgttccccgc gggcggtgcc atggacaata tcgcgcgcac gctgggcgaa    180
gacatgtcgc gcacgctggg ccaggccatc gtggtcgaga accggccggg cgccggcggc    240
aatatcggcg ccgaactggt ggcgcgcgcg cccgccgacg gctacacgct gatcatcgtt    300
gccaacggca tggccgtgaa cccggcgctg tacgccggc tgagctacga cccggtcaag    360
gacttcgcgc cggtgtcgct gctggcggtg gtgcccaacg tgctggtggc cagcaaggcg    420
```

```
cggcgccagg aaagcaccgt caaggacgtg gtggcgcacg ccaaggcggc gccgggcaag      480
tacacctatg cctccgcggg caatggcacc tcgatccacc tggcgggcga gctgttcacc      540
tcgatggccg gcgtcgacat gctgcatatc ccctacaagg gcagcggccc ggccatgacg      600
gacctgctgg gcgccaggt cgactacatg ttcgacagca tcacctcggc caggccgcat       660
atcgaatcgg gcaagctgac ggcgatcgcg gtcaccacca gcaagcgctc cagcgcgctg      720
cccaacgtgc cgacggtggc ggaggccggc ctgccgggct atgagctgtc gccgtggttc      780
gccgcctttg tgccggcgaa gacgccgcag ccggtcatcg acacgctcaa ccgcgccatg      840
ctcgaggcgc tgcgcaagcc tgcggtgcag aagcggctgg cgctgatcgg cgccgagccg      900
atcggcagtt cgccggcggt gctgcgcgag cacctggcga aggaaaccga caagtggggt      960
gtgctgatcc gccagcgggg tatccgggcg gattga                                996

<210> SEQ ID NO 88
<211> LENGTH: 993
<212> TYPE: DNA
<213> ORGANISM: C. necator

<400> SEQUENCE: 88
atgagacccc tatccgtcgt cagcagtctg gcatcgctcc tgtttgtcgc aggcagcctg       60
ggcaccctgc ccgggcgcgc cgaagccaat atcgccagta ccttcccgca aaagccgatc      120
cgcatggtgg tgacgttccc ggccggaggg gggaccgatt ctctcgcgcg cctgatcggg      180
gccgacatca gcaagtcgct ggggcagccg gtggtgatcg acaaccggcc cggcgccagc      240
ggcaatattg gcgccgagtt cgtcgccaag agtcctgccg acggctatac gctgctcatt      300
gtcaacagca gctttgccat caacccgagc gtcttcaaga gctgcagtt caatcccaag       360 tccgatttca gcgccgtcat caccttcgct tcggtgccat cggtgatcgc cgtgccatcg      420
cactcgaaac tccgcacctt cagcgacctg ctggcggcgg gcaagagccc atcaccccc       480 agctatgcgt cgtgcggcaa cggcaccccg cagcatctgg ccggcgaact gctcaaggtc      540
tcggcaagga tggacatgct gcacgtgccg tacaagggtt gcgccccgc catcgccgac       600 gtgctcggca accaggccga tgtcagcgtc aacacgctga ccaacaccat ccctacctg       660 aaaagcaaca gctgcgcgc gctggccgtc acgtcgaagg cacgctcgcc gttcctgccc      720
gacgtaccca ccgtgagcga gcttggcgtg gccggctatg acgtcgacca gtggttcggc      780
atcctcgccc cgcaaatac gccgcccgag atcgtgcaaa ggctcaacac ggaaatcgcc      840
agggccatcg ccaggcccga ggtcaaggca tcgctgacgc agctcggctt tgccacgacg      900
acaagcacgc ccgctgaatt ccagaagctg gtgagcgccg acatcgatcg ctggcagaaa      960
ttcacgacga agataaatct gctcgtcgac tga                                   993

<210> SEQ ID NO 89
<211> LENGTH: 1038
<212> TYPE: DNA
<213> ORGANISM: C. necator

<400> SEQUENCE: 89
atgaccctca cacaatgcct gcgccgcccg ctgacgaggc tgactggcgg cctgcttgcc       60
gccgtgctgg ccagcccgat ctgcgccggc gcggccggcg cgaccgcagc cgcgggggcg      120
accggggcgt cctatcccgc caagccgatc gcactgatgg tgccctatcc cgccggcggc      180
gcctccgacg ccatcgcccg cgtgctgagc cagcccgtcg gcaagcagct cggccagacc      240
```

```
gtgctggtgg agaacctggg cggcgtcagc ggcgccatcg ccgcgcagaa ggtgctgtcg      300
gcgccgggcg acggctacta cctgttccag ggctctccca cgaagtgat  cctgtctccg     360 ctggccaatg ccgcggtcaa gctgcaggcg gaggacttcc agctggtgca gccgatttcc      420
accgcggtgc tggcactgat cgcacgcaag gacctggaag ccaactccgc ggacgaactg      480
atcgccctgg cgcgcagccg caaggacaag ccgctgtctt acggcagcgt gggagtgggc      540
tcgctgtacc acatcctggt cgagcatatg cagcaactca ccggcaccag gatgacccac      600
gtcccttaca agggcgcggc gccgctggta caggacctcg gcggcggcca gctcgacttc      660
gccatcgtgc cgttcaacgc cgcgctcggc gcgatggccc agcagggacg gctgaaactg      720
ctcgccaccg cgggcgccac ccgggcgccg ctgttgccca atgtgcccac catcggcgaa      780
ggcaagctgc tgaagaactt cgccttcacg atctggaccg gcttcatggt gaagaaggga      840
accccgcccg aggtggtgca gcgcctgaac ctggcgctcg gcaatgtcct caaggatccc      900
gccgtgcgcg ccgggctgga agcccagatg cagaccgtgg ccacgccgat gacgctgcag      960
gaggcggccc gcttctacga aggcgagacg gcgcgctacc gcggcctggc caaggccatc     1020
gggctgcagc cgcaatga                                                   1038

<210> SEQ ID NO 90
<211> LENGTH: 969
<212> TYPE: DNA
<213> ORGANISM: C. necator

<400> SEQUENCE: 90
atgaaacgca tgacgatcgc cgcggccgcc ctggcggccc tggctgcggc cgccccggcc       60
cacagcacca acgcctatcc caccaagccg gtcaccctgg tggtgcccag cgcaccggcc      120
ggatccaccg atatcgttgc ccgcctggtc ggcgaacaac tgcaggccgc gcttggccag      180
cccgtggtgg tggacaacaa gcccggtgcc agcggcaata tcggcaccga agccgtggcg      240
cgcgccgcgc cggacggcta tacgctgctg cttcagtatt ccggctacca cgtcggcaat      300
ccggcgctgt tcccgcagat ccgctggaag ccgtccagct tcgtcccggt ggcgctggtc      360
atgcgcgcgc gcacgtcat  cgccatcaac ggcaagctgc ccgcgacatc gatagccgaa      420
ctggttacct acggcaaaag caatggcaag gcctgttct  atgcctcgtc cggcaatggc      480
tcgatccagc atatcgccgg cgagatgctg gcgcggcaga ccagggtgcc gatgacgcac      540
gtaccgtaca agggcgccgg gcccgtggtc accgacctga tcagcgggca ggtcgacatg      600
ttcatcacga ccccgccgag cgtgatcggg catgtgcagg cgggcaagat caaggcgctt      660
gcctatgccg gaccgaagcg ccatccctcc atgcccaatg tgccgaccac cgcggaggct      720
gggctgccag ggtatgaggt ggaatcctgg tttgcactgt ttgcaccggc gaatacaccg      780
ccggccatcg tcgagcgctt gtcccaggag gtgaagaaga tcgtggccag cgacacgtac      840
aggaagaaga tcgaggaaca aggtgccttt gccgcctaca tggggccgca ggagctgggc      900
aagttcgtcg atcaggaact ggcgtcctgg tcgcgtgtgg tcaagacatc gaatattcgc      960
gcggactaa                                                              969

<210> SEQ ID NO 91
<211> LENGTH: 972
<212> TYPE: DNA
<213> ORGANISM: C. necator

<400> SEQUENCE: 91
atgaagacac ggacgacact ggcagccctg accgccacgc tgctgctgca gggcgcggcg       60
```

```
tgggccgccg acgcctaccc gtcgcggccg atcaagctgc tggtgggtta cgcgcccggc      120
ggcccggtcg acacagccgc gcgcatctat gccgagcaac tcgggcgcgt gctcaagcag      180
ccggtggtgg tggataaccg cgcgggcgcc agcggcgcga tcgccgccga catgaccgcc      240
aaggcggcgc cggacggcta cacgctgtat ttcgtcgcca gcccgaccat gaccatgacg      300
ccgctgatcc agcactcggt caatttcaat ccggtcaagg actttaccta catcggcctg      360
atcaccgatt acaccaacgt gctgctggtg aacaaggact cccggcgaa gaacgtgggc       420 gagctggtcg actatgcgcg caagcatcct gaggggtct cgttcggctc ggccggcatt       480
ggggcatcga accacctgtc cgcggaattg ctggctcaaa tgaacagcgt gaagatgctg      540
catgtgccgt acaagggcaa tgcgccggcc atggctgacg tgatgagcgg caaggtcacg      600
ttcatgttcg atattaccgg cacggccatc gggcatatca atggcggcaa ggtgcgggcg      660
ctggcggtca cgtcgaagac tcgcaacccg cgctgccga acgtgccgac catgatcgag       720
tcggggcaga aggactatga cctgaccggc tggtatgcgc tggtggggcc gcagaagctg      780
ccggccgatg tggtggacaa gctggtcaag gcgcagaagg cggttgggga ggatgctgct     840
ttccggcaac ggatgacggc tgggggtat gacgtgaata tcagcacgcc gaaggcgctg       900
ggagatcgga ttcagcggga gctggcgctt tggggtgggg tggtgaaggc ggcgaagatt      960
caggcggatt ga                                                          972

<210> SEQ ID NO 92
<211> LENGTH: 1008
<212> TYPE: DNA
<213> ORGANISM: C. necator

<400> SEQUENCE: 92
atgcaggcag atcgtcgtag tgcgctgtgg cgctttgggg ccggattgct ggcgtggagc       60
ggcgttgccg ccgggatgct gggggcgggc gccgcgctcg cgcagagcga attcccggcg      120
cgcaccgtgc gcatggtcgt gcccttcccg gcaggtggcg ccaccgatgt gctggcccgc      180
gccattgccg aagggctggg caaggcctgg aagcgcccgg tggtggtgga aaaccgcccg      240
ggtgcgagcg gcatgctcgg cgccgaggtg gtcgcccgtg ccgaggccga cggctacacc      300
gcgctgctga cgatcacgcc gctggtgcag gcgccaagcc tgtatgcccg ggcgccctat      360
gacccggtga aggatttcgc cgcggtgtcc gagctcggca cgaccaacct ggtgttcgcc      420
gtcaacagca tgcgggtgcc tgccaccaac ctgaaagact tcatcgcgca ggttcgcgcc      480
aagccgaagc agttctccta cggctcgttc ggggccggct cgagcggcca cctgtacggc      540
gaggtcttca cgaggccgc caagatcgac atgctccatg tctcatacaa gggcgaggct      600
ccggagctga acgacctgct gggcggccag gtgccggcgg cggtgatctc ggtgatgggc     660
gccaagcccc acgtcgccac cggccgcctg cgcgccctcg cggtgactgg ccccgcgcgc      720
gcgccgcaac tgccggatgt gccgactttc cgcgaagccg gcattgaagg catggatgcg      780
atgggctggt tcgggctgct gctgccggcc gccacgccgc ggccgatcgt tgagaagttc      840
tcggcggacg tcaaccgcgt gctggcccag cccgacgtgc gcaagcgcat gaacgagctt      900
ggcgtgatcc tgaccggcag cacgccggac gcgtttgccc agaccatcca ggccgactat      960
gtccgctggg gcaaggtgat ccgcaccagg aacatccgcc tggattaa               1008

<210> SEQ ID NO 93
<211> LENGTH: 984
<212> TYPE: DNA
```

<213> ORGANISM: C. necator

<400> SEQUENCE: 93

| | | | | | |
|---|---|---|---|---|---|
| atgcagcaaa | gcagacgcaa | ctggctggca | caggccggca | ccctggccgg | cgcggccatc | 60
| ctcggcggcg | cgggcagcgc | cttcgcgcag | caatcgtatc | cgagcaagcc | gatccgcatg | 120
| atcgtgccgt | accggccgg | cggcggcacc | gacaccgtgg | gccgcctgat | cggccagcgc | 180
| ctggccgaaa | gcctgggcca | gccggtggtg | gtcgaaaaca | gcccggcgc | cagcggcatg | 240
| ctgggcaacg | acaccgtcgc | caaggcgccg | gccgacggct | acaccatcct | gctggcgatc | 300
| acggccctga | tccaggcgcc | ggccctgtac | aagcgcacgc | catacgacgt | ggccagggac | 360
| ttcacgccgg | tctcgcagat | cgccaagtcg | tccgacctgt | tcgtggtgcc | caaccgcgtg | 420
| cccgccagca | atatgcgcga | gttcctggcg | ctggccaagg | cgggcaagct | cagctatggc | 480
| tcctacggca | acggcacctc | gtcgcacctg | cacgcgagc | tgctcaagca | gcaggcaggc | 540
| atcgagctcg | cgcatatccc | ttacaagggg | gcggcgccgc | tgatgagcga | cctgctcggc | 600
| ggccaggtgg | acagcgcctt | tgtcgacgtg | acctcggcca | cgcctacct | gggcagcaac | 660
| aagttcaaga | tcctcggcat | caccggcacc | cagcgctaca | aggcgctgcc | caatgtggcg | 720
| accttcactg | aactgggcct | gccggggttc | gagcccaacg | gctggtacgg | gctgttcctg | 780
| ccggccaatg | cgcccaagga | tgtgacggcg | aagctggcgg | cagagaccgc | gcgcatcgtg | 840
| cgcctgcccg | aagtgacgca | gaagctggcc | ggcatgggcc | tgcagccggt | cgggtccacg | 900
| ccgcaggaac | tggcggccgt | ggtcgccggc | gacacaccca | gtgggccag | gatcgtgcgc | 960
| gacgccaata | tccagctcga | ctga | | | | 984

<210> SEQ ID NO 94
<211> LENGTH: 990
<212> TYPE: DNA
<213> ORGANISM: C. necator

<400> SEQUENCE: 94

| | | | | | |
|---|---|---|---|---|---|
| atgaaggcaa | agactttcat | cacgacactg | gctgccgcgg | cagccatcgt | attgccggcg | 60
| atgctggcgc | agccggcggc | ggcggccgat | gccgcctacc | cgtcgcaccc | gatccgcatg | 120
| gtggtgccgt | tcccgccggg | cggcccgacc | gacctggtgt | cgcgcgtgat | cgcacggcgc | 180
| atgagcgaga | cgctcggcca | gcaggtgctg | gtcgacaacc | ggcccggcgc | caacggcaat | 240
| atcggcgcgg | agatcgtcgc | caaggcgccg | gccgacggct | atacggtgct | gtacaacacc | 300
| tcgtcgatcg | cgctgagccc | ggcgctctac | cgcaagctca | gctacgacgt | gaaacgcgat | 360
| ttcgcgccgg | tggcgctgac | ggcaatggtg | ccgctggtgc | tggaggtcaa | cgcgcagctg | 420
| ccggtacaga | acgtgaaaga | gttcatccag | tacctgaagg | ccaaccccga | caagctcacc | 480
| tacggctcgg | ccggcaacgg | caacgtgacg | cacctggcgg | ccttcatgtt | cctgcaggcc | 540
| aacggtctgt | cggcagtgca | tgcgccctac | aagggcagcg | cgccggcact | gaccgacctg | 600
| gccagcggac | aggtgcagtt | catggccgac | accatcaatt | catcgctgcc | cttcatccgc | 660
| gacaagcgca | tgcgcgcgct | ggccgtcacc | agcaccacgc | gcagcgccca | gttgccggac | 720
| gtgcccaccc | ttgccgaaac | cgtgcagccg | ggcttcgagg | tcggcgcctg | cagggcatg | 780
| atggtgccgg | ccaggacacc | ggccgagatc | gtgcgcaagc | tcaatgccgc | cgccaccaag | 840
| gcgctggccc | accccgagac | gcgcgcaagc | ctggccgcgc | aggggcgga | gccgcgcgga | 900
| tcgaccccgg | aggcctacgc | cgcctacctc | agcgcggaaa | tgacgcgctg | gcagaaggtc | 960
| gtgaaggatt | caggcgcgac | gctggactga | | | | 990

<210> SEQ ID NO 95
<211> LENGTH: 993
<212> TYPE: DNA
<213> ORGANISM: C. necator

<400> SEQUENCE: 95

| | | | | | |
|---|---|---|---|---|---|
| atgaagtccg | tacgccgcaa | agtactcgcc | acgctggccg | ccgcgaccgc | cctggtcgct | 60 |
| gccaccggcg | gcaccgccct | ggcccagggt | gcgtacccga | acaagcccat | caccatcgtt | 120 |
| gtagcctatc | cggccggcgg | cgacgtcgac | gtgctggcgc | gcctgttcgc | ggaaaagctc | 180 |
| gccccgcgcc | tgaagcagtc | ggtggtggtg | aaaaaccgca | ccggcgccgc | cggcaccatc | 240 |
| ggcagcgcct | acgtggcgcg | cgccaacccg | gacggctaca | ccctgctgct | gccccccaac | 300 |
| accgtcgccc | tcgcgccgct | ggtgctcaag | gccggcaccg | cgccagcta | tgacgtgcag | 360 |
| cacgacctca | ctcccatcag | ccagatcggc | acgcagtcgc | tgttcgtggt | cgtcaacaag | 420 |
| ggcagcggca | tcaccaaggt | cagcgagctg | gtggcgcgcg | ccaaggccgg | caaggtggaa | 480 |
| acctatgcca | cgcccggcaa | tggctcgccg | atgcacatca | tgggcgaaat | gttcaacaag | 540 |
| tccgccggca | tcaagatcag | ccaggtgccc | taccgcggct | tggcgccggc | catcgtcgac | 600 |
| gtgatcggcg | ggcaggtgcc | ggtgacctac | atcacctatg | cgcaatctc | gcagtatgtc | 660 |
| ggcaacggca | gcctggtgcc | gctggcggtt | cggaccaga | agcgctcgcc | gttcgcgccc | 720 |
| aacgtgccga | cgctggccga | gctgggctac | aaggacgtgg | aaatcggcgc | ctggcaggcc | 780 |
| ctgctcggac | cgaagggcat | gccggccgac | ctggtgcgca | cgctcaacac | gcacgtcaac | 840 |
| gagatcctga | agatgcccga | cgtggtggcg | cgcatggcca | ccatcgcggt | cacgcctgcg | 900 |
| ggcggcgagc | cggcggtgct | gtcgaagctg | atcgccgccg | acaccgcccg | ctacaccaag | 960 |
| gtggtcaagg | agttcggcat | ccaggcggac | tag | | | 993 |

<210> SEQ ID NO 96
<211> LENGTH: 993
<212> TYPE: DNA
<213> ORGANISM: C. necator

<400> SEQUENCE: 96

| | | | | | |
|---|---|---|---|---|---|
| atgagacacg | aacgccccg | ccgccttttc | cttgcagcca | ctgccatggc | cgcgcttgcg | 60 |
| cttgccgcgg | gcagcgcgct | ggccaccgcc | gcgtatccgg | ccaagaccgt | gaccatggtc | 120 |
| gtggcctatc | cgcctggcgg | cgacaccgac | gccatggccc | ggctctatgc | cgacaagctg | 180 |
| tcggcgcgcc | tgaagcagcc | ggtcatcgtc | gagaaccgcc | ccggtgccgg | cggcgtggtc | 240 |
| ggcgccagct | tcgtcagccg | cgcgccggcg | gacggctaca | cgctgctgta | cacgcccaac | 300 |
| cctttcacgc | tggcgccgat | ggtgctcaag | ctggcgccgt | cggccagcta | tgacccgctg | 360 |
| cacggcttca | ccccgtgat | ccagaccgcg | gtgcaggcgg | tgctgctggt | ggccaacccg | 420 |
| caggccggca | tcaagaccgt | cggcgagatg | attgccgtgg | caggggcgg | caagacgctg | 480 |
| acctatggca | gcccgggcgc | gggttcgccg | atgcacatcg | ccggcgagat | gctcaaccgc | 540 |
| gccgcgggcg | tgaagatcca | gcacgtgccg | tacaagggcg | tggcgccggc | ggtcaacgac | 600 |
| gtggtggcgg | ggcacgtgaa | ctttgcctac | gtcacgctgg | gtccggtggc | gcagtacatc | 660 |
| aacaccggcc | ggctgatccc | gctggcgatc | acggacgcaa | agcgctcgcc | gctgctgccc | 720 |
| aacgtgccga | cgctgccgga | gctcggctac | aaggacgtgg | tggtcggcgc | ctggcatggc | 780 |
| gtgatggcgc | ccaagggcac | gccgcccgag | gtggtcaagg | tgctgaacca | gcagctcaac | 840 |

```
gacgtgctgc gcctgccgga cgtgaccgag aagatggcca ccttcggcgc cagcccggtg      900
ggcggcgccc cggccgcgct ggaaaaggtc aacgcggccg actacgagcg gctgggcaag      960
gtgatccgcg acctcgcgat cacggcggaa tga                                   993

<210> SEQ ID NO 97
<211> LENGTH: 1017
<212> TYPE: DNA
<213> ORGANISM: C. necator

<400> SEQUENCE: 97
atgcagcaac gcaagacata caacaggccg ccgcgccggc ggcaatggct ggccggcacg       60
gcgctggccg ctgcgctggc ggcgtgcgtg ccgtggcagg cggcgcaagc cgccggctgc      120
gccaatgtgc gcatcgtggt gccgttcccg gccggcggcc cggcagacca gctcgcgcgc      180
acgctggcgc acgggctgca gcagcggcgc ggcacgccgt tcgtggtaga caacaagcct      240
ggcgccaacg gcaatatcgg catcgacacg gtgcggcgcg cgccgggcga cggctgcacg      300
ctgctggtgg ccccggccgg caacctgacc atcaaccca gctgatgcc ggcgctgagc       360 tacaacgtcg agcgtgattt ccggccggtg tcgctgctgg cgggctcgcc caacgtgctg      420
gcggtgcatc cgtcagtaaa ggcgaattcc gtgcaggacc tggtcaggct ggcacagcag      480
gcagagaagt ccggcaagcc gctgggctac gccagcccgg gcgtcggcag cggcctgcac      540
ctggccggca gctgttccg caacaaggcc ggcatcacgc tgctgcacgt gccctacaaa       600
ggcaccacgc aggcgctcaa cgacgtggtg ggcggacagg tgccgatgct gttcggcacg      660
tggccgacgc tggcgccgtt tatccagtcc ggcgcgctgc gcgcgctggc ggtgacgcag      720
tccaggcgct cgccggccgc gccgaacgtg ccgtcgctgg ccgagcaggg cgtgcccggc      780
atcgacgtca gttcctggta tgcgctgctg gtgcccaggg ccacgccgca gctggcggcc      840
gatgcgctca gcgccgacgt gcgcgcgctg ctggccacgc cccggtgcg ggccgagctg       900 cagcgccagg gcatggagcc ggtgggcagc acggcgcagg cgctcgaggc ccgcatccgc      960
gaggaaaccg cggcgtgggc gaagctgatc aaggcgtacg ggattaccgc ggagtag       1017

<210> SEQ ID NO 98
<211> LENGTH: 1008
<212> TYPE: DNA
<213> ORGANISM: C. necator

<400> SEQUENCE: 98
gtggacaaga cgaagaacaa gccgcaagcc cgccgggaca tcctgagaca cgcactgctg       60
gccctggccg ccgcgccgct ggcactggcg gcggggaccg cgcaagcggc ctggccggaa      120
aagccgatcc ggctggtggt ggcattcccg cccggcggcc cggtcgacac gcacgcgcgc      180
ctgctggccg aaaagctgca gccgatcctg gccagacca tcgtgatcga ctacaaggcc       240
ggcgccgccg gcaatatcgg ctcggacaac gtcgccaagt ccgcgcccga cggctacacg      300
ctgctgctgg ccaacactgg gcagatggcc atcaacaact cgctctatcc caagctgccc      360
tacagcatgc cgaaggactt cgcgccggtg gcacgcacgg cgctgatccc gctggtgatg      420
gtggtcaaca caacgtgcc ggcgcgcgac ctgaaggcgt tcatcagcta tgccaaggcc       480
aacccgggca agctgaactt tgcctcgggc ggcaatggcg gcatctcgca cctgatgccg      540
gaaatgttca gcaggcttc gggcacgttc atcgtccata tcccgtacaa gggcagctcg      600
ccggcgctga ccgacgtgat gggcggccag gcgcagatga tggccgactc gatcccgctg      660
ttcacgcagt acatcaaggc aggcaaggtg cgtgcgctgg cggtgacgtc gccgcagcgc      720
```

```
tctcccgcgc tgccggatgt gccgacgatg caggaggccg ggctgaaggg cttcgaggtg    780
gttggcttct atggcatgct ggcgccggcg ggcacgccca gggaggtggt ctcacgcctg    840
tccggtgcct tgcgcacggt gctggccgac cccgacacca aggcgaagct cgagcagcag    900
ggtgccgagc ccgcatggca gtcgccgag gcatttgccg ccacgatcac ggcggagcag    960
aagcgctggg ggcaggcagt gaaggcgtcg ggcgcaagta tcgactga                1008
```

<210> SEQ ID NO 99
<211> LENGTH: 1008
<212> TYPE: DNA
<213> ORGANISM: C. necator
<400> SEQUENCE: 99

```
atgaaggatg cgaaggattt gcgcgccggg ccacgatggc tggcgggcgt gatggtgatg     60
gcctcggcgc tggctggcac aagcgccgcg gcagcggctg acgcctaccc cggcaagccg    120
atcacgctgg tcgtcccta ctccgccggc ggcccgaccg acgtcgtggc acgcacgctg    180
gcgcaggcga tgtcgcagga tctcggtcag agcgtggtgg tggaaaaccg caccggcgcc    240
ggcggcaccg tggctgccgc ctttgtcgcc cgcgcacagg cggacggcta tacgctgctg    300
atccaccata atggcatggc gaccgcgccg gcactgtaca agaagctgtc gtacgcgccg    360
ctgaaggatt tcgagtatgt cggccaggtc gcggacgtgc cgatgaccct gatgggccgc    420
aaggacctgc cggccaagac cgtgccggaa ctgatccgct acgtgacgca gaacaaggac    480
aaggtgtcgc tggccaatgc cgggctgggc gccgtatcgc aactatgcgg cgtgctgttc    540
gagcaatcgg tccacgtcaa gctcaatgca attccttacc agggcgccgg ccccgcgctg    600
accgcactgc tgggcggcca ggtcgacctg ctgtgcgacc agaccacggc cacgctgccc    660
catatccagg ccgaccgcgt gcgcctgttc ggcgtgacca cgccggcgcg gatcaaggcg    720
ctgcccagtg cgccaacgct gcaggaaggc ggtctcaagg ctttgacgt caaggtctgg    780 cacggcatct acgcgcccaa gggcacgccg cccgctgcag tggcgcggct gaccaaggcg    840
ctgcagaagg ggctgcaaga tcccgtggtg atcaagaaac tcgatggcct gggtgcggaa    900
atcgtgccgg tcgacaagca gacgccgaa ggcctgcgca cactgctcaa ggctgagagc    960
gacaagtggc agccgctgct gaagtcgatg cagatcgagg ccgactaa                1008
```

<210> SEQ ID NO 100
<211> LENGTH: 1071
<212> TYPE: DNA
<213> ORGANISM: C. necator
<400> SEQUENCE: 100

```
atgacacggc aggatgccgg cacggcacga ggccggctgc cggagacgag acacaggaga     60
caaggtatgc agcaaggcag gcgcagggtt ctgcagcaaa tgggtctggg cgtcgcgggt    120
gcggcgctgg cagggggttgg gctgggtgcg cgcgcgcagg tggtgcgggg ggtggatttc    180
ccggcacgca cggtgcgcat cgtgatgcca tacgccgcgg gcgggaccgg cgacgtggtc    240
gcgcgcatgg tcgcggacgg cctggccaag catggggca aggccgtggt ggtggacaac    300
cggccgggtg ccggcggcat gatcggcgcg gacatggtgg ccaaggcaga gccggacggc    360
tatacgctgt tgttcgcgct gaccggcctg gtccaggcgc cgctgctgta cagcaaggca    420
aactacaacg cagtgcgtga cttcgcgccg atctctgagc tggcgacctc caacctggcg    480
ctggtggtgc agcccgacgt gccggcggcc aacgtgaagc aactgatcga ctacatccgc    540
```

| | |
|---|---|
| aagctgggca agccgctgcc gtatggcagc tacgggctgg gttccagcgg gcatctgcag | 600 |
| atggaggtct tcggccgcaa cgccagggtt gaactgaccc acgtgcccta caagggcgag | 660 |
| ggcccgctgg tcaacgacct gcttggcgga caactgcccg ccggcgtcgt ggccgcggtc | 720 |
| accgcgcgca cgcatgcgcg cgccggcaag ctcaaggtgg tcgccgtggc cgggcagtcg | 780 |
| cgctcgccgc tgctgccgga ggtgccgacc ttccaggagg cgggcgtgcc cgggctggag | 840 |
| cgccagggct ggctgggcct gttcgcgccg cggcgacgc cgcgcgccgt ggtcgacaag | 900 |
| gtgtctgccg acgtcaaccg cgtgctggcc aaccccgagc tgcacacacg gctggtcgat | 960 |
| ctcggcatca tcgtcaaggg aagctcgccc gcggcctttg ccgatgtcgt gaaggtggag | 1020 |
| cagacctact gggctgaagc gatccgggcg tccaatatcc gcctggactg a | 1071 |

<210> SEQ ID NO 101
<211> LENGTH: 1026
<212> TYPE: DNA
<213> ORGANISM: C. necator

<400> SEQUENCE: 101

| | |
|---|---|
| atgccccgag caatgaaccc ggctccgacg gaactgcctg caacgccgc gcgccggcgc | 60 |
| gacgtgctgc gcgcgcttgc cgcacttggt cttggtgctg cggccggccc gctatgcgcc | 120 |
| agcaatgcct ggcccgccaa gcccatccgg ctggtggtgc cggccccgcc cggcggcggc | 180 |
| accgacctgt cgcgcgcgc gctggccgca tcgctcggca aggcgctggg ccagaccatc | 240 |
| gtggtcgaca caagcccgg cgcgaccggc atcatcggca cgataccgt ggccaaggcc | 300 |
| agccccgacg gctacacgct tctgttcacc tatgccgcca cggtggtgat caaccagacc | 360 |
| ctgcagccca ggctgcccta tgacggcctg cgcgacctgt tgccggtggc gcaggtcggc | 420 |
| gcgggcggca atttcctggt ggtgacgccg gacttcccgg cgcgcacgct caaggagctc | 480 |
| gtcgcccacg tgctcaagcg cccggatgca tacgactacg gctcatgggg catcggctcg | 540 |
| ggcggccacc tgaccatgga agccctcaag atgcagaccg gcatgaagct cgccacgtg | 600 |
| ccgtacaagg gcgtggcgca gatcctgacc gacatgcagg gcggcgtggt caaggtggcc | 660 |
| tttgtcgata cctcgtcgtc gctgccgctg atccgcgccg gcaagctgcg cgcgctggcc | 720 |
| atcagcggca cgcgccgcgc gccggccacg ccggacgtgc cgaccatgac tgaacagggc | 780 |
| taccggttcg ataccgacag ctggtatggc ctgttcgcgc cggccggcac cagtgccgcc | 840 |
| atcgtgcagc ggctcaatgc ggaagtgacc cgcctgctgg ctgacgcgcc catgcgcgag | 900 |
| cgcttcctgc agctgaacat gggcatggcg cccgccagga gtgccgagca gttcgcgcag | 960 |
| accgtgcgcg acgacgtggg cgtgtggggc aaggtgatcc aggccaacca catcacggtc | 1020 |
| gactga | 1026 |

<210> SEQ ID NO 102
<211> LENGTH: 1008
<212> TYPE: DNA
<213> ORGANISM: C. necator

<400> SEQUENCE: 102

| | |
|---|---|
| atgagcagcc agcacactgg cgcccgcagg gcttgtgcca cgcgcacagc agccctggcc | 60 |
| gcggcgctgg ccctggcggg cgccgccagc gcgcacgccg aggccccgta ccccagcaag | 120 |
| cccatccgca tggtgctgcc ctcgggcgcg ggcaccgtca ccgaccagac ggcacggctg | 180 |
| gtggccgagc gcctgaccgc cgcgctcagg cagccggtcg tggtcgacaa ccgcccggc | 240 |
| gccaacggca tcatcgccaa cgagaccgtg gcgcgcgccg cgcccgacgg ctacacgttg | 300 |

| ctgttcacct atgccgcgac catgacggtg aacccgtgga ccacgccgtc gctgccctat | 360 |
| gacccgatca aggacttcac ccccatcgca cgccccagcc agcccggcgg caacctgctc | 420 |
| gcggtcagcg ccaatgtgcc ggtgcacagc ctgcaggagc tgattgccta cgccaggtcc | 480 |
| agcaagacgg aactggcgta ctgctcttgg ggcgtgggct cgggcggcca cctggccatg | 540 |
| gaatacctga aggccaagac cggcatccac ctgcgccata tcccctacaa gaccgccacc | 600 |
| cagtgcagca cgacctggcc gcgggccac gtcaccgtcg gcatcaccga cgccatctcg | 660 |
| tcggtcccgc acctgaagtc cggccgcata cggggcattg cgatctccgg accggagcgc | 720 |
| ctgctgacgg ctccggacgt gccgaccatg tcgcagcagg gcgtgccctt ccagcaagcc | 780 |
| agctgggtcg cgatcttcgg ccccagggc ctgcccgcgc cgatcgtcaa ccggctcaac | 840 |
| gccgaggtga atcgcatcct gcagacaccg ggcgaccgcg agaaattcac tgccatgaac | 900 |
| ctgcagccgg ccgcgccgtc gagcccggcc gacctgggca agctggtcag cgccgacctg | 960 |
| gccgcgtggg gcgaggtggt gaaggtggcg gggctgcagg cgaagtaa | 1008 |

<210> SEQ ID NO 103
<211> LENGTH: 993
<212> TYPE: DNA
<213> ORGANISM: C. necator

<400> SEQUENCE: 103

| atgaaccgcc gaaactggct tgccaccgcc ggcgccgccg cgctgggcag cctgctgctg | 60 |
| ccggcccgcg ccgccagcgc ttcatccagc taccccagcc gcccgatccg gctgatcgtt | 120 |
| ccgtttatcg ccggcagcac gcccgacaac gtggcccgca cgctgtcggc ggagctgggc | 180 |
| aagaagctcg gccagccgct ggtggtcgag aacatgcccg cgccggcgg catcatcggc | 240 |
| gccagcgcgc tgcgccgggc cgcgcccgat ggctatacgc tgggcatact ggccaatgcg | 300 |
| cacgtgatca acgtgcacat gtaccgcaag atgccatacg atccgatcca cgacttcacg | 360 |
| ccgatcacgg ccctgtccgg cggaccgtcc gcgctggtgg tgccggtctc gtcgccctac | 420 |
| aagaccgctg ccgaactgat cgccgccatg aagaaagcgc cgggcaagtt caactacggc | 480 |
| tccggcggca agggcagcat cgcccatctt gcggtggaaa ccatgctgca ccagaccggc | 540 |
| tgtgacgccg tgcatatccc ttacaagggt gcgccggaaa tcatcaccgc catgctgacc | 600 |
| ggacaaaccc agttcggcat gccggtgctc ggcaccgcaa cgcaatacgt gcgcaataac | 660 |
| caggtcaggg tgcttgccgt cactgcggcc acccgttcgc cgttcttccc ggacgtgcca | 720 |
| accatggccg aagccctgcc ccgggctttt gtcatcgaca ctggagcgg cctgttcgca | 780 |
| ccggccaact tcccggccga actgacccag aagctgcatg ccgccgtcgg cgccctgcag | 840 |
| acggccggcg tgtttgatgc ccagctcaag gccaatgccg gcgaactgcg ccgcagcgcc | 900 |
| tcgcccgcgc agttcggcac cattgtcgcc agcgacaacg cgcgttacgg cgacctgatg | 960 |
| aagtcgatcg gcatgctcgg cgacctgggg tga | 993 |

<210> SEQ ID NO 104
<211> LENGTH: 1005
<212> TYPE: DNA
<213> ORGANISM: C. necator

<400> SEQUENCE: 104

| atgcaacagg ttttccgttc ccgccgccgc ttccttggac tggctgccgc cgcactggcg | 60 |
| gccatcggca ccgccacgcc gctggcggcg cccgccgccg agtccgccga cgccttcccg | 120 |

```
tcccgcccga tccgctttgt cgtgcccttc ccttccggca gcggcaccga caccaccgcg        180
cgcatgttcg ccaagaagat cggcgagctg accggccagg cgtggtggt ggagaacaag         240 cccggcggca acggcttcat tggcgtgcag accgcgctga acgcgccgcc agacggctac        300
accgtcttta tcggcagcaa ttccacgctg tcgaccaacg ccgccacctt ccgcaagctg        360
ccgtatgacc cgctgaccga ctttgcgccg atcacgctgc tgtcgcgcgg gccatgcgtg        420
atcatcgtgc cggcaagctc gccctaccgc acgctgacgg aactgctgga agatgcccgc        480
aagcgccccg gcgcgctcaa ttacggctcg ggctcgatct cctacacgct ctactccgag        540
tggctcaacg acctggcccg catcaagacc accgccgtgc cgtacaaggg cgctggcgat        600
gccatcaacg gcgtgatggc ggccaatgtc gacttcgccg tggtggatgc caccggcgcc        660
atcgaactgg tccgcggcgg caaggtccgc gcgctggcct acaccgcacc gcagcgctcg        720
ccgctgctgc cggacgtgcc ctccatcgcc gaagccggcc tgccggactt cctggcctac        780
aactgggtag ccgcggcggt ctcggcaaag acgccgccgg cagtggtgaa acggctgcag        840
gacctgtttg cgcaggccgg cagggccccg gatgtgcgcg agtactacac gcgccagtcg        900
accaagctga tcctgtcatc gcctgccgaa atgctgcagt accagaagga cgagatccag        960
cgctggaagc ggctggcgga ggtggccaag atcccgctgc aataa                       1005

<210> SEQ ID NO 105
<211> LENGTH: 1014
<212> TYPE: DNA
<213> ORGANISM: C. necator

<400> SEQUENCE: 105
atgacgaccg ctgcccacct gctgcgcggc ccgctgctgc aagccgccct gcccctgctc        60
accgtgctgg ccctggccgc cgcgcccgcc ccggccggcg cacagggcgc ctacccggcc        120
aagcccatcc acctgatcgt cgcctacccg ccgggcgggc tgaccgacac gctggcgcgc        180
accatcggcg atggcctgtc gcgccagctc ggcaagacgg tggtggtgga gaacaagggc        240
ggtgccggcg gcatcatcgg caccgactac gtcgccaagt cggcgcctga cggctatacg        300
ctgctgatga ccattcccgg cccgatcacg tccaacctgg cgctgtacaa gaagctgccc        360
tacgatccgc gcactgagct cgcgcccgatc tccgacatcg ccaccgcgcg caccgtgctg        420
gcggtcaaca gcagcgtgcc ggccaagacc gttgccgaac tgctggccta tgccaaggca        480
tcgccgggca agctgcgcat ggggtcgtgg ggcgcgggca cgcagccgca tacgatccag        540
acctacatcg ccaggcagta ccaggctgac atgctgcatg tgccctaccg cggcgaaggg        600
cccatggtga ccgacctgct cgccggccag gtcaacgtga cggtgggctc cgtgaccgcg        660
ctcaagcaac acttcgccac cggcaagctg cggcccctcg ctgtcaccgg cacgcgccgc        720
gcacagggcc tgccagacgt gccgaccttc gccgaggccg gctacgccga cgaaccgttc        780
cggctgaccg gcccgatcac gctgatggcc ccgcgaaga gccgcagga catcatcgac        840 cgcctgggcc gcgagaccgc cagcctggtc gccagcgcca catgcagcg gcgcatcgtg        900 gacatgggcg cggaaccgct cggcaatacc ccggcacagg cagaggcggc gtacaaggcg        960
tacctgccgg tggtgctcaa gctgacggcg gatacggggg tgacactcga ctga             1014

<210> SEQ ID NO 106
<211> LENGTH: 981
<212> TYPE: DNA
<213> ORGANISM: C. necator

<400> SEQUENCE: 106
```

```
atgaatcgga ccacaatctt cgcccgggcc gtgctgacgg ccggcctggc gatgctgtgc    60
ctggccagcc cggcgcaggc gcaaacgtat ccgtcgcggc cggtcaagct ggtgtcgcca   120
tatggcgccg gcggctccaa tgacatctct gcccgcatcc ttgccgaggc acttggccac   180
aagctgggcc aacaggtggt ggtggagaac aagcctggcg ccggcacgcg cctggccacc   240
gagcaggtgg cccgtgccgc gccggacggc tacacgctgc tgtgggctgc cgcgcccttc   300
gccatcaata ccgcggcagg catcgcccag cgctacgacg tccacaagga cttcgtgccg   360
gtgggaccgc gcgtgctggg cccggtcttc ctgatcgtca atgccagctc gccggcccgc   420
accgtgtccg acttcgtgcg catggcccgg gacaagccgg atggcgtgac gctggcctcc   480
ccgggcgcag gctccggccc gcacctgacc gccgagctat cgggcaggt cggcaagttc   540
cagctgctga atgtccatta ccgcggcgac gccaccgcct ataccgaact gctggccggc   600
cgcgcggacg ccaccctgac cgccatcacc tcggcgctgc cctttatcaa ggccggcaag   660
ctgcgcgtgc tggcagtggc ctcggaacag cgttcgccgg tctatccgga tgcgcccacc   720
tttgccgagc agggttaccc gggcatggtc ggctacggct ggttcggcct ggtcgcgccg   780
gccggcacgc cgcccgccgt ctccgagcgc ctgaaccgcg aggcatcggc cgtgctggcc   840
gatgccgaga tccgcaagaa gctgctgggg ctggggctcg agccgcagcc agagccgggc   900
agcgcgtttt ccgccttcat cgaccaggag atcggcaaat ggggcaagct gatcaaggcg   960
cgcggcatca agctggagtg a                                             981

<210> SEQ ID NO 107
<211> LENGTH: 978
<212> TYPE: DNA
<213> ORGANISM: C. necator

<400> SEQUENCE: 107
atgcgttcca ctgctatccg cagcctgctt gcagtcgcca tgctggcggc ctcttcactg    60
gcacttgcgc aaggcgcccg cgactggccc agccagccgg tgcgtattgt cgtgccgttc   120
caggccggct cggccacaga cctgatctcg cggcagatcg gccttggcct cggcaaggaa   180
tacgcccaga ccttcgtggt tgaaaaccgc ccgggcgccg ccgcgatgat cggcagcgag   240
gcggccgcgc gcgcgccggc cgatggctat acgctgctga tgtccgggcc ggcgtcgatg   300
gtgaccaacc ggttcctgta caagaagctc agctatgacc ggatgcgtt cgagaaggtg   360
gcagtggtcg cggtcacgcc gaatatcctg ttgtccaacc cctcgctgcc gttcaagacg   420
ctgcccgaga tggtcgcgta tgccaaggcc aatccgggca agctgaccta tgcctcgttc   480
ggtgccggca ccacctcgca tatcgccggc gagatgctga aggccgcggc cggcatcgat   540
atcgtccatg tgccgtacaa gggcgccggc gaagcgatcc cggcgctgct gtcgggccag   600
gtgtcgatgt atttcgacac catcatgacc ggcctgccgt atgtgaaggc cggcaagctg   660
cgcgcgctcg gcatgtccac cgcaaagcgc tcgcccaacg cgccggagat tcgacgatt   720
gccgagcagg gttatgccgg cttcgatatc gcgccgtggt acggcattgt cgcgcccaag   780
ggcacgccgg ccgacgtggt cagcaagctc aatgtctcga tcaacaagct gctcaaggcg   840
ccggagttcc gtgaacgcct ggctgccacc ggcgccgagc gcgcgcggcgg cagcgtcggc   900
gatttcagcg cgatggtcag cgcggagatc ccgcgcaccg aaaagctggt caagcagtcc   960
ggcgtgaccc tgcaataa                                                 978

<210> SEQ ID NO 108
```

```
<211> LENGTH: 987
<212> TYPE: DNA
<213> ORGANISM: C. necator

<400> SEQUENCE: 108
atgattcatc catgcatgcg taaagtggcc atcgggctgc tgttgccgct ggccgcggcc      60
acagccgcga tggcgcaggc cgcggacgcc agccaatatc cggacaagcc agtccgcgtc     120
atcgtgccgt tcccgcggg cagcggcacc gacagcagtg cgcgctttgt cgccgagcgg     180
atcaccgcgc agacgggcaa gcccgtggtg gtggacaacc gtccgggcgc caacggcttc     240
attgccgcca aggccgtggc cggcgcaacc ggcgacggct acaccatgct ggtgacgacc     300
aacaccacgc atgctgccaa tgcgtccttg ttcaagaagc ttccttatga cccgatcaag     360
gatttcgccc cggcatcgct gatcgccaag agcgggctgg tattggtggt gccgcccgac     420
agtccggtac gcacgctggc agacctgacg gcgctggcca aggcaagaaa tgggacgctg     480
acgtttgcca gcggcagttc gtcgaccccg atcgccagcg aactctacaa gatgctggcc     540
ggcgtgcagg cgctgcatgt gccctacaaa ggggtgccgc tggccctgac cgacctgatg     600
gggcaccaga tcgatttcat gatctccgat atttctccgg ccatgacgct gatccagggc     660
ggcaagctgc gcgcggtcgc ggtgaccact gcgcagcgca atccggtact caaggatgtc     720
cccacgatgg ctgagagcgg cctgcccggc tatgagatgg tggcatggtc ggcggccttc     780
ttcccggccg ggacgccgaa gcccgtggtg gaccgcatga gcgaactgat gcggaacggc     840
ctgaccgggc cggctgccac cgactacttt gcccgcaccg aggtcagcc tgcgccatcg     900 acgtccgagg aactggccgc ctttgtccgc agcgagaccc tgaaatgggc caaggtgatc     960
aaggcagcgg gaatcgagcc cgagtga                                          987

<210> SEQ ID NO 109
<211> LENGTH: 1011
<212> TYPE: DNA
<213> ORGANISM: C. necator

<400> SEQUENCE: 109
atgaatcaag cacaaccgtc ggcgcgccgc agggcgtcgc tgtcatgcat gctcggcctg      60
gcgctgtcgg tggcgctgcc ggctgcgctc ccatcgaccg cccaggctca ggcgtggccg     120
accaaggtgg tcaggatcgt ggtcggcggc ccgccggcg gcaccgccga tatcctcggg     180
cgcctgctgg ccgagggct gacgcagtcg ctgggcaagc cggtgatcgt cgagcagaag     240
ccgggcggcg ccgggcgcgat cgcggtcaac acactgcttt ccgcaccgca tgacggacat     300
acgctgctgc tgatccaggg cggcatcgtt tccgaaacgc cgctggcgct gaaggtctcg     360
ttcgatcctt tcaaggacct gaaacctgtt gcccaggtgg cccgtacggg gctggtgctg     420
gtgggcaacc ccaagctgcc ggcgaagaac ttcagcgaac tgcttgccta catcaagagc     480
aagcccgggc agatcgacta tgcctcttat gccgccggca tgcgcggcca gaccatcggc     540
gtccagttca accgcctggc cggcgtggat atgaagcatg tcggctacaa gggatcgccg     600
cccgcgctgc aggacgtgat gggcggccat gtgccgctga tgttcgacgg cctggccacg     660
tcgctgccgc tgatcaagtc cggcaagctc aaggcctatg ccgtggcgta tcccaagcgc     720
atccccgcgc tgccggatgt gccgaccttc gccgaagtcg gcttcccggc gatgacggag     780
cccggctgga tggggtgtg gctgccgccg gacgtgccgg cggcggtgca ggaaaagatc     840
cgcaacgcca cgctgccat cgtgcagcag cccggctacc gcgagcgcgt ggaggccatg     900
ggcatggacg ccgggcagcc gctcagcagc gaggccctgt ccagggatgc gcgcgccgcc     960
```

| catgagcggc aggcggagtt gctgcggtcg atacatttcg tgccggagta g | 1011 |

<210> SEQ ID NO 110
<211> LENGTH: 993
<212> TYPE: DNA
<213> ORGANISM: C. necator

<400> SEQUENCE: 110

| atgtcatcac tgaagaagct gctcgccatc acattgtgcg cagaggcaat cattgccctg | 60 |
| tgcgcgccag ggccgctgca ggcacaggaa gcctggcccg cacgcccgat tcaaatgatc | 120 |
| gttccgtcgt ctcccggctc gggaaccgac gcgctggcgc gggccatggc gcagcgcctt | 180 |
| tccgaatcgc tgaagcaggc cgtggtcgtg agaaccggc cgggcggcag cggggtgatc | 240 |
| ggaaccaatg ccgttctcaa gcggcgccg acggctaca cgattctcta cacaacggca | 300 |
| tccaacatgg tggttgcgcc tgccgtcatg aagtccatat cccaggaggc aagaaagggc | 360 |
| ctcatgccga tcgcgcagac agccgcgggt ggggtgttgc tgctggtgag cccggacctg | 420 |
| ccggtgcacg acttgccagg actcatcgag ctggtgaagg cgaatccgga caagtacagc | 480 |
| tatggcagct gggccaccgg ctcgtccgcg cacttgacca tggaatggct gaagaagcag | 540 |
| accggcatga agaccgagca cgtcgcatat cggacaacaa gtcaactgct caccgagctt | 600 |
| tcctcagggg tgctgaagat cggctggacc gatcccagcg tcgcggttcc gttcctgcgt | 660 |
| tccgggaagg tgcgtggcat tgccatcgtc ggcaacgtgc gctcgccaca gcttgccgac | 720 |
| gtcaagacca tgagtgaaca gggctacaag ttcaacacgg tgggatggtt cggcatgttc | 780 |
| gccccggccg gaaccagtcc ggcgatcgtg aagcggctgt ccgatgaggc caacaaggtg | 840 |
| caggcattgc cggagatcgc ggcgctgatg aagaaactga acttcgagcc gccgccggta | 900 |
| aagacctccg cgcagctggg cgagatcgtc cgcagcgatc tgcaagtctg gtcgaagatc | 960 |
| gctagcgacg cagggatcag ggtcgacgaa tag | 993 |

<210> SEQ ID NO 111
<211> LENGTH: 996
<212> TYPE: DNA
<213> ORGANISM: C. necator

<400> SEQUENCE: 111

| atgaggaagc gaaccaataa cctatggtgg cgcggatacg ccctggcgat cggagtcggt | 60 |
| gtcgtcggtg gggtgcccgt ggctcacgcc caggaggatt ggccaagcaa gccgatccgc | 120 |
| ctggtggtgg cggggcctgc cggcggcagc gccgacgccc tggcgcggct gctggcggaa | 180 |
| ggcctgcaga aggcgtggag caagccggtg atcgtggaaa acaagcctgg tgccgccggc | 240 |
| gcgctggcga tcagcgattt gcaggccacc ggcaaggatg ccataccct tctggtcatc | 300 |
| cagggcggtg tcgtcagcga agcgccgttg gcctacaagg tctattacaa gccctttgcc | 360 |
| gacctgaagc cctggcccca ggtcagccgc acggggttgg tgctggttgc caacaaggat | 420 |
| gtgccggtct ctaacctcaa gcagttggtg gactacggca atcgcagaa ggacggcctg | 480 |
| gttttcgctt cctacgctgc gggattgagg ggccacacct cggcatact gctcgggcaa | 540 |
| ctcacccacg tgccaatgcg gcatgttggc tacaaggggc tcctccggc attgaacgac | 600 |
| ctgatgggcg gccatgtgcc gctgatgttc gatggggtga ctacctcaat gccgctgatc | 660 |
| aaggcgggga agatcagagc gattgccgtg gcctatccga cccggattgc cggattggcg | 720 |
| gatgtgccga cgttcaagga gctcggttac ccgcagctgg cgcaagcggg ctggttcgcc | 780 |

| | |
|---|---:|
| gtgtggtcgc gcccggatgt cgctccggcg gtccagcaaa aaatccgcga ggcgacgctg | 840 |
| gcgtatttca agcagcccgc agtgcagaac cgcgtcaagg atatgggcat ggagcagggg | 900 |
| aatgccgcca cctcggaaga gatgatggcg gacctgaagc aggcatacca gcaacaggcc | 960 |
| gcgctgctga agtccatcaa ctaccagccg gaataa | 996 |

<210> SEQ ID NO 112
<211> LENGTH: 1080
<212> TYPE: DNA
<213> ORGANISM: C. necator

<400> SEQUENCE: 112

| | |
|---|---:|
| atggagcgcg gcctgatgct gcgctgcaca tggtatcggc cttgctctgt tcacctgcat | 60 |
| caacactctg cctggtgctt agccatgttc cgccgccttg gtcgctgcct tgcctgcctg | 120 |
| ctgttgccgt gcctcggcct ggtccatgcg ggcgcagcgc tggccgaggg cgcgcacggg | 180 |
| tatccgtcgc ggccgatcac gctggtggtg ccatggccag cgggcggcgc caccgatatc | 240 |
| tccatgcgca tcctggcgga gctggccggg cgcgagctgg ggcagccggt cgtggtggag | 300 |
| aaccggccgg cgccggcgg cacgctggtg ggaggcttgc ttgccgcggc gcggccggac | 360 |
| ggctacacca tcggccagct gccgctgacg gtatatcgct tcccgcatca gcagaagacc | 420 |
| gcctggcagc cgctgcgcga catccagccg gtgctgatga tctcgggcta taccttcggc | 480 |
| atcgtggtgc ccgcagacag cccgttacgc tcgctgcgcg acctggtcgc ctggggccgc | 540 |
| gcgcatccgg gcgagctgac cgtgggctcc accggcatcg gcaccaccgc ccatctggcg | 600 |
| atggaggacg tgctcgggcg cagcggccgt gcgctatatcc acgtgccgta tcacggcacc | 660 |
| gctgaccaga tgctggcggt ggccaacggt tcgctgatgg cgggggtcaa ttccaccggc | 720 |
| ttcgcgccct tcgtcgagac cggcaagctg cgcttgctgg ccgtgttcag cgcgcagcgc | 780 |
| tcaccgcgct ggcccgaggt gccgacggta agcgagctgg gctttgccga tgcggttcat | 840 |
| aactcgccct acggcatcgg cgtgccgcgc ggcaccgatc cggcaatcgt ccgccgcctg | 900 |
| catgacgcat tccgtgccgc gatgcagcag ccgcgccacc ttgcggaact ggccaggtac | 960 |
| gaccaggagc tgacctacct gaataccgcg caatacgatg acttcctgcg ccatgcgtgg | 1020 |
| gagaccgagc ggagctttgc cgagcgcgtg ggcaccgcgc ggcccagggg gcagctgtga | 1080 |

<210> SEQ ID NO 113
<211> LENGTH: 1002
<212> TYPE: DNA
<213> ORGANISM: C. necator

<400> SEQUENCE: 113

| | |
|---|---:|
| ttgaagtcca gcatcaagca ccgcgtggcg cgcagcgcgc gtttcgccgc catggccatt | 60 |
| gccggcctgg ccgccgccca caccgccccc actgccctcg ccgccgaagc gtggccggcc | 120 |
| aagccgatca aggtgatcgt gccttacaca ccgggcgggt ccaccgacac cgtctcgcgc | 180 |
| gtcgtgttcg aaagagtctc gcagcggctg ggccagccga tcatcatcga aaacaagccc | 240 |
| ggcgccaaca gcaccctggg cgtcggcgtg gccgcgcgct cggcgccgga tggctacacc | 300 |
| ttcgtgtcgg tacttgccgc ctacagcgcg aacatgtcgc tgtattccaa gctcagctac | 360 |
| aagcccacgg acctggtgcc ggtggcggaa atggccgagc tgccgctgtt cctgttctcc | 420 |
| agcaagaagc tgccggtcaa gaccgtcgcc gaactggtcg actacggcaa gaagcacccc | 480 |
| gacacgctga cctttggttc cagcggcgtc ggcagctccg cgcacctgac gggcgagcga | 540 |
| ctggcgatgg aatcgaagct caagctgacc cacgtgccgt acaacggcag cgcgccgatc | 600 |

```
ctgcccgcgc tggtgtccgg cgaagtctcg gtcgccttcg acccgctgct ggtgccgatg      660
ccgcatgtga atcgggcaa  gatcaatgtg ctggccgtgg cctccgccaa gcgctggcca      720
ggcgagccca acatcccgac catggaagaa gcaggttttc ccggcttcgt gatgagttcc      780
tggaccgggc tgatggcgcc tgccggcacg ccccaaccga tcgtggcccg catggccagg      840
gaaatcgccg cggccacgcg cagcccggag gtcgcgaaga agctgaccga tctcggtttt      900
gtgccggtgg gcggtacttc tgaagaattc cgcaagctga tcgagcgcga taccacgcgc      960
tacggggaga ttgttaaggc ggggaaaatt acgctggatt ga                        1002
```

<210> SEQ ID NO 114
<211> LENGTH: 987
<212> TYPE: DNA
<213> ORGANISM: C. necator

<400> SEQUENCE: 114

```
atgccccgcc tcaacttcaa gcgcctggcc attggcgcac tggccctgcc gatgctggcc       60 gccgccccg  cgcatgccgc cgacgcctac cctgccaagc cgatccgctg gatcgtcccc      120
tacgccgccg gcggcggctc ggacttcctg gcgcggacca tcggccaggg gctgtcggcc      180
aaggtcggcc agccggtggt ggtggacaac aagccgggcg gcaataccgc catcggcgcg      240
gccgagacgg cgcgctcggc cgccgacggc tataccgtgc tgtcggccga caacggcacg      300
ctggtgttca accccggtgct gtacaaatcg ctctcctaca accctggcaa ggacctggct      360
ccggtgacgc tgctgggccg cttcccgatg atcctggtgg tcggcgcggc cagcccggtc      420
aagagcgcca aggaattcat cgcccagacc aaggccaccc agggcggcat caattacggc      480
tcggccggcg cgggcagccc gcaccacctg gcgatggagc tgctgaaggt ggaagccggc      540
ctgtcgatga cgcatgcccc ctaccgtggc gccgcgccgg cgctgtcgga cgtggccgcc      600
ggacaggtgg tggcgatgat ggtggactac gctgccggcg ccggctttat caagggcggc      660
aaggtccggc cgctggcggt ggccaatgcc accggctgc  cgcagctgcc cgacgtgccg      720
acctttgccg aactgggcta cccgcgcgtg gaagctgccg cgctggtggg catggtggtg      780
ccggcgggca cgccgccgga ggtggtcaac acgctgaaca aggatgtggt cgcggcaatc      840
cgcgagcccg ctgtcaacaa gcggctggtg gacttcggcg ttgagccggt cggcaactcg      900
ccgtctcagt tcagcgagct gctgcgcagc gagtccaccc gctggaccaa gctgatccgc      960
gacctgaaga tcacgctgga caattga                                         987
```

<210> SEQ ID NO 115
<211> LENGTH: 987
<212> TYPE: DNA
<213> ORGANISM: C. necator

<400> SEQUENCE: 115

```
ttgatttcca cctcacgccg ccacgccatg ctggccgccc tggctctgtg cggcgcaacc       60
ctggctactc cccctgcctc ggcacagccc aacggccagc cggtgcgcct cgtggtcggc      120
tacgcggccg gcggccccgc cgaccaggcc gcgcgcctgt tgcggtggc  gttgggcaag      180 gcgctcaacg ccaacgtcat cgtcgacaac aagcccggcg ccaatgccac gctggccggc      240
tatgaagtgg tccgcgccag gcccgacggc gccacgctgt ggttcgccgc cagcgcggcg      300
ctgacggtcg cgcccaacat catgaagagc ctgccgtacg accc ggccaa ggacctcgcc      360 ccggtggcac cggtggcgcg ctactacaac atgctggtgg ccaacgtcaa ggagccgttc      420
```

| | |
|---|---|
| aagggcaccc aggacctggt tgcctacgcc agggcgcatc ccggcaagct cagctacggc | 480 |
| tcctcgggcg tcggcagctc caaccacgtc gccatggccc tgttcgcccg gcaggcgcag | 540 |
| gtccagctga accatattcc ctacaagggc aatgccccgg ccatgaccga caccatcggc | 600 |
| ggccagatcg acgtgatgtt cgatatcatc agcaccgcca gcggctatgt gcagagcggc | 660 |
| aaggtcaagc ccatcgccgt gggctcgccc aagcgcagcg catcgctgcc cggcgtgccc | 720 |
| accttccgcg aatccgggat tgccggcctc aaggactacg aagccggcgg ctggtacgcc | 780 |
| atctacgccc ccaagggcgt aaccccgag cagacccaga agctggccgc agcagtgcgg | 840 |
| caggccgtgg aagacgttga gctcaggaag cgctatgccg aactgggcta cgaacagtgg | 900 |
| agcggcacca cgcaggatgt cgtgaacacc gccgcgcgcg agcgcacgca gtgggccagc | 960 |
| gtgctcaagg gcgtgacgct ggactga | 987 |

<210> SEQ ID NO 116
<211> LENGTH: 996
<212> TYPE: DNA
<213> ORGANISM: C. necator

<400> SEQUENCE: 116

| | |
|---|---|
| atgcatccgt tctgcaccgg attgttccgc cggcttgcca aggcagccat tccgttcctc | 60 |
| atggccgcga cagcgccttt gccggcgctc gcagcctttc ccgacaagcc gatccgcatg | 120 |
| gtggtgccgt tcgcccccgg cggcggcacg gacctggtgg cgcgtgccat gggcattacc | 180 |
| atgggcgagg accttggcca gcccgtcatc gtcgataaca agccgggcgg cagcaccatt | 240 |
| atcggcaccg atgcggtggc caagagcgca ccagacggct acacgctggt gatggcgacg | 300 |
| ctggcccacg cggtcaaccc gagcctgcac aagaaactgc cgttcgatac ggagaaggcg | 360 |
| ttcgcgccgg tcatgctggt gggccgctcg cccaacgtgc tggtggtgaa gccggacagc | 420 |
| cccatcaaga ccgtgcagga cctgatcgcg gccgccaagg ccaagccggg caagctcaac | 480 |
| tacgcctcgc agggcgcggg cacttcggcg cacctggccg cgagctgtt caagaacatg | 540 |
| gccagggtcg acttgaacca cattccttat cgcggcgccg gccggcgat cacggacctg | 600 |
| ctcggcggg aggtcgatgt gatgttcgcc acggcagccg cagtcgcgcc gcacctggag | 660 |
| agcggcaagc ttcgggcggt ggcggtcacg accgcacagc gctcgcaggc gccggcgctg | 720 |
| agcaaggtgc caacgatcgc ggaaagcggc gtgcccaatt atgtggcgga tagctggtat | 780 |
| ggcctgttcg taccggccgg cacgccgccg gcggtgatca cgcggctgaa cgccgcggcg | 840 |
| aagaaggccg tgcacaccga cgcgttccgc aagcgcgccg aacaggaggg gcttgccatc | 900 |
| agtggcggca caccagatga gttcggccgc tacgtcaagg ccgagagcca gcgctggagc | 960 |
| aaggtcatca aggacgccaa tatcacggcc gactga | 996 |

<210> SEQ ID NO 117
<211> LENGTH: 1005
<212> TYPE: DNA
<213> ORGANISM: C. necator

<400> SEQUENCE: 117

| | |
|---|---|
| atgaacagga caggcagaac agggcggcgt gcggcgctgg gtgggatcgg cgcgatcgcg | 60 |
| atgatggcca tgatggtcgg atcgcagccg gcggcgttcg cgagcgaggc gtatcccaat | 120 |
| cgcccgatca agatgatcat cccttacacc ccgggcggct cgatcgatac agtcgggcgc | 180 |
| ctggtggctg cacagctgca gcgtcagctt gggcaagcga tcgttatcga gaaccgaccg | 240 |
| ggcgcgtcgg gcatgatcgg gtccgaagcg gtggcgaagg catcggctga cggctatacg | 300 |

| | |
|---|---|
| ctgctcttca atgcctccag ccaggtctac ctgccgctgg tcgcgaagaa cgccccttac | 360 |
| gacgccatca gggatttcac cccgatcgca caggtggggc atgtgccgct gatcgtcgtc | 420 |
| gccaacacca gcctccccac cagctcgctg cgcgacctgg tcaagctggc gaaagccaag | 480 |
| ccgcggacct acacctgggc cacctccggg ctaggcacca ccagccacct ggccgaggag | 540 |
| atgatccgcc acgccttcaa gctggagatg gatatcgtgt cctacaaggg cgccgtgccg | 600 |
| cagttgaacg acgtgatggg cggtcacgtg tcggcggcg tgtcgccgat gccaggcgca | 660 |
| tatccgttcg tcaaggcggg gcggctgaag gtgctggcgg tcaccagcag caagcgtatt | 720 |
| ccgcagcttc ccggcgtgcc gaccgttgcc gagagtggcc tgcccgggtt cgagctgctg | 780 |
| tcgtggtacg ggctctgggg tcccgccaac ctgcctgcgg acatcacccg caagctgtcg | 840 |
| caggaggtca acaaggccgt gcgcgaagcc agtcttaaga cgcgcttcga cgaactggcc | 900 |
| tttgaaaccg tgcagtccac gcctgaacag ttcaaggtgg tgatcaagga tgagatcgac | 960 |
| aaggtcgcgg gcatcgtcaa ggcagccagc atccgtatcg attga | 1005 |

<210> SEQ ID NO 118
<211> LENGTH: 1002
<212> TYPE: DNA
<213> ORGANISM: C. necator

<400> SEQUENCE: 118

| | |
|---|---|
| gtgcgcactc gaaatttcac ccgtatggtc cactcccggc gtcgtgccat tctggccctg | 60 |
| gccgcagtgc cgctgctcgc cggcagcgct ttcgcgcaat cctggcccag caagccgatc | 120 |
| aagcttgtcg tgccgttccc gccgggcggg cccacggata cggcgtcgcg catcgtcggc | 180 |
| cagaagctgg ccgagcgcct gaagcagccc gtcgtggtcg agaaccgcgc cggtgcatcg | 240 |
| ggttccatcg ctgccgcgca ggtagccaag agcgcgcctg acggctacac gctgatgatg | 300 |
| ctggccacgc ccacgctgct ggcgccgcac ctgtacaaga agcgggcta cgacacgacc | 360 |
| aaggacttca cgcccgtggc cacggtctat gacctgccga tcgtggtggt ggtcaacccg | 420 |
| acgctgctgc ccaacgtgac cgacctgccc aagctgatcg cacaggccaa ggcacagccg | 480 |
| ggcaagctca actacaccag ctccggcgcg ggcagcttcg gccacctgag catggaactg | 540 |
| ctcaagcaga tgggcggctt cgagatgcag cacgtgccct acaagggcgg cgtgcccgcc | 600 |
| atcagcgaca cccctcggtgg ccaggtcccg atcatgtacg ccgacctcgt cgccgcgctg | 660 |
| ccgcacatcc aggcgggcaa gctgcgcgcc atcgcggtcg gctcgccgca gcgcgtgagc | 720 |
| atgctgccga acgtcaagac cattgccgag caaggcttca agggctacga cgccgtttcc | 780 |
| tggggcggcc tgctggcgcc gccgggaacg cccaaggagg tggtggaccg cgtgtcgggc | 840 |
| gaggtcggca agatcctggc cgacaaggat gtacaggaca agttgctgaa ggccggcgcc | 900 |
| attgccaact accaggcgcc ggcgcagatg ggccagcgca tccagcagga ctattccaag | 960 |
| tggggcaagg tgatccgcga gaaaggcatc gcggtcgagt aa | 1002 |

<210> SEQ ID NO 119
<211> LENGTH: 960
<212> TYPE: DNA
<213> ORGANISM: C. necator

<400> SEQUENCE: 119

| | |
|---|---|
| ttgaagccgt cgagcaaaca cattgttgcg ctgctgctgg ccgtcgccag caccgcccac | 60 |
| gccgcctatc cggaccgccc tatcaagctg atcgtgccgt tcccgccccgg acaggccact | 120 |

| | |
|---|---|
| gacatcttcg cgcgcgccct ggccgagagg ctgggcaagc agctaggcca gtcaatcgtg | 180 |
| gtggaaaacc gcgccggcgc cggcggcaac atcggcatgg aagtggccgc gaaagccccg | 240 |
| gcagacggct acacgctcgt catgggcggc agcgcgatgg ctatcaacca gacgctgtac | 300 |
| aagaagacca attacgatcc gcgtcaggac ttcgcgccga tctcgggtgt gttctcggtg | 360 |
| ccgctggtgt tcctggctac gccacaatcg ggcttcacgt cattgcgcga cctgatcgcc | 420 |
| aaggccaagg ccgcaccggg caagtacagc tatgccagcg ctggcatcgg cggcacgcag | 480 |
| cacctgtctg ccgagatgct caaagcgcag accggcgtgt ttatcgtgca tattccctac | 540 |
| aagggcagcg ccccgcgca gcggatttc ctgggcaacc agattccgct gatggtcgat | 600 |
| tccgtgaccg ccgccctgcc gctgatccag accagcaagg ccgtgccgct tgctgtaaca | 660 |
| acgtcaaagc gcgtgccgca gttgcggtcg gtgccaaccg tgcgtgagga aggcgtaccg | 720 |
| ggtttcgaag cgcttggatg ggcggtgatg atggcgcccg cgggcacgcc gccggcaatc | 780 |
| gtcaatcagc tcaatgcgga gacggtgaag gcactgcaat cgcccgaact gcacaagttc | 840 |
| attacggatc gcgggtcgga gccgatgccg atgactccgg ttgagacggg gaagtttgtg | 900 |
| gatagcgaga ttcggaagtg ggcgacagtc gtgaagcggt cgggcgcaac ggcggattga | 960 |

<210> SEQ ID NO 120
<211> LENGTH: 1011
<212> TYPE: DNA
<213> ORGANISM: C. necator

<400> SEQUENCE: 120

| | |
|---|---|
| atggcttcac tgaaccgccg ccgcttcctt caatatgccg gtgtttccgc cggcaccctcc | 60 |
| gtgctggcca gcctgccggc ctttgccgca gacaacttcc ccgccaagtc gctgtccctg | 120 |
| gtggtccccct acccggccgg cggtgccagc gacacttcgg cgcgcatctt cggggaatcc | 180 |
| atcagcaaga gcgtcgggca gcaggtggtc gtcgagaact acggcggcgg caccgggctg | 240 |
| atcggcgcca acaaggtgct gggcgcaccg gccgatggc acaccttctt ccacggctcg | 300 |
| atcaacgagg tcttcctggc tcccatgctc aacccggcgg cgcgctacaa gccgcaggac | 360 |
| ttccagctgg ccgcgcccat cagcgacgcc aacatcgtgc tgatggtcag gaacggcatt | 420 |
| gccgtggata ccctggacaa tttcctggac tatgcgaaga aaagcaaggg gaaaccgctg | 480 |
| acctacgcca cggtcggcat cgactccatc tatcacctca tgggcgatgc gctggctgcc | 540 |
| cggctcggcg tgcccttcct gcacgtgccg tacaagggcg gcgctccagc gctgcaaggc | 600 |
| cttgccggcg gggaggtcga cttttgccatc ctgccctacc aatccagttt cgacagcatg | 660 |
| cagcaacagg gccggctgaa ggtgctgagc agcttcgcca aggccctgcc ccggcgctc | 720 |
| aagcatattc cgctgatctc gcaaagccgg ctggtgcccg acttcgagta ctcgatcggc | 780 |
| ggcggctact tcgtcaggca gggcacgccc gctagccggg tggcagtgct gcgcaaggcg | 840 |
| attggcgaag ccctggccaa gcccgagatc cgggccaagc tcgaagccga gggacgtacg | 900 |
| gtcgcacagc cgatcaacag ccaggagcag gcgaatcagg tcttcgacca gtacctggga | 960 |
| cgtgtcacgc aactgatccg gaacgtgggc cgcaagacca cgcgtcctg a | 1011 |

<210> SEQ ID NO 121
<211> LENGTH: 972
<212> TYPE: DNA
<213> ORGANISM: C. necator

<400> SEQUENCE: 121

| | |
|---|---|
| atgaaaccga acttgcgccg ccgcctgatg ctgtgcgccg ccatgctggg cgcgatgccc | 60 |

```
gcgttggcct ggagtgacac ctatcccagc aagccgatcc gcatggtggt gccgtttgcg      120
ccaggcgggg ccacagacgt ggtggcgcgg ctgatttcgc agaagctggg cgaagcgctc      180
aagcagtcgg tggtggtgga aaaccgtccc ggagccaacg gcatcatcgg cacggacatc      240
gtggcgcgcg cggcgccgga cggctacacc ctgctgctga acagcgccgg cgcgcagacc      300
ctcagcccgg tgctgtacaa ggcgggctat gagccgctga agagctttgc gccgatctcg      360
cagatcagca atatcggctt cgtgatggtg gtccatccgt cggtgccggc caagaccgtg      420
caggagttcg tggcgctggc caagtccaag accaagccgc tgagcctgtc ggccggcagc      480
agcatgatcg agctgatcgg cgccaccttc aagtccgcgg cgggcacgcc ggacgtcgtc      540
agcgtgtctt accgcggcac cgggccgcag atgcaggcag tggtggcagg cgaggtcgac      600
atgaccatcg acccgttcaa cggcatggcg atgatcaagg ccggcaagct gcgtccgctg      660
gcggtgttcg cgtccaagcg ctcgcccgcg ctgccggacg tgccgaccat gcatgaggcc      720
ggctatgacg gcatggcctt caattcctgg gcggggctgc tggcaccggc tggcacgccc      780
aaggaaatcg tcacgcggct gaaccaggag gtgaaccgca tcctggcgca gcccgagatc      840
aagcagcgcc tggcagcgat cgactatgag gtggtgggcg cacgccgga gcagtttgcc       900 gcgaccattg ccgaggatgc ggcaaggtgg gcgaagatcg tcaaggatac gaactacaag      960
gcgggttcct ga                                                         972

<210> SEQ ID NO 122
<211> LENGTH: 978
<212> TYPE: DNA
<213> ORGANISM: C. necator

<400> SEQUENCE: 122
gtgagccctc gcaccttcct tccccgcttc gccgcgtgcc tgctggcggt tgccgctgca       60
tggtccgcgc ccgccagcgc gcagtcggac cgtccgctgc gcatcctggt gggctacccg      120
gccggcggca ccgccgacct cgccgcacgc ctggtcggcg acaagctgcg cgagaccctg      180
aaccagaccg tggtcatcga gaacaagccc ggcgccggcg gcggctggt gatggactac      240 gcgcgcacgc agccggccga cggaaatacc ctggtggtgg ccaactcggc ggtcatgacc      300
attgcgccgc tggtctaccg caagctcaac tacgatatcc agcgcgattt cacgcccgtg      360
gcggaggccg ccaacttcca gctggcgctc gctaccgggc cggccagccc ggcgcgcacg      420
ctgaaggact atgtggcatg gctcaaggcc ggtgcgcaga caactcccta cgcctcgccg      480
gcgctgggca gcatcccgca tttcttcggg ctgatgatcg gcaagcaggt tggcatcgac      540
atgctgcacg tccccttcaa cggctctgcg ccgctgatga gcgcgctggt cggcgggcag      600
gtgccggctt cggtcgacac ccttgccgac ctgaccgaaa tgcaccgcgc cggcaagatc      660
cgcgtgctgg cgacttccgg cacccaccgc tcggtggcgc tgcccgatgt gccgaccttc      720
accgagcttg gctacaaggg catcgaaggc gaaggccgct acggcctgct ggcacccgcg      780
ggcacgccgc gcccggtgct cgacaagctc aacgccgcca tcgtcagggc cgtgcagtcg      840
ccggacgtgc gcgacaagtt cctcaagctg gggctggaac ccgcaaccgg cccggccgac      900
gcctttgccg cgtgctcaa ggccgacgcc ggcaagtggg caccggtggt caaggcgtcc      960
ggctataccg gcgactga                                                   978

<210> SEQ ID NO 123
<211> LENGTH: 981
<212> TYPE: DNA
```

<213> ORGANISM: C. necator

<400> SEQUENCE: 123

| | | |
|---|---|---|
| atgcagggtt ggatcaggcg tgcagccgcg gggctggtat ttgcgttcgc ggccacggcc | 60 |
| gccggtaccg cgctggcgga ctatcccgac aagccggtgc ggctggtggt gccctttccg | 120 |
| cccggcggcg ccaccgacct gctggcgcgc gagatcggca acgcactgtc ggcgcggctg | 180 |
| caccagccgg tggtgatcga caaccggccc ggcgccggcg caacctggcc ggccatcgcg | 240 |
| gtggcgcggg ccccggccga cggctatacg ctgctgttcg gcaccttcgg ctcgctggcg | 300 |
| gtcaacaaaa gcctctatga caagcctggc tacgatccgc tgaaggactt cgcgccggtg | 360 |
| gcttcggtcg cctacctgcc caacgtgctg gtggtgcatc ccagcgtgcc ggcgcgcacc | 420 |
| gtgcaggagc tgctggcgct ggcgcgcaag gagcccggca agctgaccta tggctcgttc | 480 |
| ggcaacggct cgtcgtcgca cctggcgggc gagctcttca cccacctggc ggctgtcaat | 540 |
| atcacgcaca ttccgtacaa gggcagcgcc gcgtcgatga ccgacctgat cggcgggcgc | 600 |
| atcaccatga tgttcgacag cgtctcgacc gcgctgccgt atatccgcga caaccgcgtg | 660 |
| cgcgcgctgg cggtgacgac gcagaaaccc tctgaccagc tcccaggcgt gcccacgctg | 720 |
| gccgccgccg cgtgcccggg ctacgagctg accgcgtggt tggcgtggc cgcgccggcc | 780 |
| ggcacgccca aggcagtgat cgaccgcctc aacggcgaga tcgtggcggc gctgaagcag | 840 |
| cctgacctgg ccgccaggct ggccagccag ggcaccgtgc ccttccccgc cacgccggcg | 900 |
| cagttcggca gctatatccg cgcgcagttc gagaagtggg acagcctgat caagtcggcc | 960 |
| aacatcaagc tggacaactg a | 981 |

<210> SEQ ID NO 124
<211> LENGTH: 999
<212> TYPE: DNA
<213> ORGANISM: C. necator

<400> SEQUENCE: 124

| | | |
|---|---|---|
| atgatctcga acatcatccg actcacacgc ggtacctgcc ttgcaacgct gttgtccgcc | 60 |
| ctgcccctgt ccggcgcgct ggcggaaggg gattggccca accgcccat tcgcatcctc | 120 |
| gtcccagctc cggcgggagg cgcatccgac atgatcgcgc gcacgattgc ggaaagcatg | 180 |
| cgccagaacc tcaaacaatc cgtggtggtt gagaacaagc ccggcgcagg cggcatcatt | 240 |
| gccacggagg caatgctcgc cgcgccacgc gatggctaca cattcgtgct gtctcccaac | 300 |
| tcgcttgtga cggagaaccc gtacagctac aaattccgct cgatccgtt caaggatctg | 360 |
| gcaccggtcg ctgaagtggc cagcgtgccg ctggtgctgg tcgccgaccc gcgtctgccg | 420 |
| gtcaccaatg tcagcgagat ggtggcctac gtgaaggcac atccggggaa ggtctccctat | 480 |
| gcgtcctaca gcccgggtac gctttctcac atcaaaggca tgcagttcaa caaggcggcc | 540 |
| gggctggaca tggagcacgt cggctacaaa ggctcgcccc ccgcgctcac cgacctgatg | 600 |
| ggcggccaga ttcagttcat gtttgacggc atgggcaccg cgcttgcgct cgtgaaaccc | 660 |
| ggcaaggtcc gggcgctggc ggtgacatcg gccgagcgtt cgccgttcct gcccgctgtg | 720 |
| ccgacaatgg cggaagcggg ctacccaaat tcagccaga tcatgggcac cagcgtctgg | 780 |
| tccacgcccg acgtgccagc tgccatccgc agcaagctgc agcaggagct aatcaaggcc | 840 |
| gtctcatccc cttcggtgaa gagccagctt gcggcacttg gaatgaacgc agggagtccc | 900 |
| acacagacct ccgccgatct ggagaaaacg ctcaagcggg agaacgagcg gacaggtcag | 960 |
| gcactgcgtg ccatcaacta caagccctcc ttgaactga | 999 |

<210> SEQ ID NO 125
<211> LENGTH: 954
<212> TYPE: DNA
<213> ORGANISM: C. necator

<400> SEQUENCE: 125

| | |
|---|---|
| atgaaaaatt cgatcgcgct gctgttctgt gcattggtca ccacagtctc gatgccgtct | 60 |
| cacgccaatg acagcacgac gccccgtcgc ctcatcgttc cctataccgc gggcggaggc | 120 |
| agcgacacgc tttccagggc aatcggccag aagctttctc aggtactggg cgaacctgtt | 180 |
| gtcgttgaaa accggcccgg ggcaaacggc tacattgccg ctggcgttgt cgccaagagc | 240 |
| ccaccagacg gccgtacctt gcttgtcggc ggcaatgcgc tgattatcgg gccgatgttg | 300 |
| tactcatcgc acaagcttaa tgcgttgaag gatttcactc ctatttccag tctggtcaga | 360 |
| gtgactcttg tactggtcag tagtccgggc cttccggcca acaatggccg agaatttgtc | 420 |
| cagatggcgc gaaaagagaa aggcctgagc tacgcctcgc cgtcgccggg catcatgttt | 480 |
| gcgaccgagc aaatcaaggc gctggccggt tcgacctga tgcgcgtgtc gtaccgtggc | 540 |
| gcaccggaag gctttatcga tgtgacttct ggaagggtat ccgtgatgtt tgacagcgtt | 600 |
| gccgcggagc tgccaaacat cagatcgggt cgcgccaagg ctcttttggt taccggcgaa | 660 |
| aaccgccacc ctctccttcc ggacgtaccg acgcttgctg aatctggcat cccaggctac | 720 |
| gtagaggaca actatatcgg catacttggt ccggccggca tggatccgca cgtcgtcgat | 780 |
| acactgaacg ccgcattgct caaggtcctc cgagaccctg aattcaaggc ctttgcagaa | 840 |
| aggctgggat ttctcccttc acctgcatct cccaaggcct tccgggatat gctcggcgcg | 900 |
| accacaacgc ggtaccaaca gattgccaat cagctcgacc tcaagccgga atag | 954 |

<210> SEQ ID NO 126
<211> LENGTH: 999
<212> TYPE: DNA
<213> ORGANISM: C. necator

<400> SEQUENCE: 126

| | |
|---|---|
| atgacccgat tcaagaacat tggccgccgt tggctcggcg gcctggttgc agcactgctt | 60 |
| tttgcagggc tggcgccggc acacggcttt cctgaccggc cggtaacgct gatggtgccg | 120 |
| ttcccggcgg gcggcctctc cgacgttgtt gcccggaacc tgaacgggtc cctgccccgg | 180 |
| cagttcgggc agccagtcat cgtcgagaac ctcgggggag ctggtggcgc gattgccgcg | 240 |
| cagaaggtcc ttcatgcacc ggccgacggc cacctgctat tgcaggcagg gcccggcgag | 300 |
| ctcatcacta cgccgctggc caatgccgca atcaaattca ggagcgaaga tttcaggctg | 360 |
| gtgcatatgg tcggcactgt cgatcttgcc atcctggtgc gcagggatct gccggtaaag | 420 |
| gatgtcgacg aactcgccgc ctatgccgcg caggcagcca aggccggcaa accactgacg | 480 |
| tacgccagcg tcggcatcgg ctcgctctat cacctcctgg gggcgcacat gtcccaaacc | 540 |
| atcggagcgc cgatgactca cgtcccttac aagggcggcg cgcccgtgat ccaggacctc | 600 |
| gttggcggaa tcgtcgatat cttcatctcg ccatttggca agcctgacat cgaacgcatg | 660 |
| cgcaccggcc aggtccggat gctggccgta ctgtcgccta cgcgagtgga ggcagtgaag | 720 |
| tcggtcccca gcgtcaatga gagcaaggcg ctgcgaggct tcaactattc aacctgggct | 780 |
| ggcatcttcg tgaagaagga cactgccgag cctgtcgtgc aggcggtgca caacgcgatt | 840 |
| gtgcatacgc tggccgaccc ctcggtgcgc gcaagcctgg atgccgcgaa cctgcctgcg | 900 |

| | |
|---|---|
| tccaagccgg tgtcgcttgc cgaaagtcag aaggcctatc agcagagcat cgaacaatac | 960 |
| cgcggcattg cccgtgccat cggcttgcag ccgcaataa | 999 |

<210> SEQ ID NO 127
<211> LENGTH: 984
<212> TYPE: DNA
<213> ORGANISM: C. necator

<400> SEQUENCE: 127

| | |
|---|---|
| atgattcgat ccatccaagg caccgtgctg gcgctggcgt catcgctcat gctggcggcc | 60 |
| gcacccgccg cccacgcgca accgcaatat cccagcaagc cgatccggct ggtggtgccg | 120 |
| ttctcggccg gcagcgccac cgacatcctg gcgcgcatca tcggcagcaa gatgggcgag | 180 |
| ggcggcactt accaggtgat cgtggacaac cgccccggcg ccggcggcac cctgggtgcc | 240 |
| accggcgtgg ccaaggcggc gccggatggc tacacgctga tcctggtttc ggtcgggcac | 300 |
| gccatcaacg ccacgctgta tcccaagctc tcgtatgaca cggtgaagga cttcgcgccg | 360 |
| gtctcgctgg tggccacggt ccccaatgtg ctggtggtca atgccgccag caagtacaag | 420 |
| tcggtgcggg acgtcgtcaa cgccgccaag gcgacgccgg gcgggctgaa tttcgactcg | 480 |
| gcgggttcgg gcagctccac ccacctgagc ggcgagatgt tcaagatgca ggccggcatt | 540 |
| gacatcgtcc atatcccgta caagggcacg ggcgaagcgc tgaccgacgt catggctggc | 600 |
| cggggcgaca tgatgtttgc gcccagcgta tcggccatgc cgttcgtcag cagggcaag | 660 |
| ctgcgggcgc tggcggtcac cacggccagg cgccagcg cgctgccgga gattcccacg | 720 |
| gtggcggagt ccggcttccc cggctacgcg ttcgactcct ggttcggcgt gctggcgccc | 780 |
| gccggcaccc cgaaggaaat cgtcgatgcg ctcaatgccg agatcggcaa ggccttggcc | 840 |
| gcgccggatg tgcgcgagcg cctggccgcc cagggcgcgg agccaaagcg ctcgtcgccg | 900 |
| caggagttcg ctgcctatat ccaggcggag atcggcaagc tggcgccggt ggtcaggcaa | 960 |
| tccggcgtga agcgggggca gtag | 984 |

<210> SEQ ID NO 128
<211> LENGTH: 963
<212> TYPE: DNA
<213> ORGANISM: C. necator

<400> SEQUENCE: 128

| | |
|---|---|
| atgcgatcgc cccgcaagct gtttcacatg gccgccctgc tggcctcact tgccgtcgtc | 60 |
| ggccaggcgc ccgcggcgcc ctacccggat catcctgtcg aactcgtggt gccaagcacg | 120 |
| gcgggcggtg gtaccgacac ggttgcgcgg gccttcagcg aagccatgcg aaagtacctg | 180 |
| ccgcagccgc tgaccgtggt gaacaagcca ggtgccagcg cgccatcgg catgacggaa | 240 |
| gtggcccgcg ccaggcccga tgctacaag ctcggcatca tcatcgcgga agccgtgatc | 300 |
| gtcccgcatc tcgggccgac caccctcgac gccgccgagc tggtgccgat cgcgcgcctg | 360 |
| aatgccgatc cgtcggcgat cacggtcaag gccgactcgc gctggaacac catcgaggcg | 420 |
| ttcctggcat tcgccgcggc gcacccgggg gaggtgcagg tcgggaattc cggcccgggc | 480 |
| tcgatctggc acctggcggc gacggcgctg gaggacaagg cgcacgtcaa attcaatcat | 540 |
| gtgccgttct ccggtgcggc gccggccctg gtggcgttga tgggcgggca tatcgacgcg | 600 |
| gtggccgtca gtccggccga agtatcggcc tatgtggccg caggcaaggt gaagacgctc | 660 |
| gcggtgatgg ccgggcagcg tgtcagggc ttcgagaacg ttccgacgct gcgtgagcgc | 720 |
| ggtatcgacc tctcgatcgg cacatggcgc ggactggccg cgcccagggg cacgccacct | 780 |

```
gaagtgctcg aaaccctcgc ggccgccagc cgcaaggcgg tggcggaccc tgtcttcgtg    840
gcggcgctgg gccggcagaa ccttgggatt gcctatgccg acgcggcgac cttcaaggcg    900
atgatcgcgg cagacaacgc ggtgatgaag gtactggtgg ccaggaccaa cctgcggaag    960
tga                                                                  963

<210> SEQ ID NO 129
<211> LENGTH: 1005
<212> TYPE: DNA
<213> ORGANISM: C. necator

<400> SEQUENCE: 129
atgcacccga cccaagacca atggcgccgg cgctttcccc ttcgcctggc cggcgcgctc     60
gcgctggcct gcggcctcgc cgccgcgacc ggcgcacagg cagaggcgcc ctatcccaac    120
cgccctatcc agatgatcgt ggcctacggt cccgggggcg ggacggacct ggtggcacgg    180
ttgctggccc gccacctcga aagcaactc ggcggcgcca cggtggtggt gcagaacaag    240
cccggcgcgg gcggcgccat cggcttcgcc gaactggcac ggtccgcgcc ggacggctac    300
accatcggct ttatcaatac gccgaacctg ctgaccattc ccatcgagcg caagaccacc    360
ttcacctggc gcagcttcga cctgatcggc aacctggtcg acgatccggg cggcttcacg    420
gtgcacaaca gcaacggcat cgactcgctg gccgcgctga tccgccatgc caaggcgcat    480
ccgggggagg tgtcagtcgg caccaccggc gtcggctcgg acgaccacct cgccatgctg    540
ctgttcgaga gggccgcggg cgtcaagctc acccatgtcg gctacaaggg cgcaggcgac    600
gtgcgtgcgg cgctggtcgg gcagcagctc accatcgggg ccattaacgt gggcgaagcg    660
ctgcagtacc agaaaggcgg ctcgccgatc aagttccttg gccaaatggg cgcaacacgg    720
gcaacgctgg ccccgaacgt gcccaccttc gcgaacagg gcttcgacat tgagctggct    780
tcgctgcgcg gcctggcggc gcccaaggc ctgcctgagc cggtcaggaa gaaactggtg    840
gaggcgatgg cgcgcgtggt cgcggatccg cagttccgcc agcaggccga agcgatgtat    900
gcgccgttgc actatctggc gccggccgcc tacagcgcgg agctggagcg cggggagacg    960
ggcttccgtc agctgtggaa agagatgccg tggcaggaga actga                  1005

<210> SEQ ID NO 130
<211> LENGTH: 1005
<212> TYPE: DNA
<213> ORGANISM: C. necator

<400> SEQUENCE: 130
atgtgcgttc aagcgggcaa ggccacgctg gccggtatga agtggatcat gtgcggagcg     60
cttggactcg cgttttccgc gggggcgctg gcagcggatg cctatccgtc caagcccatc    120
acgctggtgg tgccgttctc ggccggcggc ccgaccgatg tggtgtcgcg ggcccttggc    180
caggccatgt cgaaggatct ggacagagc gttgtcgtgg agaacaagct cggcgccggc    240
ggcacggtgg cggccgcatt cgtggcgcgg gcgcagcccg acggctacac catcctgatc    300
caccacaatg gcatggcgac ggcgccggcg ctgtacaaga agctctccta cagtccgatg    360
aaggacttcg agtacatcgg gcaggtggcg gatgtgccga tgacgctgct gggccgcaag    420
gacctgccgc cggccaacgc ggcggagctg atcaagtatg tctcgcagaa caaggagaag    480
gtctcgctgg ccaatgccgg ccttggcgcg gtttcgcagc tatgcggcct gctgttcgag    540
gaggcagtca aggtcaagat gacttccatt ccctaccagg gcaccggccc cgcgctgacg    600
```

| | |
|---|---|
| gccttgctgg gcgggcaggt ggacctgctg tgcgaccaga ccacctcgac gctgccgcat | 660 |
| atcaacgcca accgcgtcaa gctgtatggc gtgacgacgc ctagccgcat caaggcactg | 720 |
| cccaatgcgc cgacgctgca ggaaggcggc ctgaagggct tctcgatgaa ggtgtggcac | 780 |
| gggatctatg cgcccaaggg cacgccgccc gaggtcactg ccaggctgac cagggcgctg | 840 |
| cagcaggcac tgaaggatcc cgccgtggcc aagcggcttg acgacctggg tgcggaggtt | 900 |
| gtgccggtag acaagcagac gccggaaggg ctgcgcacct ggctcaaggc ggaaagcgac | 960 |
| aagtggcagc cgctgctgaa gacgatgaag gtggaggccg actga | 1005 |

<210> SEQ ID NO 131
<211> LENGTH: 996
<212> TYPE: DNA
<213> ORGANISM: C. necator

<400> SEQUENCE: 131

| | |
|---|---|
| atgcagcgtc attcccgcca gcggcgtgcc atagttgcgg cgctcgccac cctgcctgcc | 60 |
| ttgtcgcct ggtccgcacc ggcctgcgcg gcagaggcat ttccttcgcg tccgatccgg | 120 |
| ctggtggtgc ccttcacgcc cggcggcacc actgacatcc tggcgcgcct ggttgcgcag | 180 |
| aaggccggcg aggcgctggg ccagcagatc gtggtcgaca accgtccggg cgcgggcggc | 240 |
| aacatcggcg ctgaggccgt ggcgcgcagt gcagctgacg gctatacgct gctgatgggc | 300 |
| acgttgggca cgcaggtgac caaccagttc atttacccgc gcatgccgta cgacagcacc | 360 |
| cgggacttcg tgcccgtgac gctggtcgcc aattccccca acgtgctgct tgtcaacagc | 420 |
| acgctgaacg caaggtcggt gggcgaactg gtgacgctgg ccaggcgcga gccgggcaag | 480 |
| atcaactatg cctcgaccag caccggcggg tcgccccacc tgtcaggcga gttgctgaac | 540 |
| atgatggcgg cgtcagcat gcagcacgtg ccgtacaaag gggccgcccc cgccatgacg | 600 |
| gacctgctcg cgggccaggt caacctgatg ttcgacaacc tgccgtccgc gctcgcacag | 660 |
| atccaggctg gcaaggtgac ggcgctgcg gtcaccagtg ccaggcgggc ctcggtgctg | 720 |
| ccttccgtgc cgaccgtgcg cgagtcgggg ctgccgggct atgaagtcaa ttcctggttc | 780 |
| gggctgctcg cgccggccgg cacgccgccc gagcgcgtgc gccggctcca gcaggcggtg | 840 |
| gacaaggtgc tggccacgcc cgacgtgcgc aagcgcatcg aacagcttgg cgccgagccg | 900 |
| ggcggcgaag gctccgccgc gttcgcggcg cagatcagga gcgatacgga aaaatggtcg | 960 |
| cgcgtgatcc agaccgccgg catcaagccg caatga | 996 |

<210> SEQ ID NO 132
<211> LENGTH: 993
<212> TYPE: DNA
<213> ORGANISM: C. necator

<400> SEQUENCE: 132

| | |
|---|---|
| atgctatttc cgaaccccctt gcgacggctg gccgccgcgc tggcattggc cctgggtgcc | 60 |
| agtgccgttc ctgccatggc tgcccccgcc agcggcgacg cgcccgtgcg catcgtggtc | 120 |
| ggcttcgcgg ccggtggcgc gctggacatc ttcgcgcgcg cgcttgctga aaagctgcgt | 180 |
| gtttcgctcg atacgcctgt cctggtcgag aaccgccccg gcgcatcggc gcggctggcg | 240 |
| ctggagaacg tcaaacgcgc gccgccggac ggcaagacgg tgctgatctc gcccgcgccg | 300 |
| ccgttcacca tctttccgct gacctacaag cgcctggcct atgaccccga caaggacctg | 360 |
| gttccggtcg cctacctggc cgacgtgccg ctggtggcgt ccgccagcgt caaccagccc | 420 |
| tatcggacca tgccggaata cctggcatgg gtgaagcgca acccggacaa gggcggtgtc | 480 |

```
gggctggtca cgctcggcgg cagcattcat ttcggggtgc tgtcgctcag caagtcgatt      540
ggcgtgccgt tgctgcccac tgcctatcgc ggcgccgtca tgatgctgac cgatgagatc      600
ggcggcacgc tgccgctggg tatcgatgcg gtgggggggc agatggagct gtaccgggcg      660
ggcaagatcc gtttcctcgg cgtcaccggg acccgccggt cggcgctgct gcctgatgtg      720
ccaacgctgg cggaggcggg cgcgccgggt ttcgagacgg cgtcaggctg gtactcggcc      780
tttgtgccgg cggggacgcc gccggctacg gtggcgagga tcgagaaagc gctgctcgac      840
gccgtcaagg atcccgtggt gcgcgacaag atgtcggcgc tgggcatgga gatgaacggc      900
aagccggggg atgccctgcg caagctcatc caggcgcagc gcatgcagtg gggaccggtg      960
gtcgcggctt cgggctttac ggccagcgaa tga                                   993
```

<210> SEQ ID NO 133
<211> LENGTH: 990
<212> TYPE: DNA
<213> ORGANISM: C. necator

<400> SEQUENCE: 133

```
atggaaacca tgagccattt gcgctcgatc atgcgcggca tgcttgccgg cgcagccttg       60
ctcgcagcca cttgcgcaac tgccgcaccc gcgtggcccg accggccgct gcgcctggtg      120
gtgccgttcc cggccggtgg ttcctacgac atcatcggcc gcacactcgc gcgcaagctg      180
gaacagcggc tggggcagcc ggtgatggtg gagaacatcg ccggtggcgc gaccgtgccg      240
ggtgtgtcgt cggtgctcaa ggagaaggcc gacggcaaca cgctgctgct ggccagcgac      300
ggcacgctca gtatcaatcc gttcacgatc aagggcctgc gctatcgccc cgagaccgac      360
ctgacgccgg tgaccatcgt cagcaccgtg ccgcactgga tcatcacgcg cgccgaccgc      420
aaggagatga ctctgggcga gctgaagacg catatccagc gcaatcccgg caaggtgtcg      480
atcagcatca acgtcgtcgc gggggctgcg cacctcggcc tggccgactg gaagcgccgc      540
aatggcctgg atttcaccat cgttccatac cgcggctcgc cgccggccat ggcggacctg      600
atcggcggcc agacctatgc gcatgtcgat gtgatcggct cttcggtcaa ttacgtccag      660
gatggcaagg ccaggcccct ggctacgctg caggcggagc ccgtcacgca gtttcccagc      720
ctcgaaacgc agaaggcggg cggcacggat gtgctgcagg tacgcggcaa cctggcgctg      780
gtggtcaagg cgggtacgcc ggccccggtc atcgaccggc tctacaggga agtgaaggcc      840
agcgtgcagg aagcggactt tgccgcgcgc ctgcagacgc ttgcctatga gccggtcctt      900 tccaccccg agcaggcccg ccgcttcctg caagcggaaa cgatccgcta cggcgccatt      960
gcgcgcgcag tcgatctcga atccaactga                                      990
```

<210> SEQ ID NO 134
<211> LENGTH: 984
<212> TYPE: DNA
<213> ORGANISM: C. necator

<400> SEQUENCE: 134

```
atgacccgca ttacccgatt cgcacgcgtg gcgctggccg gcatgctggc agccacggcg       60
ctgggcgccg cggcgcaggc gcccttccca aggcaaaaac cgattacgct ggtggtgccg      120
ttcgcccccg gcggcggcaa cgatatcctc gcgcggctga tcgcgccgaa gatgggcaag      180
ctgctgggcc agaccgtcgt gatcgagaac aagcccggcg cgggcggcaa tctcggcgcc      240
gactatgtcg cccacgcggc tccggacggc tatacgctgg tgatcgcatc cagccaggtg      300
```

| | |
|---|---|
| acgatgaacc cgtttctcgg cacgaagatt ccgttcagca tcgaacgcga cttcgagccg | 360 |
| gtggggcgga tcgcgtcagt gccgatcatg ctggtcgcca accccgacca gccgttccgc | 420 |
| acgctgcagg atttatcca gtacacccgc gccaatcccg gcaagctcag ctatagcagc | 480 |
| ccgggcaacg gcacgcccca gcacctggcc ggtgaagtct tgccaggct caacaagacc | 540 |
| gaactgctgc acgtgcccta tcgcggcacc gggccgtcga tcaccgacct gatgggcggg | 600 |
| caagtgcaga tctcgttcgc gacctttgct tcggcgatcc agtatgtgcg cgccggcaaa | 660 |
| ctgcgcgcgc tgggcatcgc cggcaagaag cgcaccgcgc tcatgcccga cctgccgacc | 720 |
| tttgcggaag caggcatcgc cggctacgac gccgagctgt ggtacagcct gctggcgccg | 780 |
| gcgcagacgc cgaagccagt ggtcgacaag ctcaacgccg cactggtggc cgcgctgaaa | 840 |
| tcgcccgaca tcgccgagca gatggcaaag caaggcttcg agccgcaggc gtcgtcgccg | 900 |
| gccgagctga agacctatat cggcaaggaa atggcgcgct ggcagcggct gatccaggac | 960 |
| aacggcatca aggtggcctt atga | 984 |

<210> SEQ ID NO 135
<211> LENGTH: 975
<212> TYPE: DNA
<213> ORGANISM: C. necator

<400> SEQUENCE: 135

| | |
|---|---|
| atgcagatcc gtgcattgca tcgccgtcgc ctggtgctgg gcggcgccgc ggccatgctg | 60 |
| ctggccggcc gcaccggcgc acaagcgcgc agcaacggcc cgctggtgct ggtcgtgccg | 120 |
| tttgcgccag gcggcgtggt cgacaagacc gcgcgcgcag tccatgttgg cctcggacgc | 180 |
| cggctcggcc agaccgtggt gatcgagaac cacgacggcg ccggcggcac catcggcacg | 240 |
| ggcatcgtgg cgcgcagcaa ggccaacggc cacaccatcg gcctggtcta tgactcgtat | 300 |
| gcgaccgagc cgctggccta cccgaacctg ccttaccgcg ccgggcgtga tctcaccggc | 360 |
| gtgtcgtata tggtgcgcgc gccaatggcg ctggtggtgc cggccgcgtc gccgtggcgc | 420 |
| acgctgcagg actatgtgcg ggcgtgccga caatggcgcg aggtgtctta tgcctccgtg | 480 |
| ggtgtcggca gttccaacca cctgaccgcc gaatggttcc accaggccgc cggcacccat | 540 |
| ggcctgcacg tgccgttccg cggcggcgcc ccggcactga agacctgct gggcggccat | 600 |
| gtcgattcga tgttcgccag cctgccgctg gtgctggcgc aactgcaggc cggcaagctg | 660 |
| cgggcgctcg cggtcagctc ttctgcgcgc aatccgcatc tgccgacggt gcccacgctg | 720 |
| gccgacacct ggccgggcct ggtcacctat tcctgggtcg gcatgatcgc gccggccggc | 780 |
| acgccggccg cgcagctcga ccgcctggcc gccgcagtca gccagacgct gcgcgaagcg | 840 |
| gccgtcacgc agtacctgta cgacaatggc tttgaagtcg tggccagcgg acgcgaggcg | 900 |
| atgaatgcac tggtcgcttc cgaagcggcg cgctgggcgg aactggcgcg gcaacgcacg | 960 |
| ctggcgctga gctag | 975 |

<210> SEQ ID NO 136
<211> LENGTH: 975
<212> TYPE: DNA
<213> ORGANISM: C. necator

<400> SEQUENCE: 136

| | |
|---|---|
| atgcgtttcg gcacccttgc cgcggcaatg cttgtcacat ccgcgctggt cggcgcggcc | 60 |
| cccgcgctcg cgcaaacctg gccgccaag ccgatccgga tcgtggtcgg cttcccgacc | 120 |
| ggcggcgcgc ccgatacgct ggcgcgcatc gtctcggaga agatctcgcc atcgtggggc | 180 |

```
cagcccgtga tcgtggacaa caagcccggc gcgggcggca atatcggcgc cgaggcggtg      240
gcgcacgcgc cggcggacgg ctacaccctg gcactgggca cggtcggcac gcactcgatc      300
aacggcgcgc tgtacagcaa gatgccgtac gacatggtga aggacttcgc gccggtcatg      360
atgatcgcct cgacgcccaa cgtgctggtg gtcaaccccg gcgtgccggc gaagaccacg      420
gccgagctga tcgcactggc gaagagcaag cccggcgcgc tgaccttcgg caccccggc       480 gtcggcacct cgccgcacgt ggccggagaa atgttcaatt cgatggccgg cgtcaagatc      540
acgcacgtgc cctacaaggg ccgagccatg gccatccccg acctgctcgg cggccatatc      600
accatgatgt cgacaacct gccgtcggcc ttgcccgtgg tgcgcgaggg caagctgcgc       660
gcgctgggca ttaccagcgc gaagcgctcg gcctcggcac cggatatccc gacactggcc      720
gagcagggct gcctggatt tgaagccgat tcatggttcg ccgtgttcgc gccggccaat      780
acgccgaagg atgtggtggc caggctcaac actgaactca accgcatctt cacgctgccc      840
gatgtgcagg cgaagctgaa gacgctgggg ctggatccga tcctggggac gccggagaaa     900
ctggcggcat accagcgcca ggagattgca aaatgggcga gggtggtgaa ggaatcgggg      960
gcgaaggcgg agtag                                                      975
```

<210> SEQ ID NO 137
<211> LENGTH: 990
<212> TYPE: DNA
<213> ORGANISM: C. necator

<400> SEQUENCE: 137

```
atgcaagtga gtcccaagcg cccccatctc gcaggtgcag cagccctgtt tgtcaccctc       60
ttcctcagtg gtttgcctgc tgcccacgcg gccggctatc cggatcgtcc cattacgctg      120
gtggtgccat tcggcgccgg cggcatcact gacctggtgg cacgcgccac cggcaaggcc      180
ctgtctgaac agcttggcca gtcgatcgtc gtggaaaacc gccccggcgc gggcggcaac      240
atcgcggcag atttcgtacg tcgtgcccgg cccgatggct acacactgat gttgccacc       300 gtgggcgtcc ttgcggtcaa tccgcatacg gacgtcaagg tcagctttga tagcgcgaag      360
gacttcacct atatctcgct cgtcggttcc acgccccatc tggtggtggt cggcgccgac      420
gtcccggcca ggacgctgcc cgaactgatc aagctcgcgc aacgccagcc cggcgccgtc      480
agcgtaggca ccgcaggcgt cggcagctcg ccgtaccagg gcatgcgcgt gctgcaggac      540
gcggcccggg ccgaattcct gcacgtaccg ttcaagagcg cgctgaatc ggtgaccaac       600 gttgtctcgg gcaggtcaa catgacattc gaggccacg cgcaggtgat gccattcgtc       660
gcctccggca agctgcgggc gttggccgtt gccaatccgc ggcggctggc caccgcgccg      720
gacgtgccgc cgacaccgga actgggcctg ccgaccatcg tgtccggttc ggtggcaggc      780
ctgattgcgc ctgccggcct tgatgccgcc atcgtgaaga agctcaacac agccattgcc      840
ggcgtggtat cgaaccccaa gttcaaggcc acgctgatgg cacagggcac tgaaccgatg      900
tcatcgtcgc ccgaacaatt ccgcaagctg atcaaagaag aagaccagcg ctggtcggcc      960
ttgctcaagg ctgacaacaa gaccaggtaa                                      990
```

<210> SEQ ID NO 138
<211> LENGTH: 975
<212> TYPE: DNA
<213> ORGANISM: C. necator

<400> SEQUENCE: 138

```
ttgaccatta aaaaccgatt caccctgggc ctgttggcaa cggcagccct catcgcggcg    60
gccccggctt gcgcacaaga acagtggcca gcaaagacga tccgctttgt cgtgcccttt   120
gccgccggcg gcgccaatga cctgatggcg cgcgccgcgg ccgagggcgc aaccaaggcg   180
ctgggccaga ccgtgctgat cgagaaccgg cccggcgcgg gcggcaccgt gggcgccgac   240
atcgtggcca agagcgcgcc ggatggctat accttcctga tcagcgcagc cggcgtcatc   300
tccaacagca tgatcaagaa gtcaatgccg ttcaaggatg acgcgctggt tcccgtggcc   360
atgatcggcc ttgcgccttc ggtcatcgtg gtgccgaaga acgcgcccta caaggatctg   420
cgcgacttcg tcgaggcctc aaagaagggg aacggtttca acttcgcgac cgcggggacc   480
ggcagcaccc cgcacttcgt ggcggagatc ctgaatgtga agtacggcgc aaagctgcag   540
ccggtgccct acaagagcgg gtcggaaagc actacggcag tgctgggcgg ccaggtggaa   600
ggaacctccg aggccagcat catcgccctt ccgcatatcc tgcacgatgg caagttcaag   660
gcgctcgcca ccacctggac gcagcgcatc tcggcctacc gcagcttttc caccgcggtg   720
gagcaaggct tcccggacct gcagatcgcg cattgggccg cgtccatgc ccccaagggg    780 acgcccgacg ccatcctgga caaggtggcc gccgcggtgg acaaggccat gaaggacccg   840
gccgccgccg ccaagctgaa ggccgtgggc atcgaaccgg tcggcggcac gcgtgcggac   900
ttcgtgaagt tgtcgaggc ggagcgcaag cggctgggcg agattgtcaa ggccgccagg    960
atgcaggaga agtaa                                                    975
```

<210> SEQ ID NO 139
<211> LENGTH: 1005
<212> TYPE: DNA
<213> ORGANISM: C. necator

<400> SEQUENCE: 139

```
gtgaacaacc gataccagaa acgacttccg gcttggccgc ggctgcgcgc ggcactgatg    60
ctggcggcag ccgcggccgc gctgccggct gccgccgtcg cgcaggactt cccgcagcat   120
cccgtgcgca tggtgctgcc ctaccccgcc ggcgggccca ccgacctgct cgcgcgcgtg   180
gtcgcggtca agatgggcga gagcctgggc cagagcgtgg tggtcgacaa caaacccggc   240
gccagcggca tgatcggcgc cgaagccgtg gcgcgcgctc ccgccgacgg ctacaccatc   300
ctggccaatg cctcgctgca tgtgatcaac cccagcattc agccgaagat gcgctatgac   360
tccttcaagg acttcgtgcc gatcacgcag ctggccgacg tgccgctggt gctggtggtc   420
aacaacgcct cgccggtgaa gacagtgcag gacctgatcg cctacgcaaa tagccagggc   480
ggtgcgctca acttcggctc ggcgggcaat gcctcggccc agcacctggc cggcgaatcg   540
ttcaagctgg cggcaaaggt gccgatgcag catgtgccgt acaagggcag cgcgccggcg   600
ctgacggacc tgatgggcgg ccagatccag ctgatgtttg attccatgcc gtcggcgatg   660
cccttcatca gtccggcaa gctgcgtgcc gttgccgtga ccaccgcgcg gcgcgcgagc    720
gcgctgccaa acgtgcccac cgtcgccgag tccggcctgc ccggcttcga catcagcacc   780
tggtatgggc tgtgggcgcc gcgcggcacg ccggccccgg tcgtggaaaa gctggccgcg   840
catgcggccg gcgcgctgaa gcggcccgat gtgcgccagc aatatgccga catgggcgcc   900
gagccggtcg gctcctcacc tggcgacttt gcccgctaca acgcttccga aggcaaaaaa   960
tgggcggaaa tcgtgcggcg ctcgggggcc aaggcagacc agtag                  1005
```

<210> SEQ ID NO 140
<211> LENGTH: 984

```
<212> TYPE: DNA
<213> ORGANISM: C. necator

<400> SEQUENCE: 140
atgcaacgca cccgccgcgc cctggcagcc gccgctgccc tggccgcatg cctgccgctg      60
ttcagcgcca gagccctcgc cgccgccccc tatccgtcca agcccatcca gatgatcgtg     120
ccgcaggcac cgggcggcac caacgacatc gtcgcgcgac tggtcgccgc gaccctgtcg     180
caacggctcg gccagcaggt ggtggtggaa accgcccggg cgccggcgg caatatcggc      240
acccaggcag cggcccgcgc cacgccggac ggctacacgc tgctgatgac catcagcagc     300
acgcaggcca tcaacccgtc gctgtaccgc agcattccgt tcgacccggt caaggatttc     360
gagccgatcg ccccggtggc aagcgtgccg aacgtgctgg tggccaatcc cgccttcccc     420
gccaagtcgc tgcccgaatt gatcgcgatg gccaaggcca ggccggacta ctaccgctat     480
gcctccgccg gcaatggcac gctgaaccac ctgctgggcg agatgctcaa cagcatggcc     540
ggcatcaagc tcgaacatgt gccctacaag ggcgtcgcgc cggcgctgaa cgatgtgctg     600
ggcaaccagg tgccgctggc cttcgccagc ctgccgtcgg tgctggccca tatcaaggcg     660
ggcaaggtgc gcgcgctcgg cgtcagctcc gccaagcgct cgccgttcgc gccggacatt     720
cccgcgatca acgaaaccgt gcccgggtat agcggcgacc tctgggtcgg cctgttcgcg     780
gtcaagaata cgccgaagga cgtgacccaa aagctcggcc aggccatgca ggagatcctg     840
gcggacaaga ccctgcgcga caagctggcg gcacagggcg ccgaagtgat gacgggcacg     900
ccgcagcagt tcagcaagat gctggcgtcc gacatggaca gtgggcccg catcgtgaag     960
gcatcgggcg cgcaggtgga ctga                                            984

<210> SEQ ID NO 141
<211> LENGTH: 990
<212> TYPE: DNA
<213> ORGANISM: C. necator

<400> SEQUENCE: 141
atgcaagatc aaaggcagca gcaaaagcga cggttcatgg ccaccctgtt gtggctgggc      60
gccgtgggcc tggctggccc ggcaatggcg acagctatc cgtcgcgccc gatccgcctg      120
gtggtgccgt cagccgccgg cggcagtccc gacgtgctga tgcgcgcatt gggcgccgaa     180
gtcggcaagt cgctgggcca gtcgttcgtg atcgacaaca agcccggcgc ctcgggcgtg     240
atcggcatct ccgaactgga acgcgccgcg cctgacggct acacgctcgg ctatgccaac     300
aacgtgacgc tgtcgatcaa caagagcacc ttccgcaagc tgccgtaccg gcccgatgcc     360
ttcgtgccgg tggtgctgct gttcaaggtg ccgaatgtga tcgcggtcag gccggagatg     420
ccggtgaaga cctttgccga gctggtggcc tacgtcaagg ccaacccgga caaggtcacc     480
tatgcctcgc cgggccaggg cacgtccggc cacctgactg ccagctgct cgcggacaag     540
gcggggctgg cctggacgca cgtcggctac aagggcagcc cgcaggccgc caccgatgtg     600
atgggcggcc aggtcaatgt gctgatcgac aacatgccga ccatcctgcc gctgatcaag     660
gccggcaagc tcaagccgct gacggtgacc agcctggcgc gctcgccgct gctgccggcg     720
ctgcccacca tcgcggagtc tggcgtgccg ggtttcgaag gggtggcctg gggcggcctg     780
gtcgcgccgc aaggcacgcc cgccggggtg gtgggcaagc tcaacggcgc cttcaaccgc     840
gcgctggcg atccggccat caaggacaag ttcgccgcac tgggcgccga acggtcggc      900
ggcacgccgc aggcgctggc cggctatgcc gcgcgtgaaa ccgacaaatg gcggccgtg     960
```

```
                              gtcaggcagg ccggcatcac gccgcagtaa                990
```

```
<210> SEQ ID NO 142
<211> LENGTH: 963
<212> TYPE: DNA
<213> ORGANISM: C. necator

<400> SEQUENCE: 142
atgcaacgga gacaatttgg cgccacgctg ctggcgggcg cggcagcgtt gggtttcccc    60
tacatcgccc gggcgcaggg caaggcgatt cgcgtcatcg tgcccttcac ggcgggcagc   120
ggctcggacg agggcgcgcg cttttacgcg gagctgatcg gcaaggcgct gggacgctcc   180
atcgtggtcg agaacaagcc gggggccagc ggcctcatcg ccgtgcgcac tgtgctggcg   240
gagccggcgg acggcaacac catcctgctg ggcagcaact cgctgatcgc ggtgaacccg   300
gtgatggtga aggacctggg ctacgacccg ttcaaggacc tggtgccgct gcacggcctg   360
gcgatctccg ccgccgcttt tgtggccggc aacgattcac cctacaacag cattgcggat   420
gtggtggccc gctacaaggc cacgggcaac ccgatctcga tcggcaatta ttccgaaggc   480
tatcgcctgg taggcgagtg gctggcgcag gtaacgggta tcaagaccac gcccgtgccg   540
tacaagggcg gagcgcccat ggtgacggac ctgatcggac accggctgga catcgccctc   600
aacgacatca ccggcatcgc ccccatggaa aaggccaaga agctccgcgt gctcgcgatt   660
accggcgggg cgcgcgacaa gctgttgccg aatgtcccga cgatgaagga actgggctat   720
gcggactttg aatcctacgt ggtcgtcc ttctcgatga aggccggcac cccgcaggac   780
aagctcaagg agcttgccgc agcgatttcc gccgcgaag ggaccgaggc ggcaaaggca   840
taccagtcca agcgcgcggg tacctttttg aagaaggcgc tcggcgaatt gggggaattc   900
cagcgtgcgg aatacctgcg cttcaagggt gtggcggaaa aagccaatat ccggccgagt   960
tga                                                                963
```

```
<210> SEQ ID NO 143
<211> LENGTH: 963
<212> TYPE: DNA
<213> ORGANISM: C. necator

<400> SEQUENCE: 143
atgaaagttg cccacctcac ggccttgctg ctgtgtgccg cgtcgatcgg cacggccgcg    60
gcgcagtcct atccccagcg cccggtgcgt ctggtcgtgc cgtacgcccc gggcggcagt   120
gccgacatcg ccgcccgcct ggtctcggat gcctggtcga agagcctggg cggcaccatc   180
gtggtcgaga accgtgccgg cgccggcggc aatatcggcg tcgatgccgt ggccaaggcc   240
gccgccgacg gctacaccat cggcctgcag acggtgtccc tggccatcaa cccgggtctg   300
ttcccgcgca tgccgtatga cacgctgaag gacctggccc cgatcggcat ggtcgccagt   360
tcgcagcacg tgctggtggt caacaacaac gtgcccgcca ggaacctgca ggaactgatc   420
gccgctgcca gggccacgcc gggcaagctg acctacgggt ccgcgggcaa cggcagcacc   480
ttccatatgt cggccgagct gttcaagtcg gtggccaacg tctccatcgt ccacgtgccg   540
taccgcggcg gcgccccggc cctggtcgac accatcgcgg gccaggtcga catgagcttc   600
ccggtgatct cggccgcgca gcagcatgtg cagggcggca agctcaaggc gctcgccgtc   660
accggcagca agcgcgcgcc gcagttgccc aatgtgccga ccgcggccga ggcgggcctg   720
cccggctatg ccttcgagac ctggttcatg gtgtttgccc cggccggcac gcccaggccc   780
gtgatcgaca agctgaacgc ggcgctgaac accgcgctgg ccgcgcaggc aacccgtgag   840
```

```
cgcatgctca aggaaggctt cgagcccacc ccgaccacgc ccgaggccgc gcgccagcgc    900
ctggaaaagg agatgcccgt gtgggccaac ctgatcaggc agcgcggcat caccgcggaa    960
taa                                                                  963
```

<210> SEQ ID NO 144
<211> LENGTH: 990
<212> TYPE: DNA
<213> ORGANISM: C. necator

<400> SEQUENCE: 144

```
atgaccgcaa tgcccccgaa gccgtttctc gcctgcgccg ccgccctgac cgcggtgctg     60
tccgcaacgc ccgccgccgc gcaggcccaa tcctggccgg accgaccgat ccggctggtg    120
gtgcccttcg ccgcgggcgg cgccactgac gtgctgggcc gctgctggc agtcggcctc     180 ggcgaaaagc tcggccagtc ggtagtggtc gagaacaagc ccggcgccag caccgtgatc    240
ggcgccaccc aggtatccaa ggccgcgccc gacggctaca cgctgctgct ggcggccagc    300
accacgctga cgctgaaccc ggccatccgc caacacctgg gctacgaccc catcaagagc    360 ttcacccgc tgggcctggt cgccgacatg agcctggtgc tggtagccaa cccggacacg    420
cagatcacca cgctcaagga tctggtgacg caggccaagg cgcaccccga caagttctcc    480
tacggctcgt tcgcgccgg ctcctcggtg catttcggcg cggagatgct caagtccgcc    540
accggcatcc gcatggtcca cgtgcccttc aacggcagcg ccccagcct gaccgcgctg    600 gccgcggcc aggtgccgat cgcggtcgat accgtggtgg ccaccctgcc gctgatcaag    660
ggtggcaaga tccggccagt ggcagtgctg tcgccgcagc gactgccagc gctgccgcaa    720
gtaccgaccg tcgcggagag cggctatccc ggcttccaga tgggcacgtg gttcgcgctg    780
ctggcacccg cgggcctgcc cgcgccggtg cagcagaagc tggagaaggc gctggccgag    840
gtcgccaatg cacccgccac caaggcacgc atggtcgagc tggcgctgac gccggcctac    900
ggcaatggcg cggcggtgaa ggcgcgggtg gagaaggaat tgcctgagat gcgggcggtg    960
gcggcgcggg cggatattcg ggcggagtaa                                     990
```

<210> SEQ ID NO 145
<211> LENGTH: 978
<212> TYPE: DNA
<213> ORGANISM: C. necator

<400> SEQUENCE: 145

```
atgaagaagg gaatgactgc agcatttctg ctcatgtgtg gcgtgatggc gggaacttcc     60
gcggcccatg cagaaacaac atggccaacc aagccaatcc ggttggttat ccctttccg    120 cctggtggcg gcacggacat cctgtctcgc atcgtcgcaa acgaggtgtc tcagaccacc    180
aagtggacgt tcgtcccaga caacaagcct ggtgccggcg ggacaatcgg tatatccgat    240
gtggtcaagg ccgccccgac tggatacgac atcgtgatgg gcagaagga caatgtcgtg    300 gtcgcgccat gggtgaacaa agccgtgacc tacgacccgc gcaaggatct cgtggcgatc    360
gctcatgtcg cctacgtccc cctggttatc gtcacgccta agaattcgcc ttacaaatcg    420
ttccaggatc tggtgacggc cgctcggaaa tcacctggca cggtcacata cgcgtcgccg    480
ggcaacggca ccacagccca tcttgccgcc gagatcattg ccatgccgc cggcatcaag    540 ctcttgcatg tccctacaa aggctccaac gctgcgctgg tcgacaccat ggccgggaat    600
gtgaacatca tgatctcgtc agtcccatcg gccctggcgc agatcaagtc gggcaaggtg    660
```

| | |
|---|---|
| cgggccatgg ccgtcacctc agcgacgcgt agttccgcct tgcccgaagt acccaccgtc | 720 |
| gccgagagcg ggtacaagca ggttgacgtc agttcctggt atggactctt cgcccctgcg | 780 |
| aagacaccga aggacgttgt ggaacgcatt ggcgtggaag tgaacaaggc aatggccaag | 840 |
| ccagccgtca tccataacat caacgaacag ggcgcgaag cgaagtccat gtccgcagca | 900 |
| gaattctccc agcttgtgca aagcgactat ctgaagtgga aggacatcgt aaaggcgtcc | 960 |
| ggagccacgg tcgaatga | 978 |

<210> SEQ ID NO 146
<211> LENGTH: 957
<212> TYPE: DNA
<213> ORGANISM: C. necator

<400> SEQUENCE: 146

| | |
|---|---|
| ttggcacgct gtcttgtggt gttacccatg gcgctcgctg cacagaccgg tatggcgcag | 60 |
| gagggtcctg tcaggatcct cgtcggtttc ccgccgggcg gcgtgaccga cgtcgttgct | 120 |
| cgcctgctgg ccaaaggcat gcaggcagaa atcgcgagac cagtcattgt ggaaaatcgt | 180 |
| ccaggagccg gcggtcaaat cgcggcacaa gtcctcaaat ccgcccgccc cgacggcaat | 240 |
| acactgttcc tgaccaacag tcataccact gccatgattc cctttacgaa tctccatccg | 300 |
| ggatttgacc cccagaagga cttcgttcca gttggcctgg tagggacgat gccgaacttc | 360 |
| ttcgtcgtga atccgaaaat ggtagggccc gaagtcgaca gcctgaaggc ctttttctcaa | 420 |
| tgggcaagag caaaggccgg ccggggcaac gtcggcgttc ccgcaccggc gagcgcgccg | 480 |
| gagttctcca tctcgctgct gaacaaggcc ttcgacgcgg acctcaaggc cgttgcctac | 540 |
| aagggagatg cgccgatggt gcaggacctg ctggcaggac agattcccgc ggggatctgc | 600 |
| gcaatggccg ccgcgctgcc tcacgtccgc gccggcaagc tcaagcttct ggctgtcgat | 660 |
| ggaccggaac ggctgcctgg cttttgacgtc cccacctacg ccgagcgcgg ggtcaacggc | 720 |
| ctgagcgatg ccatgacaat cggcatcgtc gcgccggccg gcatcgcgcc ggcgctggtg | 780 |
| acaaagtaca acacagccat caacaaggtc gtcggatcga gggccttcca ggatcgggtt | 840 |
| gccgaatccg gcatcatcgc cagcactggc actccggatg acatggcgcg cgttacggaa | 900 |
| ggcagcagga aggccaatgc ccagttggtg aaagcggccg gataccagcc gcagtaa | 957 |

<210> SEQ ID NO 147
<211> LENGTH: 978
<212> TYPE: DNA
<213> ORGANISM: C. necator

<400> SEQUENCE: 147

| | |
|---|---|
| atgaacacga agcagaggct tgtcctcgcg atggccgtgg ccggcctggg cctggcaggg | 60 |
| cacgcggcgg cccaatatcc gcaacagccc atccgtatcg tggtgggcta tgcggccggg | 120 |
| ggcaccaccg acatcctggc gcgggcgctg gccgaacaac tggccagcga gctgaagcag | 180 |
| tcggtgatca tcgagaacaa gcccggcgcg gccggcaact cggccgccgc ctatgtgcag | 240 |
| cagtcggcgc cggatggcta tacgctgttc atggcaaccg tgtcgagcca cggcatcaac | 300 |
| ccagccttgt acaagaaaac gctgggctac gagccggtca gcggctttgc gcccgtcagc | 360 |
| atggtcgcct cgatcccgct cgtgctgatc acgaccccga acctgcccgc caggaacgtg | 420 |
| cctgacctgg tgacgctggc ccggaagaag tcgggagagc tgaactacgc atccagcggc | 480 |
| aacggttcgc cggtccacct ggccggtgcg atgtttgccc agagcgccaa tgccaagctg | 540 |
| gtgcatgtgc cgtatcgggg cggagcgctt gccaatactt cggtgatcgc cggcgagacg | 600 |

```
caactgagct tcgccacgct gcctggcgcc ctgccgcagg tgaaggccgg caggctgcgc    660
gccatcgccg tgaccaccag ggagcggtcg ccgcagctgc cggatgttcc cgccatgcgt    720
gaagtgccgg gcttcggcag cttcgagatc aatacctgga atgcattgct ggcaccgaaa    780
aatacgccac agccggtgat cgatgcgctg aaccgggccg tcgccaggtc actggcatcg    840
ccgaagctta ttcagcgctt caacggggag ggggcgacgc cggcaagcag caccccggcc    900
gaactcagcc gcttcgtcaa cgccgagctg gccaaatggg ctggcgtcgt gaaagacctg    960
gacgtcaagg tcgactga                                                  978
```

<210> SEQ ID NO 148
<211> LENGTH: 993
<212> TYPE: DNA
<213> ORGANISM: C. necator

<400> SEQUENCE: 148

```
atgcaccccc gtcgcatcct tctcaagtca gcgctggcgc tggccgccac cgtggccgcc     60
gcgctggccg cgcccggcat cggcgcgctc gcgcagggca taccggcaa accggtgcgc    120 ctgatcctgc cgatcagcgc cggttccggc gtggacacca tcgcgcgcgc ggccggtccg    180
gccctgggca aggcctttgg ccagccggtg gtgatcgaga acctgcccgg cgccggcggt    240
atcaccgggg ccgcagccgt ggtcaaggcg cagccggatg gcagcacgct cgggctggtc    300
tcgaacaacc atgtcatcaa cccgagcgtg ttccgcacca tgccgttcga tgccatcaag    360
gacatcaccc cgatcagcgt gatcggcacc acgccgctgg tgcttgtcgt gaatcccaag    420
gtgccggcaa ggaacgtgaa ggaactggtg gcgctgctca aggccaggcc cgacggctac    480
aactacggct cgtccggcaa cggcaccatc atccacctgg ccggggagat gttcctggac    540
gaggccggcg tgagtgcgcg ccacgttccg tacaagggca cgggcccgat gatgaacgac    600
ctgatcgccg gacaggtgga actgggcgtg gttgcgctca acgcggtggc gccgcacctg    660
aaggccggca cactgcgcgc gatcggcgtg tgcggcgaca agcgctcgtc cgccgcgccg    720
gagatcccca ccatcgccga caaggcttg ccccactaca acgtcgccgg ctggtttgcc    780
gtggtcggcc ccgccggcat gccgccggca gaggtaaagc gcgtgcatga cgcatttgcc    840
agggccttca cctcgcccga agtgctggag gccatgaaga agcaggccac cgtgatcgag    900
cccggcacac ccgaggcggc cgccagcttc ttccgcagcg aggccacgcg ctacgccgca    960
ctggtgaaga aggccaacgt caaggtcgaa tag                                 993
```

<210> SEQ ID NO 149
<211> LENGTH: 975
<212> TYPE: DNA
<213> ORGANISM: C. necator

<400> SEQUENCE: 149

```
atgcccaccc acccttcatt cctgctgcgt atcgccgccg tggcggccgg cctggcgctg     60
gcggctcccg ctgccatggc ctggaccagc aagccggtcc ggatgctggt gcccgccccc    120
gcgggcggca ccatggacgt gctcgcgcgc ctgctggcag accagctgtc ggccgacctt    180
ggccaccccg tggtggtcga caacaagccg ggcgccggcg cggcattgc catcactacc    240 atgctggccg cgcccgctga tggccagacc atcatggtca ccgccagcaa tgtgctgacc    300
gagatcccgc atgtgctcaa gcagccgttc gaccgctga aagacgtcag gcccgtcgcc    360
gccgtggcgc gttcgcgcat ggtgatgatt ggcgcgcctg gcctgccggc caaggacctg    420
```

| | |
|---|---|
| aagggcctgg tcagctacgc ccgggccaat ccgggcaagc tcagctttgc ttcgtacagc | 480 |
| gccggcaccg cttcgcacta cgcgggcatg atcatgaacc agaaggccgg gctggacttg | 540 |
| cagcatgtgc cctttgccgg ttccgcgccg gcgctgacgc aggtgatggg caatcagatt | 600 |
| gccgtgatgt acgacggcat ggtgacctcg ctgccgatga tccgtgccgg caaggtgcag | 660 |
| gtctatgccg tggcgtcgaa gagccgctcg gcgctgctgc cgcaggtgcc aacctttgcg | 720 |
| gaaatgggtt accccgacat ggagttcagc aactgggtgg cgtgattgc gtcgtcgaag | 780 |
| ctgtcgcccg aactggccga aaggtccac gcggctgcct acaaggccgc ggcttctgcc | 840 |
| aaggtgcgtg accgcatgga ggcgctcggt tatgagccgc tgccggcgca gcccctgccg | 900 |
| caactgagcg aatcagtgcg cacggagttc gagcgcaatg ccggcatcgt caaggcgttc | 960 |
| aatatccagc cctga | 975 |

<210> SEQ ID NO 150
<211> LENGTH: 969
<212> TYPE: DNA
<213> ORGANISM: C. necator

<400> SEQUENCE: 150

| | |
|---|---|
| atgaaaccga ccttcaccgc catcgcgctg ctggcggcat gcgcaagcgg cgccgcacat | 60 |
| gcaagcgcgt atcccgaccg gccgatcaag ctgatcgtcc cctacgccgc cggcggcacc | 120 |
| accgacatca ttgcccgcat cgtcggcacg cgcctgggcc cggtgctggg caaccggtg | 180 |
| gtggtcgaga accgcccggg cgccggcggc gcggtcggca gcgcctacgc ggccaggcag | 240 |
| ccggccgacg gctacacgct ggtgatggag gtggagagct cgcacgccgt caaccccaac | 300 |
| gtctacctga agaccgccta tgacccggtc aaggacttcg cgccggtcag caacctggcc | 360 |
| gacgtgccca acgtgctggt ggtcaacccg gcgttccgg ccacggacct gcagtcgttc | 420 |
| atcaagctgc tgaaggccaa cccgggcaag tactcgttcg gctcgtccgg caacggcgga | 480 |
| ctgagccata tgaacggcga gctgttcatg aacgccaccg gcacgcgcat gctgcacgtg | 540 |
| ccatacaagg gcctgggccc ggcgctcaac gatgcggtgg caggccagat ccaggtggtg | 600 |
| ttcgacaata tcccgtcgtc gtccggcctg atccagggcg ggcgcctgaa gccgctggcg | 660 |
| gtcgccgcgc agcagcgcct gaaggtgctg cccaatgtgc cgacctatgc cgaggccggc | 720 |
| ctgccggcga tgaacaaccc gtcgtggttc ggcctgggcg caccggcggg cacgccctcg | 780 |
| gccattctcg acaagctcaa cgacgccgtg cgccaggtat tggccgagcc cgaggtgatc | 840 |
| gccgccatcg agaaacaagg tgcgatcccg gcaccgagtt cgcgcaaggc cttcggcgac | 900 |
| ctgatccggg cgcagaatgc gcactggaag caagtcgtcg aggacatcca tttcaccagg | 960 |
| ctccagtaa | 969 |

<210> SEQ ID NO 151
<211> LENGTH: 444
<212> TYPE: DNA
<213> ORGANISM: C. necator

<400> SEQUENCE: 151

| | |
|---|---|
| gtgacttcgg cacgcggacc gcgcggcgcg acgagtcccg cccactgccc ggcgctggcc | 60 |
| acacaggcca aggcacaact gcagaagatc acctacgcca cgcccggcat cggcacgctg | 120 |
| ttgcacctga taggcgttgt gctcgacaag aacagcagcg tgccgctgca gcacgtgccg | 180 |
| tacaagggcg ccgggtcggc catcaatgat ctgctcggtg gtcaggttga tgtgctgatc | 240 |
| acgtctacgt ctaccgtggc tggcttcatc cagtcgagcc gcatgtgtgc gctggcagtg | 300 |

```
accagcttgc gacggctcgg cgtgttcgcc aagacaacgc gccatgcggt caagcatgga    360
ggttactccg cgatcgcgat aatctggttt agctgctcgc aagcggcagc aaaaacctcc    420
aagggcgctt gcttccaggg gtga                                           444
```

<210> SEQ ID NO 152
<211> LENGTH: 1008
<212> TYPE: DNA
<213> ORGANISM: C. necator

<400> SEQUENCE: 152

```
atgaagacat tgttccagct gcggggaaac accggccgcg caggcacagt ggcactcgcc     60
acaggccttt cgtttgcact ggctttcgca actgcggccg cgcatgccgc ctatcccgac    120
cgcgccatcc gctgggtagt gccgtttcca gcgggcggtg ccattgacaa tatcgcccgc    180
acgctgggag acgacatgtc gcgcacgctc ggtcaaccgg tcgtcgtgga aatcgacct    240 ggcgccggcg gcaatatcgg cgccgaaatg gtcgcgcgct cgccggccga cggctacaca    300
atgattatcg taggcaacgg catgtccgtg aactccgagc tatacggcca actgacgtat    360
gatcctgtca aggactttgc gcccgtttcg ctgctggccg tggtgcccaa tgtattggtc    420
gtcaacaaga accgaaggca agaaggcacc gtcaaggagg tgatcgccca cgccaaggct    480
tcgcccggca agtacacgta tgcttcggct ggcaacggta cttctatcca cctgcgggct    540
gcgctcttca actcgatggc cggcatcgac atgctgcaca tcccttacaa gggcagcggc    600
cctgccatgt ccgacatgct gggcgggcag gtggactata tgttcgacag catcacgtcg    660
gccaagccgc aaattgacgc cggtaagcta cgcgccatcg cagtaaccac tgccaagcgc    720
tccagtgccc tgctgaacgt gccgacggtg gccgaagccg gacttccggg ctatgagcta    780
tcgccctggt tcgccgcctt cgtgccggct aagacccgc agccagtgat cgagtcgctg    840
aaccgagcca tgctcgaggc actgaagaaa ccggaggtgc agaagcgtct ggccttgatc    900
ggtgccgagc cgatcggcag cacgccctcc gccctgcgcg accacctggc gaaagaaagc    960
cagaagtggg gcgtgctgat ccgcgagcgt ggtattcgcg ccgactga               1008
```

<210> SEQ ID NO 153
<211> LENGTH: 978
<212> TYPE: DNA
<213> ORGANISM: C. necator

<400> SEQUENCE: 153

```
atgcaatccc ttatcagact gaccggcatg ctggtcgccc taacggttgc cggcaccgca     60
gcggcacaga gcttcccgag caagccggtg accatcgtcg tgccgtactc ggccggcggg    120
ccggtggaca gcttcgtgcg agggctcacg ccacggcttg ccgatgcgtg aagcagccg    180 gtggtggtgc tgaacaagcc tggcgccaat gaaatcatcg gcgccgagtt cgtcgccaag    240
agcgcgccgg acggctacac gctgtttgct ggcacggaag ctgcgctaac catgaaccaa    300
ttcctgtaca agaagctgcc gtacagccca gacaaggact tgccgaggt gtcgcgactc    360 gtggcactac cgttggtgtt cttcgtgccg aagacctcgc cgccaattc actcaaggag    420 ttcatcgcgc tcgcgaagaa ggtttcggca agcaagccga tgacctacgg ctcctctggc    480
gccggcggca tcgcgcacct acccatggcg atgttcacgc ataacgagaa tctgaccatg    540
gtgcacgtcc cttacaaggg tgccgcgcca ctgatcccag aagtgatctc agggcagatc    600
gatgccgccg tgctcggcgt ctcggtgatc gagcagcacg tcaagtcggg cgcgctcaag    660
```

```
gccctcgccg tctcggcgga cacgcgctcg gcggcgctgc ccgatgtgcc caccttcaag    720
gagttaggga tcaaggagat caatgcggtc ttcaatatcg gccttgtggc gccgcatggc    780
acgccgaccg cgctagtgga gaagatttcc tctgacgtca gccgcatcgt ccagtctcca    840
gacttccgga gaaagtatat cgatgcgttc tcctatgtcg cggtgggctc cacaccagcg    900
gccttcaagg attttctggc acaagaccga agaatccaga gcgaacgcgt gaaactttcc    960
ggtgtgtcgc tcgattga                                                  978
```

```
<210> SEQ ID NO 154
<211> LENGTH: 954
<212> TYPE: DNA
<213> ORGANISM: C. necator

<400> SEQUENCE: 154
atgaagcgga tcatacccgc gctactgctt tgtagtgcga caatcgcaac gaatgcgcag     60
gccgagtatc ccgtcaggcc catcacgcta gtggtgcctt ttcccgccgg cgcaacgacg    120
gatacagtgg cccgcgtggt cggccaggcg gcatcggccc agcttggcca gcccatcgtg    180
atcgacaaca agccaggcgc ggaagggcaa gtggccgcgc aggaggtggc ccgagcgaca    240
ccggacggct accgtttgct gctcgccacg tcgggcaacc tgtcgttggt gccggcgttg    300
cgcaagaagc cgccctacga cgtgctgacc gatttcacgc ccatcgccga tgtcggtcgc    360
ttcggctttt tcctgtacgt gaaccctgcc gtcccggcca gcaacctgaa cgagttcctc    420
gcctacgcca aggccaatcc cggcaagctg agttacggca ccggcaacaa caccggcgtg    480
gtcgcgttct cgcacttcaa gacactcaca ggcatcgagc tgacccaggt gccctacaag    540
ggcgagccgc cggccatgct ggatctgatc gccggccgca cccaggccat gatcggtacg    600
accatcggcg cgtcctatct gcgcgagggc aaactgcgcg cactggtctc catcaatgcc    660
cagcgaaaca gcctacttcc cgatgtgccg acgctgcgcg aggcaggcat gcaggatttg    720
gagatcatgc cgtgggcggg tctggtcggg ccggcgggca tgcccaagga cgtcgtggcc    780
cgtctaaacc aggcattcgt tgccgcgatg aacaatccga aggtacgcga acagatggac    840
cggctgggct tccgttgac gccttcttca cctgaagcgt tcggtcgtct gatcaaacac    900
caactggcgg tccatggccg cctggtgaag gacgccgggc tgcagccaga ataa         954
```

```
<210> SEQ ID NO 155
<211> LENGTH: 1014
<212> TYPE: DNA
<213> ORGANISM: C. necator

<400> SEQUENCE: 155
atgaagcaag gccttgaaat gctgcggctg gcaatcgcca ggctggtatt ggcgacagcc     60
gggatgacgt gggctgttgg tgtggtggca ttggccgagc ccggcgctgc gctggcggca    120
taccctgaca gccgatccg gctgatcgtc cctgcggcag cgggtggtac cacgcgatatc    180 gcgtcgcgtc tggttggcaa acgcatggcc gaactcctgg ccagccggt agtggtagaa    240 aaccgtgccg gcggcgccgg catcattggc gtgcaggcgc tcaagcaatc tgctcccgac    300
ggctacaccc tgatgatggg caatatcgga cccaatgcga tcaactatag cttgtaccgg    360
caactgcctt atcgtgcgga ggactttgcg ccggtcacca tggtggtgtc ggtccccaac    420
gttcttgtgg taaatgcgaa tgtgccggcg cgtacggtgg cccagctggt agcgctgtcc    480
aaggcccagc ccggcaagct ctccttcgcc tcgtcgggca ctggccagtc ggtccatttg    540
tctggcgagc tgttccgcaa gcgcaccggt attgatatta tccatgtgcc ctacaagggc    600
```

| | | |
|---|---|---|
| gcggcaccgg ccgtggccga cttggttgcc ggccaggtaa ccatgatggt ggataatctc | 660 | |
| cccagctccc tgcctcatat ccagtcgggc aaattgcggg cactggccgt gaccagcgcg | 720 | |
| agccgcgtcc ccgagctgcc agacgtgcct accatgaagg aggccggttt ggaggacttt | 780 | |
| caggtgactg cgtggtttgg cctgatggct ccggcaggac cgccttcggc cgtgatcgac | 840 | |
| aggctgcaga ggaccgtggc tatcatcctc gccgagcccg aggtcaaatc acgcctggct | 900 | |
| gattttggcg gcgtgcccgg cggcgatacg cccacgcatt tcggaaattt catcaagagc | 960 | |
| gagcgcgagc gttgggcacg cgtggtcaag gacaccggca ttccgctgga ataa | 1014 | |

<210> SEQ ID NO 156
<211> LENGTH: 1014
<212> TYPE: DNA
<213> ORGANISM: C. necator

<400> SEQUENCE: 156

| | | |
|---|---|---|
| atgaaatccc tgctgcagcg gctgttcccg cggccattga ccacacctga cgcccgcacc | 60 | |
| ggcgccgccg cgctgatgct cgtcctggcc gcggccagcg cgcccgccca tgcagcgtgg | 120 | |
| cccgaccacc cgatccgctg gatcgtgccg tttccggccg gcggcgcgat ggacaatatc | 180 | |
| gcgcgcacgc tgggtgaaga tatgtcgcgc acgctcggtc aggccatcgt ggtggagaat | 240 | |
| cgccccggcg ccggcggcaa catcggcgcg gagctggttg cgcgcgcgcc ggccgacggc | 300 | |
| tacaccatga tcatcgtggc taacggcatg gcggtgaatc ccgccctgta cggcaagctc | 360 | |
| ggctacgacc cggtgaaaga ctttgccccc gtgtcgctgc tggctgtggt acccaatgta | 420 | |
| ctggtggcga gcaaggccaa gacgccagtg aagacggttg cggaggtggt ggccaatgcc | 480 | |
| aaggcgcggc cgggcaagta cacctatgcg tcggcgggca acggcacctc gatccaccta | 540 | |
| gcaggcgagt tgttcacttc catggcgggc gtcgacctgc tgcacgttcc ctacaaaggc | 600 | |
| agtggcccgg ccatgaccga cctgcttggc ggccaggtcg actacatgtt cgacagcatc | 660 | |
| acctcggcaa agccgcatat cgattccggc aaactcaccg ccatcgcggt aacgaccacc | 720 | |
| aagcgctcga cggcgttgcc caatgtgcct accgtagccg agtccggggtt ggctggctat | 780 | |
| gagctatcgc cgtggttcgc cgcctttgtt ccggcacgca cgccttccgc cgccattgag | 840 | |
| aagctgaacc aagccatgct cgatgcgcta cgcaatcctg ccgtgcagaa acggctggcg | 900 | |
| gcgattggcg cggagccgat tggcagtacc ccggcagcac tacgcgacca cctggcgcgt | 960 | |
| gagaccgcca gtggggcga gctgatccgg gcgcgcggga tccgcgccga ttga | 1014 | |

<210> SEQ ID NO 157
<211> LENGTH: 588
<212> TYPE: DNA
<213> ORGANISM: C. necator

<400> SEQUENCE: 157

| | | |
|---|---|---|
| atgagtatcg acagtatcca gcaacaattt ctagacagcg ccgagaccaa gcgacaggcc | 60 | |
| gcggcggtga tggcccccta tcgacgcc gccgtggaac gcatggtcgg cgcgctgacc | 120 | |
| agcggcaaca agatcctggc ctgcggcaac ggcggctccg cagccgatgc gcagcacttt | 180 | |
| gccgccgaac tggtcgggcg cttcgagcgc gagcgccccg gctgccgc gatcgcgctg | 240 | |
| accaccgaca gctcgatcct gaccgcgatc ggcaacgact atgacttcag caaggtgttt | 300 | |
| tccaagcagg tcgaggcgct gggccagccc ggcgacatcc tgctggcgct ttccacctcg | 360 | |
| ggcaattctg ccaacgtgat cgccgccatc gaagccgcgc gccagcgcga gatggccgtg | 420 | |

```
gttgcgctga ccggcaaggg tggcggcacc atcgccggcc tgctcgatga attcgatatc        480
cacctgtgcg tgccgagcga gcgcaccgcg cgcatccagg aagtgcacct gctgaccctg        540
cattgcctgt gcgacggcat cgacgaggca ctgctcgggg aagcctga                     588

<210> SEQ ID NO 158
<211> LENGTH: 690
<212> TYPE: DNA
<213> ORGANISM: C. necator

<400> SEQUENCE: 158
atgcccgggg aaacaccact gcaagggctg tatccattcc tgcacgggga gcggcaggac         60
ggcgccaggc ttgacgcagc cttactcgct tccgtgcagc agaaggccag cgacagcatt        120
gacgccaagc gccgcttctt cgagcagaac gggcccgtgg tggtggcggt ggcccaggca        180
attgccttga cctaccgcaa cggcggccgg ctgtttgcca tgggcaacgg cgggtcgagc        240
tgcgacgcgg cgcatatcgc ggtggagttc ctgcatcccg tcacggcggg tcggccggcg        300
ctcgcggccg tcaacctcgt cgcggatacg gcgatgatga ccgcagttgg gaacgacgtg        360
ggcttcgccc acgtcttcgt gcgccagctg gtggcgcagg cgaggcgcgg cgacgcgctg        420
atcggtgtct cgaccagcgg caactcggaa aatctgctcg cggccttcgc caagggcaag        480
gagatgggtc tggcgaccat cggcctgtct ggtcacgacg gcggccgcat ggcggcgagc        540
gcggacctcg atcactgcct ggtggtggac agcgacagca ttcaccgggt gcaggaaacc        600
catgttgcga tctaccacat cctgtgggat ctggtgcaca cgttgctcgc cgaggaccgc        660
ggcgggctgg ccgcaggagg cgcgcgatga                                         690

<210> SEQ ID NO 159
<211> LENGTH: 948
<212> TYPE: DNA
<213> ORGANISM: C. necator

<400> SEQUENCE: 159
atgaacaaga ccgtcattcc gcaggagcag atccggcagt cccatatcct ggtggtcggc         60
gacatgatgc tggaccgcta ctggttcggc gatgtggagc gcatctcgcc ggaagcaccg        120
gtgccggtgg tccaggtcaa gcgcagcgac gagcgcctgg gcggcgccgc caacgtggcc        180
cgcaatgccg cggcactggg cgcacgcgtg ggcatgctgg gcgtggtcgg cgacgacgag        240
ccggcccgca cgcttgaagc gctgctgggc gagagccatg tgcagcccta cctgcaccgc        300
gatcccaagc tcaacaccac catcaagctg cgcgtggtgg cgcaccagca gcagttgctg        360
cgcgtggatt tcgagagcgc gccggcgcat gaagtgctgg ccgcggtaca ggaccgcttc        420
ctggccctga tcaacgacta ccaggtgctg gtgctgtccg attacggcaa aggcggtctg        480
acccacgtca cgcgcatgat cgacgccagc cgcgcggccg ggcgcaaggt gctgatcgat        540
cccaagggcg acgactactc gcgctaccgc ggcgccaccc tgatcacccc caaccggggcc        600 gagatgcgtg ccgtggtcgg cgcctggaag accgaggcca acctgaccat ccgcgcgcag        660
aacctgcgcc gcgggctgca gctggaggcg ctgttgctga cgcgctcgga agagggcatg        720
acgctctaca ccgaggccga ggtgctgcac gtctccgccc aggcgcgcga ggtctatgat        780
gtatcgggtg cgggcgatac cgtgatcgcc acgctcgcca ccatgctggg tgccggcgtg        840
ccgctcaagg aagccgtgca gcatgccaat cgtgccggcg ccatcgtggt gggcaagctt        900
ggtaccgccg tcgtctctta ttctgaattg ttcggcgccg ccccgtga                    948
```

<210> SEQ ID NO 160
<211> LENGTH: 588
<212> TYPE: DNA
<213> ORGANISM: C. necator

<400> SEQUENCE: 160

```
atgccgcaga cgccgcccaa gtttgtcatc ctggaccgcg acggggtggt caacctcgac    60
agcgaccagt tcatcaagac gcccgatgaa tgggtgccga tcgacggcag cctggaggcc   120
atcgccgcgc tgaaccaggc cggctaccgc gtggtcctcg ccagcaacca gtccggcatc   180
ggccgcgggc tgttcgagat gagcgcgctc aacgccatgc acgagaagat gcacacgttg   240
ctcgcgcgcg tgggcgggcg cgtcgacgcg tgttcttct gcccccatac cgccgcggac   300
ggctgcgact gccgcaagcc caagcccggc atgctggagc agatcagcga gcgcttcggc   360
atcgagctcc gcggcgtgcc catcgttggc gattcgctgc gcgacctgga agccggcgtg   420
gcggtcggtt gcgcgccgca cctggtacgc agcggcaagg ccagaagac cctcgaccag   480
ggcgccctgc cgcccgggcac gcaagtgcac gacgacctgc tcgcgtttgc cgctggctg   540
accggcaacg gcggcgcaca cgcccaccc actcatagcg ccggctga                588
```

<210> SEQ ID NO 161
<211> LENGTH: 495
<212> TYPE: DNA
<213> ORGANISM: C. necator

<400> SEQUENCE: 161

```
atgtccgtac ccgctttcga atccaagctg accctgcctg acacccccgc cgcgctggcc    60
gcgcgcatcg ccgccttgcc gcgcccgctg gtgttcacca atggcgtctt cgacatcctg   120
caccgcggcc atgccaccta cctggcacag gcgcgcgcac tgggcgcaag cctggtggtt   180
ggcgtcaaca gcgatgcttc cgtaaagatg ctgggcaagg gcgacgaccg tccgctgaac   240
catgaatcgg accgcatggc gctgctggcc gcgctggagt cggtcgacct ggtggcgatg   300
ttccgcgaac agaccccggt ggaactgatc cgcctggtgc gccccgacat ctacgtcaag   360
ggcggcgact acgacatcga cacgctggaa gaaacccggc tggtgcgcag ctggggcggg   420
caggcctacg ccatcccctt cctgcacgac cgctcgacca ccaagctgct gaccagggtg   480
cgccagggca gctaa                                                    495
```

<210> SEQ ID NO 162
<211> LENGTH: 996
<212> TYPE: DNA
<213> ORGANISM: C. necator

<400> SEQUENCE: 162

```
atgaccatca tcgtcaccgg cgccgctggc tttatcggca gcaacctcgt caaaggcctg    60
aacgaccgcg gcgagaccaa cgtcatcgct gtcgacaacc tgacccgtgc cgacaagttc   120
cacaacctgg tcgactgcga gatctccgac tacctggaca gcaggactt cctcgcgcgc   180
tttgcccgcg gcgagttcgg caaggtgcgg gcggtattcc atgagggcgc gtgctccgac   240
accatggaga ccgacggccg ttacatgatg gagaacaact accgttacac gctgtcgctg   300
atggagagct gcctggaaca gggcacgcag ttcctgtatg cgtcgtcggc ggctacctac   360
ggtgcttcgc aggtgttccg cgaagaccgc gagtttgagc gccgctgaa cgtgtacggc   420
tactccaagt cctgttcga ccagatcgtg cggcgccggc tgccgtcggc gctgtcgcag   480
atcgtgggct tccgctactt caacgtgtac ggcccgcgtg aaacgcacaa gggccgcatg   540
```

```
gcctcggtcg ccttccacaa cttcaaccag ttccgcgccg acggcacggt gaagctgttc      600
ggcgagtacg gtggctatgc ccccggcatg cagagccgcg actttatctc ggtcgaggac      660
gtggtcaagg tcaacctgca cttcttcgac catccggaca agtccggcat cttcaatctc      720
ggcaccggcc gcgcgcagcc gttcaacgac atcgccgcca ccgtggtcaa taccctgcgc      780
gaggccgaag gcaagccgcg cctgtcgctc gatgaactgg tgcaggaagg cctgctcgag      840
tacgtcaagt ccccgatgc gctgcgcggc aagtaccagt gctttacgca gtcggatgtg      900
tcgaagctgc gcagcgccgg ctacagcgag ccgttcctga gcgtcgagga aggcgtggcg      960
cgctactgcc gctggctgat cgaacgcgcc ggctga                               996
```

<210> SEQ ID NO 163
<211> LENGTH: 987
<212> TYPE: DNA
<213> ORGANISM: C. necator

<400> SEQUENCE: 163

```
atgaaacgta ttctcatcgt caagctgacc tctctcggcg acatggtgtt cacccagccg       60
ctggtcgcgg acctgcagcg ggcctttccc ggcgtcaaga tcgactggat cgccgactca      120
tattgcgcca acgtgccgcg ctggaatccg aatatcgagc gtgtgatttc cgcgccgctg      180
cgcggcttca agaaatcgcg caattgggct ggcttgcgtg cgatcttcag cgcgctgcgt      240
gaactgcgtc gcgagaagta cgatgcgctg ctggacgtcc acggcgtcta caagagcgcc      300
atcgtgacgt tcctggcacg cacgcgcaat cgctatggct accccgtggc agagttgggc      360
gagagcggcg ctcgcttcgc ctacaaccat gtgttccagc catttgtcga agaagattgc      420
gcgcggcagc ggatgcgccg cgccgtcagc cgcgccctgg gctatgagct gaccagggac      480
atggactacg gcctggagat gccagcagac acgccggcgc cggccgccaa gggtccgtac      540
gcgatgctgt ccatgccac ctcgagcgag gaaaagaagt ggccggtcgc cgactggatc      600
agcgtgggca gcgcgatctc ggccgcgggg ctgcgcgtgc tggtgccctg ggcaacgac       660 gcggagcgca aggaagccga aaccatcgcc gccagcgtgc ccaacgccga agtgatgcca      720
cgcctgagca tcaccggtgt ggcgcagatg gtaggcaagg catcgctggt ggttggcatg      780
gacaccggct tcgtgcatat cgccgatgcg ctgcgccgcc cgaccgtgat cctgttcacg      840
accacgtcgc gccacctgta cggcgtcgat gcgccgggcc gcgtggtctc gctgggcggc      900
ggcggcgtgg tgccgcggcg ggatcaggtg ctggctgcca tcgatgaagt gctgggcgtg      960
cagccgcccg tcacctcgcc aaactga                                          987
```

<210> SEQ ID NO 164
<211> LENGTH: 1107
<212> TYPE: DNA
<213> ORGANISM: C. necator

<400> SEQUENCE: 164

```
atgctcagct cccgttctga gcgcgcgacg gtgccggcgg catcgtcgga cgcggccggt       60
gtggcgcagc ccacgccggc cgcggtgcct tcacactgc cggaacggcc gcgcatcctg      120
ctggtcaagg tgtcgtcgct cggtgacgtg gtgcacaaca tgccgctggt gcacgatctg      180
cgcgcgcgct ggccgggtgc cgagatcgac tgggtggtgg aagagggcta tgtcgagctt      240
gtccggctgt tgccggaggt gcgccgggta attccgtttg cgctgcggcg ctggcgcaag      300
cgcatcctgc agggcggcac ctggcgcgag gtgggcgagg tgcgtgactt gttgcgccag      360
gagcgctatg acgcggtgat cgaaagccag ggtttgctca agaccgcggt ggtcgcgcgc      420
```

```
gtggccgcgc gggcgcccgg cgcgccgatt atcgggctgg gcaatgccac gcagggctcc    480
ggctatgagc cggcggcgcg gctgctatac accgatccgg tgcgcgtgcc acgccagacg    540
cattcggtgc ggcgctcgcg cttgctgggc gctgcgctga ccgggcttgt gccggcggag    600
ccgccgcagt ttttcgggcc tgccgcgcag tcgctgcatg tggacgatcc gctgtggggc    660
gatctgcctg cgcgctatgc cgtgtgcttc catgcgaccg ctggcgcgcg caagaaatgg    720
gcggtgcaga actggcatgc gctgggcagg cggctggcgg atgagggtct ggtgatgttg    780
ctgccgtggg gcaatgacaa ggaacgccag gctgccgaag atcgctgc tggtgtgccg      840 caggcgaggg tgttgccgcg attctcggtg atgcagggtt tcgggctgat caacggggcc    900
gaggtggtga tcggggtcga tacgggcctg gtccatattg ccgcggcgtt gtgccggccg    960
acggtggaga tctatacggc cacgtggcgc tggaagactg agggctactg gtccgggcgc   1020
atcgccaatg tcggtgacga cggcgtggtg ccgtctgtcg atgaggtcta cgacgcggct   1080
tgccgcgtgc gcggagtggc tgcctga                                       1107
```

<210> SEQ ID NO 165
<211> LENGTH: 1023
<212> TYPE: DNA
<213> ORGANISM: C. necator

<400> SEQUENCE: 165

```
atgaagaaag ccctcgtcat cgcccccaac tggatcggcg acgccctgat ggcgcagccg     60
ctctttgcgc tgctcaaggc gcgccatccg cgcctggtca tcgacgcact cgcgcccaag    120
tgggtcgcgc ccgtgctcgc gcgcatgccg gagatcggcc gcgtgttccc gtccgacctc    180
gcgcacggca agctgcagct gtcggcacgg ctgatgttcg cgcagcagct caagaacgaa    240
ggctatgacc tcgcctacgt gctgccgaac tcgctcaagt cggcactggt ccctggctg     300 gccggcatcc cgctgcgcat cggctaccgc ggcgaagccc gcttcggcct gctcaacgtg    360
cgccacgcca accgccgcg cgacaagcgc ccgccgatgg tggagcacta cgcccgcctg    420
gcgctcaagc ccggcgcgcg cctgcccgaa gacctgcccg agccgcgcct gcgcgtcgac    480
ccgacgcgca tggcggccac cgccgagcgc tttggcatcg ccccgcacac gcgcgtgatc    540
gcgttctgcc cggtgccga gttcggcccg gccaagcgct ggccggccgg gcatttcgcc    600
aggctcgcgc agatgctgcg cgcgttcctac ccgtatgcgc agatgatcac gctgggctcg    660
gccaaggacg ccgagatcgc cgccgagatc gtcagcgagg ccccgttcgt gcgcaacctg    720
tgcggccaga cctcgctgga tgacgccgtg gacctgctgg cgctctccga agccgcggtc    780
tgcaacgact ccggcctgat gcacgtcacc gcggcgctga accggcccca ggtggcggtg    840
ttcggctcga gcgacccgcg ccacacgccg ccgttgtcac aggcagcgag tatcatgtgg    900
ctgcaactgg agtgcagtcc ctgcttcaag cgcgagtgcc cgctgggcca cctgcgctgc    960
ctgaaagaga tcgaacctga aatggtgttc gtcgagctgc gcaagctgct gcaccggccc   1020
tga                                                                 1023
```

<210> SEQ ID NO 166
<211> LENGTH: 1290
<212> TYPE: DNA
<213> ORGANISM: C. necator

<400> SEQUENCE: 166

```
atgctgcgtt tgctctatag catgttatgg gtggtggtgc tgccgctggc gctgctgcgc     60
```

```
ctggcctggc gtgcgcgcaa ggagccgggc tacttgcagc atgtcggcga acgcctgggt      120
atatacggca gcctgccccg gaaaggtccg tggctatggg tccacgccgt gtcggtgggc      180
gagacccgcg ccgcgcagcc gctgatcgag gcgctgctcg gcgcctatcc gcaccaccgc      240
ctgctgctga cgcacatgac gccgaccggc cgccagaccg tgcgcagct gttcggcaag       300 gagccgcgca tcctgcaatg ctacctgccg tatgacctgc catggctggt ggggtgtttc      360
atgcggtatt tccggccgca ggcgggcatg ctgatggaga cggaggtgtg gcccaacctg      420
gtgcgcggcg cgcgcaaggc cggagtgccg ctgttcctgg tcaatgcgcg cctgtcgccg      480
cgcagcttcc ggcgcacggc gcggtttggg gcgcgctgcg cggtcatgta tgcggatttt      540
gcgggcgtgc tggcgcagac ggcgggtgat gccgagcgct tcaggcgtt gggcgtgccg       600 gcggtgcaga tcaccggcaa cctgaagttc gatatgcagc cggcgccggc aggcgttgcg      660
ctgggcgagc agttgcgcaa ggtcattggc acgcgtgcgg tgctggcagc cgccagcacg      720
cgcgagggag aggagccgat gttgctcgac gcgttctccc gttggcaatc actggcgggc      780
gatgtcccgc gtcccgctct gctgctgatc ccccgtcacc cgcagcgctt cgatgaagtc      840
gccgcgatgg cggcgcgtgc ggggttctcg gtcgagcgcc ggagtgcact ggatcttgac      900
ggcatccagt cgccgctgac tgccgatatc gtgctgggcg attcgatggg cgagatggcg      960
atgtactttg ctgcgtcgga tcttgccttt atcggtggca gcctgttgcc gctcggggg       1020 cagaacctga tcgaagcctg cgcggtcggc acgccggtgc tggtcggtcc gcataccttc      1080
aactttgcgc aggcgacgga agacgcgatt gccgcgggcg cttgcctgcg cgtcgacaat      1140
gccgatgcgc tgatgcgcat cgcggcaagc gtgctggccg atccagcccg gctggcggat      1200
atgcgcgcgc atgcgcagac cttttgcagg c ctgcatcggg gcgccaccgt gcgcacccct   1260
gctgcgctgg ccccggcgct ggaaggctga                                       1290

<210> SEQ ID NO 167
<211> LENGTH: 894
<212> TYPE: DNA
<213> ORGANISM: C. necator

<400> SEQUENCE: 167
atgagccgtg tgttcacgtg gcttggcatc ggcttgctga cggtgctggg caagctgcca      60
tatccgttcg tcgcgcgctt cggcgaggcg ctgggaagcc tgctctacct ggtgccgagc      120
gagcggcgcc gcgtggtgca ggccaacctg cgcctgtgtt tcccggaccg gaccgaggcc      180
gaaatcgatg aactgtcgcg gcagagcttc gcatcctgt tccgcagctt tgccgaacgc       240
ggcatcttct ggaccggcag tgaggcgcag atgcgccgct gggtgcagat cgacgaccag      300
gccggcctgg tggccctgga tgcaccccg catatcctgg tgacgctgca cctgtcgggc      360
gtggaagccg gtgcgatccg actcaccatc gacctgcgcg agcatctcgg ccgctccggc      420
gcatcgctct ataccaggca gaagaacgac ctgttcgacc acttcctgaa gcacgcgcgc      480
gggcgcttcg gcgccaacat gatctcgcgc aacgacagcg cgcgcgacat cctgcgctgc      540
ctgaagaagg gcgaggccct gcagctgatc gccgacatgg atttcggcga gcgcgactcg      600
gagttcgtgc cgttcttcgg cgtgcaggcg ctgacactga cctcggtgtc gcggctggcg      660
cgcctgaccg gggccaaggt cgtgccgatc tacaccgaga tgctgcccga ctaccagggc      720
tatgtgctgc gcatcctgcc gccctgggaa gactaccccg cgcaagcgt caccgacgac      780 acgccgcca tgaatgcctt cttcgaggac tgcatccgcc cgcgcgtacc cgagtactac      840
tgggtgcaca gcgcttcaa gcaccgcctg ccggggcgagc ccgagatcta ctga           894
```

```
<210> SEQ ID NO 168
<211> LENGTH: 879
<212> TYPE: DNA
<213> ORGANISM: C. necator

<400> SEQUENCE: 168
atgaaacacc ggctccaggc tgcgctcacc atcgcagtct tcaagctcgt cgccgccctg      60
ccgtacggtg tcaccgcacg cctgggcgat gcgatcggca agctgctgta tcgcatcccc     120
agccgccgcc ggcgcattgt ccataccaac ctgtccctgt gcttcccgga catggatgca     180
gacacgcgcg acaagctggc acggaaccac ttcggccacg tcctgcgcag ctacctggag     240
cgcggcgtgc agtggttcgg cagcgccgag cgcctgggca agctggtgga actggactcg     300
cgcatcgacc tggcctcgtg cgcggagcat ccgaccatct tcatgggctt ccatttcgtc     360
ggcatcgagg ccggctgcat gttctattcg atgcgccacc cggtggcctc gctgtacacc     420
aggatgtcca gccagatgct ggaagacatc tcgcgcacgc agcgcgggcg ctttggcgcc     480
gagatgatcc cgcgcagcgg cagcggcaag caggtggtgc gcacgctgcg cgccggctgc     540
ccggtaatgc tggcgtcgga catggatttc ggcatcaacg attcggtgtt cgtgccgttc     600
tttggcgtgc cggcctgcac gctgacctcg gcctcgcgcc tggccagcat gaccggcgcg     660
cgcgtggtgc ccttcaccac cgaagtgctg cccgactacc gcggctaccg gctgcgcata     720
ttcgacccgc tggaaggctt cccctcgggc agcgtcgagg aagattcgcg ccgcatgaac     780
gccttcctcg aagcccagat cgccaccatg ccggagcagt attactggat ccaccggcgc     840
ttcaagaacc ggcccgcagg catgccgtcg gtgtactga                            879

<210> SEQ ID NO 169
<211> LENGTH: 897
<212> TYPE: DNA
<213> ORGANISM: C. necator

<400> SEQUENCE: 169
atgacctttt tgttctggct gatctcccgt tttcccctgc ggctgctgca agccgcgggc      60
ggcgcgctcg gactgctgag cgcgcgcctg cccggccgct acggccagcg cctgcgggag     120
aacttccgcc aggcgtttcc cgacgccacc gatgcgatga tcgacgaagc ggcccgttcg     180
gccggacgca tgatcgtcga gatgccctac ttctggagcc gcagcaagat cggtgcgaag     240
ctgcatggct tgacgactac cctgtggccc gagctgggca agctgcaggc gcgcggcaag     300
ggcatcatca tcctgacccc gcacctgggc tgctttgaag tgctgccgca gtcccacgcg     360
ctgcagcgcc cggtcaccgc cctgttcaag ccgccgcacc agccctggct gcgcgactgg     420
attgaaaaaa tgcgcacccg gcccggcatg cacatggcgc cggccacgcc gcgcggtgtg     480
cgcatgctgg tgaaggcact caagcgcggc caggcggtgg gcatcctgcc cgaccaggtg     540
cccagcggcg gcgagggcaa ctgggcgccg ttcttcggca agccggccta ccatggca      600 ctggtgcacc ggctgcagca gctgaccggc gcgccggtgg tggcggtctt tgccgagcgc     660
ctgccgcgcg gcgccggcta tcgcggccac ctgcgcgtga tcaacgacgg cggcatgctg     720
ccggacgatc ctgccgccgc tgccgcggtc atcaaccgga ctatcgagga actggtgggc     780
ctgtgcccca cgcagtacct gtgggcttac aaccgctaca agcaacccgc cggagcgggt     840
accccggacg cgccgggcaa tgataccgag ccggccactg atcgatcgat ttcatga       897
```

MATERIALS AND METHODS FOR DIFFERENTIAL BIOSYNTHESIS IN SPECIES OF THE GENERA *RALSTONIA* AND *CUPRIAVIDUS* AND ORGANISMS RELATED THERETO

This patent application claims the benefit of priority from U.S. Provisional Application Ser. No. 62/665,800 filed May 2, 2018, teachings of which are herein incorporated by reference in their entirety.

FIELD

The present invention relates to methods for increasing carbon-based chemical product yield in an organism by increasing carbon uptake and/or altering a pathway to or from an overflow metabolite in the organism, nonnaturally occurring organisms having increased carbon-based chemical product yield with increased carbon uptake and/or an altered pathway to or from an overflow metabolite, and methods for producing a carbon-based chemical product with these organisms.

BACKGROUND

Under conditions of nutrient limitation, a phenomenon known as overflow metabolism (also known as energy spilling uncoupling or spillage) occurs in many bacteria (Schlegel and Vollbrecht Microbiology 1980 117:475-481). The range and quantity of overflow metabolites produced in a particular fermentation can depend upon the limitation applied (e.g. nitrogen, phosphate, oxygen), the extent of the limitation, the carbon source provided and the fermentation conditions such as, but not limited to, pH, source of phosphates or ammonia. See (Vollbrecht et al. European Journal of Applied Microbiology and Biotechnology 1978 6(2):145-155; Vollbrecht and Schlegel European Journal of Applied Microbiology and Biotechnology 1978 6(2):157-166; and Vollbrecht et al. European Journal of Applied Microbiology and Biotechnology 1979 7(3):267-276). Such overflow metabolites represent a net loss of carbon which could otherwise be converted into one or more desired compounds.

Tripartite tricarboxylate transporters (TTT) are carbon transporter proteins that use ion-electrochemical gradients to move substrates in a symporter mechanism (Rosa et al. Front Cell Infect. Microbiol. 2018 8:33; Winnen et al. Res. Microbiol. 2003 154(7):457-65).

Replacement of traditional chemical production processes relying on, for example fossil fuels and/or potentially toxic chemicals, with environmentally friendly and/or sustainable solutions is being considered, including work to identify suitable building blocks for such use in the manufacturing of such chemicals. Methods and organisms are needed which channel carbon into selected biosynthetic pathways by blocking undesirable pathways, thereby improving production of one or more desired compounds.

SUMMARY

Methods for increasing product yield of organisms and organisms capable of increased product yield are provided.

An aspect of the present invention relates to methods for increasing carbon-based chemical product yield in an organism. These methods comprise modifying an organism selected from a species of *Cupriavidus* or *Ralstonia* with diminished polyhydroxybutyrate synthesis or an organism with properties similar thereto to increase carbon uptake and/or alter a pathway to or from an overflow metabolite. Organism are modified in accordance with the present invention by modulating activity of one or more polypeptides or functional fragments thereof functioning to increase carbon uptake and/or in a pathway to or from an overflow metabolite, thereby increasing carbon-based chemical product yield in the organism as compared to an organism without said modulated polypeptide activity.

In one nonlimiting embodiment, the organism is modified to increase carbon uptake via one or more modifications to alter expression and/or activity of a carbon transporter protein or functional fragment thereof.

In one nonlimiting embodiment, modifications to alter expression and/or activity of a carbon transporter protein or functional fragment thereof comprise altering expression and/or activity of one or more genes encoding a TctA, a TctB or a TctC.

In one nonlimiting embodiment, one or more genes as listed in Table 2 are modified.

In one nonlimiting embodiment, the organism is modified to alter a pathway to or from an overflow metabolite by disrupting one or more genes associated with the production of lactate, hydroxybutyrate, acetate and/or 2,3 butandiol, as shown in Table 3.

Another aspect of the present invention relates to nonnaturally occurring organisms capable of yielding a carbon-based chemical product. These nonnaturally occurring organisms are selected from a species of *Cupriavidus* or *Ralstonia* with diminished polyhydroxybutyrate synthesis or an organism with properties similar thereto and are modified to increase carbon uptake and/or alter a pathway to or from an overflow metabolite.

In one nonlimiting embodiment, the nonnaturally occurring organisms are modified to increase carbon uptake via one or more modifications to alter expression and/or activity of a carbon transporter protein or functional fragment thereof.

In one nonlimiting embodiment, one or more modifications to alter expression and/or activity of a carbon transporter protein or functional fragment thereof comprise altering expression and/or activity of one or more genes encoding a TctA, a TctB or a TctC is made to the organism.

In one nonlimiting embodiment, one or more genes as listed in Table 2 or Table 3 are modified.

Yet another aspect of the present invention relates to methods for producing a carbon-based chemical product. In these methods, a nonnaturally occurring organism of the present invention is fermented with a carbon source.

In one nonlimiting embodiment, the carbon source is derived from a biological or nonbiological feedstock. In one nonlimiting embodiment, the feedstock fed to the fermentation process comprises a gaseous or liquid stream. In one nonlimiting embodiment, the feedstock is selected from gases, sugars, sugar acids, carboxylic acids, aromatics, and alcohols. In one nonlimiting embodiment, the carbon source is derived from a by-product or waste stream of a food or agricultural industry.

BRIEF DESCRIPTION OF THE FIGURES

FIG. 1 is a schematic of enzymatic production of PHB from fructose. Examples of enzymes and/or their genes which may be interfered with and pathways which may be blocked are indicated by strikes.

DETAILED DESCRIPTION

The present invention provides methods of increasing carbon-based chemical product yield in an organism as well as nonnaturally occurring organisms modified to exhibit increased product yield as compared to unmodified organisms.

The methods of the present invention comprise modifying an organism selected from a species of *Cupriavidus* or *Ralstonia* with diminished polyhydroxybutyrate synthesis or an organism with properties similar thereto to increase carbon uptake and/or alter a pathway to or from an overflow metabolite. Organism are modified in accordance with the present invention by modulating activity of one or more polypeptides or functional fragments thereof functioning to increase carbon uptake and/or in a pathway to or from an overflow metabolite, thereby increasing carbon-based chemical product yield in the organism as compared to an organism without said modulated polypeptide activity. In one nonlimiting embodiment, genes in these pathways to or from an overflow metabolite may be modified. Such modifications may comprise overexpressing an endogenous or exogenous nucleic acid sequence in the organism. Alternatively, such modification may comprise downregulating, deleting or mutating an endogenous or exogenous nucleic acid sequence in the organism. The modified organisms are then cultured under conditions suitable for biosynthesis of the one or more products.

In certain aspects, the organism is modified by altering, engineering, or introducing one or more nucleic acid sequences within the organism to have one or more different characteristic properties relative to those of the corresponding unmodified wild type organism. The altering of modifying of the nucleic acid sequences can be, for example and without limitation, via genetic engineering, by adaptive mutation, or by selective isolation of naturally occurring mutant strains.

In some nonlimiting embodiments, one or more enzymes or nucleic acids of the organism are modified via non-direct or rational enzyme design approaches with aims of improving activity, improving specificity, reducing feedback inhibition, reducing repression, improving enzyme solubility, changing stereo-specificity, or changing co-factor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches. In some nonlimiting embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids encoding polypeptides functioning as a transhydrogenase, reductase, dehydrogenase, or hydrogenase enzyme or functional fragments thereof. The modifications can be to nucleic acids not directly involved in encoding polypeptides functioning as a transhydrogenase, reductase, dehydrogenase, or hydrogenase enzyme or functional fragments thereof, but indirectly affecting the polypeptides through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics. Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one nonlimiting embodiment, modification of the organism is carried out by allele exchange. In this embodiment, genome edits are made in a *Cupriavidus* or *Ralstonia* organism with perturbed PHB synthesis or an organism with properties similar thereto by allele exchange (also referred to as allelic exchange). In one non-limiting embodiment, the organism is a ΔphaCAB H16 *C. necator* strain generated using allele exchange.

The term 'allele' is often used interchangeably with the term 'gene' more generally, and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one nonlimiting embodiment, recombinant/synthetic alleles can be constructed via gene synthesis and/or standard molecular biology techniques. These alleles are then cloned into a plasmid vector for transfer into the organism and execution of the allele exchange procedure.

In some nonlimiting embodiments, the organism is modified to include one or more exogenous nucleic acid sequences.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In certain aspects, the organism is modified to include one or more functional fragments of enzymes, other polypeptides, or nucleic acids. The phrase "functional fragment" as used herein refers to a peptide fragment of a polypeptide or a nucleic acid sequence fragment encoding a peptide fragment of a polypeptide that has at least 25%, e.g., at least 30%, at least 40%, at least 50%, at least 60%, at least 70%, at least 75%, at least 80%, at least 85%, at least 90%, at least 95%, at least 98%, at least 99%, or at least 100% of the activity of the corresponding mature, full-length, polypeptide. The functional fragment can generally, but not always, be comprised of a continuous region of the polypeptide, wherein the region has functional activity.

Tripartite tricarboxylate transporters (TTT) are carbon transporter proteins that use ion-electrochemical gradients to move substrates in a symporter mechanism. Each transporter is comprised of two transmembrane proteins and a periplasmic solute-binding protein. TctA is a well-conserved 12 transmembrane protein while TctB is a poorly conserved smaller transmembrane protein with 4 putative TMs domains. TctC is a periplasmic tricarboxylate-binding receptor. The TctC protein is highly represented in the protobacteria genomes possibly providing specificity to the transporter. Recent genome analysis of *Ralstonia* has shown an overrepresentation of tctC homologs. In one nonlimiting embodiment of the present invention, one or more modifications to increase carbon uptake comprise altering expression and/or activity of one or more of carbon transporter proteins or functional fragments thereof.

Within biotechnology the approach of redirecting carbon flux to a desired product by utilizing nutrient limitation is a well-established process. With *Cupriavidus*, it is the principle methodology for obtaining high polyhydroxyalkanoate (PHA) titers, as it exploits the organism's natural mechanism for intracellular storage of carbon and energy. To utilize *Cupriavidus* or *Ralstonia* for the purposes of generating other chemicals however, this natural mechanism is detrimental for obtaining high productivity and/or yields. Elimination or significant attenuation of PHA synthesis is therefore required, in order to maximize the efficiency of generating the desired product.

An unintended consequence of such an approach is that there is a cascade of effects upon metabolism due to high amounts of reducing equivalents and build-up of key central metabolites including pyruvate and acetyl-CoA. These manifestations include among others metabolic bottlenecks, heightened generation of overflow metabolites and a redox imbalance.

Furthermore, under conditions of nutrient limitation, a phenomenon known as overflow metabolism (also known as energy spilling uncoupling or spillage) occurs in many bacteria (Schlegel & Vollbrecht Microbiology 1980 117: 475-481). In growth conditions in which there is a relative excess of carbon source and other nutrients (e.g. phosphorous, nitrogen and/or oxygen) are limiting cell growth, overflow metabolism results in the use of this excess energy (or carbon), not for biomass formation but for the excretion of metabolites, typically organic acids. Such overflow metabolites represent a net loss of carbon which could otherwise be converted into one or more desired compounds. Accordingly, in one nonlimiting embodiment of the method of the present invention, one or more modifications in a pathway to/from an overflow metabolite are made to increase carbon-based chemical product yield.

By "carbon-based chemical product" as used herein, it is meant to include C3 to C12 alkenes, alcohols, diols, monoacids, diacids, hydroxyacids, amino acids and diamines. In one nonlimiting embodiment, the carbon-based chemical product may be any C6-C12 difunctional aliphatic fatty acid or derivative thereof including, but not limited to, C6-C12 amino acids, C6-C12 diamines, C6-C12 hydroxyacids, C6-C12 diols, and C6-C12 diacids. Nonlimiting examples of carbon-based chemical products produced in accordance with this disclosure include 1,3-propanediol, 1,2-propanediol, methionine, threonine, lysine, glutamic acid, tryptophan, aspartic acid, leucine, isoleucine, valine, citric acid, maleic acid, succinic acid, isoprene, linalool, limonene, 3-hydroxypropanoic acid, malonic acid, lactic acid, n-butanol, 2-butanone, butadiene, 2-3 butanediol, 1-3 butanediol, benzoic acid, 1,4-benzenediamine, benzeneamine, pyridine, vanillin, hydroquinone, 1,4-diaminobutane, 2-hydroxyisobutyric acid, itaconic acid, 3-hydroxybutyrate and nylon intermediates.

In some nonlimiting embodiments, the organism has been modified to exhibit an increased synthesis of the extracellular product relative to that of the corresponding wild type organism.

In some nonlimiting embodiments, the carbon-based chemical product includes pimelic acid, 7-aminoheptanoate, 7-hydroxyheptanoate, heptamethylenediamine, 1,7-heptanediol, or a combination thereof. Additional descriptions of the synthesis of these carbon-based chemical products with Ralstonia, Cupriavidus, or an organism similar thereto can be found in U.S. Pat. No. 10,196,657, the disclosure of which is incorporated by reference herein in its entirety for all purposes.

In some nonlimiting embodiments, the carbon-based chemical product includes 1,4-butanediol, putrescine, 4-hydroxybutyrate, 4-aminobutyrate, or a combination thereof. Additional descriptions of the synthesis of these carbon-based chemical products with Ralstonia, Cupriavidus, or an organism related thereto can be found in U.S. Pat. Nos. 10,072,150 and 9,637,764, the disclosures of which are incorporated by reference herein in their entirety for all purposes.

In some nonlimiting embodiments, the carbon-based chemical product includes glutaric acid, 5-aminopentanoic acid, cadaverine (also known as 1,5 pentanediamine), 5-hydroxypentanoic acid, 1,5-pentanediol, glutarate semialdehyde (also known as 5-oxopentanoate), or a combination thereof. Additional descriptions of the synthesis of these carbon-based chemical products with Ralstonia, Cupriavidus, or an organism related thereto can be found in U.S. Pat. No. 9,920,339, the disclosure of which is incorporated by reference herein in its entirety for all purposes.

In some nonlimiting embodiments, the carbon-based chemical product includes isoprene. Additional descriptions of the synthesis of this carbon-based chemical product with Ralstonia, Cupriavidus, or an organism related thereto can be found in U.S. Pat. No. 9,862,973, the disclosure of which is incorporated by reference herein in its entirety for all purposes.

In some nonlimiting embodiments, the carbon-based chemical product includes adipic acid, 6-aminohexanoic acid, hexamethylenediamine, caprolactam, 1,6-hexanediol, or a combination thereof. Additional descriptions of the synthesis of these carbon-based chemical products with Ralstonia, Cupriavidus, or an organism related thereto can be found in U.S. Pat. No. 9,580,733, the disclosure of which is incorporated by reference herein in its entirety for all purposes.

For products of the present invention containing carboxylic acid groups such as organic monoacids, hydroxyacids, aminoacids and dicarboxylic acids, these products may be formed or converted to their ionic salt form when an acidic proton present in the parent product either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to below the lowest pKa through addition of acid or treatment with an acidic ion exchange resin.

For products of the present invention containing amine groups such as but not limited to organic amines, aminoacids and diamine, these products may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate and/or bicarbonate, ammonia, sodium hydroxide, and the like. The salt can be isolated as is from the system as a salt or converted to the free amine by raising the pH to above the lowest pKa through addition of base or treatment with a basic ion exchange resin.

For products of the present invention containing both amine groups and carboxylic acid groups such as but not limited to aminoacids, these products may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases include aluminum hydroxide, calcium hydroxide, potassium hydroxide, sodium carbonate and/or bicarbonate, ammonia, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. The salt can be isolated as is from the system or converted to the free acid by reducing the pH to below the pKa through addition of acid or treatment with an acidic ion exchange resin.

Nonnaturally occurring organism produced and used in accordance with the present invention are selected from a species of Cupriavidus or Ralstonia with diminished polyhydroxybutyrate synthesis or an organism with properties similar thereto.

For purposes of the present invention, by "diminishing" or "diminished" polyhydroxybutyrate synthesis, it is meant that the organism is altered to synthesize less polyhydroxybutyrate as compared to an unaltered wild-type organism of the same species. Organisms used in this disclosure can exhibit at least 20%, 25%, 30%, 40%, 50% or even greater decreased polyhydroxybutyrate synthesis as compared to an unperturbed wild-type organism of the same species.

Nonlimiting examples of species of Cupriavidus or Ralstonia useful in accordance with this disclosure include Cupriavidus necator, Cupriavidus metallidurans, Cupriavidus taiwanensis, Cupriavidus pinatubonensis, Cupriavidus basilensis* and *Ralstonia pickettii*.

*C. necator* (also referred to as *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar, N. S. & Casida, L. E. Int. J. of Systematic Bacteriology 1987 37(4): 323-326), bacterial predation (Byrd et al. Can J Microbiol 1985 31:1157-1163; Sillman, C. E. & Casida, L. E. Can J Microbiol 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of either aerobic or nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (ΔphaCAB) is used. In one nonlimiting embodiment, the organism is further modified to eliminate phaCAB, involved in PHBs production and/or H16-A0006-9 encoding endonucleases thereby improving transformation efficiency as described in U.S. patent application Ser. No. 15/717,216, teachings of which are incorporated herein by reference. However, other means of eliminating PHB synthesis are included within the scope of the invention.

By "an organism with properties similar thereto" it is meant an organism having one or more of the above-mentioned properties of *C. necator*.

In the process described herein, a fermentation strategy can be used that entails anaerobic, micro-aerobic or aerobic cultivation coupled with nutrient limitation such as iron, sulphate, nitrogen, potassium, oxygen, phosphorus, carbon and/or or NADP limitations, gradients thereof and any combinations thereof.

A cell retention strategy using a ceramic hollow fiber membrane can also be employed to achieve and maintain a high cell density during fermentation.

The principal carbon source fed to the fermentation can derive from a biological or non-biological feedstock. In one nonlimiting embodiment, the feedstock is fed to the fermentation as a gaseous or liquid stream.

Feedstocks for fermentation may be gases such as carbon dioxide or hydrogen; sugars such as glucose, xylose or fructose; sugar acids such as gluconate; fatty acids or fats/oils, carboxylic acids such as propionic acid, lactic acid, and formic acid; amino acids, aromatics such as phenol and benzoic acid and/or alcohols such as glycerol.

The feedstocks may be carbon sources derived from by-product or waste streams such as brewing, dairy, plant oil, ethanol, corn, soy, fish, or sugar industries or any other food or agricultural waste such as used cooking oil.

The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles or waste streams from the food processing or dairy industries municipal waste such as fruit peel/pulp or whey. The non-biological feedstock can be, or can derive from, natural gas, syngas, $CO_2/H_2$, CO, $H_2$, $O_2$, methanol, ethanol, waste streams from processes to produce monomers for the Nylon-66 and Nylon-6 industries such as but not limited to non-volatile residues (NVRs) and caustic wash waste streams from the cyclohexane oxidation process used to manufacture adipic acid or caprolactam or waste stream from other chemical industry processes such as, but not limited to a carbon black industry or a hydrogen-refining industry, or petrochemical industry, a nonlimiting example being a PTA-waste stream.

In one nonlimiting embodiment, at least one of the enzymatic conversions of the production method comprises gas fermentation within the modulated *Ralstonia* or *Cupriavidus* organism or other organism with properties similar thereto. In this embodiment, the gas fermentation may comprise at least one of natural gas, syngas, CO, $H_2$, $O_2$, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

The methods of the present invention may further comprise recovering produced product from the organism. Once produced, any method can be used to isolate these products or derivatives or compounds related thereto.

The isolation of at least one product can involve any one or more downstream processes generally known to be suitable for the at least partial separation and/or isolation of material from a reaction or bioprocess. The collection can, for example, involve centrifugations, cell disruptions, concentrations, precipitations, extractions, filtrations, crystallizations, distillations, chemical conversions, or combinations thereof. One or more biosynthetic products can be collected from the liquid or solid phase of the culture, or from the gas phase present in the headspace of a bioreactor or the off-gas.

The present invention also provides nonnaturally occurring organisms and methods for producing the nonnaturally occurring organisms modified to comprise one or more modifications to increase carbon uptake and/or one or more modifications in a pathway to/from an overflow metabolite. Such modification may comprise overexpressing an endogenous or exogenous nucleic acid sequence in the organism. Alternatively, such modification may comprise downregulating, deleting or mutating an endogenous or exogenous nucleic acid sequence in the organism. These nonnaturally occurring organisms exhibit increased product yield as compared to product yield in the same organism without modification to comprise one or more modifications to increase carbon uptake and/or one or more modifications in a pathway to/from an overflow metabolite. The nonnaturally occurring organisms are selected from a species of *Cupriavidus* or *Ralstonia* with diminished polyhydroxybutyrate synthesis or an organism with properties similar thereto.

Nonlimiting examples of species of *Cupriavidus* or *Ralstonia* useful in accordance with this disclosure include *Cupriavidus necator, Cupriavidus metallidurans, Cupriavidus taiwanensis, Cupriavidus pinatubonensis, Cupriavidus basilensis* and *Ralstonia pickettii*.

In one nonlimiting embodiment, the present invention relates to a substantially pure culture of the nonnaturally occurring organism modified to comprise one or more modifications to increase carbon uptake and/or one or more modifications in a pathway to/from an overflow metabolite.

As used herein, a "substantially pure culture" of an altered organism is a culture of that microorganism in which less than about 40% (i.e., less than about 35%; 30%; 25%; 20%; 15%; 10%; 5%; 2%; 1%; 0.5%; 0.25%; 0.1%; 0.01%;

0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of nonnaturally occurring microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In addition, the present invention provides bio-derived, bio-based, or fermentation-derived products produced using the methods and/or nonnaturally occurring organisms disclosed herein. Examples of such products include, but are not limited to, compositions comprising at least one bio-derived, bio-based, or fermentation-derived compound or any combination thereof, as well as molded substances, formulations and semi-solid or non-semi-solid streams comprising one or more of the bio-derived, bio-based, or fermentation-derived compounds or compositions, combinations or products thereof.

While the invention has been described in detail, in some instances making reference to a specific aspect thereof, it is apparent to one of skill in the art that various changes and modifications can be made thereto without departing from its spirit and scope. The following section provides further illustration of the methods and materials of the present invention. These Examples are illustrative only and are not intended to limit the scope of the invention in any way.

EXAMPLES

Example 1: Identifying Tcts Proteins that Alter Assimilation of Different Carbon Sources In one nonlimiting embodiment, *R. eutropha* is grown in different carbon sources and RNAseq and/or proteomic experiments are performed to identify Tcts that are affected on different carbon sources. The Tcts are then validated by altering expression and/or activity and carbon utilization assessed. By modifying particular tcts, assimilation of different carbon sources can be altered. Such modifications may comprise overexpressing an endogenous or exogenous nucleic acid sequence in the organism. Alternatively, such modification may comprise downregulating, deleting or mutating an endogenous or exogenous nucleic acid sequence in the organism. For example, tctC genes H16_A1360, H16_A3350, H16_B1846 and H16_B1848 are induced through growth on pimelate, whilst H16_B0202 and H16_B1474 are induced through growth on adipate. TctC genes H16_A0036, H16_A1555, H16_B1078 and H16_B1448 are induced by growth on adipate and pimelate. TctC genes H16_A2384 and H16_B2116 are induced on fructose relative to pimelate and adipate. In addition, tctA gene H16_A2775 is induced on fructose relative to pimelate and adipate whilst H16_B2053 is induced on pimelate and adipate. TctB gene H16_B2054 is induced on pimelate and adipate whilst H16_A2774 is induced on fructose. RNA expression levels of selected *C. necator* H16 genes encoding Tct family transport components upon growth with fructose, adipate and pimelate as sole carbon sources are shown in Table 1. Gene expression levels were measured by RNAseq and are expressed as relative expression units (REU) that are normalized to total transcript levels.

TABLE 1

| Gene locus | Description | Expression on fructose (REU) | Expression on adipate (REU) | Expression on pimelate (REU) |
|---|---|---|---|---|
| H16_A0036 | TctC-type | 3 | 17 | 17 |
| H16_A1360 | TctC-type | 60 | 19 | 234 |
| H16_A1555 | TctC-type | 7 | 58 | 23 |
| H16_A2384 | TctC-type | 278 | 8 | 18 |
| H16_A2774 | TctB-type | 99 | 13 | 10 |
| H16_A2775 | TctA-type | 162 | 22 | 23 |
| H16_A3350 | TctC-type | 11 | 10 | 164 |
| H16_B0202 | TctC-type | 41 | 422 | 43 |
| H16_B1078 | TctC-type | 8 | 179 | 40 |
| H16_B1448 | TctC-type | 13 | 154 | 113 |
| H16_B1474 | TctC-type | 6 | 40 | 7 |
| H16_B1846 | TctC-type | 1 | 1 | 10 |
| H16_B1848 | TctC-type | 2 | 3 | 9 |
| H16_B2053 | TctA-type | 27 | 605 | 436 |
| H16_B2054 | TctB-type | 8 | 180 | 123 |
| H16_B2116 | TctC-type | 272 | 6 | 5 |

Example 2: Putative TTT Transporter Genes Present in *R. Eutropha* Genome

Nonlimiting examples of putative TTT transporter genes that can be altered in accordance with the present invention are set forth in Table 2.

TABLE 2

| tctA | tctB | tctC | | |
|---|---|---|---|---|
| h16_A2775 | h16_B2054 | H16_A0036 SEQ ID NO: 1) | H16_A3375 (SEQ ID NO: 53) | H16_B0924 (SEQ ID NO: 105) |
| h16_B2053 | h16_A3719 | | | |
| h16_A3720 | h16_A2774 | H16_A0079 (SEQ ID NO: 2) | H16_A3385 (SEQ ID NO: 54) | H16_B0925 (SEQ ID NO: 106) |
| PHG080 | | | | |
| PHG079 | | H16_A0091 (SEQ ID NO: 3) | H16_A3428 (SEQ ID NO: 55) | H16_B0983 (SEQ ID NO: 107) |
| | | H16_A0098 (SEQ ID NO: 4) | H16_A3650 (SEQ ID NO: 56) | H16_B0991 (SEQ ID NO: 108) |
| | | H16_A0102 (SEQ ID NO: 5) | H16_A3718 (SEQ ID NO: 57) | H16_B1006 (SEQ ID NO: 109) |
| | | H16_A0144 (SEQ ID NO: 6) | H16_B0053 (SEQ ID NO: 58) | H16_B1030 (SEQ ID NO: 110) |
| | | H16_A0198 (SEQ ID NO: 7) | H16_B0066 (SEQ ID NO: 59) | H16_B1033 (SEQ ID NO: 111) |
| | | H16_A0266 (SEQ ID NO: 8) | H16_B0088 (SEQ ID NO: 60) | H16_B1040 (SEQ ID NO: 112) |

TABLE 2-continued

| tctA | tctB | tctC | |
|---|---|---|---|
| | | H16_A0337 (SEQ ID NO: 9) | H16_B0128 (SEQ ID NO: 61) | H16_B1078 (SEQ ID NO: 113) |
| | | H16_A0404 (SEQ ID NO: 10) | H16_B0129 (SEQ ID NO: 62) | H16_B1280 (SEQ ID NO: 114) |
| | | H16_A0563 (SEQ ID NO: 11) | H16_B0202 (SEQ ID NO: 63) | H16_B1370 (SEQ ID NO: 115) |
| | | H16_A0592 (SEQ ID NO: 12) | H16_B0206 (SEQ ID NO: 64) | H16_B1440 (SEQ ID NO: 116) |
| | | H16_A0622 (SEQ ID NO: 13) | H16_B0215 (SEQ ID NO: 65) | H16_B1445 (SEQ ID NO: 117) |
| | | H16_A1110 (SEQ ID NO: 14) | H16_B0284 (SEQ ID NO: 66) | H16_B1448 (SEQ ID NO: 118) |
| | | H16_A1115 (SEQ ID NO: 15) | H16_B0302 (SEQ ID NO: 67) | H16_B1450 (SEQ ID NO: 119) |
| | | H16_A1238 (SEQ ID NO: 16) | H16_B0312 (SEQ ID NO: 68) | H16_B1474 (SEQ ID NO: 120) |
| | | H16_A1254 (SEQ ID NO: 17) | H16_B0331 (SEQ ID NO: 69) | H16_B1509 (SEQ ID NO: 121) |
| | | H16_A1293 (SEQ ID NO: 18) | H16_B0335 (SEQ ID NO: 70) | H16_B1527 (SEQ ID NO: 122) |
| | | H16_A1360 (SEQ ID NO: 19) | H16_B0346 (SEQ ID NO: 71) | H16_B1542 (SEQ ID NO: 123) |
| | | H16_A1396 (SEQ ID NO: 20) | H16_B0349 (SEQ ID NO: 72) | H16_B1618 (SEQ ID NO: 124) |
| | | H16_A1497 (SEQ ID NO: 21) | H16_B0363 (SEQ ID NO: 73) | H16_B1752 (SEQ ID NO: 125) |
| | | H16_A1555 (SEQ ID NO: 22) | H16_B0368 (SEQ ID NO: 74) | H16_B1754 (SEQ ID NO: 126) |
| | | H16_A1646 (SEQ ID NO: 23) | H16_B0369 (SEQ ID NO: 75) | H16_B1793 (SEQ ID NO: 127) |
| | | H16_A1674 (SEQ ID NO: 24) | H16_B0391 (SEQ ID NO: 76) | H16_B1814 (SEQ ID NO: 128) |
| | | H16_A1717 (SEQ ID NO: 25) | H16_B0392 (SEQ ID NO: 77) | H16_B1820 (SEQ ID NO: 129) |
| | | H16_A1781 (SEQ ID NO: 26) | H16_B0398 (SEQ ID NO: 78) | H16_B1821 (SEQ ID NO: 130) |
| | | H16_A1787 (SEQ ID NO: 27) | H16_B0399 (SEQ ID NO: 79) | H16_B1822 (SEQ ID NO: 131) |
| | | H16_A1883 (SEQ ID NO: 28) | H16_B0418 (SEQ ID NO: 80) | H16_B1846 (SEQ ID NO: 132) |
| | | H16_A1890 (SEQ ID NO: 29) | H16_B0480 (SEQ ID NO: 81) | H16_B1848 (SEQ ID NO: 133) |
| | | H16_A1928 (SEQ ID NO: 30) | H16_B0482 (SEQ ID NO: 82) | H16_B1906 (SEQ ID NO: 134) |
| | | H16_A2075 (SEQ ID NO: 31) | H16_B0486 (SEQ ID NO: 83) | H16_B1937 (SEQ ID NO: 135) |
| | | H16_A2080 (SEQ ID NO: 32) | H16_B0512 (SEQ ID NO: 84) | H16_B1973 (SEQ ID NO: 136) |
| | | H16_A2131 (SEQ ID NO: 33) | H16_B0513 (SEQ ID NO: 85) | H16_B1999 (SEQ ID NO: 137) |
| | | H16_A2140 (SEQ ID NO: 34) | H16_B0532 (SEQ ID NO: 86) | H16_B2001 (SEQ ID NO: 138) |
| | | H16_A2146 (SEQ ID NO: 35) | H16_B0537 (SEQ ID NO: 87) | H16_B2005 (SEQ ID NO: 139) |
| | | H16_A2153 (SEQ ID NO: 36) | H16_B0557 (SEQ ID NO: 88) | H16_B2116 (SEQ ID NO: 140) |
| | | H16_A2162 (SEQ ID NO: 37) | H16_B0606 (SEQ ID NO: 89) | H16_B2125 (SEQ ID NO: 141) |
| | | H16_A2303 (SEQ ID NO: 38) | H16_B0613 (SEQ ID NO: 90) | H16_B2155 (SEQ ID NO: 142) |
| | | H16_A2384 (SEQ ID NO: 39) | H16_B0678 (SEQ ID NO: 91) | H16_B2274 (SEQ ID NO: 143) |
| | | H16_A2419 (SEQ ID NO: 40) | H16_B0695 (SEQ ID NO: 92) | H16_B2308 (SEQ ID NO: 144) |
| | | H16_A2420 (SEQ ID NO: 41) | H16_B0697 (SEQ ID NO: 93) | H16_B2439 (SEQ ID NO: 145) |
| | | H16_A2597 (SEQ ID NO: 42) | H16_B0705 (SEQ ID NO: 94) | H16_B2441 (SEQ ID NO: 146) |
| | | H16_A2772 (SEQ ID NO: 43) | H16_B0726 (SEQ ID NO: 95) | H16_B2477 (SEQ ID NO: 147) |
| | | H16_A2779 (SEQ ID NO: 44) | H16_B0742 (SEQ ID NO: 96) | H16_B2492 (SEQ ID NO: 148) |
| | | H16_A2866 (SEQ ID NO: 45) | H16_B0748 (SEQ ID NO: 97) | H16_B2523 (SEQ ID NO: 149) |
| | | H16_A2980 (SEQ ID NO: 46) | H16_B0766 (SEQ ID NO: 98) | H16_B2533 (SEQ ID NO: 150) |
| | | H16_A3051 (SEQ ID NO: 47) | H16_B0775 (SEQ ID NO: 99) | PHG382 (SEQ ID NO: 151) |

TABLE 2-continued

| tctA | tctB | tctC | | |
|---|---|---|---|---|
| | | H16_A3191 (SEQ ID NO: 48) | H16_B0822 (SEQ ID NO: 100) | PHG392 (SEQ ID NO: 152) |
| | | H16_A3193 (SEQ ID NO: 49) | H16_B0844 (SEQ ID NO: 101) | PHG396 (SEQ ID NO: 153) |
| | | H16_A3203 (SEQ ID NO: 50) | H16_B0851 (SEQ ID NO: 102) | PHG400 (SEQ ID NO: 154) |
| | | H16_A3285 (SEQ ID NO: 51) | H16_B0908 (SEQ ID NO: 103) | PHG402 (SEQ ID NO: 155) |
| | | H16_A3350 (SEQ ID NO: 52) | H16_B0912 (SEQ ID NO: 104) | PHG403 (SEQ ID NO: 156) |

Example 3: Modifications in a Pathway to/from an Overflow Metabolite

Nonlimiting examples of pathways that can be blocked to increase yield of the desired product are set forth in FIG. 1 and Table 3.

TABLE 3

A. Prevention or limitation of formation and/or accumulation of overflow metabolites

| By-products which formation and/or accumulation are prevented or limited: | Enzymes that are targeted for altering their expression and/or activity | Reactions potentially catalyzed | EC numbers | Genes in *Cupriavidus necator* encoding the enzymes |
|---|---|---|---|---|
| lactate | L-Lactate dehydrogenase | pyruvate <-> L-lactate | EC:1.1.1.27 | H16_A0666 |
| | D-lactate dehydrogenase | pyruvate <-> D-lactate | EC:1.1.1.28 | H16_A1681, H16_A1682 |
| | Propionate CoA-transferase | Lactoyl-CoA <-> Lactate | EC:2.8.3.1 | H16_A2718 (pct) |
| acetate | Acetyl-CoA hydrolase/transferase | acetyl-CoA -> acetate | EC:3.1.2.1 | H16_B1368 |
| | Acetyl-CoA hydrolase | acetyl-CoA <-> acetate | EC:2.8.3.18 | H16_A1358 |
| | Propionate CoA-transferase | acetyl-CoA <-> acetate | EC:2.8.3.1 | H16_A2718 (pct) |
| | Acyl-CoA synthetase | Acetyl-CoA <-> acetyladenylate <-> acetate | EC:6.2.1.1 | H16_A1197 |
| | Acetyl-coenzyme A synthetase | Acetyl-CoA <-> acetyladenylate <-> acetate | EC:6.2.1.1 | H16_A1616, H16_A2525, H16_B0386, H16_B1102 |
| | Acetate-CoA ligase | Acetyl-CoA <-> acetyladenylate <-> acetate | EC:6.2.1.1 | H16_B0834 |
| | Acetaldehyde dehydrogenase | Acetyl-CoA <-> acetaldehyde | EC:1.2.1.10 | H16_A1806, H16_B0551, H16_B0596 |
| | NAD-dependent aldehyde dehydrogenase | acetaldehyde <-> Acetate | EC:1.2.1.3 | H16_A0745, H16_A1495, H16_A3345, H16_B0737, H16_B0833, H16_B1534, H16_B1735, H16_B1751, H16_B1835, H16_B2444 |
| | Aldehyde dehydrogenase, NAD(P)-dependent | acetaldehyde <-> Acetate | EC:1.2.1.3 | H16_B0421 |
| | Aldehyde dehydrogenase | acetaldehyde <-> Acetate | EC:1.2.1.— | H16_B1960 |
| | Phosphotransacetylase | acetyl-CoA <-> Acetyl-P | EC:2.3.1.8 | H16_B1631 (pta1), H16_B1871 (pta2) |
| | Acylphosphatase | Acetyl-P <-> Acetate | EC:3.6.1.7 | H16_A3325 |
| | Acetate kinase | Acetyl-P <-> Acetate | EC:2.7.2.1 | H16_A0670. H16_B1630 |

TABLE 3-continued

| A. Prevention or limitation of formation and/or accumulation of overflow metabolites | | | | |
|---|---|---|---|---|
| butanoate | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| | 3-hydroxyacyl-CoA dehydrogenase | Acetolacetyl-CoA <-> (S)-3-hydroxybutanoyl-CoA | EC:1.1.1.35 | H16_A0461 |
| | Enoyl-CoA hydratase/Delta(3)-cis-delta(2)-trans-enoyl-CoA isomerase | Acetolacetyl-CoA <-> (S)-3-hydroxybutanoyl-CoA | EC:1.1.1.35 | H16_A1526 |
| | Enoyl-CoA hydratase/isomerase family | Acetolacetyl-CoA <-> (S)-3-hydroxybutanoyl-CoA | EC:1.1.1.35 | H16_B0724 |
| | 3-Hydroxyacyl-CoA dehydrogenase | Acetolacetyl-CoA <-> (S)-3-hydroxybutanoyl-CoA | EC:1.1.1.157 | H16_A0282 (paaH1), H16_A1102 (paaH2) |
| | Enoyl-CoA hydratase | (S)-3-hydroxybutanoyl-CoA <-> Crotonoyl-CoA | EC:4.2.1.17 | H16_A0142, H16_A1889, H16_A2291, H16_A3307, H16_B0657, H16_B0659 |
| | Propionate CoA-transferase | Butyryl-CoA -> Butyrate | EC:2.8.3.1 | H16_A2718 (pct) |
| | Phosphotransacetylase | Butyryl-CoA <-> Butyryl-Phosphate | EC:2.3.1.8 | H16_B1631 (pta1), H16_B1871 (pta2) |
| | Acetate kinase | Butyryl-Phosphate <-> Butyrate | EC:2.7.2.1 | H16_A0670, H16_B1630 |
| branched chain amino acid (leucine, isoleucine, valine) | Acetolactate synthase | Pyruvate -> 2-aceto-2-hydroxybutyrate | EC 2.2.1.6 | H16_A1035, H16_A1036, H16_A2231, H16_B0313, H16_B0589, H16_B0735, H16_B2452 |
| | Ketol-acid reductoisomerase | 2-aceto-2-hydroxybutyrate <-> <-> 2,3-dihydroxy-3-methylpentanoate | EC:1.1.1.86 | H16_A1037 (ilvC) |
| | Dihydroxy-acid dehydratase | 2,3-dihydroxy-3-methylpentanoate -> 3-methyl-2-oxopentanoate | EC:4.2.1.9 | H16_A2987, H16_B0280 |
| | Branched-chain amino acid aminotransferase | 3-methyl-2-oxopentanoate -> L-isoleucine | EC:2.6.1.42 | H16_A0561 |
| | Leucine dehydrogenase | 3-methyl-2-oxopentanoate -> L-isoleucine | EC:1.4.1.9 | H16_B0449 |

TABLE 3-continued

| A. Prevention or limitation of formation and/or accumulation of overflow metabolites | | | | |
|---|---|---|---|---|
| | Acetolactate synthase | Pyruvate -> 2-acetolactate | EC 2.2.1.6 | H16_A1035, H16_A1036, H16_A2231, H16_B0313, H16_B0589, H16_B0735, H16_B2452 |
| | Ketol-acid reductoisomerase | 2-acetolactate <-> <-> 2,3-dihydroxy-3-methylbutanoate | EC:1.1.1.86 | H16_A1037 (ilvC) |
| | Dihydroxy-acid dehydratase | 2,3-dihydroxy-3-methylbutanoate -> 2-oxoisovalerate | EC:4.2.1.9 | H16_A2987, H16_B0280 |
| | Branched-chain amino acid aminotransferase | 2-oxoisovalerate -> L-valine | EC:2.6.1.42 | H16_A0561 |
| | Leucine dehydrogenase | 2-oxoisovalerate -> L-valine | EC:1.4.1.9 | H16_B0449 |
| | Aspartate/tyrosine/ aromatic aminotransferase | 2-oxoisovalerate <-> L-Valine | EC:2.6.1.66 | H16_A2267 |
| | Acetolactate synthase | Pyruvate -> 2-acetolactate | EC 2.2.1.6 | H16_A1035, H16_A1036, H16_A2231, H16_B0313, H16_B0589, H16_B0735, H16_B2452 |
| | Ketol-acid reductoisomerase | 2-acetolactate <-> <-> 2,3-dihydroxy-3-methylbutanoate | EC:1.1.1.86 | H16_A1037 (ilvC) |
| | Dihydroxy-acid dehydratase | 2,3-dihydroxy-3-methylbutanoate -> 2-oxoisovalerate | EC:4.2.1.9 | H16_A2987, H16_B0280 |
| | 2-Isopropylmalate synthase | 2-oxoisovalerate -> (2s) isopropylmalate | EC:2.3.3.13 | H16_A1041 (leuA1), H16_B0081 (leuA2) |
| | 3-Isopropylmalate dehydratase | (2s) isopropylmalate <-> <-> (2R,3S)-3-isopropylmalate | EC:4.2.1.33 | H16_A1236 (leuC1) large subunit, H16_A1237 (leuD1) small subunit, H16_A1549 (leuC2) large subunit, H16_A1550, (leuD2) small subunit, H16_A2620 (leuD3) small subunit, H16_A2621 (leuC3) large subunit, H16_B0051 (leuD4) small subunit, H16_B0052 (leuC4) large subunit, H16_B2275 (leuC5) large subunit, H16_B2276 (leuD5) small subunit |
| | 3-Isopropylmalate dehydrogenase | (2R,3S)-3-isopropylmalate <-> 2-isopropyl-3-oxosuccinate | EC:1.1.1.85 | H16_A2619 (leuB3) |
| | Branched-chain amino acid aminotransferase | 4-methyl-2-oxopentanoate <-> L-Leucine | EC:2.6.1.42 | H16_A0561 |
| | Leucine dehydrogenase | 4-methyl-2-oxopentanoate <-> L-Leucine | EC:1.4.1.9 | H16_B0449 |
| isobutyrate | Acetolactate synthase (AlsA) | Pyruvate -> 2-acetolactate | EC 2.2.1.6 | H16_A1035, H16_A1036, H16_A2231, H16_B0313, H16_B0589, H16_B0735, H16_B2452 |

TABLE 3-continued

| A. Prevention or limitation of formation and/or accumulation of overflow metabolites | | | | |
|---|---|---|---|---|
| acetoin | Acetolactate synthase (AlsA) | Pyruvate –> 2-acetolactate | EC 2.2.1.6 | H16_A1035 (ilvB), H16_A1036 (ilvH), H16_A2231, H16_B0313, H16_B0589, H16_B0735, H16_B2452 |
| | Acetoin dehydrogenase E1 component alpha-subunit | acetoin <-> acetaldehyde + acetyl-CoA | EC:1.1.1.—] | H16_B0144 (AcoA) |
| | Acetoin dehydrogenase E1 component beta-subunit | acetoin <-> acetaldehyde + acetyl-CoA | EC:1.1.1.—] | H16_B0145 (AcoB) |
| 2,3 butanediol | Acetolactate synthase (AlsA) | Pyruvate –> 2-acetolactate | EC 2.2.1.6 | H16_A1035, H16_A1036, H16_A2231, H16_B0313, H16_B0589, H16_B0735, H16_B2452 |
| | Alcohol dehydrogenase | production of ethanol and/or 2,3-Butanediol | EC:1.1.1.1 | H16_A0757 (adh) |
| | Butanediol Dehydrogenase [4] | acetoin <-> 2,3 butanediol | EC:1.1.1.4 | |
| 3-hydroxy-butyrate | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| | Acetoacetyl-CoA reductase | Acetoacetyl-CoA <-> 3-Hydroxybutyryl-CoA | EC:1.1.1.36 | H16_A1439 (phaB1), H16_A2002 (phaB2), H16_A2171 (phaB3) |
| | Poly(3-hydroxybutyrate) polymerase | 3-Hydroxybutyryl-CoA <-> Polyhydroxybutyrate (PHB) | EC:2.3.1.— | H16_A1437 (phaC1), H16_A2003 (phaC2) |
| | Intracellular poly(3-hydroxybutyrate) depolymerase | Polyhydroxybutyrate (PHB) <-> 3,3-hydroxybutanoyl oxybtanoate | EC:3.1.1.75 | H16_A1150 (phaZ1), H16_A2862 (phaZ2), H16_B0339 (phaZ3), H16_B1014 (phaZ5), H16_B2073 (phaZ6), H16_B2401 (phaZ7) |
| | D-(−)-3-hydroxybutyrate oligomer hydrolase | 3,3-hydroxybutanoyl oxybtanoate <-> 3-hydroxyburyrate | EC:3.1.1.22 | H16_A2251 (phaY1) |
| | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, |

TABLE 3-continued

| A. Prevention or limitation of formation and/or accumulation of overflow metabolites | | | | |
|---|---|---|---|---|
| | | | | H16_B0381, H16_B0406, H16_B0662, H16_B0668, H16_B0759, H16_B1369, H16_B1771 |
| | Succinyl-CoA: 3-ketoacid-coenzyme A transferase | Acetoacetyl-CoA <-> Acetoacetate | EC:2.8.3.5 | H16_A1331 (subunit A), H16_A1332 (subunit B) |
| | D-beta-hydroxybutyrate dehydrogenase | Acetoacetate <-> 3-hydroxyburyrate | EC:1.1.1.30 | h16_A1334, h16_A1814 |
| Acetaldehyde and ethanol | Acetaldehyde dehydrogenase | Acetyl-CoA <-> Acetaldehyde | EC:1.2.1.10 | H16_A1806, H16_B0551, H16_B0596 |
| | Alcohol dehydrogenase, class IV | Acetaldehyde <-> Ethanol | EC:1.1.1.1 | H16_A0861 |
| | Zn-dependent alcohol dehydrogenase | Acetaldehyde <-> Ethanol | EC:1.1.1.1 | H16_B0517, H16_B1433 (adhP), H16_B1699, H16_B1745 |
| | Alcohol dehydrogenase, class III | Acetaldehyde <-> Ethanol | EC:1.1.1.1 | H16_B1195 (adhC), H16_B2470 |
| | Alcohol dehydrogenase (cytochrome c) | Acetaldehyde <-> Ethanol | EC:1.1.2.8 | H16_B1047 (quiA) |
| | Alcohol dehydrogenase | production of ethanol and/or 2,3-butanediol | EC:1.1.1.1 | H16_A0757 (adh) |
| Acetone | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| | Succinyl-CoA: 3-ketoacid-coenzyme A transferase | Acetoacetyl-CoA <-> Acetoacetate | EC:2.8.3.5 | H16_A1331 (subunit A), H16_A1332 (subunit B) |
| Methanol | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| 2-propanol | Acetyl-CoA acetyltransferase | Acetyl-CoA <-> Acetoacetyl-CoA | EC:2.3.1.9 | H16_A0170, H16_A0867, H16_A0868, H16_A0872, |

TABLE 3-continued

A. Prevention or limitation of formation and/or accumulation of overflow metabolites H16_A1297,
H16_A1438 (phaA),
H16_A1445,
H16_A1528,
H16_A1713,
H16_A1887,
H16_A1720,
H16_A2148,
H16_B0380,
H16_B0381,
H16_B0406,
H16_B0662,
H16_B0668,
H16_B0759,
H16_B1369,
H16_B1771

B. Re-direction of flux from an overflow metabolite

Metabolites:
malate, citrate, succinate, cis-aconitate, 2-oxoglutarate and isocitrate (TCA cycle intermediates).
Potential strategy:
In an aspect of the invention, an excess of TCA cycle intermediates such as malate, citrate, succinate, cis-aconitate, 2-oxoglutarate and isocitrate is prevented by funneling the carbon through the TCA cycle towards an intermediate of interest and/or tuning down the utilization of that same intermediate in the TCA (resulting in driving flux out of the TCA cycle)

| Exemplification | Enzymes that are targeted for altering their expression and/or activity | Reactions potentially catalyzed | EC numbers | Genes in *Cupriavidus necator* encoding the enzymes |
|---|---|---|---|---|
| Under N-limiting conditions cis-aconitate accumulates. To increase production of arginine one could accelerate the flux from cis-aconitate to 2-oxoglutarate (alter expression and/or activity of EC4.2.1.3, 1.1.1.41, 1.1.1.42) which could then be converted into glutamate (EC 2.6.1.2) and enter the arginine metabolism. | Aconitate hydratase | citrate <-> cis-aconitate <-> isocitrate | EC:4.2.1.3 | H16_A2638 (acnA), H16_B0568 (acnB) |
| | Isocitrate dehydrogenase [NAD] | isocitrate <-> 2-oxoglutarate | EC:1.1.1.41 | H16_B1016 (icd3) |
| | Isocitrate dehydrogenase [NADP] | isocitrate <-> oxalusuccinate <-> 2-oxoglutarate | EC:1.1.1.42 | H16_A3056 (icd1), H16_B1931 |
| | Aspartate/tyrosine/aromatic aminotransferase | 2-oxoglutarate –> Glutamate | EC:2.6.1.2 | H16_A2267 |

See Voldina et al. Appl Microbiol Biotechnol. 2014 98(8): 3579-89; Steinbüchel and Schlegel Eur J Biochem. 1984 141(3): 555-64; Raberg et al. PLoS One. 2014; 9(5): e95907; and Schlegel and Vollbrecht Microbiology 1980 117: 475-481

TABLE 3

A. Prevention or limitation of formation and/or accumulation of overflow metabolites

| By-products which formation and/or accumulation are prevented or limited: | Enzymes that are targeted for altering their expression and/or activity | Reactions potentially catalyzed | EC numbers | Genes in *Cupriavidus necator* encoding the enzymes |
|---|---|---|---|---|
| lactate | L-Lactate dehydrogenase | pyruvate <-> L-lactate | EC:1.1.1.27 | H16_A0666 |
| | D-lactate dehydrogenase | pyruvate <-> D-lactate | EC:1.1.1.28 | H16_A1681, H16_A1682 |
| | Propionate CoA-transferase | Lactoyl-CoA <-> Lactate | EC:2.8.3.1 | H16_A2718 (pct) |
| 3-hydroxy-butyrate | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, |

TABLE 3-continued

A. Prevention or limitation of formation and/or accumulation of overflow metabolites

| By-products which formation and/or accumulation are prevented or limited: | Enzymes that are targeted for altering their expression and/or activity | Reactions potentially catalyzed | EC numbers | Genes in *Cupriavidus necator* encoding the enzymes |
|---|---|---|---|---|
| | | | | H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| | Acetoacetyl-CoA reductase | Acetoacetyl-CoA <-> 3-Hydroxybutyryl-CoA | EC:1.1.1.36 | H16_A1439 (phaB1), H16_A2002 (phaB2), H16_A2171 (phaB3) |
| | Poly(3-hydroxybutyrate) polymerase | 3-Hydroxybutyryl-CoA <-> Polyhydroxybutyrate (PHB) | EC:2.3.1.— | H16_A1437 (phaC1), H16_A2003 (phaC2) |
| | Intracellular poly(3-hydroxybutyrate) depolymerase | Polyhydroxybutyrate (PHB) <-> 3,3-hydroxybutanoyl oxybtanoate | EC:3.1.1.75 | H16_A1150 (phaZ1), H16_A2862 (phaZ2), H16_B0339 (phaZ3), H16_B1014 (phaZ5), H16_B2073 (phaZ6), H16_B2401 (phaZ7) |
| | D-(-)-3-hydroxybutyrate oligomer hydrolase | 3,3-hydroxybutanoyl oxybtanoate <-> 3-hydroxyburyrate | EC:3.1.1.22 | H16_A2251 (phaY1) |
| | Acetyl-CoA acetyltransferase | Acetyl-CoA <-> Acetoacetyl-CoA | EC:2.3.1.9 | H16_A0170, H16_A0867, H16_A0868, H16_A0872, H16_A1297, H16_A1438 (phaA), H16_A1445, H16_A1528, H16_A1713, H16_A1887, H16_A1720, H16_A2148, H16_B0380, H16_B0381, H16_B0406, H16_B0662, H16_B0668, H16_B0759, H16_B1369, H16_B1771 |
| | Succinyl-CoA: 3-ketoacid-coenzyme A transferase | Acetoacetyl-CoA <-> Acetoacetate | EC:2.8.3.5 | H16_A1331 (subunit A), H16_A1332 (subunit B) |
| | D-beta-hydroxybutyrate dehydrogenase | Acetoacetate <-> 3-hydroxyburyrate | EC:1.1.1.30 | h16_A1334, h16_A1814 |
| acetate | Acetyl-CoA hydrolase/transferase | acetyl-CoA -> acetate | EC:3.1.2.1 | H16_B1368 |
| | Acetyl-CoA hydrolase | acetyl-CoA <-> acetate | EC:2.8.3.18 | H16_A1358 |
| | Propionate CoA-transferase | acetyl-CoA <-> acetate | EC:2.8.3.1 | H16_A2718 (pct) |
| | Acyl-CoA synthetase | Acetyl-CoA <-> acetyladenylate <-> acetate | EC:6.2.1.1 | H16_A1197 |

TABLE 3-continued

A. Prevention or limitation of formation and/or accumulation of overflow metabolites

| By-products which formation and/or accumulation are prevented or limited: | Enzymes that are targeted for altering their expression and/or activity | Reactions potentially catalyzed | EC numbers | Genes in *Cupriavidus necator* encoding the enzymes |
|---|---|---|---|---|
| | Acetyl-coenzyme A synthetase | Acetyl-CoA <-> acetyladenylate <-> acetate | EC:6.2.1.1 | H16_A1616, H16_A2525, H16_B0386, H16_B1102 |
| | Acetate-CoA ligase | Acetyl-CoA <-> acetyladenylate <-> acetate | EC:6.2.1.1 | H16_B0834 |
| | Acetaldehyde dehydrogenase | Acetyl-CoA <-> acetaldehyde | EC:1.2.1.10 | H16_A1806, H16_B0551, H16_B0596 |
| | NAD-dependent aldehyde dehydrogenase | acetaldehyde <-> Acetate | EC:1.2.1.3 | H16_A0745, H16_A1495, H16_A3345, H16_B0737, H16_B0833, H16_B1534, H16_B1735, H16_B1751, H16_B1835, H16_B2444 |
| | Aldehyde dehydrogenase, NAD(P)-dependent | acetaldehyde <-> Acetate | EC:1.2.1.3 | H16_B0421 |
| | Aldehyde dehydrogenase | acetaldehyde <-> Acetate | EC:1.2.1.— | H16_B1960 |
| | Phosphotransacetylase | acetyl-CoA <-> Acetyl-P | EC:2.3.1.8 | H16_B1631 (pta1), H16_B1871 (pta2) |
| | Acylphosphatase | Acetyl-P <-> Acetate | EC:3.6.1.7 | H16_A3325 |
| | Acetate kinase | Acetyl-P <-> Acetate | EC:2.7.2.1 | H16_A0670. H16_B1630 |
| 2,3 butanediol | Acetolactate synthase (AlsA) | Pyruvate -> 2-acetolactate | EC 2.2.1.6 | H16_A1035, H16_A1036, H16_A2231, H16_B0313, H16_B0589, H16_B0735, H16_B2452 |
| | Alcohol dehydrogenase | production of ethanol and/or 2,3-butanediol | EC:1.1.1.1 | H16_A0757 (adh) |
| | Butanediol Dehydrogenase | acetoin <-> 2,3 butanediol | EC:1.1.1.4 | |

What is claimed is:

1. A method for increasing carbon-based chemical product yield in an organism, said method comprising modifying an organism selected from a species of *Cupriavidus* or *Ralstonia* with diminished polyhydroxybutyrate synthesis by modulating activity of one or more polypeptides functioning to increase carbon uptake comprising one or more carbon transporter proteins selected from TctA, TctB or TctC, thereby increasing carbon-based chemical product yield in the organism as compared to an organism without said modulated polypeptide activity.

2. The method of claim 1, wherein modulating the activity of one or more polypeptides comprises overexpressing or mutating an endogenous or exogenous nucleic acid sequence in the organism.

3. The method of claim 1, wherein modulating the activity of one or more polypeptides thereof comprises, deleting or mutating an endogenous or exogenous nucleic acid sequence in the organism.

* * * * *